US011555195B2

(12) United States Patent
Abramson et al.

(10) Patent No.: US 11,555,195 B2
(45) Date of Patent: Jan. 17, 2023

(54) TISSUE-SPECIFIC EXPRESSION CONTROL OF DELLA POLYPEPTIDES

(71) Applicant: FUTURAGENE ISRAEL LTD., Rehovot (IL)

(72) Inventors: Miron Abramson, Karmei Yosef (IL); Tany Sinai, Neve Yarak (IL); Sivan Livne, Rehobot (IL)

(73) Assignee: Futuragene Israel Ltd., Rehovot (IL)

(*) Notice: Subject to any disclaimer, the term of this patent is extended or adjusted under 35 U.S.C. 154(b) by 0 days.

(21) Appl. No.: 16/644,643

(22) PCT Filed: Sep. 17, 2018

(86) PCT No.: PCT/IL2018/051040

§ 371 (c)(1),
(2) Date: Mar. 5, 2020

(87) PCT Pub. No.: WO2019/053725

PCT Pub. Date: Mar. 21, 2019

(65) Prior Publication Data

US 2021/0062202 A1 Mar. 4, 2021

Related U.S. Application Data

(60) Provisional application No. 62/582,767, filed on Nov. 7, 2017, provisional application No. 62/577,549, filed on Oct. 26, 2017, provisional application No. 62/559,746, filed on Sep. 18, 2017.

(51) Int. Cl.
*C12N 15/82* (2006.01)
*C07K 14/415* (2006.01)

(52) U.S. Cl.
CPC ........ *C12N 15/8213* (2013.01); *C07K 14/415* (2013.01); *C12N 15/8218* (2013.01); *C12N 15/8261* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 4,658,082 | A | 4/1987 | Simpson et al. | |
| 4,945,050 | A | 7/1990 | Sanford et al. | |
| 5,034,323 | A | 7/1991 | Jorgensen et al. | |
| 5,231,020 | A | 7/1993 | Jorgensen et al. | |
| 5,262,306 | A | 11/1993 | Robeson et al. | |
| 5,283,184 | A | 2/1994 | Jorgensen et al. | |
| 5,693,512 | A | 12/1997 | Finer et al. | |
| 5,736,369 | A | 4/1998 | Bowen et al. | |
| 5,981,840 | A | 11/1999 | Zhao et al. | |
| 6,300,543 | B1 | 10/2001 | Cass et al. | |
| 8,697,359 | B1 | 4/2014 | Zhang | |
| 2004/0029283 | A1 | 2/2004 | Fillatti | |
| 2005/0034192 | A1 | 2/2005 | Damaj et al. | |
| 2007/0039070 | A1* | 2/2007 | Bloksberg et al. .. | C07K 14/415 800/284 |
| 2008/0313773 | A1 | 12/2008 | Chua et al. | |
| 2009/0172841 | A1* | 7/2009 | Lawit et al. ......... | C12N 15/827 800/290 |
| 2010/0286082 | A1 | 11/2010 | Breaker et al. | |
| 2010/0287672 | A1 | 11/2010 | Chang et al. | |
| 2011/0245326 | A1 | 10/2011 | Belmont et al. | |
| 2014/0273235 | A1 | 9/2014 | Voytas et al. | |
| 2015/0052634 | A1 | 2/2015 | Park et al. | |
| 2015/0059010 | A1* | 2/2015 | Cigan et al. ....... | C12N 15/8216 800/260 |

FOREIGN PATENT DOCUMENTS

| | | |
|---|---|---|
| EP | 0271988 | 6/1988 |
| EP | 0604662 | 7/1994 |
| EP | 0672752 | 9/1995 |
| ES | 2364932 | 8/2012 |
| WO | WO 1991/010725 | 7/1991 |
| WO | WO 1994/003282 | 2/1994 |
| WO | WO 1998/031812 | 7/1998 |
| WO | WO 1999/53050 | 10/1999 |
| WO | WO 2011/054998 | 5/2011 |
| WO | WO 2013/176772 | 11/2013 |
| WO | WO 2017/048969 | 3/2017 |
| WO | WO 2018/116501 | 6/2018 |
| WO | WO 2018/119501 | 7/2018 |
| WO | WO 2019/053725 | 3/2019 |

OTHER PUBLICATIONS

MacMillan et al. (2015) New Phytol 206:1314-27.*
Harberd & Freeling (1989) Genetics 121(4):827-38.*
Chandler & Harding (2013) J Exp Bot 64(6):1603-13.*
Zentella et al. (2007) Plant Cell 19:3037-57.*
Crane (2004) Phil Trans Biol Sci 359:735-37.*
Achard & Genschik (2009) J Exp Bot 60(4): 1085-92.*
Koyama et al. (2005) J Biosci Bioengin 99(1):38-42.*
Svitashev et al. (2015) Plant Physiol 169:931-45.*
Holtorf et al. (1995) Plant Mol Biol 29:637-46.*
U.S. Appl. No. 62/559,746, filed Sep. 18, 2017, Futuragene Isreal LTD.
U.S. Appl. No. 62/577,549, filed Oct. 26, 2017, Futuragene Isreal LTD.
U.S. Appl. No. 62/582,767, filed Nov. 7, 2017, Futuragene Isreal LTD.
PCT International Preliminary Report on Patentability in International Appln. No. PCT/IL2018/051040, dated Mar. 24, 2020, 17 pages.
PCT International Search Report and Written Opinion in International Appln. No. PCT/IL2018/051040, dated Feb. 22, 2019, 27 pages.

(Continued)

*Primary Examiner* — Russell T Boggs
(74) *Attorney, Agent, or Firm* — Fish & Richardson P.C.

(57) ABSTRACT

Constructs for genetically engineering plants to selectively alter DELLA gene expression to promote plant growth while maintaining root integrity are provided, as are methods of designing, making and using such constructs.

31 Claims, 27 Drawing Sheets

Specification includes a Sequence Listing.

(56) References Cited

OTHER PUBLICATIONS

Myburg et al., "The genome of Eucalyptus grandis," Nature, 2014, 510(7505):356-362.
Achard et al., "Gibberellin signaling controls cell proliferation rate in *Arabidopsis,*" Current Biology, 2009, 19(14):1188-1193.
EP European Search Report in European App No. 18856388.6, dated May 3, 2021, 6 pages.
Lor et al., "Targeted mutagenesis of the tomato PROCERA gene using transcription activator-like effector nucleases," Plant Physiology, 2004, 166(3):1288-1291.
Busov et al., "Activation tagging is an effective gene tagging system in *Populus,*" Tree Genetics & Genomes, Feb. 2010, 7:91-101.
Busov et al., "Transgenic modification of gai or rgll causes dwarfing and alters gibberellins, root growth, and metabolite profiles in *Populus*," Planta, Jul. 2006, 224:288-299.
Crista.tau.ac.il [Online], "CRISTA—CRISPR Target Assessment," available on or before Mar. 10, 2017, via Internet Archive: Wayback Machine URL <http://web.archive.org/web/20170310035837/https://crista.tau.ac.il/>, retrieved on Jan. 31, 2022, URL<https://crista.tau.ac.il/>, 2 pages.
Eriksson et al., "Increased gibberellin biosynthesis in transgenic trees promotes growth, biomass production and xylem fiber length," Nature Biotechnology, Jul. 2000, 18:784-788.
Goodstein et al. [Online], "Phytozome: a comparative platform for green plant genomics," Nucleic Aciss Research, 2012, 40:D1178-D1186, retrieved on Jan. 31, 2022, URL<https://phytozome.jgi.doe.gov/>, 3 pages.
Harberd et al., "The angiosperm gibberellin-GIDl-DELLA growth regulatory mechanism: How an 'inhibitor of an inhibitor' enables flexible response to fluctuating environments," The Plant Cell, May 2009, 21:1328-1339.
Kazusa.or.jp/codon [Online], "Codon Usage Database," available on or before Mar. 23, 2017, via Innernet Archive: Wayback Machine URL <https://web.archive.org/web/20170323041725/http://www.kazusa.or.jp/codon/>, retrieved on Jan. 31, 2022, URL<www.kazusa.or.jp/codon/>, 1 page.
Lo et al., "A novel class of gibberellin 2-oxidases control semidwarfism, tillering, and root development in rice," The Plant Cell, Oct. 2008, 20:2603-2618.
PlantGenIE.org [Online], "Search PlantGenIE," available on or before Apr. 15, 2017, via Internet Archive: Wayback Machine URL <http://web.archive.org/web/20170415000005/https://plantgenie.org/>, retrieved on Jan. 31, 2022, URL<https://plantgenie.org/>, 1 page.
Sun et al., "Molecular mechanism of gibberellin signaling in plants," Annual Review Plant Biology, 2004, 55:197-223.
Swain et al., "Tall tales from sly dwarves: novel functions of gibberellins in plant development," TRENDS in Plant Science, Mar. 2005, 10:123-129.
Tyler et al., "DELLA proteins and gibberellin-regulated seed germination and floral development in *Arabidopsis,*" Plant Physiology, Jun. 2004, 135:1008-1019.
Wen et al., "*Arabidopsis* RGLl encodes a negative regulator of gibberellin responses," The Plant Cell, Jan. 2002, 14:87-100.
Wild et al., "The *Arabidopsis* DELLA RGA-LIKE3 is a direct target of MYC2 and modulates jasmonate signaling responses," The Plant Cell, Aug. 2012, 24:3307-3319.
Yamagushi, "Gibberellin metabolism and its regulation," Annual Review of Plant Biology, 2008, 59:225-251.
Bakhsh et al., "Endeavours of RuBisCO small subunit promoter as a tool of green tissue specific expression," Czech Journal of Genetics and Plant Breeding, 2012, 48(1):1-9.
Nomura et al., "The promoter of rbcS in a C3 plant (rice) directs organ-specific, light-dependent expression in a C4 plant (maize), but does not confer bundle sheath cell-specific expression," Plant Molecular Biology, 2000, 44:99-106.

* cited by examiner

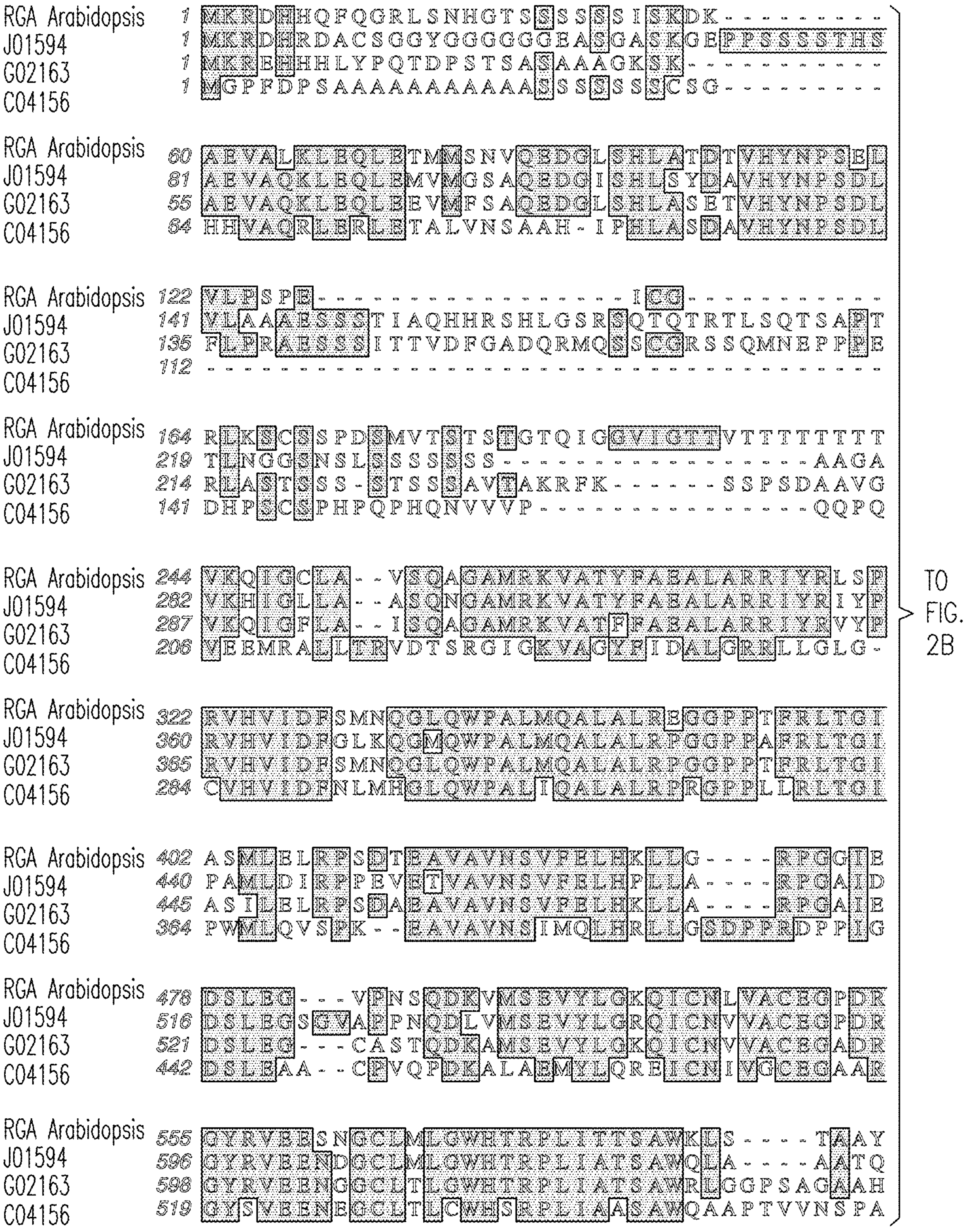

FIG. 2A

```
RGA Arabidopsis   1  MKRDHHQFQGRLSNHGTSSSSSSISKDK--------------
J01594            1  MKRDHRDACSGGYGGGGGEASGASKGEPPSSSSTHS
G02163            1  MKREHHHLYPQTDPSTSASAAAGKSK--------------
C04156            1  MGPFDPSAAAAAAAAASSSSSSCSG---------------

RGA Arabidopsis  60  AEVALKLEQLETMMSNVQEDGLSHLATDTVHYNPSEL
J01594           81  AEVAQKLEQLEMVGSAQEDGISHLSYDAVHYNPSDL
G02163           55  AEVAQKLEQLEVMFSAQEDGLSHLASETVHYNPSDL
C04156           64  HHVAQRLERLETALVNSAAH-IPHLASDAVHYNPSDL

RGA Arabidopsis 122  VLPSPE----------------ICG---------------
J01594          141  VLAAAESSSTIAQHHRSHLGSRSQTQTRTLSQTSAPT
G02163          135  FLPRAESSSITTVDFGADQRMQSSCGRSSQMNEPPPE
C04156          112  ---------------------------------------

RGA Arabidopsis 164  RLKSCSSPDSMVTSTSTGTQIGGVIGTIVTTTTTTTT
J01594          219  TLNGGSNSLSSSSSS----------------AAGA
G02163          214  RLASTSSS-STSSSAVTAKRFK------SSPSDAAVG
C04156          141  DHPSCSPHPQPHQNVVVP-------------QQPQ

RGA Arabidopsis 244  VKQIGCLA--VSQAGAMRKVATYFAEALARRIYRLSP
J01594          282  VKHIGLLA--ASQNGAMRKVATYFAEALARRIYRIYP    TO
G02163          287  VKQIGFLA--ISQAGAMRKVATFFAEALARRIYRVYP    FIG.
C04156          206  VEEMRALLTRVDTSRGIGKVAGYFIDALGRRLLGLG-    2B

RGA Arabidopsis 322  RVHVIDFSMNQGLQWPALMQALALREGGPPTFRLTGI
J01594          360  RVHVIDFGLKQGMQWPALMQALALRPGGPPAFRLTGI
G02163          365  RVHVIDFSMNQGLQWPALMQALALRPGGPPTFRLTGI
C04156          284  CVHVIDFNLMHGLQWPALIQALALRPRGPPLLRLTGI

RGA Arabidopsis 402  ASMLELRPSDTEAVAVNSVFELHKLLG----RPGGIE
J01594          440  PAMLDIRPPEVETVAVNSVFELHPLLA----RPGAID
G02163          445  ASILELRPSDAEAVAVNSVFELHKLLA----RPGAIE
C04156          364  PWMLQVSPK--EAVAVNSIMQLHRLLGSDPPRDPPIG

RGA Arabidopsis 478  DSLEG----VPNSQDKVMSEVYLGKQICNLVACEGPDR
J01594          516  DSLEGSGVAPPNQDLVMSEVYLGRQICNVVACEGPDR
G02163          521  DSLEG----CASTQDKAMSEVYLGKQICNVVACEGADR
C04156          442  DSLEAA--CPVQPDKALAMYLQREICNIVGCEGAAR

RGA Arabidopsis 555  GYRVEESNGCLMLGWHTRPLITTSAWKLS----TAAY
J01594          596  GYRVEENDGCLMLGWHTRPLIATSAWQLA----AATQ
G02163          598  GYRVEENGGCLTLGWHTRPLIATSAWRLGGPSAGAAH
C04156          519  GYSVEENEGCLTLCWHSRPLIAASAWQAAPTVVNSPA
```

FROM FIG. 2A

FROM FIG. 3A

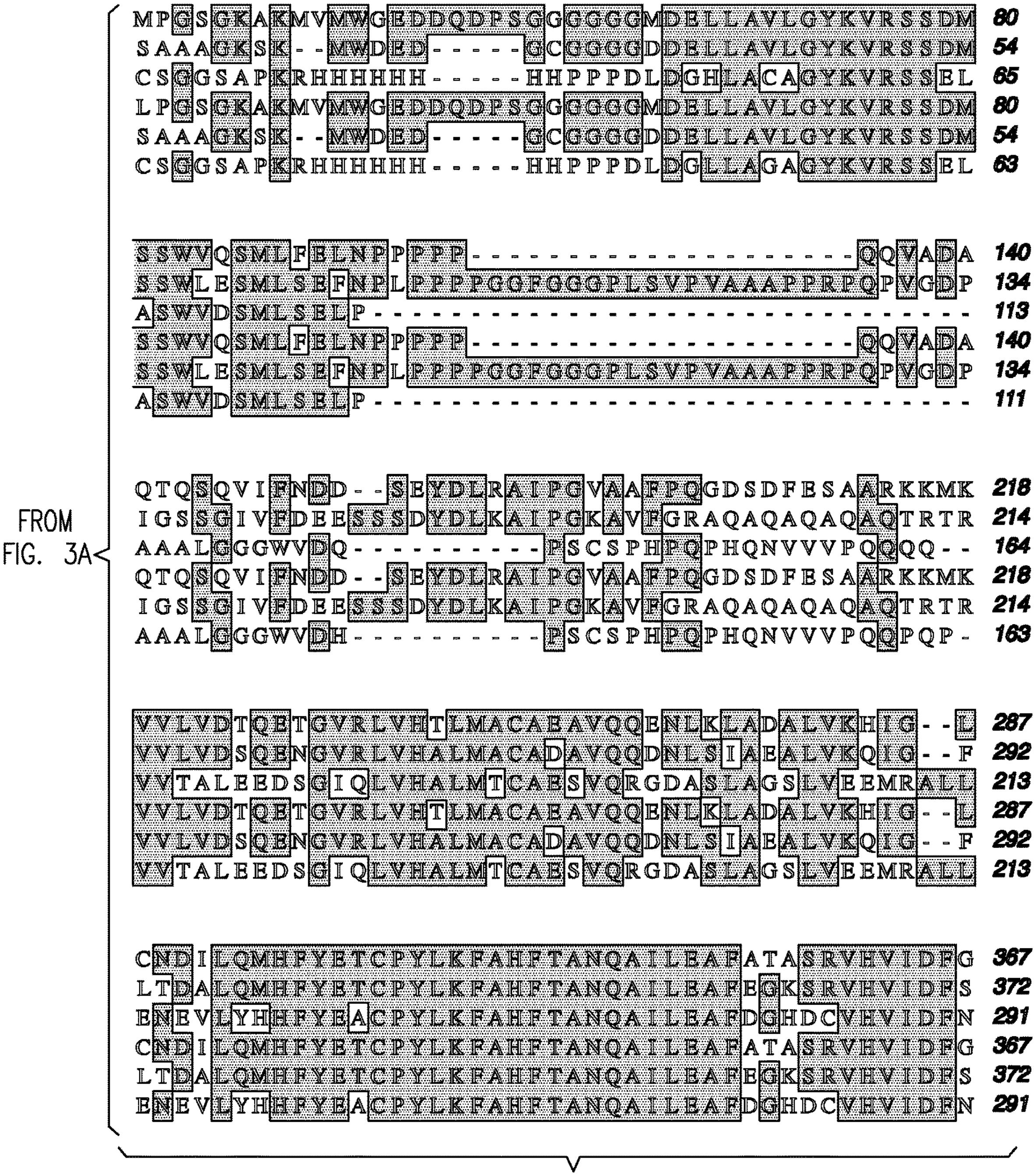

```
         MPGSGKAKMVMWGEDDQDPSGGGGGGMDELLAVLGYKVRSSDM  80
         SAAAGKSK--MWDED-----GCGGGGDDELLAVLGYKVRSSDM  54
         CSGGSAPKRHHHHHHH-----HHPPPDLDGHLACAGYKVRSSEL  65
         LPGSGKAKMVMWGEDDQDPSGGGGGMDELLAVLGYKVRSSDM  80
         SAAAGKSK--MWDED-----GCGGGGDDELLAVLGYKVRSSDM  54
         CSGGSAPKRHHHHHHH-----HHPPPDLDGLLAGAGYKVRSSEL  63

         SSWVQSMLFELNPPPPP--------------QQVADA  140
         SSWLESMLSEFNPLPPPPGGFGGGPLSVPVAAAPPRPQPVGDP  134
         ASWVDSMLSELP--------------------------  113
         SSWVQSMLFELNPPPPP--------------QQVADA  140
         SSWLESMLSEFNPLPPPPGGFGGGPLSVPVAAAPPRPQPVGDP  134
         ASWVDSMLSELP--------------------------  111

         QTQSQVIFNDD--SEYDLRAIPGVAAFPQGDSDFESAARKKMK  218
         IGSSGIVFDEESSSDYDLKAIPGKAVFGRAQAQAQAQTRTR  214
FROM     AAALGGGWVDQ--------------PSCSPHPQPHQNVVVPQQQQ--  164
FIG. 3A  QTQSQVIFNDD--SEYDLRAIPGVAAFPQGDSDFESAARKKMK  218
         IGSSGIVFDEESSSDYDLKAIPGKAVFGRAQAQAQAQTRTR  214
         AAALGGGWVDH--------------PSCSPHPQPHQNVVVPQQPQP-  163

         VVLVDTQETGVRLVHTLMACAEAVQQENLKLADALVKHIG--L  287
         VVLVDSQENGVRLVHALMACADAVQQDNLSIAEALVKQIG--F  292
         VVTALEEDSGIQLVHALMTCAESVQRGDASLAGSLVEEMRALL  213
         VVLVDTQETGVRLVHTLMACAEAVQQENLKLADALVKHIG--L  287
         VVLVDSQENGVRLVHALMACADAVQQDNLSIAEALVKQIG--F  292
         VVTALEEDSGIQLVHALMTCAESVQRGDASLAGSLVEEMRALL  213

         CNDILQMHPYETCPYLKFAHPTANQAILEAFATASRVHVIDFG  367
         LTDALQMHRYETCPYLKFAHPTANQAILEAFEGKSRVHVIDFS  372
         ENEVLYHHPYEACPYLKFAHPTANQAILEAFDGHDCVHVIDFN  291
         CNDILQMHPYETCPYLKFAHPTANQAILEAFATASRVHVIDFG  367
         LTDALQMHRYETCPYLKFAHPTANQAILEAFEGKSRVHVIDFS  372
         ENEVLYHHPYEACPYLKFAHPTANQAILEAFDGHDCVHVIDFN  291
```

FROM FIG. 3A

```
DELLA1  368  LKQGMQWPALMQALALRPGGPPAFRLTGIGPPQPNNT
DELLA2  373  MNQGLQWPALMQALALRPGGPPTFRLTGIGPPAPDNS
DELLA3  292  LMHGLQWPALIQALALRPRGPPLLRLTGIGPPSPDGR
J01594  368  LKQGMQWPALMQALALRPGGPPAFRLTGIGPPQPNNT
G02163  373  MNQGLQWPALMQALALRPGGPPTFRLTGIGPPAPDNS
C04156  292  LMHGLQWPALIQALALRPRGPPLLRLTGIGPPSPDGR

DELLA1  448  PEVETVAVNSVPELHPLLA----RPGAIDKVLSSIKA
DELLA2  453  SDAEAVAVNSVPELHKLLA----RPGAIEKVLGVVRQ
DELLA3  372  K--EAVAVNSIMQLHRLLGSDPPRDPPIGSVLPWIRS
J01594  448  PEVETVAVNSVPELHPLLA----RPGAIDKVLSSIKA
G02163  453  SDAEAVAVNSVPELHKLLA----RPGAIEKVLGVVRQ
C04156  372  K--EAVAVNSIMQLHRLLGSDPPRDPPIGSVLPWIRS

DELLA1  524  APPNQDLVMSEVYLGRQICNVVACEGPDRVERHETLV
DELLA2  526  CASTQDKAMSEVYLGKQICNVVACEGADRVERHETLA
DELLA3  448  CPVQPDKALAEMYLQREICNIVGCEGAARVERHEPLD
J01594  524  APPNQDLVMSEVYLGRQICNVVACEGPDRVERHETLV
G02163  526  CASTQDKAMSEVYLGKQICNVVACEGADRVERHETLA
C04156  448  CPVQPDKALAEMYLQREICNIVGCEGAARVERHEPLD

DELLA1  604  GCLMLGWHTRPLIATSAWQLA
DELLA2  606  GCLTLGWHTRPLIATSAWRLG
DELLA3  527  GCLTLCWHSRPLIAASAWQAA
J01594  604  GCLMLGWHTRPLIATSAWQLA
G02163  606  GCLTLGWHTRPLIATSAWRLG
C04156  527  GCLTLCWHSRPLIAASAWQAA
```

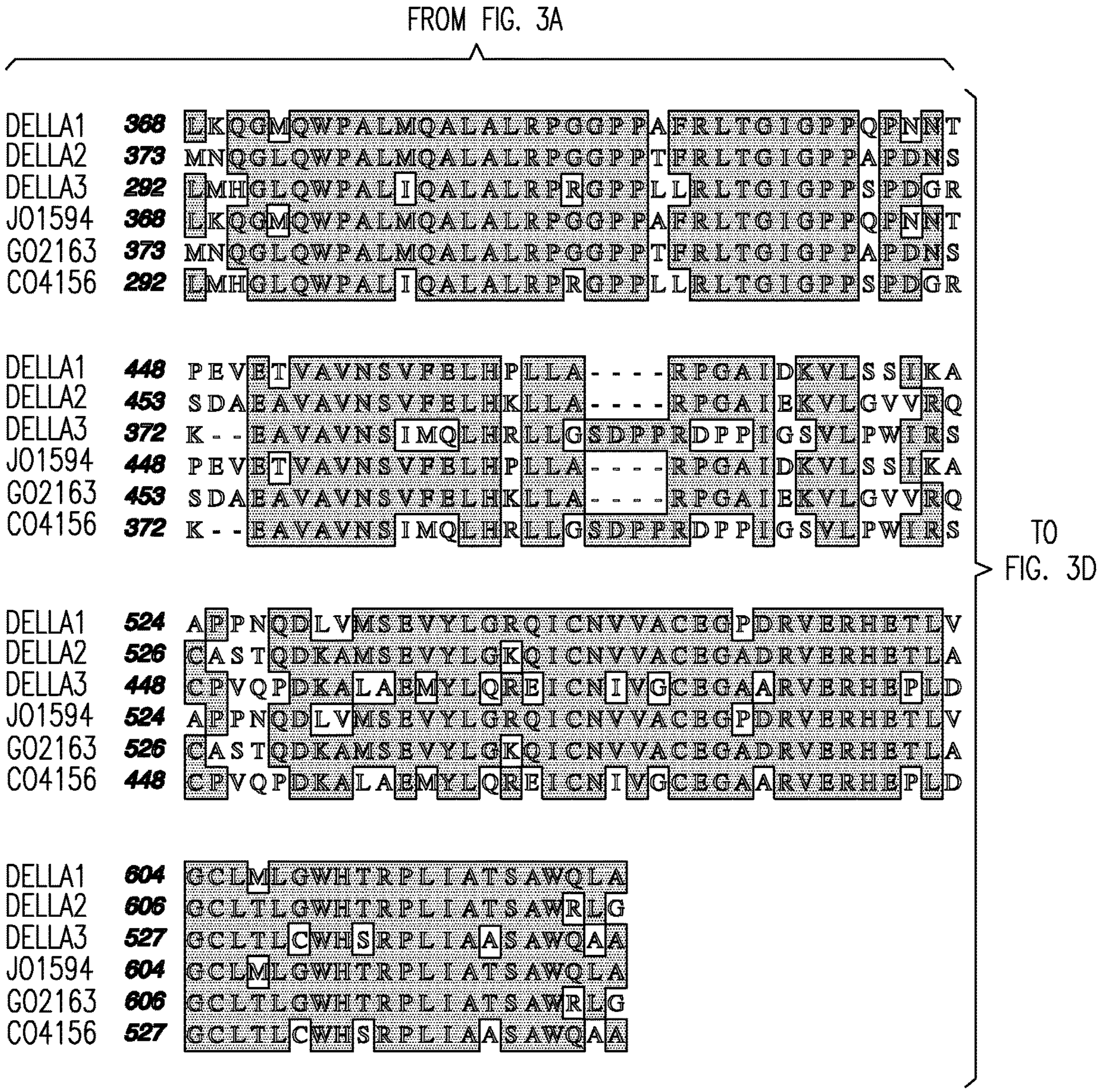

FIG. 3C

FROM FIG. 3B

```
DALQQVGWKLAQLADTIGVEFERRGFVANSLADLEPAMLDIRP   447
DRLQEVGWKLAQLAETIHVEFEYRGFVANSLADLDASILELRP   452
DALREIGLRLAELARSVNVRFAFRGVAASRLEDVKPWMLQVSP   371
DALQQVGWKLAQLADTIGVEFEFRGFVANSLADLEPAMLDIRP   447
DRLQEVGWKLAQLAETIHVEFEYRGFVANSLADLDASILELRP   452
DVLREIGLRLAELARSVNVRFAFRGVAASRLEDVKPWMLQVSP   371

MRPKIVTMVEQEANHNGPGFVDRFTEALHYYSSLFDSLEGSGV   523
VRPAIVTVVEQEANHNGPVPVDRFNESLHYYSTLFDSLEG---  525
LNPKIMTVAEQEANHNRPGFLDRFTEALYYYSTLFDSLEAA--  447
MRPKIVTMVEQEANHNGPGFVDRFTEALHYYSSLFDSLEGSGV   523
VRPAIVTVVEQEANHNGPVPVDRFNESLHYYSTLFDSLEG---  525
LNPKIMTVAEQEANHNRPGFLDRFTEALYYYSTLFDSLEAA--  447

QWQARMGSAGFDPVHLGSNAFKQASMLLALPAGGEGYRVEEND   603
QWRARLGGAGFVPAHLGSNAFKQASMLLALPAGGDGYRVEENG   605
RWRARLGRAGFRPLHLGSNAFKQASMLLTLFS-TEGYSVEENE   526
QWQARMGSAGFDPVHLGSNAFKQASMLLALPAGGEGYRVEEND   603
QWRARLGGAGFVPAHLGSNAFKQASMLLALPAGGDGYRVEENG   605
RWRARLGRAGFRPLHLGSNAFKQASMLLTLFS-TEGYSVEENE   526

AATQ                        628
GPSAGAAH                    634
PTVVNSPAGVINHDDNNNQL        567
AATQ                        628
GPSAGAAH                    634
PTVVNSPAGVINHDDNNNQL        567
```

FROM FIG. 3C

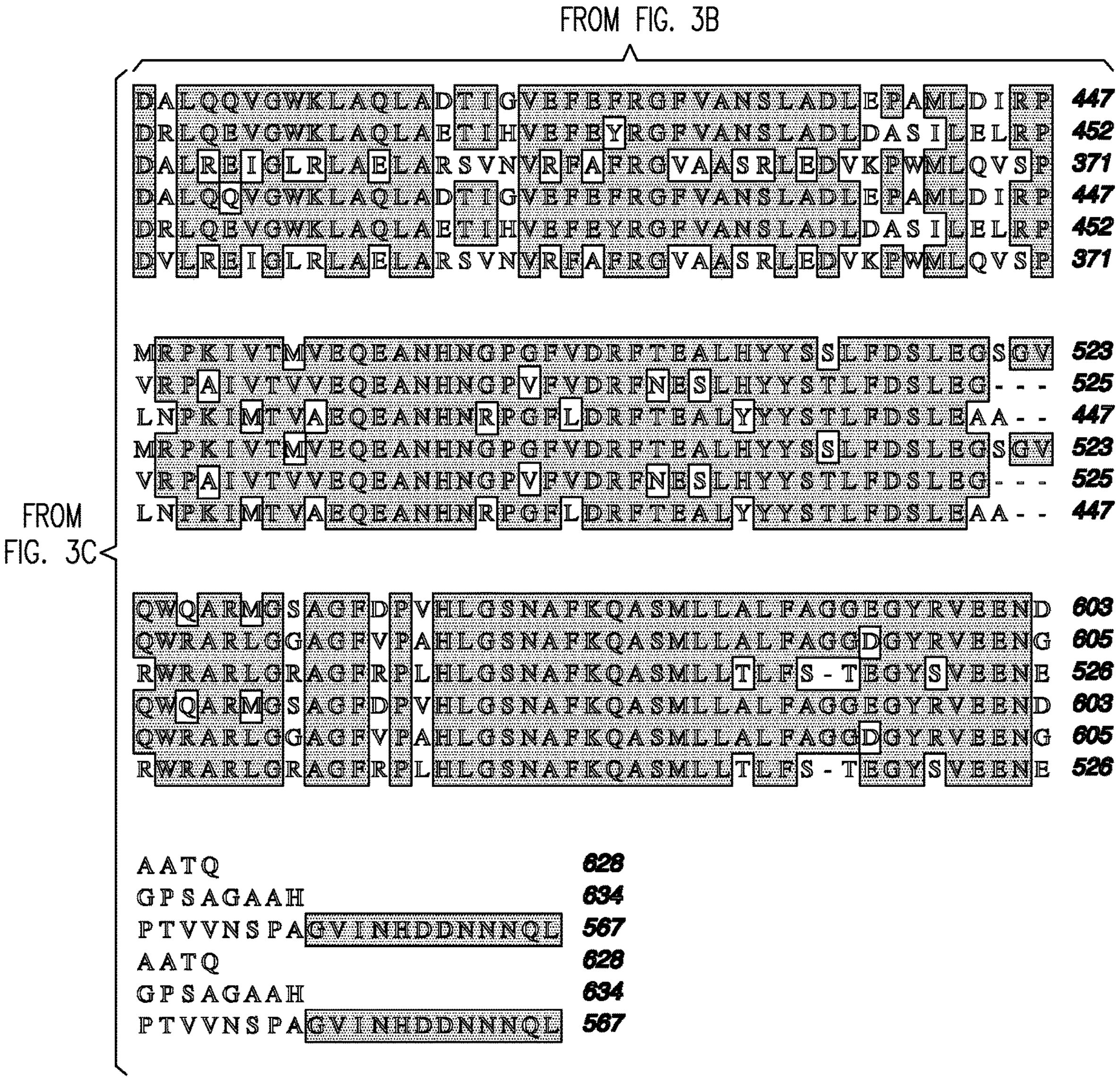

FIG. 3D

| | | |
|---|---|---|
| J01594 | 1 | MKRDHRDACSGGYGGGGGGEASGASKGEPPSSSSTHS |
| DELLA1 | 1 | MKRDHRDACSGGYGGGGGGEASGASKGEPPSSSSTHS |
| J01594 | 81 | AEVAQKLEQLEMVMGSAQEDGISHLSYDAVHYNPSDL |
| DELLA1 | 81 | AEVAQKLEQLEMVMGSAQEDGISHLSYDAVHYNPSDL |
| J01594 | 161 | SRSQTQTRTLSQTSAPTQTQSQVIFNDDSEYDLRAIP |
| DELLA1 | 161 | SRSQTQTRTLSQTSAPTQTQSQVIFNDDSEYDLRAIP |
| J01594 | 241 | SESTRPVVLVDTQETGVRLVHTLMACAEAVQQENLKL |
| DELLA1 | 241 | SESTRPVVLVDTQETGVRLVHTLMACAEAVQQENLKL |
| J01594 | 321 | LDSSCNDILQMHFYETCPYLKFAHFTANQAILEAFAT |
| DELLA1 | 321 | LDSSCNDILQMHFYETCPYLKFAHFTANQAILEAFAT |
| J01594 | 401 | PNNTDALQQVGWKLAQLADTIGVEFEFRGFVANSLAD |
| DELLA1 | 401 | PNNTDALQQVGWKLAQLADTIGVEFEFRGFVANSLAD |
| J01594 | 481 | MRPKIVTMVEQEANHNGPGFVDRFTEALHYYSSLFDS |
| DELLA1 | 481 | MRPKIVTMVEQEANHNGPGFVDRFTEALHYYSSLFDS |
| J01594 | 561 | QWQARMGSAGFDPVHLGSNAFKQASMLLALFAGGEGY |
| DELLA1 | 561 | QWQARMGSAGFDPVHLGSNAFKQASMLLALFAGGEGY |

FROM FIG. 3E

LPGSGKAKMVMWGEDDQDPSGGGGGGMDELLAVLGYKVRSSDM 80
MPGSGKAKMVMWGEDDQDPSGGGGGGMDELLAVLGYKVRSSDM 80

SSWVQSMLFELNPPPPPPQQVADAVLAAAESSSTIAQHHRSHLG 160
SSWVQSMLFELNPPPPPPQQVADAVLAAAESSSTIAQHHRSHLG 160

GVAAFPQGDSDFESAARKKMKTLNGGSNSLSSSSSSSAAGAAP 240
GVAAFPQGDSDFESAARKKMKTLNGGSNSLSSSSSSSAAGAAP 240

ADALVKHIGLLAASQNGAMRKVATYFAEALARRIYRIYPNDGS 320
ADALVKHIGLLAASQNGAMRKVATYFAEALARRIYRIYPNDGS 320

ASRVHVIDFGLKQGMQWPALMQALALRPGGPPAFRLTGIGPPQ 400
ASRVHVIDFGLKQGMQWPALMQALALRPGGPPAFRLTGIGPPQ 400

LEPAMLDIRPPEVETVAVNSVFELHPLLARPGAIDKVLSSIKA 480
LEPAMLDIRPPEVETVAVNSVFELHPLLARPGAIDKVLSSIKA 480

LEGSGVAPPNQDLVMSEVYLGRQICNVVACEGPDRVERHETLV 560
LEGSGVAPPNQDLVMSEVYLGRQICNVVACEGPDRVERHETLV 560

RVEENDGCLMLGWHTRPLIATSAWQLAAATQ 628
RVEENDGCLMLGWHTRPLIATSAWQLAAATQ 628

FIG. 3F

| | | |
|---|---|---|
| G02163 | 1 | MKREHHHLYPQTDPSTSASAAAGKSKMWDEDGCGGGG |
| DELLA2 | 1 | MKREHHHLYPQTDPSTSASAAAGKSKMWDEDGCGGGG |
| G02163 | 81 | SETVHYNPSDLSSWLESMLSEFNPLPPPPGGFGGGPL |
| DELLA2 | 81 | SETVHYNPSDLSSWLESMLSEFNPLPPPPGGFGGGPL |
| G02163 | 161 | RSSQMNEPPPEIGSSGIVFDEESSSDYDLKAIPGKAV |
| DELLA2 | 161 | RSSQMNEPRPEIGSSGIVFDEESSSDYDLKAIPGKAV |
| G02163 | 241 | AVGAAPESSRPVVLVDSQENGVRLVHALMACADAVQQ |
| DELLA2 | 241 | AVGAAPESSRPVVLVDSQENGVRLVHALMACADAVQQ |
| G02163 | 321 | PQNPPLDHSLTDALQMHFYETCPYLKFAHFTANQAIL |
| DELLA2 | 321 | PQNPPLDHSLTDALQMHFYETCPYLKFAHFTANQAIL |
| G02163 | 401 | IGPPAPDNSDRLQEVGWKLAQLAETIHVEFEYRGFVA |
| DELLA2 | 401 | IGPPAPDNSDRLQEVGWKLAQLAETIHVEFEYRGFVA |
| G02163 | 481 | GVVRQVRPAIVTVVEQEANHNGPVFVDRFNESLHYYS |
| DELLA2 | 481 | GVVRQVRPAIVTVVEQEANHNGPVFVDRFNESLHYYS |
| G02163 | 561 | LAQWRARLGGAGFVPAHLGSNAFKQASMLLALFAGGD |
| DELLA2 | 561 | LAQWRARLGGAGFVPAHLGSNAFKQASMLLALFAGGD |

FROM FIG. 3G

DDELLAVLGYKVRSSDMAEVAQKLEQLEEVMFSAQEDGLSHLA 80
DDELLAVLGYKVRSSDMAEVAQKLEQLEEVMFSAQEDGLSHLA 80

SVPVAAAPPRPQPVGDPFLPRAESSSITTVDFGADQRMQSSCG 160
SVPVAAAPPRPQPVGDPFLPRAESSSITTVDFGADQRMQSSCG 160

FGRAQAQAQAQAQTRTRLASTSSSSTSSSAVTAKRFKSSPSDA 240
FGRAQAQAQAQAQTRTRLASTSSSSTSSSAVTAKRFKSSPSDA 240

DNLSIAEALVKQIGFLAISQAGAMRKVATFFAEALARRIYRVY 320
DNLSIAEALVKQIGFLAISQAGAMRKVATFFAEALARRIYRVY 320

EAFEGKSRVHVIDFSMNQGLQWPALMQALALRPGGPPTFRLTG 400
EAFEGKSRVHVIDFSMNQGLQWPALMQALALRPGGPPTFRLTG 400

NSLADLDASILELRPSDAEAVAVNSVFELHKLLARPGAIEKVL 480
NSLADLDASILELRPSDAEAVAVNSVFELHKLLARPGAIEKVL 480

TLFDSLEGCASTQDKAMSEVYLGKQICNVVACEGADRVERHET 560
TLFDSLEGCASTQDKAMSEVYLGKQICNVVACEGADRVERHET 560

GYRVEENGGCLTLGWHTRPLIATSAWRLGGPSAGAAH 634
GYRVEENGGCLTLGWHTRPLIATSAWRLGGPSAGAAH 634

FIG. 3H

```
C04156    1    MGPFDPSAAAAAAAAA--AASSSSSSSCSGGSAPKRH
DELLA3    1    MGPFDPSAAAAAAAAAVAASSSSSSSCSGGSAPKRH

C04156   79    NSAAHIPHLASDAVHYNPSDLASWVDSMLSELPSSSF
DELLA3   81    NSAAHIPHLASDAVHYNPSDLASWVDSMLSELPSSSF

C04156  159    QQPQPQQQQQLTVVTALEEDSGIQLVHALMTCAESVQ
DELLA3  161    QQQQ--QQQQLTVVTALEEDSGIQLVHALMTCAESVQ

C04156  239    GLGSAPASAFENEVLYHHFYEACPYLKFAHFTANQAI
DELLA3  239    GLGSAPASAFENEVLYHHFYEACPYLKFAHFTANQAI

C04156  319    GIGPPSPDGRDVLREIGLRLAELARSVNVRFAFRGVA
DELLA3  319    GIGPPSPDGRDALREIGLRLAELARSVNVRFAFRGVA

C04156  399    SVLPWIRSLNPKIMTVAEQEANHNRPGFLDRFTEALY
DELLA3  399    SVLPWIRSLNPKIMTVAEQEANHNRPGFLDRFTEALY

C04156  479    RHEPLDRWRARLGRAGFRPLHLGSNAFKQASMLLTLF
DELLA3  479    RHEPLDRWRARLGRAGFRPLHLGSNAFKQASMLLTLF

C04156  559    NHDDNNNQL  567
DELLA3  559    NHDDNNNQL  567
```

FIG. 3I

FROM FIG. 3I
```
HHHHHHHPPPDLDGLLAGAGYKVRSSELHHVAQRLERLETALV    78
HHHHHHHPPPDLDGHLACAGYKVRSSELHHVAQRLERLETALV    80

SSPCLPSGFPDPYSPAAAALGGGWVDHPSCSPHPQPHQNVVP    158
SSPCLPSGFPDPYSPAAAALGGGWVDQPSCSPHPQPHQNVVP    160

RGDASLAGSLVEEMRALLTRVDTSRGIGKVAGYFIDALGRRLL   238
RGDASLAGSLVEEMRALLTRVDTSRGIGKVAGYFIDALGRRLL   238

LEAFDGHDCVHVIDFNLMHGLQWPALIQALALRPRGPPLLRLT   318
LEAFDGHDCVHVIDFNLMHGLQWPALIQALALRPRGPPLLRLT   318

ASRLEDVKPWMLQVSPKEAVAVNSIMQLHRLLGSDPPRDPPIG   398
ASRLEDVKPWMLQVSPKEAVAVNSIMQLHRLLGSDPPRDPPIG   398

YYSTLFDSLEAACPVQPDKALAEMYLQREICNIVGCEGAARVE   478
YYSTLFDSLEAACPVQPDKALAEMYLQREICNIVGCEGAARVE   478

STEGYSVEENEGCLTLCWHSRPLIAASAWQAAPTVVNSPAGVI   558
STEGYSVEENEGCLTLCWHSRPLIAASAWQAAPTVVNSPAGVI   558
```

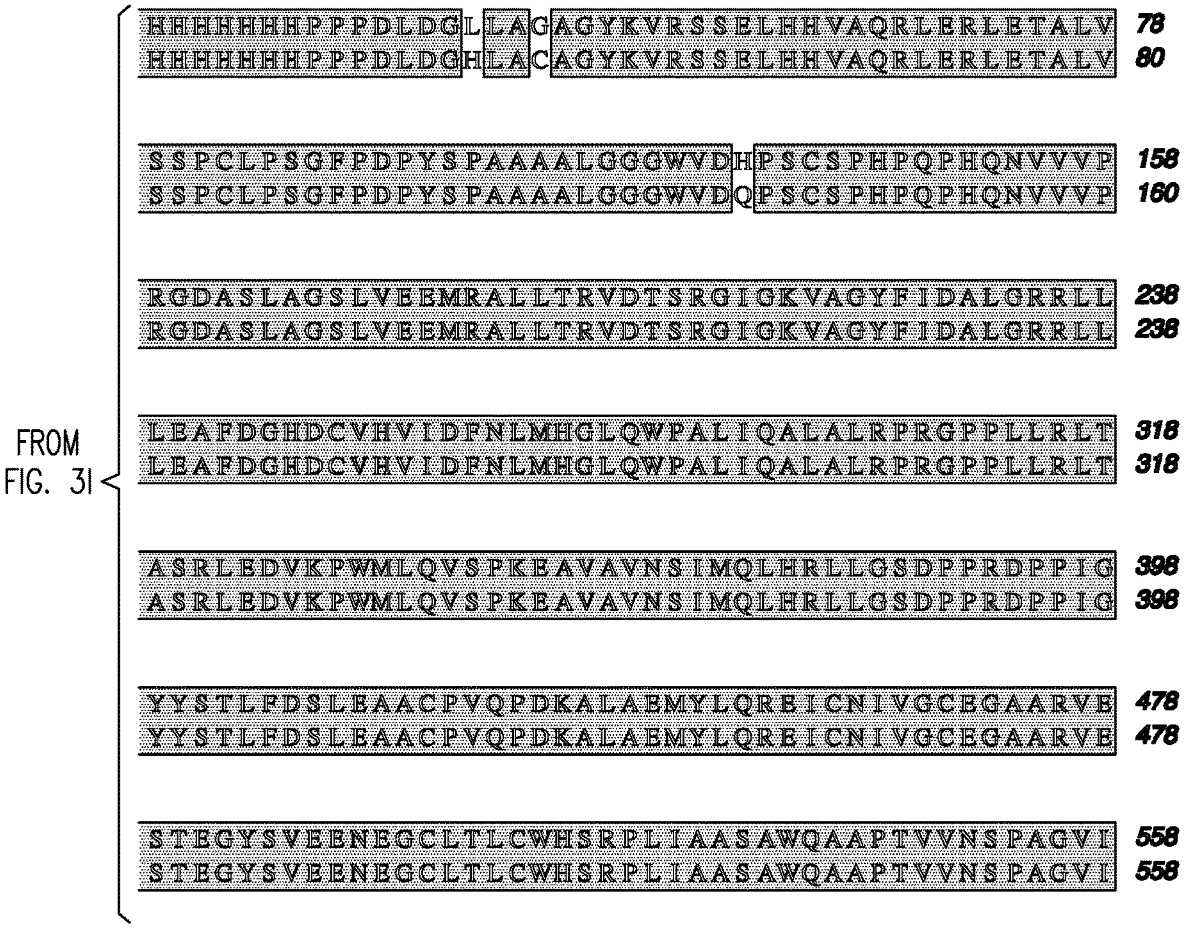

FIG. 3J

| DELLA1_Camaldulensis | 1 | MKRDHRDACSGGYGGGGGGEASGASKGEPPSSSSTHS |
| DELLA1_GxU | 1 | MKRDHRDACSGGYGGGGGGEASGASKGEPPSSSSTHS |

| DELLA1_Camaldulensis | 68 | ------------------------------------- |
| DELLA1_GxU | 81 | AEVAQKLEQLEMVMGSAQEDGISHLSYDAVHYNPSDL |

| DELLA1_Camaldulensis | 68 | ------------------------------------- |
| DELLA1_GxU | 161 | SRSQTQTRTLSQTSAPTQTQSQVIFNDDSEYDLRAIP |

| DELLA1_Camaldulensis | 80 | SESTRPVVLVDTQETGVRLVHTLMACAEAVQQENLKL |
| DELLA1_GxU | 241 | SESTRPVVLVDTQETGVRLVHTLMACAEAVQQENLKL |

| DELLA1_Camaldulensis | 160 | LDSSCNDILQMHFYETCPYLKFAHFTANQAILEAFAT |
| DELLA1_GxU | 321 | LDSSCNDILQMHFYETCPYLKFAHFTANQAILEAFAT |

| DELLA1_Camaldulensis | 240 | PNNTDALQQVGWKLAQLADTIGVEFEFRGFVANSLAD |
| DELLA1_GxU | 401 | PNNTDALQQVGWKLAQLADTIGVEFEFRGFVANSLAD |

| DELLA1_Camaldulensis | 320 | MRPKIVTMVEQEANHNGPGFVDRFTEALHYYSSLFDS |
| DELLA1_GxU | 481 | MRPKIVTMVEQEANHNGPGFVDRFTEALHYYSSLFDS |

| DELLA1_Camaldulensis | 400 | QWQARMGSAGFDPVHLGSNAFKQASMLLALFAGGEGY |
| DELLA1_GxU | 561 | QWQARMGSAGFDPVHLGSNAFKQASMLLALFAGGEGY |

FIG. 9A

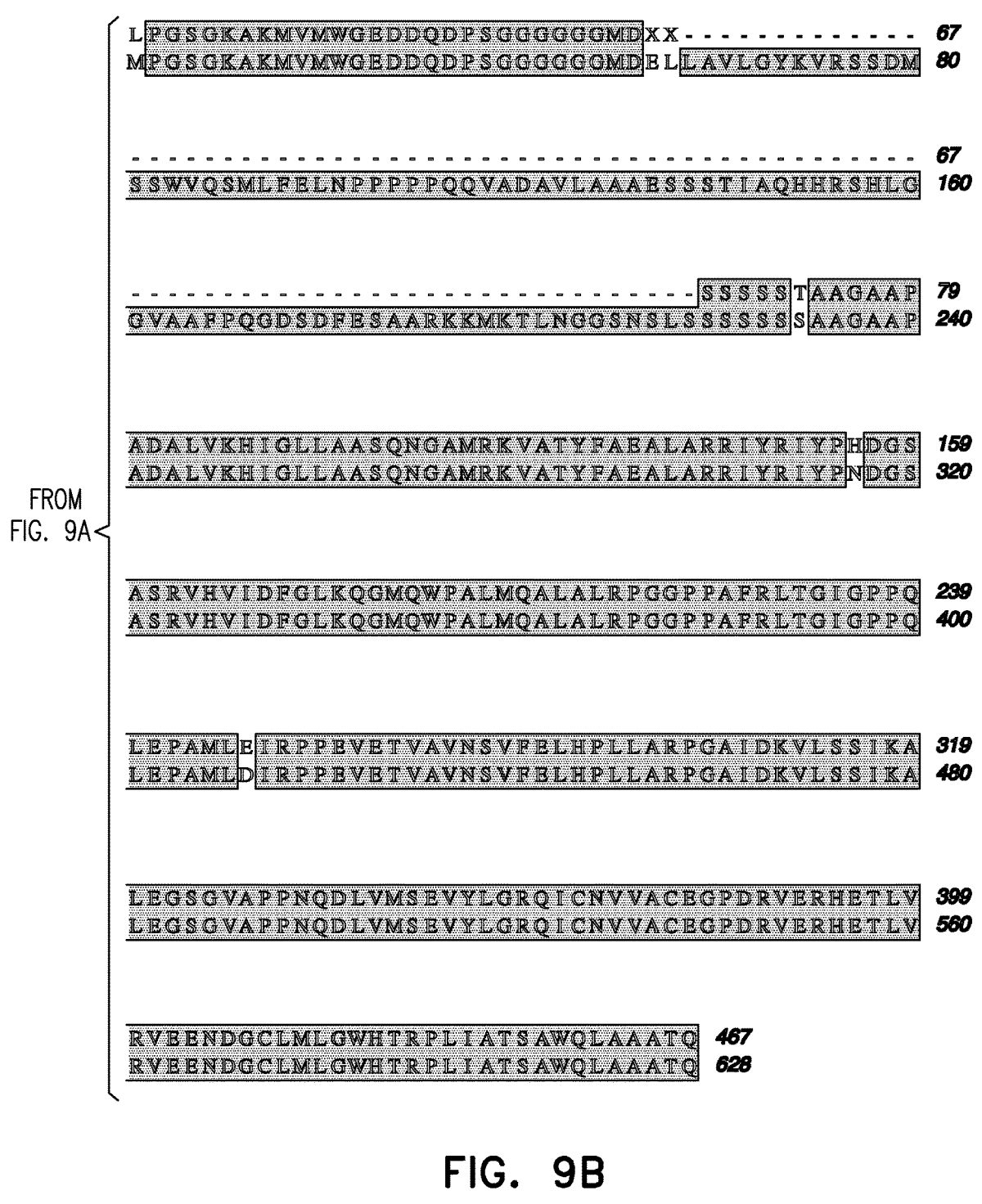

FROM FIG. 9A

LPGSGKAKMVMWGEDDQDPSGGGGGGMDXX------------- 67
MPGSGKAKMVMWGEDDQDPSGGGGGGMDELLAVLGYKVRSSDM 80

------------------------------------------- 67
SSWVQSMLFELNPPPPPQQVADAVLAAAESSSTIAQHHRSHLG 160

-------------------------------SSSSSTAAGAAP 79
GVAAFPQGDSDFESAARKKMKTLNGGSNSLSSSSSSSAAGAAP 240

ADALVKHIGLLAASQNGAMRKVATYFAEALARRIYRIYPHDGS 159
ADALVKHIGLLAASQNGAMRKVATYFAEALARRIYRIYPNDGS 320

ASRVHVIDFGLKQGMQWPALMQALALRPGGPPAFRLTGIGPPQ 239
ASRVHVIDFGLKQGMQWPALMQALALRPGGPPAFRLTGIGPPQ 400

LEPAMLEIRPPEVETVAVNSVFELHPLLARPGAIDKVLSSIKA 319
LEPAMLDIRPPEVETVAVNSVFELHPLLARPGAIDKVLSSIKA 480

LEGSGVAPPNQDLVMSEVYLGRQICNVVACEGPDRVERHETLV 399
LEGSGVAPPNQDLVMSEVYLGRQICNVVACEGPDRVERHETLV 560

RVEENDGCLMLGWHTRPLIATSAWQLAAATQ 467
RVEENDGCLMLGWHTRPLIATSAWQLAAATQ 628

FIG. 9B

```
DELLA1_Globulus    1 ------------------------------------------------
DELLA1_GxU         1 MKRDHRDACSGGYGGGGGGEASGASKGEPPSSSSTHS

DELLA1_Globulus    1 ------------------------------------------------
DELLA1_GxU        81 AEVAQKLEQLEMVMGSAQEDGISHLSYDAVHYNPSDL

DELLA1_Globulus    1 ------------------------------------------------
DELLA1_GxU       161 SRSQTQTRTLSQTSAPTQTQSQVIFNDDSEYDLRAIP

DELLA1_Globulus    1 ---------------------------MACAEAVQQENLKL
DELLA1_GxU       241 SESTRPVVLVDTQETGVRLVHTLMACAEAVQQENLKL

DELLA1_Globulus   58 LDSSCNDILQMHFYETCPYLKFAHFTANQAILEAFAT
DELLA1_GxU       321 LDSSCNDILQMHFYETCPYLKFAHFTANQAILEAFAT

DELLA1_Globulus  138 PNNTDALQQVGWKLAQLADTIGVEFEFRGFVANSLAD
DELLA1_GxU       401 PNNTDALQQVGWKLAQLADTIGVEFEFRGFVANSLAD

DELLA1_Globulus  218 MRPKIVTMVEQEANHNGPVFVDRFTEALHYYSSLFDS
DELLA1_GxU       481 MRPKIVTMVEQEANHNGPGFVDRFTEALHYYSSLFDS

DELLA1_Globulus  298 QWQARMGSAGFDPVHLGSNAFKQASMLLALFAGGEGY
DELLA1_GxU       561 QWQARMGSAGFDPVHLGSNAFKQASMLLALFAGGEGY
```

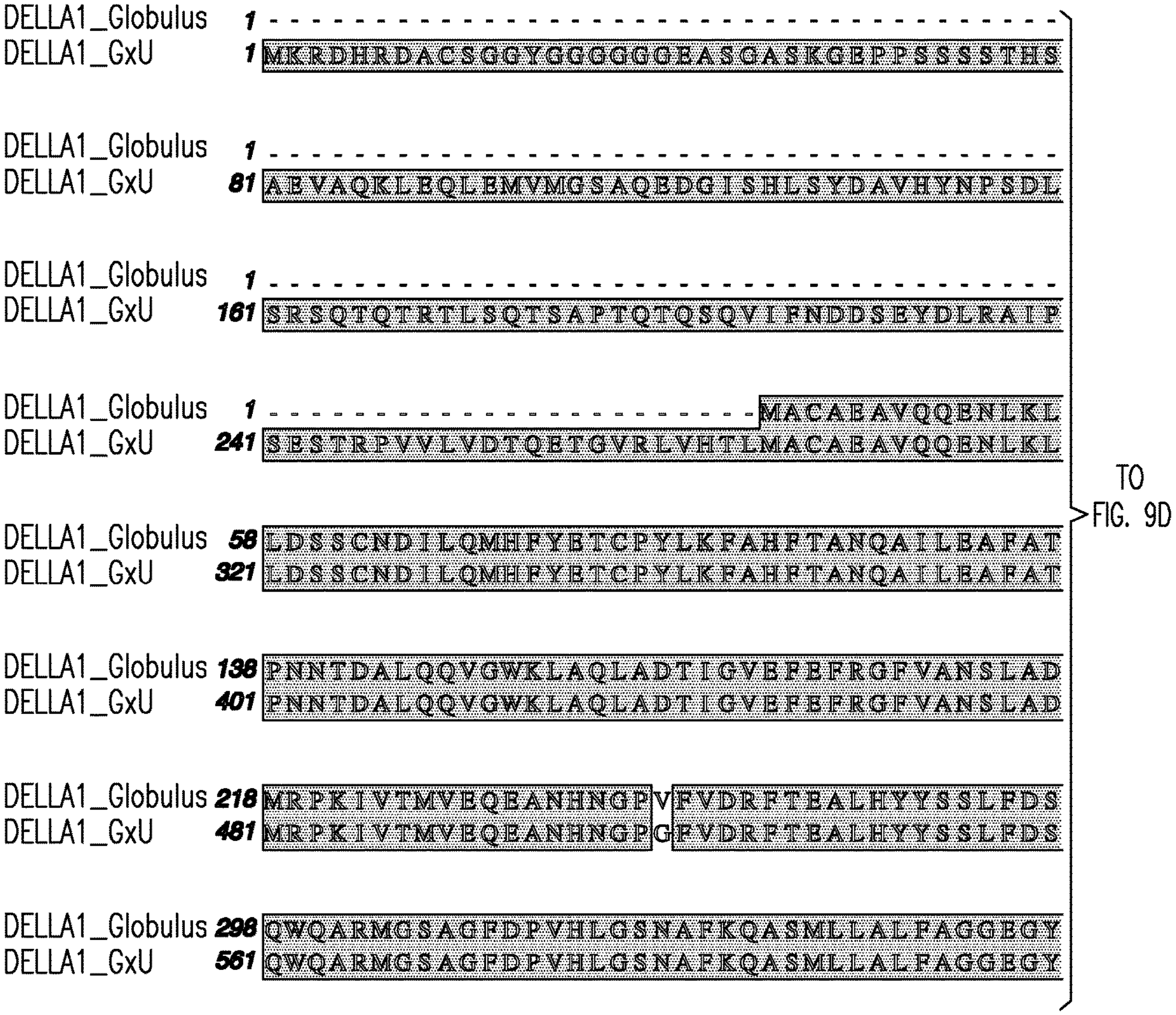

FIG. 9C

FROM FIG. 9C

```
-------------------------------------------  0
MPGSGKAKMVMWGEDDQDPSGGGGGGMDELLAVLGYKVRSSDM  80

-------------------------------------------  0
SSWVQSMLFELNPPPPPQQVADAVLAAAESSSTIAQHHRSHLG  160

-------------------------------------------  0
GVAAFPQGDSDFESAARKKMKTLNGGSNSLSSSSSSSAAGAAP  240

ADALVKHIGLLAASQNGAMRKVATYFAEALARRIYRIYPHDGS  57
ADALVKHIGLLAASQNGAMRKVATYFAEALARRIYRIYPNDGS  320

ASRVHVIDFGLKQGMQWPALMQALALRPGGPPAFRLTGIGPPQ  137
ASRVHVIDFGLKQGMQWPALMQALALRPGGPPAFRLTGIGPPQ  400

LEPAMLDIRPPEVETVAVNSVFELHPLLSRPGAIDKVLSSIKA  217
LEPAMLDIRPPEVETVAVNSVFELHPLLARPGAIDKVLSSIKA  480

LEGSGVAPPNQDLVMSEVYLGRQICNVVACEGLDRVERHETLV  297
LEGSGVAPPNQDLVMSEVYLGRQICNVVACEGPDRVERHETLV  560

RVEENDGCLMLGWHTRPLIATSAWQLAAATQ  365
RVEENDGCLMLGWHTRPLIATSAWQLAAATQ  628
```

FIG. 9D

DELLA2_Globulus 1 MKREHHHLYPQTGPSTSASAAGGKSKMWDEDGCGGGG
DELLA2_GxU 1 MKREHHHLYPQTDPSTSASAAAGKSKMWDEDGCGGGG DELLA2_Globulus 81 SETVHYNPSDLSSWLESMLSEFNPLPPPPQPPPPGGF
DELLA2_GxU 81 SETVHYNPSDLSSWLESMLSEFNPLPPPP-----GGF DELLA2_Globulus 161 QSSCGRSSQMNEPRPEIGSSGIVFDEESSSDYDLKAI
DELLA2_GxU 156 QSSCGRSSQMNEPRPEIGSSGIVFDEESSSDYDLKAI DELLA2_Globulus 239 SPSDAAVGAAPESSRPVVLVDSQENGVRLVHALMACA
DELLA2_GxU 236 SPSDAAVGAAPESSRPVVLVDSQENGVRLVHALMACA DELLA2_Globulus 319 IYRVYPQNPPLDHSLTDALQMHFYETCPYLKFAHFTA
DELLA2_GxU 316 IYRVYPQNPPLDHSLTDALQMHFYETCPYLKFAHFTA DELLA2_Globulus 399 FRLTGIGPP----------------------------
DELLA2_GxU 396 FRLTGIGPPAPDNSDRLQEVGWKLAQLAETIHVEFEY DELLA2_Globulus 408 -------------------------------------
DELLA2_GxU 476 IEKVLGVVRQVRPAIVTVVEQEANHNGPVFVDRFNES DELLA2_Globulus 408 -------------------------------------
DELLA2_GxU 556 ERHETLAQWRARLGGAGFVPAHLGSNAFKQASMLLAL

FROM FIG. 9E

```
DDELLAVLGYKVRSSDMAEVAQKLEQLEEVMFSAQEDGISHLA 80
DDELLAVLGYKVRSSDMAEVAQKLEQLEEVMFSAQEDGLSHLA 80

GGGPLSVPVAAAPPRPQPVGDPFLPRAESSSITTVDFGADQRM 160
GGGPLSVPVAAAPPRPQPVGDPFLPRAESSSITTVDFGADQRM 155

PGKAVFG--RAQAQAQAQTRTRLASTSSSSTSSSAVTAKRFKS 238
PGKAVFGRAQAQAQAQAQTRTRLASTSSSSTSSSAVTAKRFKS 235

DAVQQDNLSIAEALVKQIGFLAISQAGAMRKVATFFAEALARR 318
DAVQQDNLSIAEALVKQIGFLAISQAGAMRKVATFFAEALARR 315

NQAILEAFEGKSRVHVIDFSMNQGLQWPALMQALALRPGGPPT 398
NQAILEAFEGKSRVHVIDFSMNQGLQWPALMQALALRPGGPPT 395

------------------------------------------- 407
RGFVANSLADLDASILELRPSDAEAVAVNSVFELHKLLARPGA 475

------------------------------------------- 407
LHYYSTLFDSLEGCASTQDKAMSEVYLGKQICNVVACEGADRV 555

------------------------------------------ 407
FAGGDGYRVEENGGCLTLGWHTRPLIATSAWRLGGPSAGAAH 634
```

FIG. 9F

TISSUE-SPECIFIC EXPRESSION CONTROL OF DELLA POLYPEPTIDES

CROSS-REFERENCE TO RELATED APPLICATIONS

Reference is made to U.S. Provisional Patent Application Ser. Nos. 62/559,746, filed Sep. 18, 2017, 62/577,549, filed Oct. 26, 2017, and 62/582,767, filed Nov. 7, 2017 and all entitled TISSUE-SPECIFIC EXPRESSION OF DELLA POLYPEPTIDES, the disclosures of which are hereby incorporated by reference and priority of which is hereby claimed pursuant to 37 CFR 1.78(a)(4) and (5)(i).

FIELD OF THE INVENTION

DELLA polypeptides play a significant role in regulating gibberellin hormone expression level in the plant. This disclosure relates to compositions, assays, methods for genetically engineering plants to selectively alter DELLA gene expression.

BACKGROUND

Gibberellins (GA) are important plant hormones that act in many physiological and developmental processes, including seed germination, stem elongation, leaf expansion, trichome development, pollen maturation and the induction of flowering (Achard and Genschik, 2009). Although only a few GAs have biological activity (Yamaguchi, 2008), many non-bioactive GAs exist in plants, and act as precursors for the bioactive forms or are de-activated metabolites.

The synthesis and deactivation of bioactive GAs are regulated by different factors. One such factor is the GA's feedback inhibition of its own biosynthetic pathway mediated by DELLA polypeptides. DELLA polypeptides are named after their conserved DELLA domain consisting of Aspartic acid (D), Glutamic acid (E), Leucine (L), Leucine (L), Alanine (A), and are a subset of the plant GRAS family, transcriptional regulators that play diverse roles in plant development.

Like all GRAS proteins, DELLAs share a conserved C-terminal GRAS domain that is involved in transcriptional regulation but is distinguished from the rest of the GRAS family by a specific N-terminal sequence containing two conserved domains: the DELLA domain and a second conserved domain encoding for a Threonine, Valine, Histidine, Tyrosine, Asparagine, Proline [TVHYNP] (Davière and Achard, 2013). More than one such DELLA gene can be found in some plants. For example, the *Arabidopsis* genome encodes five known DELLA proteins (GA-Insensitive, GAI; Repressor of GA1-3, RGA; RGA-Like1, RGL1; RGL2 and RGL3) (Peng et al., 1997, Silverstone et al. 1998, Lee et al., 2002, Wen and Chang 2002, Tyler et al., 2004). Phenotypic analysis of DELLA mutants in *Arabidopsis* indicates that GAI and RGA control cell expansion in the hypocotyl, the shoot and the root tissues (King et al. 2001. Fu and Harberd 2003); RGL1 is involved in floral development (together with RGA and RGL2) (Cheng et al., 2004; Tyler et al., 2004), RGL2 regulates germination (Lee et al., 2002) and RGL3 contributes to plant fitness during environmental stress (Achard et al., 2008; Wild et al., 2012).

SUMMARY OF THE INVENTION

The present disclosure provides compositions, assays, and methods for genetically engineering plants to selectively alter DELLA gene expression to promote plant growth while maintaining root integrity.

More specifically, provided herein is a construct comprising a promoter operably linked to a polynucleotide sequence that is a template for both strands of a double stranded ribonucleic acid molecule (dsRNA), wherein the dsRNA reduces the expression level of at least one DELLA polypeptide. The promoter can be a constitutive promoter. The promoter can be selected from, e.g., the group consisting of 35S CaMV, CaMV19S, sgFiMV, SVBV, FMV34S, sugarcane bacilliform badnavirus promoter, CsVMV promoter, *Arabidopsis* ACT2/ACT8 actin promoter, *Arabidopsis* ubiquitin UBQ1 promoter, barley leaf thionin BTH6 promoter, rice actin promoter, GOS2, Rice cyclophilin, and Maize H3 histone. The promoter can be a tissue-specific promoter. The promoter can be, e.g., derived from a tissue selected from the group consisting of leaf tissue, stem tissue, and photosynthetic tissue. The promoter can be, e.g., a RBC promoter. The DELLA polypeptide can be a eucalyptus DELLA polypeptide. The DELLA polypeptide can be substantially (e.g., at least 80%, 85%, 90%, 95%, 99%, or more) identical to a polypeptide selected from the group consisting of: SEQ ID NO: 1 (DELLA1), SEQ ID NO: 3 (DELLA2), and SEQ ID NO: 5 (DELLA3). The dsRNA can include a unit including a first strand and a second strand of nucleotides, wherein the first strand and the second strand are complementary and the first strand is substantially identical to at least 20-25, 50, 75, 100, 125, 150, 175, 200, 225, or 250 or more contiguous nucleotides of a sequence encoding a DELLA polypeptide.

Any of the above-described constructs can include a loop region separating the first strand from the second strand of nucleotides.

Any of the above-described constructs can include two or more dsRNAs. Two or more of the dsRNAs can be derived from different DELLA polypeptides. Two or more of the dsRNAs can be derived from, e.g., SEQ ID NO: 1 (DELLA1) and SEQ ID NO: 3 (DELLA2), SEQ ID NO: 1 (DELLA1) and SEQ ID NO: 5 (DELLA3), or SEQ ID NO: 3 (DELLA2) and SEQ ID NO: 5 (DELLA3), or any combination of SEQ ID NOs: 1, 3, and 5. Two or more of the dsRNAs can be derived from the same DELLA polypeptide.

Also provided herein are host cells including any of the above-described constructs. The host cell can be, e.g., a bacterial (e.g., *Agrobacterium*) cell.

Moreover, provided herein are plant tissues including any of the above-described constructs. Also provided herein are plant tissues transformed with any of the above-described host cells. The plant tissue can be, e.g., a green tissue, a root tissue.

There is further provided a method of producing a plant with reduced expression level of at least one DELLA polypeptide, the method including expressing any of the above-described constructs in the plant. The plant can be, e.g., a eucalyptus plant.

Another aspect of the present invention is a method of producing a plant with reduced expression level of at least one DELLA polypeptide, the method including transforming a plant cell with any of the above-described constructs, regenerating a plant from the transformed plant cell, and growing the transformed plant, wherein the transformed plant has increased growth compared to a wild-type plant of the same species. The plant can be, e.g., a eucalyptus plant.

Any of the above-described constructs can reduce the transcript level of at least one endogenous DELLA polynucleotide by at least 40%.

Also provided herein is a method of engineering a plant including introducing a first expression cassette into a plant that reduces the expression of at least one endogenous DELLA polypeptide in the plant, introducing a second expression cassette into the plant, that comprises a polynucleotide encoding a DELLA polypeptide operably linked to a heterologous root-specific promoter, and growing the transformed plant, having DELLA polypeptides expression that is primarily localized in the roots of the plant compared to a wild-type plant of the same species. The first expression cassette can encode, e.g., an antisense nucleic acid, a sense nucleic acid, an siRNA, a microRNA, or a dsRNA. The endogenous DELLA polypeptide can be a eucalyptus DELLA polypeptide. The eucalyptus DELLA polypeptide can be substantially (e.g., at least 80%, 85%, 90%, 95%, 99%, or more) identical to a polypeptide selected from the group consisting of: SEQ ID NO: 1 (DELLA1), SEQ ID NO: 3 (DELLA2), and SEQ ID NO: 5 (DELLA3). The root-specific promoter can be selected from, e.g., the group consisting of PsMTA, Class III Chitinase promoter, phosphate transporter promoter, tonoplast intrinsic aquaporin 2 promoter, Pyk10 promoter, AtFLS5 promoter, btg26 promoter, and *Solanum lycopersicum* root-expressed 2-ODD (REO). The second cassette DELLA polypeptide can be an *Arabidopsis thaliana* DELLA polypeptide. The *Arabidopsis* DELLA polypeptide can be substantially (e.g., at least 80%, 85%, 90%, 95%, 99%, or more) identical to a polypeptide selected from the group consisting of: SEQ ID NO: 13, SEQ ID NO: 15, SEQ ID NO: 17, SEQ ID NO: 19, or SEQ ID NO: 21.

Any of the above-described methods can include in the first expression cassette a polynucleotide that is a template for both strands of a double stranded ribonucleic acid molecule (dsRNA).

Any of the above-described methods can include a plant engineered by the method or a progeny of the plant. The plant can include plant parts, e.g., a plant cell.

Also provided herein is a method of engineering a plant by constructing an expression cassette comprising a polynucleotide encoding a DELLA polypeptide, operably linked to a heterologous root-specific promoter, introducing the expression cassette into a plant having reduced DELLA expression of at least one endogenous DELLA polynucleotide, and growing the transgenic plant having DELLA polypeptides expression that is primarily localized in the roots of the plant compared to a wild-type plant of the same species. The plant can be, e.g., a plant having a Also provided herein is a method of producing a plant with reduced expression level of at least one DELLA polypeptide, the method comprising: transforming a plant cell with a CRISPR/Cas9 construct comprising one or two guide RNA sequences targeting a gene encoding the DELLA polypeptide, regenerating a plant from the transformed plant cell to form a transformed plant, and growing the transformed plant, wherein the transformed plant has increased growth compared to a wild-type plant of the same species. In an embodiment, the plant is a eucalyptus plant. Preferably, the guide RNA sequences are selected from SEQ ID NO: 63 and SEQ ID NO: 64. Also provided is a plant engineered by the method or a progeny of the plant. Further provided is a plant cell of the plant.

BRIEF DESCRIPTION OF THE FIGURES

FIGS. 2A and 2B. Together depict RGA from *A. thaliana* (SEQ ID NO:15) aligned with DELLA homologs from *Eucalyptus grandis*, J01594 (SEQ ID NO:7), G02163 (SEQ ID NO:9) and C04156 (SEQ ID NO:11).

FIGS. 3A, 3B, 3C and 3D. 3A/1, 3A/2. 3A/3 and 3A/4 together depict the identified *Eucalyptus grandis* DELLA protein sequences, J01594, G02163 and C04156, aligned against the *Eucalyptus grandis*×*urophylla* (gXu) library. 3B/1 and 3B/2 together depict sequence alignment between J01594 (SEQ ID NO:7) and DELLA1 (SEQ ID NO:1). J01594 has 99% identity to DELLA1. 3C/1 and 3C/2 together depict sequence alignment between G02163 (SEQ ID NO:9) and DELLA2 (SEQ ID NO:3). G02163 has 99% identity to DELLA2. 3D/1 and 3D/2 together depict sequence alignment between C04156 (SEQ ID NO:11) and DELLA3 (SEQ ID NO:5). C04156 has 98% identity to DELLA3. Sequence identity or homology was determined using Blast sequence alignment algorithm with default parameters.

FIGS. 5A and 5B schematically depict certain, non-limiting nucleic acid cassettes according to the invention. A1-A3. Schematic of down regulation construct constructed using sequences from one, two or three DELLA genes. Cassette P1 (Promoter 1) to T1 (Termination sequence 1) encodes a hairpin RNA (hpRNA), constructed by fusing at least one RNAi element (RNAi1, RNAi2, RNAi3), by synthesizing the resulting sequence as an inverted repeat, and inserting a loop sequence between the respective sense and inverted repeat sequences. P1 is the 35S constitutive promoter or the Rubisco promoter. RNAi1, RNAi2 and RNAi3 elements are 300 bp to 400 bp fragments derived from a DELLA genes selected from the group of DELLA1, DELLA2 and DELLA3. L-Loop. B1-B3. Schematic of hpRNA molecule produced by transcription of transgene P1 to T1. C1-C3. Schematic of the over expression constructs constructed for down regulation of at least one endogenous DELLA gene using cassette P1-T1 and over expression of a DELLA polypeptide in the roots using cassette P2 (Promoter 2)-T2 (Termination sequence 2). P2 is a *Eucalyptus* aquaporin promoter. $DELLA_{OE}$-DELLA gene overexpression sequence.

FIGS. 9A, 9B and 9C. Sequence alignments of DELLA sequences from different *Eucalyptus* species. 9A/1 and 9A/2 together show gXu DELLA1 (SEQ ID NO:1) has 99% identity to a partially sequenced DELLA sequence from *Eucalyptus camaldulensis* (SEQ ID NO:86). 9B/1 and 9B12 together show gXu DELLA1 (SEQ ID NO:1) has 99% identity to a partially sequenced RGA-like DELLA from *Eucalyptus globulus* (SEQ ID NO:87). 9C/1 and 9C/2 together show gXu DELLA2 (SEQ ID NO:3) has 97% identity to a RGA-like DELLA sequence from *Eucalyptus globulus* (SEQ ID NO:88).

Figure 10:
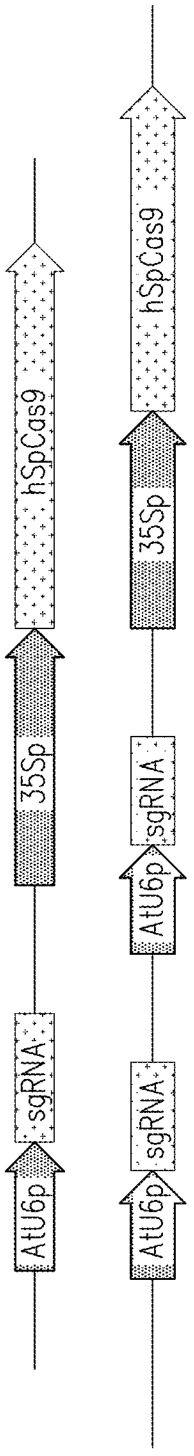

FIG. 10. Schematic representation of T-DNA maps of constructs. FIG. 10 schematically depicts certain, non-limiting DELLA genome editing constructs according to the invention.

Figure 11:
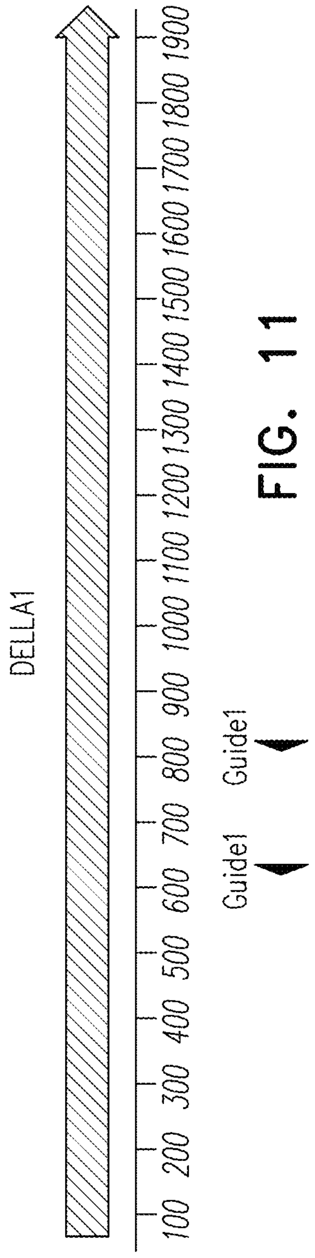

FIG. 11. Location of sgRNAs on the DELLA1 gene in *Eucalyptus grandis×urophylla* clone.

Figure 12:
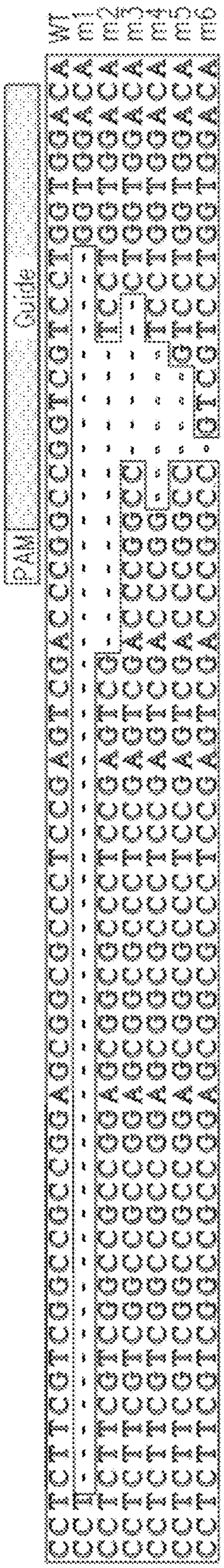

FIG. 12. Target sequences of wild-type (WT) *Eucalyptus grandis×urophylla* clone nt 692-754 of SEQ ID NO:2) and 6 Cas9 mutated events (ml-6, SEQ ID NOs:89-94) are shown. The gRNA and protospacer adjacent motif (PAM; bold text) sequences are located above the wild type sequence.

Figure 13:
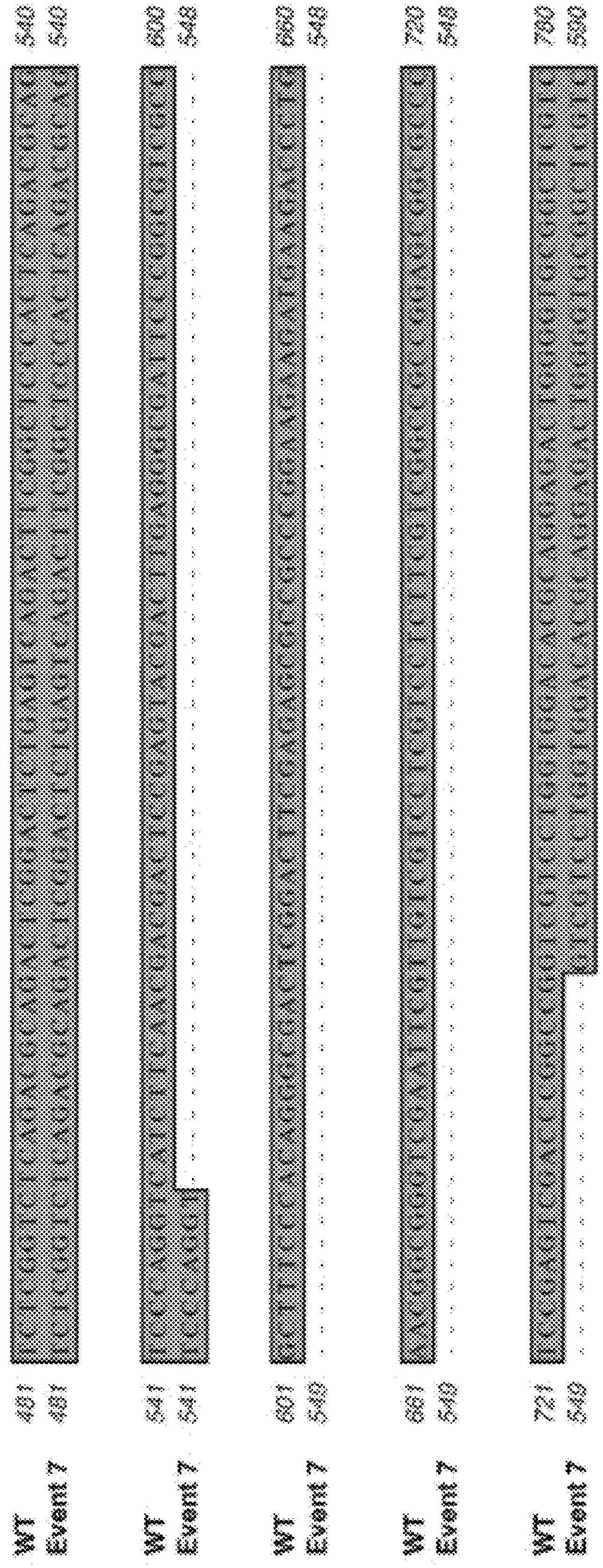

FIG. 13. Alignment between nucleotide sequence of WT DELLA1 (nt 481-780 of SEQ ID NO:2) and event 7 displaying 189 nt deletion (nt 481-590 of SEQ ID NO:95).

DEFINITIONS

As used herein, a "functional gene" is a wild-type gene or a gene having one or more mutations, as compared to the corresponding wild-type gene, that do not result in complete loss of any essential function in the protein encoded by the functional gene, as compared to the protein encoded by the corresponding wild-type gene. As used herein, a "functional protein" is a wild-type protein or a protein having one or more amino acid changes, as compared to the corresponding wild-type protein, that do not result in complete loss of any essential function in the functional protein, as compared to the corresponding wild-type protein.

As used herein, a "fully functional gene" is a wild-type gene or a gene having one or more mutations, as compared to the corresponding wild-type gene, that result in no loss of any function in the protein encoded by the fully functional gene, as compared to the protein encoded by the corresponding wild-type gene. As used herein, a "fully functional protein" is a wild-type protein or a protein having one or more amino acid changes, as compared to the corresponding wild-type protein, that result in no loss of any function in the fully functional protein, as compared to the corresponding wild-type protein.

As used herein, the term "gene" can be replaced with "protein-encoding nucleic acid".

As used herein, the terms "about" and "approximately" are defined as being within plus or minus 10% of a given value or state, preferably within plus or minus 5% of said value or state. As used herein, the term "substantially" means at least 80%, 85%, 90%, 95%, 99%, or more of a given value or state.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

DELLA proteins play a central role in regulating GAs. GAs are phytohormones that regulate a wide range of developmental processes, including seed germination, leaf expansion, stem elongation, flowering, and fruit and seed development (Sun and Gubler, 2004; Swain and Singh, 2005). GA's effect on these developmental processes varies from tissue to tissue. As such, fine-tuning of the DELLA proteins expression pattern in the plant is required to increase plant height and biomass without negatively effecting root growth.

Previous attempts to modify GA expression in order to overcome GA inhibition have consistently shown that modifying GA expression to promote stem elongation has an antagonistic effect on the roots. For example, both GA overproducing mutations and exogenous GA applications suppressed lateral and adventitious root formation (Eriksson et al., 2000, Lo et al., 2008, Busov et al., 2010).

Previous attempts to use DELLA polypeptides to overcome GA inhibition have also failed. Notably, deletions or nonsynonymous mutations in the conserved DELLA domain have been shown to render the protein insensitive to degradation. Not only do these mutations not overcome GA inhibition, they actually constitutively block the GA response. Additionally, these DELLA mutations also inhibit plant growth, resulting in an undesirable dwarf phenotype (Peng et al., 1999, Harberd et al., 2009). In *Populus* plants, blockage of GA signaling via exogenous expression of DELLA-less versions of GAI and RGL1 likewise resulted in undesirable dwarf plants (Busov et al., 2006).

This disclosure provides compositions, assays, and methods for genetically engineering plants to selectively alter DELLA gene expression to overcome GA inhibition without inhibiting plant growth. Selective expression of DELLA polypeptides in the plant can overcome GA inhibition while avoiding the problems (e.g., suppression of root formation) typically associated with attempts to overcome GA inhibition. Thus, the present invention simultaneously increases plant height and retains root growth integrity by selectively manipulating the DELLA expression levels in the plant and in different tissues of the plant.

DELLA Activity

The present disclosure relates to the genetic engineering of plants to alter DELLA gene expression and, in particular, to tissue-specific regulation of DELLA proteins expression.

Figure 1:
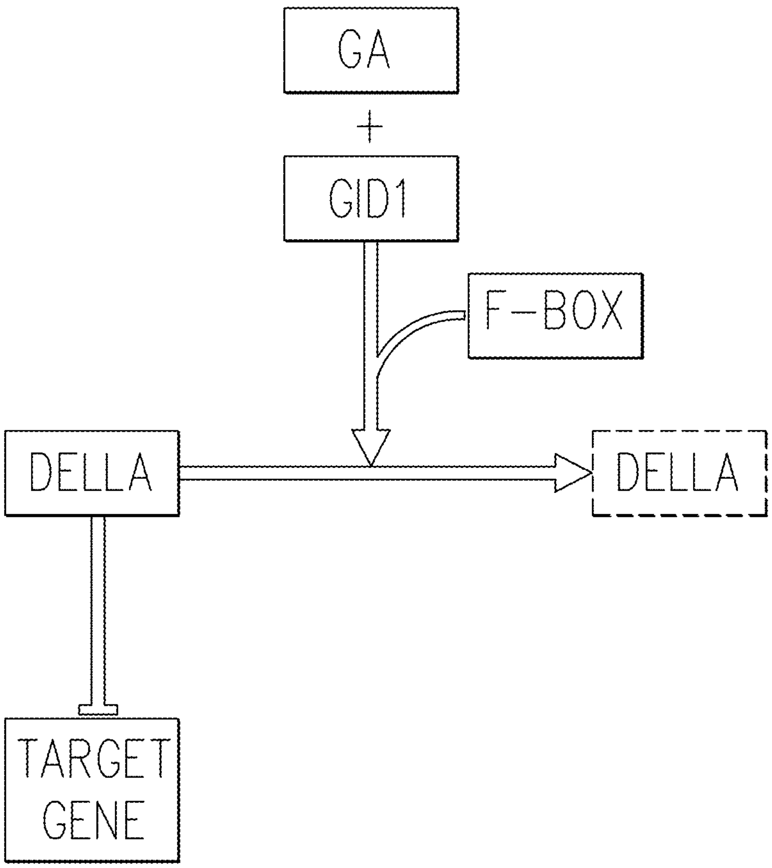
FIG. 1. A schematic representation of the key steps in DELLA degradation in the plant cell. GA binds to its receptor GIBBERELLIN INSENSITIVE DWARF1 (GID1). GA binding to GID1 leads to the formation of the GA-GID1-DELLA complex. The GA-GID1-DELLA complex interacts with the F-box SLEEPY1 (SLY1)/GID2. This interaction leads to poly-ubiquitination of the DELLAs by SCFSLY1/GID2 and in turn to the degradation of DELLA in the 26S proteasome.

Provided herein are transgenic plants whose expression of polypeptides having DELLA activity has been altered. As used herein, a DELLA polypeptide is a polypeptide having DELLA activity. A polypeptide having DELLA activity means a polypeptide able to form the GA-GID1-DELLA complex which represses gibberellin (GA)-promoted growth (FIG. 1).

The alterations in the expression level of DELLA polypeptides, compared to wild-type plants can include, e.g., increase or decrease in the expression level of a DELLA polypeptide, increase or decrease of DELLA activity, increase or decrease in the transcription level of a gene encoding a DELLA polypeptide, expression of DELLA polypeptides in specific tissues, absence of detectable expression of DELLA polypeptides in individual tissues or absence of detectable expression of DELLA polypeptides in the whole plant. More than one endogenous DELLA polypeptide expression level can be altered in a cell or plant. DELLA polypeptides used, regulated or expressed in the present invention can include endogenous DELLA polypeptides or exogenous DELLA polypeptides.

Figure 2B:
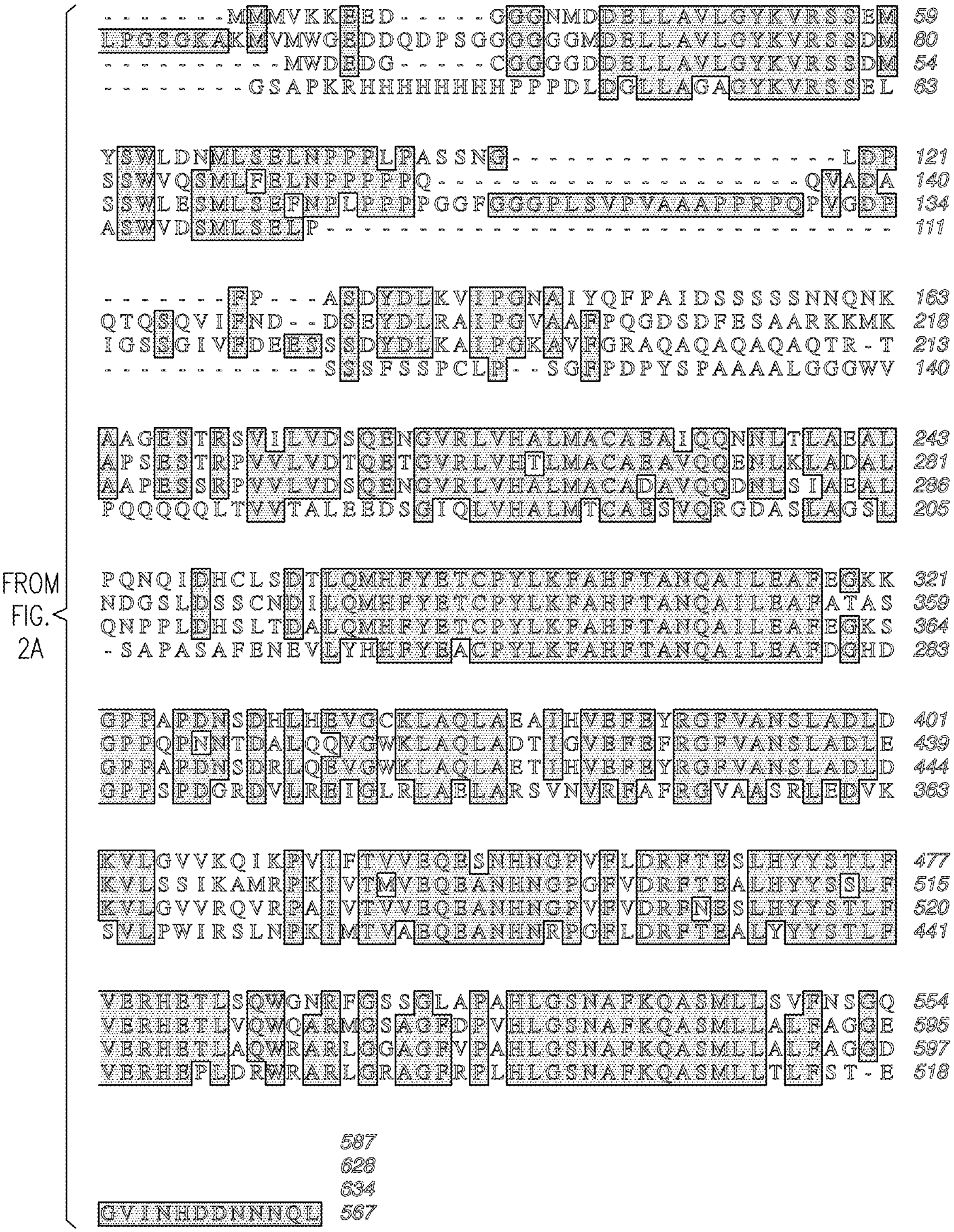
Figure 3A:
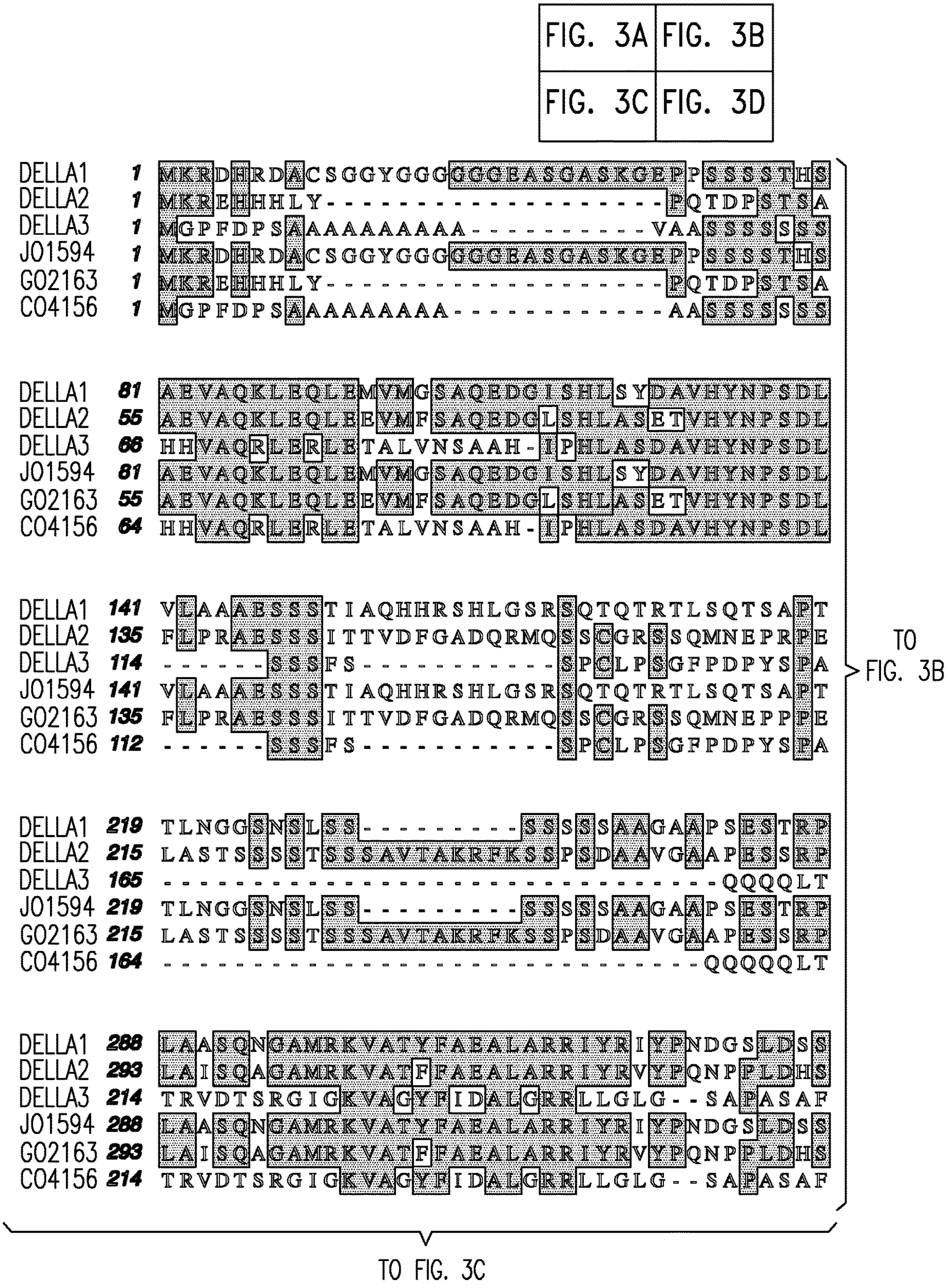

As used herein, the term DELLA polypeptide refers to a functional DELLA and functional fragments thereof having a first conserved domain encoding for the DELLA domain and a second conserved domain encoding for a Threonine, Valine, Histidine, Tyrosine, Asparagine, Proline (TVHYNP) conserved domain. FIGS. 2A and 2B depict an amino acid alignment of four DELLA polypeptides and the conserved domains.

The inventors have disclosed herein three DELLA homologs in *Eucalyptus*.

DELLA Expression Modifications

Provided herein are methods of modifying plant phenotypes by altering expression levels of DELLA polypeptides in plants. The DELLA polypeptides or polynucleotides encoding DELLA polypeptides are expressed in Wild-type (WT) plants or in plants having altered DELLA expression level compared to the WT. As referred to herein, plants having altered DELLA expression level can be the result of naturally occurring gene mutations or the result of genetic engineering of the plant. In an aspect, genetic engineering of the plant includes altering the expression level of at least one DELLA coding region present in the genome of a plant. The plant can be a wild-type plant or a genetically modified plant.

Techniques which can be used to alter the expression level of a DELLA coding region, include, but are not limited to:

i. disrupting the DELLA gene coding region;

ii. disrupting the DELLA gene coding region's transcript, such as disrupting a coding region's mRNA transcript;

iii. disrupting the activity of an endogenous DELLA polypeptide, iv. modifying the timing and/or spatial expression of the DELLA coding region by transgenically placing it under the control of a non-native promoter; or v. over-expressing a DELLA gene coding region.

Gene Down Regulation Techniques

The use of antisense RNAs, ribozymes, double-stranded RNA (dsRNA) interference, and gene knockout methods such as CRISPR type systems, TALENS and zinc fingers, are valuable techniques for generating plants with a phenotype that is different compared to the phenotype of a wild-type plant of the same variety.

Antisense RNA, ribozyme, and dsRNAi technologies typically target RNA transcripts of coding regions.

Antisense RNA technology involves introducing into a cell an RNA molecule that is complementary to the sequence found in a particular mRNA in a cell. By binding to the mRNA, the antisense RNA can inhibit translation of the encoded gene product. The use of antisense technology to reduce or inhibit the expression of specific plant genes has been described, for example in EP 271988, Smith et al., 1988, *Nature,* 334:724-726, and Smith et al., 1990, *Plant Mol. Biol.,* 14: 369-379.

The antisense nucleic acid sequence transformed into plants will be substantially identical to at least a portion of the coding region of the gene or genes to be repressed. The sequence, however, does not have to be perfectly identical to inhibit expression of the encoded mRNA. Thus, an antisense or sense nucleic acid molecule encoding only a portion of the DELLA encoding sequence can be useful for producing a plant in which expression of the DELLA gene is inhibited. For antisense suppression, the introduced sequence need not be full length relative to either of the primary transcription product or the fully processed mRNA. Generally, an antisense nucleic acid with greater homology to the target RNA can compensate for the use of a shorter polynucleotide. Furthermore, the introduced polynucleotide need not have the same intron or exon pattern; an antisense RNA targeting non-coding segments of the gene or genes to be repressed can be equally effective. In some aspects, a sequence of at least, e.g., 20, 25, 30, 50, 100, 200, or more continuous nucleotides (up to the full length of the mRNA) substantially identical to an endogenous DELLA gene mRNA, or a complement thereof, can be used.

Catalytic RNA molecules or ribozymes can also be used to inhibit expression of a gene encoding DELLA. A ribozyme is a RNA that has both a catalytic domain and a sequence that is complementary to a particular nucleic acid sequence. The ribozyme functions by associating with the nucleic acid molecule (via the complementary domain of the ribozyme) and then cleaving the nucleic acid molecule using the catalytic domain. In carrying out this cleavage, the ribozyme is not itself altered, and is thus capable of recycling and cleaving other molecules, making it a true enzyme. A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff et al., *Nature,* 334:585-591 (1988).

Another method by which expression of a gene encoding DELLA can be inhibited is by sense suppression (also known as co-suppression). Introduction of expression cassettes in which a nucleic acid sequence from a target gene is configured in the sense orientation with respect to the promoter, and is actively transcribed in the cell has been shown to be an effective means to suppress the transcription of target genes. For an example of the use of this method to modulate expression of endogenous genes, see Napoli et al., *The Plant Cell* 2:279-289 (1990); Flavell, *Proc. Natl. Acad. Sci.*, USA 91:3490-3496 (1994); Kooter and Mol, *Current Opin. Biol.* 4:166-171 (1993); and U.S. Pat. Nos. 5,034,323, 5,231,020, and 5,283,184.

For sense suppression, the nucleic acid sequence introduced by the expression cassette, needs less than absolute identity to the target gene sequence and also need not be full length, relative to either the primary transcription product or fully processed mRNA. Furthermore, the introduced sequence need not have the same intron or exon pattern, and identity of non-coding segments will be equally effective. In some aspects, a sequence of the size ranges noted above for antisense regulation is used, i.e., 30-40, or at least about 20, 50, 100, 200, 500 or more nucleotides.

Disruption of a coding region of a target gene can be accomplished by transfer DNA (T-DNA) based inactivation. For instance, a T-DNA can be positioned within a polynucleotide coding region described herein, thereby disrupting expression of the encoded transcript and protein. T-DNA based inactivation can be used to introduce into a plant cell a mutation that alters expression of the coding region, e.g., decreases expression of a coding region or decreases activity of the polypeptide encoded by the coding region. For example, mutations in a coding region and/or an operably linked regulatory region can be made by deleting, substituting, or adding a nucleotide(s). The use of T-DNA based inactivation is discussed, for example, in Azpiroz-Leehan et al., (1997, *Trends in Genetics,* 13:152-156). Disruption of a coding region can also be accomplished using methods that include transposons, homologous recombination, and the like.

In an aspect, the method for controlling DELLA gene expression in the plant uses a double-stranded RNA (dsRNA) or a nucleic acid that can promote or lead to production of a dsRNA, which can be used to down regulate an endogenous DELLA gene via RNA interference (RNAi). RNAi is known to be effective method for gene down regulation in plants (see, e.g., Chuang, C. F. & Meyerowitz, E. M., *Proc. Natl. Acad. Sci. USA* 10 97: 4985 (2000); Waterhouse et al., *Proc. Natl. Acad. Sci. USA* 95:13959-13964 (1998); Tabara et al., *Science* 282:430-431 (1998); Matthew, *Comp Funct Genom* 5: 240-244 (2004); Lu et al., *Nucleic Acids Res.* 32(21):e171 (2004)).

Without wishing to be bound by theory, expression cassettes can introduce dsRNAs into a cell that, when expressed in the cell, are processed into short dsRNAs called small interfering RNAs (siRNAs) by an endogenous endonuclease. The siRNA mediates RNAi via formation of a multi-component RNase complex termed RNA Interfering Silencing Complex (RISC), thereby leading to the degradation of the target gene transcript. Post transcriptional gene silencing by double-stranded RNA is discussed in further detail by Hammond et al., *Nature Rev Gen* 2: 110-119 (2001), Fire et al., *Nature* 391: 806-811 (1998) and Timmons and Fire, *Nature* 395: 854 (1998). siRNAs are generally short dsRNAs having a length in plants that range from 19 to 25 base pairs, or from 20 to 24 base pairs. In an aspect siRNAs having 19, 20, 21, 22, 23, 24, or 25 base pairs, and in particular 21 or 22 base pairs, corresponding to the target gene to be down-regulated can be used. However, the invention is not intended to be limited to the use of such siRNAs.

The dsRNA can be formed from two separate (sense and antisense) RNA strands that are annealed together. One of the dsRNA strands has a nucleotide sequence which is complementary to at least part of the nucleotide sequence of the target gene to be down-regulated and the other strand of the dsRNA is able to base-pair with the first strand. Alternatively, the dsRNA can be a single polynucleotide molecule having a foldback stem-loop or hairpin structure wherein the sense and antisense stands of the dsRNA are formed from different regions of single polynucleotide molecule that is partially self-complementary. The single polynucleotide molecule further comprises a loop region between the sense and antisense regions. The precise nature and sequence of the "loop" linking the two RNA strands is generally not material to the invention, except that it should not impair the ability of the double-stranded part of the molecule to mediate RNAi. RNAs having the hairpin structure are convenient if the dsRNA is to be synthesized by expression in vivo, for example in a host cell or organism, or by in vitro transcription. The features of "hairpin" or "stem-loop" RNAs for use in RNAi are generally known in the art (see for example International Patent Publication WO 1999/53050). In an aspect of the invention, the loop structure can comprise linker sequences or additional sequences as described below.

The RNAi polynucleotides can encompass the full-length target RNA or can correspond to a fragment of the target RNA. In some cases, the fragment will have fewer than 100, 200, 300, 400, 500 600, 700, 800, 900, or 1000 nucleotides corresponding to the target sequence. In addition, in an aspect, these fragments are at least, e.g., 20, 50, 100, 200, 300, or more nucleotides in length. The upper limit on the length of the dsRNA can be dependent on the requirement for the dsRNA to be processed within the cell into fragments that direct RNAi. The chosen length can, e.g., be influenced by the method of synthesis of the RNA and the mode of delivery of the RNA to the cell. Although the genes used for RNAi need not be completely identical to the target gene, they can be, e.g., at least 70%, 80%, 90%, or 95% or more identical to the target gene sequence. See, e.g., U.S. Patent Publication No. 2004/0029283.

In some cases, fragments for use in RNAi will be at least substantially similar to regions of a target protein that do not occur in other proteins in the organism or can be selected to have as little similarity to other organism transcripts as possible, e.g., selected by comparison to sequences in analyzing publicly-available sequence databases.

Additionally, the dsRNA can contain short non-target regions flanking the target-specific sequence, provided that such sequences do not affect performance of the dsRNA in RNA inhibition to a material extent.

The dsRNA can contain one or more substitute bases in order to optimize performance in RNAi. It will be apparent to one of ordinary skill in the art how to vary each of the bases of the dsRNA in turn and test the activity of the resulting dsRNAs (e.g., in a suitable in vitro test system) in order to optimize the performance of a given dsRNA.

The dsRNA can further contain DNA bases, non-natural bases, non-natural backbone linkages, or modifications of the sugar-phosphate backbone, for example to enhance stability during storage or enhance resistance to degradation by nucleases.

The dsRNA can be fully or partially double-stranded. Partially double-stranded dsRNAs can include short single-stranded overhangs at one or both ends of the double-stranded portion. The dsRNA can also contain internal non-complementary regions.

In some constructs, dsRNAs can comprise additional sequences and optionally a linker. Additional sequences can include, for example, (i) a sequence facilitating large-scale production of the dsRNA construct; (ii) a sequence effecting an increase or decrease in the stability of the dsRNA; and (iii) additional sequences to catalyze processing of dsRNA regions. In an aspect, the linker is a conditionally self-cleaving RNA sequence, preferably a pH sensitive linker or a hydrophobic sensitive linker.

Multiple dsRNA regions of the dsRNA construct can be connected directly or by one or more linkers. A linker can be present at a site in the RNA construct, separating dsRNA regions from another region of interest. Multiple dsRNA regions of dsRNA constructs can be connected without linkers.

The linker sequence can promote division of a long dsRNA into smaller dsRNA regions under particular circumstances, resulting in the release of separate dsRNA regions under these circumstances and leading to more efficient gene silencing by these smaller dsRNA regions. Examples of suitable conditionally self-cleaving linkers are RNA sequences that are self-cleaving at high pH conditions. Suitable examples of such RNA sequences are described by Borda et al., *Nucleic Acids Res.* 31: 2595-600 (2003). This sequence originates from the catalytic core of the hammerhead ribozyme HH16.

Linkers can also be located at a site in the dsRNA construct, separating the dsRNA regions from another, e.g., an additional, sequence of interest, which preferably provides some additional function to the RNA construct.

An intron can be used as a linker. An "intron" as used herein can be any noncoding RNA sequence of a pre-messenger RNA.

A non-complementary RNA sequence, ranging from about 1 base pair to about 10,000 base pairs, can also be used as a linker.

Expression vectors that continually express siRNA in transiently- and stably transfected cells are engineered to express small hairpin RNAs, which are processed in vivo into siRNA molecules capable of carrying out gene-specific silencing (Brummelkamp et al., *Science* 296: 550-553 (2002), and Paddison et al., *Genes & Dev.* 16: 948-958 (2002)).

Yet another way to suppress expression of an endogenous plant gene is by recombinant expression of microRNA that suppress a target gene (e.g., a gene encoding DELLA). Artificial microRNAs are single-stranded RNAs (e.g., between 18-25 nucleotides, e.g., 21 nucleotides), that are not normally found in plants and that are processed from endogenous microRNA precursors. Their sequences are designed according to the determinants of plant microRNA target selection, such that the artificial microRNA specifically silences its intended target gene(s) and are generally described in Schwab et al., *Plant Cell* 18: 1121-1133 (2006). See also US Patent Publication No. 2008/0313773.

Another method to reduce levels of a gene expression product of a gene of interest is to employ riboswitch techniques (see, e.g., U.S. Patent Publication Nos. 2010/0286082 and 2011/0245326).

In some aspects, expression cassettes comprising a DELLA gene are introduced into a plant, having a genetic background that is different from the wild-type. In an aspect, the plant genetic background is different from the wild-type by having reduced expression levels of at least one of the plant's DELLA polypeptides. The difference in the genetic background can be the result of naturally occurring gene mutations or genetic engineering methods as described herein to reduce expression of a desired product.

In an aspect, a non-naturally occurring gene editing system for controlling DELLA polypeptide expression in the plant are the Clustered Regularly Interspersed Short Palindromic Repeats (CRISPR) system editing technologies. Such CRISPR technologies include, but are not limited to, those described in U.S. Pat. No. 8,697,359; U.S. Patent Publication No. 2014/0273235; and International Patent Publication No. WO 2013/176772.

In general, the "CRISPR system" refers collectively to transcripts and other elements involved in the expression of, or directing the activity of CRISPR-associated ("Cas") proteins. The CRISPR system can include polynucleotides encoding the Cas polypeptide, trans-activating CRISPR ("tracr") polynucleotides (e.g., tracrRNA or an active partial tracrRNA), a tracr-mate polynucleotide (encompassing a "direct repeat" or a tracrRNA-processed partial direct repeat in the context of an endogenous CRISPR system), a guide polynucleotide (also referred to as a "spacer" in the context of an endogenous CRISPR system), or other polynucleotides relating to the CRISPR locus.

In an aspect, one or more elements of a CRISPR system is derived from a type I, type II, or type III CRISPR system. The type I and type III systems use a large complex of Cas proteins for crRNA-guided targeting. However, the type II system requires only a single protein for RNA-guided DNA recognition and cleavage (Doudna and Charpentier, *Science* 346: 1258096-1-1258096-9).

In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is complementary to, where hybridization between a target sequence and a guide sequence promotes the formation of a CRISPR complex. Full complementarity is not necessarily required, provided there is sufficient complementarity to cause hybridization and promote formation of a CRISPR complex. A target sequence can comprise any polynucleotide, such as DNA or RNA polynucleotides. In an aspect, a target sequence is located in the nucleus or cytoplasm of a cell. The target sequence can be within an organelle of a eukaryotic cell, e.g., a mitochondrion or a chloroplast. In an aspect of the invention the recombination is a homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more nucleotides from) the target sequence. Without wishing to be bound by theory, the tracr sequence, which can comprise or consist of all or a portion of a wild-type tracr sequence (e.g., about or more than about 20, 26, 32, 45, 48, 54, 63, 67, 85, or more nucleotides of a wild-type tracr sequence), can also form part of a CRISPR complex, such as by hybridization along at least a portion of the tracr sequence to all or a portion of a tracr mate sequence that is operably linked to the guide sequence. In an aspect, the tracr sequence has sufficient complementarity to a tracr mate sequence to hybridize and participate in formation of a CRISPR complex. As with the target sequence, it is believed that complete complementarity is not needed, provided there is sufficient to be functional. In an aspect, the tracr sequence has at least 50%, 60%, 70%, 80%, 90%, 95%, or 99% of sequence complementarity along the length of the tracr mate sequence when optimally aligned. In an aspect, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors.

A RNA-guided endonuclease is directed to a specific nucleic acid sequence (or target site) by a guide RNA. The guide RNA interacts with the RNA-guided endonuclease as well as the target site such that, once directed to the target site, the RNA-guided endonuclease is able to introduce a double-stranded break into the target site nucleic acid sequence.

The RNA-guided endonuclease can be derived from a CRISPR/CRISPR-associated (Cas) system. The CRISPR/Cas system can be, e.g., a type I, a type II, or a type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cu1966, or Cpf1.

In an aspect, the RNA-guided endonuclease is derived from a type II CRISPR/Cas system. The RNA-guided endonuclease can be derived from a Cas9 protein. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina.*

DELLA Polypeptides

As used herein, the term "DELLA polypeptide" includes endogenous DELLA polypeptides, endogenous DELLA polymorphic variants, endogenous DELLA alleles, endogenous DELLA mutants, DELLA homologs, and DELLA orthologs of the endogenous eucalyptus DELLA polypeptide. A nucleic acid that encodes a DELLA polypeptide refers to a gene, pre-mRNA, mRNA, and the like, including codon optimized sequences.

The term "endogenous" means a nucleic acid that encodes a polypeptide that corresponds to a polypeptide that is native to the wild-type plant.

The term "homolog" means a gene that has essentially the same biochemical function or similar biochemical function as another gene.

A polynucleotide is "heterologous" to an organism or a second polynucleotide sequence if it originates from a foreign species, or, if from the same species, is modified from its native form or function. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., it is a genetically engineered coding sequence, from a different gene in the same species, or an allele from a different ecotype or variety).

An "overexpressed" polypeptide as used herein refers to an increase in the expression level of an endogenous DELLA polypeptide. The increase in the expression level can be described as being greater than about 10%, 20%, 30%, 40%, 50%, 60%, 70%, 80%, 90%, or more than the wild-type expression level. Alternatively, an "overexpressed" polypeptide can refer to introducing a DELLA polynucleotide into a cell and expressing the polypeptide encoded by the said polynucleotide.

DELLA Downregulation

In an aspect, endogenous DELLA polypeptide expression level is reduced throughout the entire plant or only in a subset of cells or tissues of the plant. The endogenous DELLA polypeptide expression level can be reduced according to any method known in the art, such as the methods listed above. Such methods include, but are not limited to, antisense, siRNA, microRNA, dsRNA, sense suppression, mutagenesis, CRISPR, and dominant negative inhibition.

In an aspect, endogenous DELLA polypeptide expression level is reduced in the plant using dsRNA. dsRNA are expressed in the plant, plant cell or plant tissue, from expression cassettes encoding hair-pin RNA (hpRNA) targeting one or more polynucleotides encoding endogenous DELLA polypeptides.

In an aspect, the methods of the invention encompass the simultaneous or sequential provision of two or more different dsRNAs or RNA constructs to the same endogenous DELLA polynucleotide, so as to achieve a more potent inhibition of a single target gene.

In an aspect, the methods of the invention encompass the simultaneous or sequential provision of two or more different dsRNAs or RNA constructs to different endogenous DELLA polynucleotides, so as to achieve down-regulation or inhibition of multiple target genes.

Alternatively, multiple endogenous DELLA polynucleotides are targeted by the provision of one dsRNA that is substantially complementary to a sequence found in multiple target sequences.

In an aspect, one or more endogenous DELLA polypeptide expression level is reduced in *Eucalyptus* plants.

In an aspect, the *Eucalyptus* DELLA polypeptides are selected from the group consisting of SEQ ID NO: 1, 3, 5, 7, 9, and 11.

Root-Specific Expression

This disclosure provides transgenic plants and methods of making transgenic plants in which the DELLA polypeptide expression levels in the roots of the plant is maintained, enhanced or reduced compared to the DELLA polypeptide expression levels elsewhere in the plant. According to some aspects, the DELLA polypeptide expression levels in the roots of the plant are maintained or enhanced while the DELLA polypeptide expression levels elsewhere in the plant are reduced. Specific expression of DELLA polypeptides in the roots overcome problems typically associated with plants having generally reduced DELLA polypeptide expression indiscriminately throughout the entire plant including the roots, which can result in suppressed lateral and adventitious root formation.

In an aspect, the transgenic plants of the present invention contain polynucleotide molecules that reduce the expression level of at least one endogenous DELLA polypeptide in green tissues.

In an aspect, an expression cassette comprising a green tissue-specific promoter operably linked to a polynucleotide molecule is introduced into a plant of the invention such that when expressed in the plant cells reduce the expression level of at least one endogenous DELLA polypeptide as compared to a wild-type plant.

In an aspect, the invention provides a plant containing at least two expression cassettes. A first expression cassette comprising a polynucleotide that reduces the expression level of at least one endogenous DELLA polypeptide; and a second expression cassette comprising a polynucleotide encoding a DELLA polypeptide linked to a heterologous root-specific promoter that causes overexpression of the DELLA polypeptide in the plant roots.

In an aspect, the invention provides methods of engineering a plant having DELLA activity that is primarily localized in the roots of the plant (e.g., at least 50%, at least 60%, at least 70%, at least 80%, at least 90%, or at least 99% of the DELLA activity in the plant being localized in the roots of the plant). The method comprises introducing into the plant, a first expression cassette, that when expressed in said plant, the level of expression of at least one endogenous DELLA polypeptide is reduced; and a second expression cassette comprising a polynucleotide encoding a DELLA polypeptide, operably linked to a heterologous root-specific promoter; and culturing the plant under conditions such that the DELLA polynucleotide is overexpressed in the roots of the plant.

In an aspect, a DELLA overexpression cassette is introduced into a plant having a genetic background that is different from the wild-type plant. As used herein, a different genetic background can refer to a plant in which the expression level of one or more endogenous DELLA polynucleotide is reduced or increased compared to a wild-type plant, throughout the entire plant or only in a subset of cells or tissues of the plant. The altered expression level can be attributed to a plant having a naturally occurring gene mutation in an endogenous DELLA polynucleotide or a transgenic plant in which a DELLA polypeptide expression level has been modified. The transgenic plant can be modified according to any method known in the art, including but not limited to the methods listed above.

One of skill in the art will understand that an overexpressed DELLA polynucleotide can, but need not, be identical to the downregulated endogenous DELLA polynucleotide. In an aspect, the DELLA polynucleotide is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to the downregulated endogenous DELLA polynucleotide in order to avoid silencing of the overexpressed DELLA polynucleotide (e.g., using different codons the overexpressed DELLA polynucleotide sequence can vary from the endogenous DELLA polynucleotide being reduced while encoding for an identical DELLA amino acid sequence). The degree of sequence identity or homology is determined using the Blast sequence alignment algorithm.

In an aspect, the overexpressed DELLA polynucleotide is selected from, e.g., GAI (*Arabidopsis thaliana*, At1g14920); RGA (*Arabidopsis thaliana*, At2g01570); RGL1 (*Arabidopsis thaliana*, At1g66350); RGL2 (*Arabidopsis thaliana*, At3g03450); RGL3 (*Arabidopsis thaliana*, At5g17490); OsGAI1 (*Oryza sativa*, BAA90749); OsGAI2 (*Oryza sativa*, AAR31213); OsGAI3 (*Oryza sativa*, BAD82782); HvSLN1 (*Hordeum vulgare*, AAL66734); VvGAI1 (*Vitis vinifera*, AAM19210); TaGAI (*Triticum aestivum*, CAB51555); ZmGAI (*Zea mays*, CAB51557), *Populous* GAI (XP_011021384.1, XP_011002785.1), and *Hevea brasiliensis* (gb|ALG02536.1).

When introducing two or more expression cassettes into the plant cells, the expression cassettes can be joined into a single construct or the expression cassettes can remain as two or more separate constructs.

In an aspect, the plant is a *Eucalyptus* plant.

The terms "fragment" and "portion" are used interchangeably herein.

The term "green tissue" as used herein includes but is not limited to, photosynthetic tissues, leaves, stem epidermis tissue, apical meristem tissues and shoot tips.

Polynucleotides described herein, including nucleotide sequences which are a portion of a coding region described herein, can be operably linked to a regulatory sequence. An example of a regulatory sequence is a promoter.

The term "promoter" as used herein refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene in a plant cell, tissue or organ. Such a promoter can be derived from a plant, bacterial, viral, fungal or animal origin. Such a promoter can be constitutive, i.e., capable of initiating high level gene transcription in a plurality of plant tissues; tissue-specific, i.e. capable of initiating gene transcription in a specific plant tissue or tissues; inducible, i.e., capable of initiating gene transcription in response to a stimulus, or; chimeric, i.e., formed of portions of at least two different promoters.

Non-limiting examples of constitutive plant promoters include CaMV35S and CaMV19S promoters, Figwort mosaic virus subgenomic transcript (sgFiMV) promoter, Strawberry vein banding virus (SVBV) promoter, FMV34S promoter, sugarcane bacilliform badnavirus promoter, CsVMV promoter, *Arabidopsis* ACT2/ACT8 actin promoter, *Arabidopsis* ubiquitin UBQ1 promoter, barley leaf thionin BTH6 promoter, rice actin promoter (Verdaguer B. et al., *Plant* 15 *Mol. Bioi.* 1998 37(6):1055-67), GOS2 (de Pater et al., *Plant J* November; 2(6):837-44, 1992), Rice cyclophilin (Bucholz et al., *Plant Mol Biol.* 25(5):837-43, 1994), and Maize H3 histone (Lepetit et al., *Mol. Gen. Genet.* 231: 276-285, 1992).

In an aspect, the promoter is a tissue-specific promoter. Non-limiting examples of tissue-specific promoters include those described in Yamamoto et al., (1997) *Plant J.* 12(2): 255-265; Kawamata et al., (1997) *Plant Cell Physiol.* 38(7): 792-803; Hansen et al. (1997) *Mol. Gen. Genet.* 254(3):337-343; Russell et al. (1997) *Transgenic Res.* 6(2):157-168; Rinehart et al., (1996) Plant Physiol. 112(3):1331-1341; Van Camp et al., (1996) Plant Physiol. 112(2):525-535; Canevascini et al., (1996) Plant Physiol. 112(2):513-524; Yamamoto et al., (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al., (1993) Proc. Natl. Acad. Sci. U.S.A. 90(20):9586-9590; and Guevara-Garcia et al. (1993) Plant J. 4(3):495-505.

Examples of promoters that can be used in this invention include but are not limited to green tissue promoters including leaf-specific promoters, flower-specific promoters, fruit-specific promoter, stem-specific promoters or photosynthetic tissue-specific promoters. Examples of such tissue-specific promoters include, but are not limited to, two chlorophyll binding proteins (cab I and cab2) from sugar beet (Stahl D. J. et al., 2004 BMC Biotechnology 2004 4:31), ribulose-bisphosphate carboxylase (Rubisco), encoded by rbcS (Nomura M. et al., 2000 Plant Mol. Bioi. 44: 99-106), A (gapA) and B (gapB) subunits of chloroplast glyceraldehyde-3-phosphate dehydrogenase (Conley T. R. et al., 1994 Mol. Cell. Bioi. 19: 2525-33; Kwon H. B. et al., 1994 Plant Physiol. 105: 357-67), promoter of the *Solanum tuberosum* gene encoding the leaf and stem specific (ST-LSI) protein (Zaidi M. A et al., 2005 Transgenic Res. 14:289-98), stem regulated, defense-inducible genes, such as JAS promoters (US Patent Publication No. 2005/0034192), chalcone synthase promoter (Faktor et al., 1996 Plant Mol. Bioi. 32: 849) strawberry RJ39 promoter (International Patent Publication No. WO 1998/31812).

In an aspect, the promoter is a root-specific promoter. Non-limiting examples of root-specific promoters include PsMTA (Fordam-Skelton, A. P. et al., 1997 Plant Molecular Biology 34: 659-668.), Class III Chitinase promoter, phosphate transporter promoter, tonoplast intrinsic aquaporin 2 promoter, Pyk10 promoter, AtFLS5 promoter, btg26 promoter, and *Solanum lycopersicum* root-expressed 2-ODD (REO).

As used herein, the phrase "operably linked" refers to a physical positioning of the regulatory element (e.g., promoter) and the gene of interest, such that the promoter sequence is able to initiate transcription of the gene of interest. For example, a promoter sequence can be located upstream of the selected nucleic acid sequence in terms of the direction of transcription and translation.

Expression cassettes and vectors and in vitro culture methods for plant cell or tissue transformation and regeneration of plants are generally known in the art. See, e.g., Gruber et al., "Vectors for Plant Transformation," in Methods in Plant Molecular Biology and Biotechnology, supra, pp. 89-119.

The term "construct" (also referred to herein as an "expression vector", "expression construct" or "DNA construct") refers to a nucleic acid construct that contains at least one expression cassette that when introduced into a host cell, results in transcription and/or translation of a RNA or polypeptide, respectively. Antisense or sense constructs that are not, or cannot be, translated are expressly included by this definition. In the case of both expression of transgenes and suppression of endogenous genes (e.g., by antisense, RNAi, sense suppression, CRISPR system) one of skill will recognize that the inserted polynucleotide sequence need not be identical, but can be only substantially identical to a sequence of the gene from which it was derived.

Recombinant constructs can optionally include a selectable marker gene. As used herein, the term "selectable marker gene" includes any gene, which confers a phenotype on a cell in which it is expressed that facilitates the identification and/or selection of cells which are transfected or transformed, with an expression construct of the invention. Examples of suitable selectable markers include resistance genes against ampicillin (Ampr), tetracycline (Tcr), kanamycin (Kanr), phosphinothricin, and chloramphenicol (CAT) gene. Other suitable marker genes provide a metabolic trait, for example manA. Visual marker genes can also be used and include for example beta-glucuronidase (GUS), luciferase, and Green Fluorescent Protein (GFP).

In an aspect, a vector comprising the constructs includes additional sequences which render this vector suitable for replication and integration in prokaryotes, eukaryotes, or preferably both (e.g., shuttle vectors). Suitable eukaryotic cells include plant cells. Suitable prokaryotic cells include eubacteria, such as gram-negative organisms, for example, *E. coli* or *A. tumefaciens.*

Typical vectors can also contain one or more additional regulatory elements, such as transcription and translation initiation sequences, transcription and translation terminators, a 5' leader and/or intron for enhancing transcription, a 3'-untranslated region (e.g., a sequence containing a polyadenylation signal), and a nucleic acid sequence encoding a transit or signal peptide (e.g., a chloroplast transit or signaling peptide). The expression vector can also include sequences engineered to enhance stability, production, purification or yield of the expressed polypeptide. Optionally, one or more transcription termination sequences can also be incorporated in the recombinant construct. The term "transcription termination sequence" encompasses a control sequence at the end of a transcriptional unit, which signals 3' processing and poly-adenylation of a primary transcript and termination of transcription. Additional regulatory elements, such as transcriptional or translational enhancers, can be incorporated in the expression construct.

A vector can integrate into a cell's genomic DNA. A vector can also be capable of replication in a bacterial host, for instance *E. coli* or *Agrobacterium tumefaciens*. Preferably, the vector is a plasmid.

Polynucleotides described herein can be produced in vitro or in vivo. For instance, methods for in vitro synthesis include, but are not limited to, chemical synthesis with a conventional DNA/RNA synthesizer. Commercial suppliers of synthetic polynucleotides and reagents for in vitro synthesis are well known. Methods for in vitro synthesis also include, for instance, in vitro transcription using a circular or linear expression vector in a cell free system. Expression vectors can also be used to produce a polynucleotide described herein in a cell, and the polynucleotide can then be isolated from the cell.

The invention also provides host cells having altered expression level of the DELLA polypeptides described herein. As used herein, a host cell includes the cell into which a polynucleotide described herein was introduced, and its progeny, which can, but need not necessarily, include the polynucleotide. Accordingly, a host cell can be an individual cell or a cell culture.

Plant cells can be transformed stably or transiently with the nucleic acid constructs. As used herein, "transformation" refers to a process by which a polynucleotide is inserted into the genome of a plant cell. Such an insertion includes stable introduction into the plant cell and transmission to progeny.

The transformation process results in the introduction of the nucleic acid sequence into the cell so as to change the recipient cell into a transformed, genetically modified or transgenic cell. In stable transformation, the nucleic acid molecule can be integrated into the plant genome and as such it represents a stable and inherited trait. In transient transformation, the nucleic acid molecule is expressed but it is not integrated into the genome of the cell.

Transgenic plants described herein can be produced using routine methods. The isolated polynucleotides or polypeptides can be introduced into a monocotyledonous or dicotyledonous plant by one or more techniques typically used for direct delivery into cells known to the skilled person. Such protocols can vary depending on the type of organism, cell, plant or plant cell, i.e., monocot or dicot, targeted for gene modification. Suitable methods of transforming plant cells include microinjection (Crossway et al., (1986) Biotechniques 4:320-334; and U.S. Pat. No. 6,300,543), electroporation (Riggs et al., (1986) Proc. Natl. Acad. Sci. USA 83:5602-5606, direct gene transfer (Paszkowski et al., (1984) EMBO J. 3:2717-2722), and ballistic particle acceleration (see, for example, Sanford et al., U.S. Pat. No. 4,945,050; International Patent publication No. WO 1991/10725; and McCabe et al., (1988) Biotechnology 6:923-926). Also see Tomes et al., "Direct DNA Transfer into Intact Plant Cells Via Microprojectile Bombardment". pp. 197-213 in Plant Cell, Tissue and Organ Culture, Fundamental Methods. eds. 0. L. Gamborg & G. C. Phillips. Springer-Verlag Berlin Heidelberg N.Y., 1995; U.S. Pat. No. 5,736,369 (meristem); Weissinger et al., (1988) Ann. Rev. Genet. 22:421-477; Sanford et al., (1987) Particulate Science and Technology 5:27-37 (onion); Christou et al., (1988) Plant Physiol. 87:671-674 (soybean); Datta et al., (1990) Biotechnology 8:736-740 (rice); Klein et al., (1988) Proc. Natl. Acad. Sci. USA 85:4305-4309 (maize); Klein et al., (1988) Biotechnology 6:559-563 (maize); International Patent publication No. WO 1991/10725 (maize); Klein et al., (1988) PlantPhysiol. 91:440-444 (maize); Fromm et al., (1990) Biotechnology 8:833-839; and Gordon-Kamm et al., (1990) Plant Cell 2:603-618 (maize); Hooydaas-Van Slogteren & Hooykaas (1984) Nature (London) 311:763-764; Bytebierm et al., (1987) Proc. Natl. Acad. Sci. USA 84:5345-5349 (Liliaceae); De Wet et al., (1985) In The Experimental Manipulation of Ovule Tissues, ed. G. P. Chapman et al., pp. 197-209. Longman, N.Y. (pollen); Kaeppler et al., (1990) Plant Cell Reports 9:415-418; and Kaeppler et al., (1992) Theor. Appl. Genet. 84:560-566 (whisker mediated transformation); U.S. Pat. No. 5,693,512 (sonication); D'Halluin et al., (1992) Plant Cell 4:1495-1505 (electroporation); Li et al., (1993) Plant Cell Reports 12:250-255; and Christou and Ford, (1995) Annals of Botany 75:407-413 (rice); Osjoda et al., (1996) Nature Biotech. 14:745-750; *Agrobacterium* mediated maize transformation (U.S. Pat. No. 5,981,840); silicon carbide whisker methods (Frame et al., (1994) Plant J. 6:941-948); laser methods (Guo et al., (1995) Physiologia Plantarum 93:19-24); sonication methods (Bao et al., (1997) Ultrasound in Medicine & Biology 23:953-959; Finer and Finer, (2000) Lett Appl Microbiol. 30:406-10; Amoah et al., (2001) J Exp Bot 52: 1135-42); polyethylene glycol methods (Krens et al., (1982) Nature 296:72-77); protoplasts of monocot and dicot cells can be transformed using electroporation (Fromm et al., (1985) Proc. Natl. Acad. Sci. USA 82:5824-5828) and microinjection (Crossway et al., (1986) Mol. Gen. Genet. 202: 179-185).

The most widely utilized method for introducing an expression vector into plants is based on the natural transformation system of *Agrobacterium. A. tumefaciens* and *A. rhizogenes* which are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) Crit. Rev. Plant Sci. 10:1. Descriptions of the *Agrobacterium* vector systems and methods for *Agrobacterium*-mediated gene transfer are provided in Gruber et al., supra; Mild et al., supra; and Moloney et al., (1989) Plant Cell Reports 8:238. Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) Science 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. Nos. 4,658,082; 913,914, filed Oct. 1, 1986, as referenced in U.S. Pat. No. 5,262,306, issued Nov. 16, 1993. Once constructed, these plasmids can be placed into *A. rhizogenes* or *A. tumefaciens* and these vectors used to transform cells of plant species, which are ordinarily susceptible to *Fusarium* or *Alternaria* infection. The selection of either *A. tumefaciens* or *A. rhizogenes* will depend on the plant being transformed thereby. In general, *A. tumefaciens* is the preferred organism for transformation. Most dicotyledonous plants, some gymnosperms, and a few monocotyledonous plants (e.g., certain members of Liliales and Arales) are susceptible to infection with *A. tumefaciens. A. rhizogenes* also has a wide host range, embracing most dicots and some gymnosperms, which includes members of the Leguminosae, Compositae, and Chenopodiaceae. European Patent Application No. 0604662 discloses a method for transforming monocots using *Agrobacterium*. European Application No. 0672752 discloses a method for transforming monocots with *Agrobacterium* using the scutellum of immature embryos. Ishida et al. discuss a method for transforming maize by exposing immature embryos to *A. tumefaciens* (*Nature Biotechnology* 14:745-50 (1996)). Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) Theor. Appl. Genet. 69:235-40; U.S. Pat. No. 4,658,082; Simpson et al., supra; and U.S. Pat. No. 5,262,306.

Several methods of plant transformation, collectively referred to as direct gene transfer, have been developed as an alternative to *Agrobacterium*-mediated transformation. A generally applicable method of plant transformation is microprojectile mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford et al., (1987) Part. Sci. Technol. 5:27; Sanford, (1988) Trends Biotech 6:299; Sanford, (1990) Physiol. Plant 79:206; and Klein et al., (1992) Biotechnology 10:268).

Another method for physical delivery of DNA to plants is sonication of target cells as described in Zang et al., (1991) BioTechnology 9:996. Alternatively, liposome or spheroplast fusions have been used to introduce expression vectors into plants. See, e.g., Deshayes et al., (1985) EMBO J. 4:2731; and Christou et al., (1987) Proc. Natl. Acad. Sci. USA 84:3962. Direct uptake of DNA into protoplasts using $CaCl_2$ precipitation, polyvinyl alcohol, or poly-L-ornithine has also been reported. See, e.g., Hain et al., (1985) *Mol. Gen. Genet.* 199:161; and Draper et al., (1982) *Plant Cell Physiol.* 23:451.

Electroporation of protoplasts and whole cells and tissues has also been described. See, e.g., Donn et al., (1990) Abstracts of the VIIth Int'l. Congress on Plant Cell and Tissue Culture IAPTC, A2-38, p. 53; D'Halluin et al., (1992) Plant Cell 4:1495-505; and Spencer et al., (1994) Plant Mol. Biol. 24:51-61.

Following stable transformation, plant propagation is carried out. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant.

Transformed plants can be regenerated by micropropagation which provides a rapid and consistent reproduction. Micropropagation is a process of growing new generation plants from a single piece of tissue that has been excised from a selected parent plant or cultivar. This process permits the mass reproduction of plants having the preferred tissue expressing the genetically modified polypeptide. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial cultured tissue is allowed to grow until a sufficient number of tissue samples are produced to meet production goals. During stage three, the tissue samples grown in stage two are divided and grown into individual plantlets. At stage four, the plantlets are transferred to a greenhouse for hardening where the plants' tolerance to light is gradually increased so that it can be grown in the natural environment.

Transformation of a plant with the polynucleotides described herein can result in a transgenic plant displaying a phenotype including, but not limited to, increased biomass compared to the wild-type plant, increased plant height, changes in cell wall composition, increased stress tolerance, early or late seed germination, increased or reduced stem elongation, increased or reduced leaf expansion, early or late pollen maturation, and early or late induction of flowering.

Phenotype can be assessed by any suitable means. The biochemical characteristics of lignin, cellulose, carbohydrates and other plant extracts can be evaluated by standard analytical methods including spectrophotometry, fluorescence spectroscopy, HPLC, mass spectroscopy, molecular beam mass spectroscopy, near infrared spectroscopy, nuclear magnetic resonance spectroscopy, and tissue staining methods.

The terms "down-regulation of gene expression", "reduced/decreased polypeptide expression level", "silencing" and "inhibition of gene expression" are used interchangeably and refer to a measurable or observable reduction in gene expression or a complete abolition of detectable gene expression, at the level of protein product and/or mRNA product from the target gene. The down-regulation effect of the gene expression can be calculated as being, e.g., at least 20%, 30%, 40%, 50%, 60%, preferably 70%, 80% or even more preferably 90% or 95% when compared with normal gene expression. Down-regulation or inhibition of gene expression in the plant cells can be confirmed by phenotypic analysis of the plant or by measurement of mRNA or protein expression using molecular techniques such as RNA solution hybridization, PCR, nuclease protection, Northern hybridization, reverse transcription, gene expression monitoring with a microarray, antibody binding, enzyme-linked immunosorbent assay (ELISA), Western blotting, radioimmunoassay (RIA), other immunoassays, or fluorescence-activated cell sorting (FACS).

According to one aspect of the invention, down-regulation of a DELLA gene leads to increased growth. Increased growth includes, but is not limited to, improved growth, increased height and increased biomass, compared to the wild-type. Depending on the assay used, the growth increase can be quantified as described above, as being greater than about 5%, 10%, 20%, 25%, 33%, 50% or 75% compared wild-type plants.

The expression "target region", "target nucleotide sequence" or "target site" of the target gene can be any suitable region or nucleotide sequence of the gene. The target region comprises at least 19 consecutive nucleotides of the target gene.

Also contemplated are processed products of the plants (e.g., woody plants) of some aspects of the invention including, but not limited to, ornament, timber or firewood, charcoal, pellet, pulp, paper, cellulose, hemi-cellulose, lignin, derivatives therefrom, sawmill, furniture, construction materials, dyes, mulch, fertilizers, as well as nectar for honey and oil for pest repellant, mosquito repellent, pesticides, fuel, food, feed, beverage, sweets, toothpaste, cosmetics, perfume, soap, detergents, antiseptic, medicinal, and pharmaceutics industries.

Nucleic acid sequences of the polypeptides can be optimized for plant expression. Examples of such sequence modifications include, but are not limited to, removal of polyadenylation sites, altering G/C content to more closely approach that typically found in the plant species of interest, and the removal of codons atypically found in the plant species, commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al., 1996, Plant Cell Reports 15:677-681. In this method, the standard deviation of codon usage (SDCU), a measure of codon usage bias, can be calculated by first finding the squared proportional deviation of usage of each codon of the native gene relative to that of highly expressed plant genes, followed by a calculation of the average squared deviation. The formula used is:

$$SDCU = n = 1N\left[\frac{Xn - Yn}{Yn}\right]\frac{2}{N},$$

where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan. The Codon Usage Database contains codon usage tables for a number of different species, with each codon usage table having been statistically determined based on the data present in Genbank.

By using the above tables to determine the most preferred or most favored codons for each amino acid in a particular species (for example, *Eucalyptus*), a nucleotide sequence encoding a protein of interest can be codon optimized for that particular species. This is carried out by replacing codons that may have a low statistical incidence in the particular species with those corresponding codons that are statistically more favored.

However, one or more less-favored codons can be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively affect mRNA stability or expression.

A modified nucleotide sequence can be fully or partially optimized for plant codon usage. Construction of synthetic genes by altering the codon usage is described in for example International Patent Publication No. WO 1994/003282.

The term "biomass," as used herein, refers to plant material that is processed to provide a product, e.g., a biofuel such as ethanol, or livestock feed, or a cellulose for paper and pulp industry products. Such plant material can include whole plants, or parts of plants, e.g., stems, leaves, branches, shoots, roots, tubers, and the like.

The terms "polypeptide" and "protein" are interchangeably used.

The term "corresponding to" refers to sequences which are identical or highly similar to each other. A sequence and the sequence which is corresponding to said sequence are known as "corresponding sequences". The percent sequence identity between corresponding sequences can generally be, e.g., at least 80% or 85% identical, preferably at least 90%, 95%, 96%, or more preferably at least 97%, 98%, or more, still more preferably at least 99% or more.

The term "complementary" as used herein relates to all of DNA-DNA complementarity, RNA-RNA complementarity and to DNA-RNA complementarity. In analogy herewith, the term "RNA equivalent" substantially means that in the DNA sequence(s), the base "T" can be replaced by the corresponding base "U" normally present in ribonucleic acids. Two nucleic acid strands are "substantially complementary" when at least 85% of their bases pair.

As used herein, the term "wild-type" refers to a naturally occurring plant cell, seed, plant component, plant tissue, plant organ or whole plant that has not been genetically modified.

As used herein, the term "phenotype" refers to a plant's visible and physiological properties that are produced by the interaction of the genotype and the environment. A phenotype distinguishing feature, characteristic, or trait which can be altered as described herein by modifying expression of at least one coding region in at least one cell of a plant. The modified expression of at least one coding region can confer a change in the phenotype of a transformed plant by modifying any one or more of a number of genetic, molecular, biochemical, physiological, morphological, or agronomic characteristics or properties of the transformed plant cell or plant as a whole. Whether a phenotype of a transgenic plant is altered is determined by comparing the transformed plant with a plant of the same species that has not been transformed with the same polynucleotide (a wild-type).

The term "plant" as used herein encompasses whole plants, a grafted plant, ancestors, and progeny of the plants and plant parts, including seeds, shoots, stems, roots (including tubers), rootstock, scion, and plant cells, tissues and organs. The plant can be in any form including suspension cultures, embryos, meristematic regions, callus tissue, leaves, gametophytes, sporophytes, pollen, and microspores.

Plants that are particularly useful in the methods of the invention include all plants which belong to the superfamily Viridiplantee, in particular monocotyledonous and dicotyledonous plants including a fodder or forage legume, ornamental plant, food crop, tree, or shrub selected from the list comprising, but not limited to, *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia vi/losa, Pagopyrum* spp., *Feijoa sellowlana, Fragaria* spp., *Flemingia* spp, *Freycinetia banksli, Geranium thunbergii, Ginkgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficil-*

*lata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used in some aspects of the invention.

In an aspect, the plant is a woody plant.

The term "woody plant" as used herein refers to a tree, namely a perennial plant having an elongated hard lignified stem. Woody plants include angiosperms and gymnosperm species and hybrids. Non-limiting examples of woody plants include eucalyptus, poplar, pine, fir, spruce, acacia, sweet gum, ash, birch, oak, teak, mahogany, sugar and Monterey, nut trees, e.g., walnut and almond, and fruit trees, e.g., apple, plum, citrus and apricot.

In an aspect, the plant is a eucalyptus plant. Examples of *Eucalyptus* include, without limitation, the following species: *E. botryoides, E. bridgesiana, E. camaldulensis, E. cinerea, E. globule, E. grandis, E. gunii, E nicholii, E. pulverulenta, E. robusta, E. rudis, E. saligna, E. tereticornis, E. urophylla, E. viminalis* and a cross hybrids of any of the preceding species especially *Eucalyptus grandis* and *Eucalyptus urophylla.*

EXAMPLES

The present invention can be illustrated by the following examples. It is to be understood that the particular examples, materials, amounts, and procedures are to be interpreted broadly in accordance with the scope and spirit of the invention as set forth herein.

Example 1

A. Identification of DELLA Homologs in *Eucalyptus Grandis*

To identify possible DELLA homologs in eucalyptus, a known DELLA sequence from *Arabidopsis* was aligned against a eucalyptus genome database found in Phytozome, a plant comparative genomics portal. The RGA sequence from *Arabidopsis thaliana* (accession number AT2G01570) was used to search the *Eucalyptus grandis* genome in the Phytozome database using the BLAST search tool. Three *Eucalyptus grandis* sequences (accession numbers J01594, G02163 and C04156) were identified (FIGS. 2A and 2B) as likely homolog DELLA genes.

B. Identification of DELLA Homologs in *Eucalyptus Grandis*×*Urophylla* Clone

Transcriptome sequencing of the *grandis*×*urophylla* eucalyptus plant (herein referred to as gXu) was conducted. Total RNA was isolated using Plant Total RNA purification kit and protocol (25800, Norgen biotic corp.), and On-Column DNase I Digestion Set treatment (DNASE70-1SET, Sigma). Total RNA volume was 50 μl. Total RNA was then re-treated with Turbo DNAse (AM1907, Ambion) to remove residual DNA. The purified RNA was kept at −80° C. until Illumina sequencing was performed. Illumina sequencing was carried out according to standard protocols to provide transcriptomes of the target plant.

J01594, 602163 and C04156 protein sequences from *Eucalyptus grandis* were aligned against the gXu transcriptome library, using ClustalW alignment software on the MacVector homepage. Based on the conserved GRAS and DELLA motifs, sequences similar to the *Eucalyptus grandis* J01594, 602163 and C04156, were identified in gXu, herein referred to as DELLA1, DELLA2 and DELLA3, respectively (FIGS. 3A, 3B, 3C and 3D).

C. Tissue-Specific Expression of gXu DELLAs

The transcript level for each gene was measured in three different types of tissues: leaves from tissue culture material, leaves from young expanding leaves and mature fully expanded leaves taken from 3 month old plants grown in the greenhouse. Young leaves were taken from the first internode of plants grown in the greenhouse, while mature leaves were taken from the $15^{th}$ internode of plants grown in the greenhouse.

The transcript level of DELLA1, DELLA2, and DELLA3 genes was measured in gXu using RT-PCR. For the RT-PCR analysis, total RNA from leaves of the transgenic Eucalyptus plants was extracted using MasterPure kit (Epicentre) according to the manufacturer's protocol. Residual genomic DNA was treated with RNase-free DNase I (Ambion). The cDNA was obtained from 0.2 μg of total RNA using the SuperScript III one-step RT-PCR system (Invitrogen) with Platinum Taq polymerase. To detect RNA expression levels of the DELLA genes, RT-PCR was carried out using primer pairs that generate fragments indicative of the DELLA genes.

The primer pairs used in RT-PCR for the individual genes are listed in Table 1.

TABLE 1

Primer pairs used in RT-PCR

| Gene | Primers | Product size |
|---|---|---|
| DELLA1 (SEQ ID NO: 2) | Forward GTGACGATGGTGGAACAG (SEQ ID NO: 27) Reverse CATGCTCGCCTGCTTGAA (SEQ ID NO: 28) | Approximately 304 bp |
| DELLA2 (SEQ ID NO: 4) | Forward CCCCGGACAACTCCGACC (SEQ ID NO: 29) Reverse CGGTCCACGAAGACCG (SEQ ID NO: 30) | Approximately 311 bp |
| DELLA3 (SEQ ID NO: 6) | Forward CCTGAACCCGAAGATAATGAC (SEQ ID NO: 31) Reverse ATGCTGGCTTGCTTGAACG (SEQ ID NO: 32) | Approximately 312 bp |

D. Results

Figure 4:
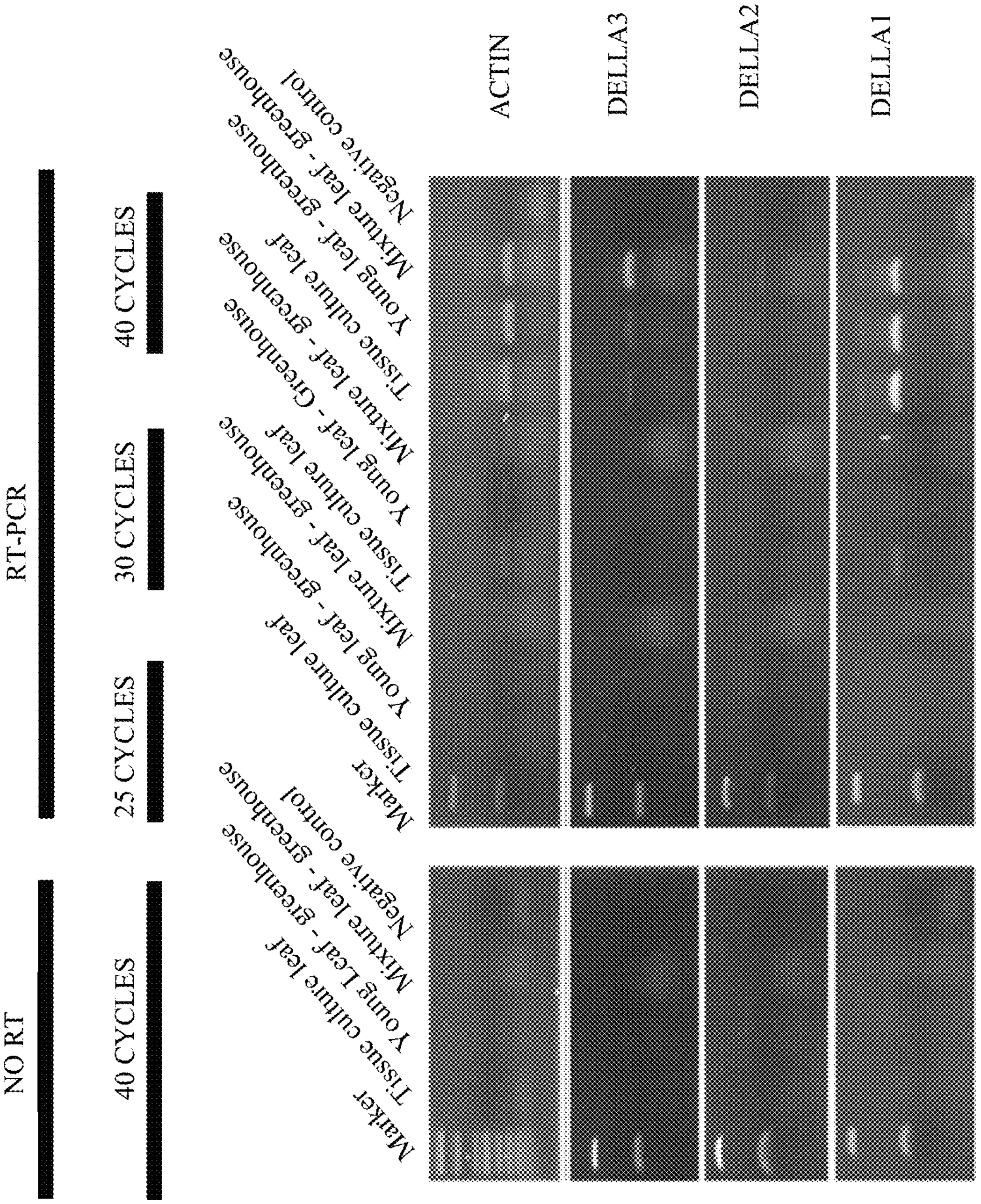
FIG. 4. The RT-PCR results of DELLA1, DELLA2 and DELLA3 expression level in tissue culture leaves, young leaves (in the greenhouse) and mature leaves (in the greenhouse). DELLA1 had a higher expression level in tissue culture and young leaves compared to DELLA3. DELLA2 expression was not detected in tissue culture leaves or young leaves, and only a low expression level was detected in mature leaves. Actin was used as a control gene.

The RT-PCR results, as seen in FIG. 4, revealed that DELLA1 and DELLA3 are expressed in tissue culture leaves, young leaves and mature leaves. DELLA1 had a higher expression level in tissue culture and young leaves compared to DELLA3. DELLA2 expression was not detected in tissue culture leaves or young leaves, and only low expression level was detected in mature leaves.

Example 2

A. Construct Preparation

Figure 5A:
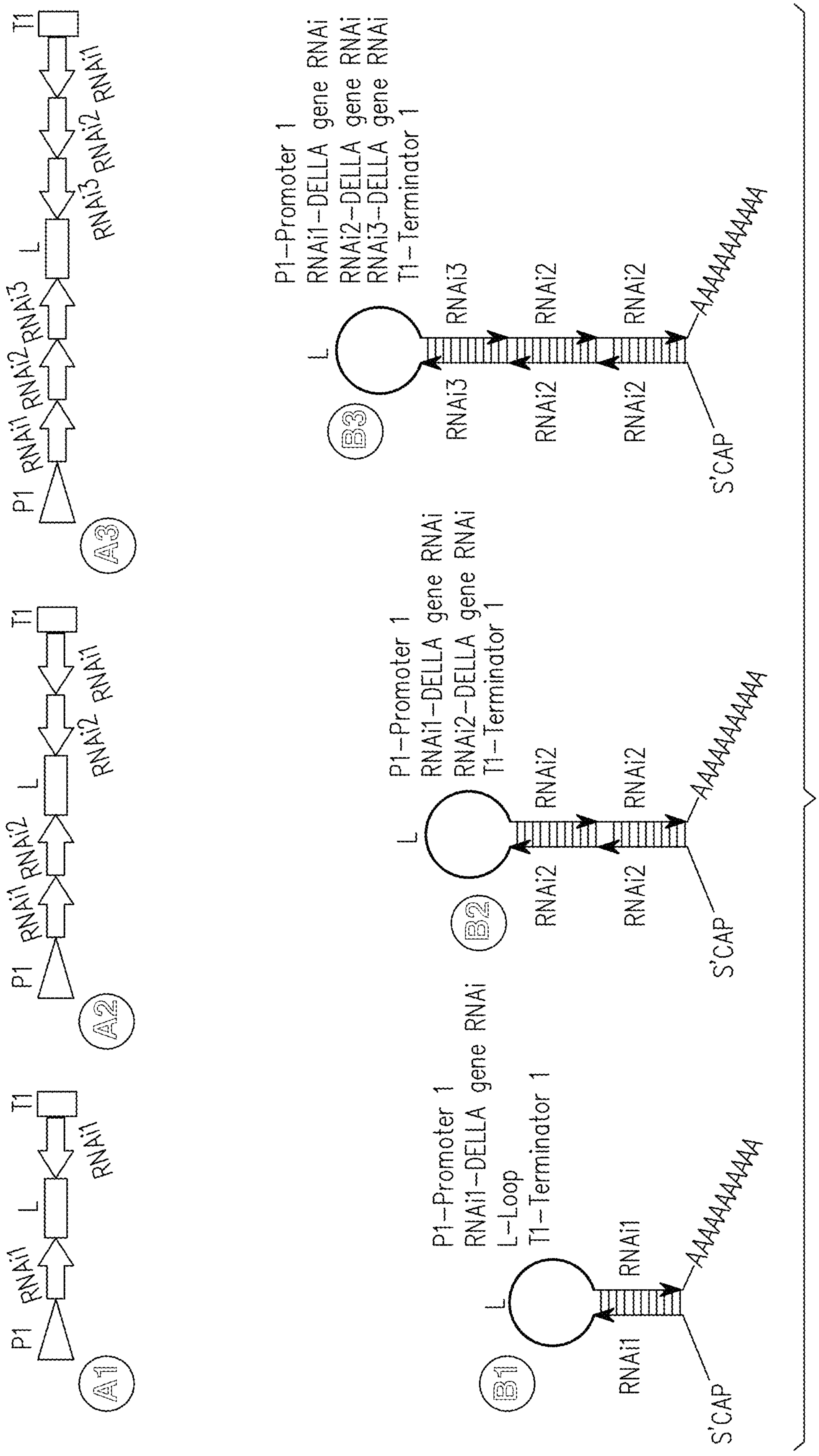
FIGS. 5A and 5B. Schematic representation of T-DNA maps of constructs.
Figure 5B:
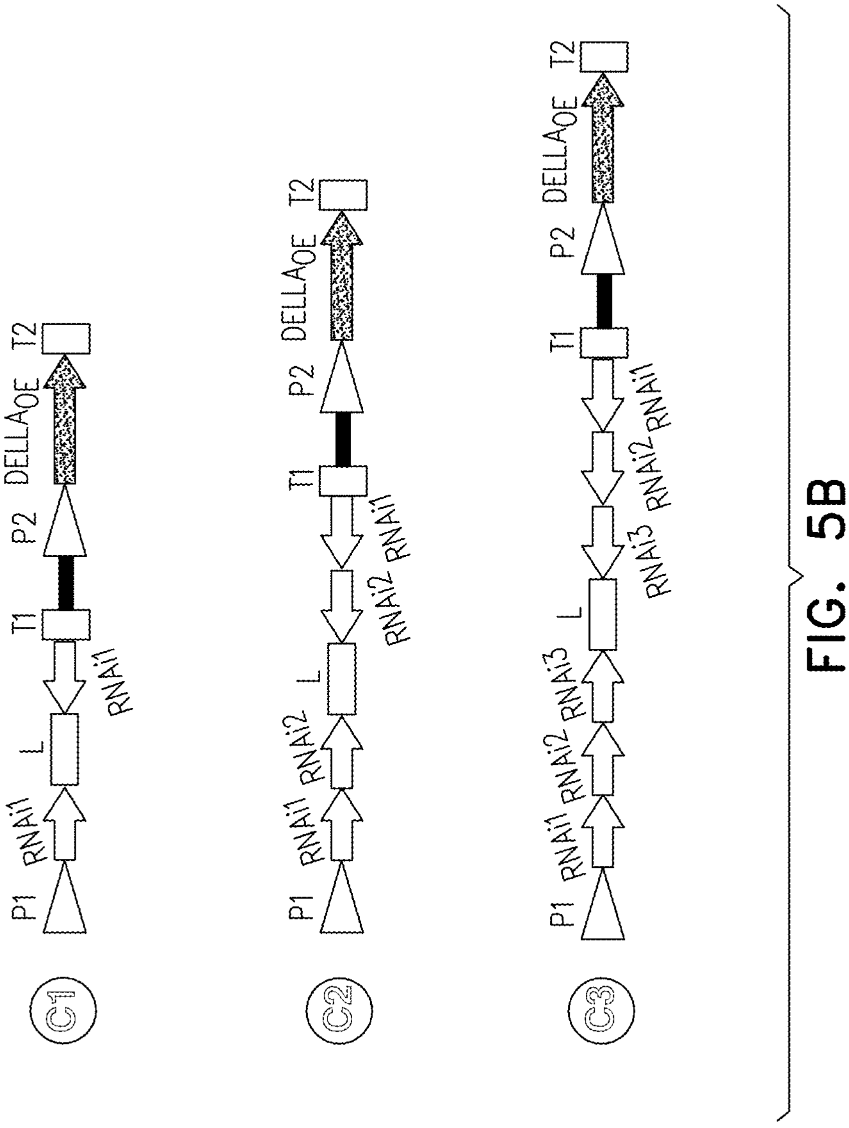

Down regulation constructs comprise an expression cassette comprising a fragment of a sequence encoding for a DELLA target sequence, the reverse complement sequence of the fragment and a loop sequence. Transcription of the constructs produce a hairpin RNA (hpRNA), having a stem comprised of the dsRNA fragment, formed by annealing of the inverted-repeat sequences of the target gene, and a loop region. The Down Regulation and Overexpression cassettes are shown in Table 2. Schematic representations of the constructs are shown in FIGS. 5A and 5B.

TABLE 2

Down Regulation and Overexpression cassettes

| Cassette no. | Cassette | Cassette use | DR Target polypeptide (SEQ ID NO) | RNAi fragment of the target gene (SEQ ID NO) | Loop sequence (SEQ ID NO) | OE Target polypeptide (SEQ ID NO) |
|---|---|---|---|---|---|---|
| 1 | DEL1 | DR | 1 | 23 | 26 | — |
| 2 | DEL2 | DR | 3 | 24 | 26 | — |
| 3 | DEL3 | DR | 5 | 25 | 26 | — |
| 4 | DEL1/2 | DR | 1/3 | 23/24 | 26 | — |
| 5 | DEL1/3 | DR | 1/5 | 23/25 | 26 | — |
| 6 | DEL2/3 | DR | 3/5 | 24/25 | 26 | — |
| 7 | DEL1/2/3 | DR | 1/3/5 | 23/24/25 | 26 | — |
| 8 | DEL1GT | DR | 1 | 23 | 26 | — |
| 9 | DEL2GT | DR | 3 | 24 | 26 | — |
| 10 | DEL3GT | DR | 5 | 25 | 26 | — |
| 11 | DEL1/2GT | DR | 1/3 | 23/24 | 26 | — |
| 12 | DEL1/3GT | DR | 1/5 | 23/25 | 26 | — |
| 13 | DEL2/3GT | DR | 3/5 | 24/25 | 26 | — |
| 14 | DEL1/2/3GT | DR | 1/3/5 | 23/24/25 | 26 | — |
| 15 | DEL1/$RGA_{OE}$ | DR/OE | 1 | 23 | 26 | 15 |
| 16 | DEL1/3/ $RGA_{OE}$ | DR/OE | 1/5 | 23/24 | 26 | 15 |
| 17 | DEL1/2/3/ $RGA_{OE}$ | DR/OE | 1/3/5 | 23/24/25 | 26 | 15 |
| 18 | DEL1/2/3/ $RGL_{OE}$ | DR/OE | 1/3/5 | 23/24/25 | 26 | 19 |

| Cassette no. | Schematic representation (FIGS. 5A, 5B) | Promoter (DR/OE) | Promoter DR/OE (SEQ ID NO) | Terminator | Terminator (SEQ ID NO) |
|---|---|---|---|---|---|
| 1 | A1, B1 | 35S CaMV | 41 | NOS | 45 |
| 2 | A1, B1 | 35S CaMV | 41 | NOS | 45 |
| 3 | A1, B1 | 35S CaMV | 41 | NOS | 45 |
| 4 | A2, B2 | 35S CaMV | 41 | NOS | 45 |
| 5 | A2, B2 | 35S CaMV | 41 | NOS | 45 |
| 6 | A2, B2 | 35S CaMV | 41 | NOS | 45 |
| 7 | A3, B3 | 35S CaMV | 41 | NOS | 45 |
| 8 | A1, B1 | RBC | 43 | NOS | 45 |
| 9 | A1, B1 | RBC | 43 | NOS | 45 |
| 10 | A1, B1 | RBC | 43 | NOS | 45 |
| 11 | A2, B2 | RBC | 43 | NOS | 45 |
| 12 | A2, B2 | RBC | 43 | NOS | 45 |
| 13 | A2, B2 | RBC | 43 | NOS | 45 |
| 14 | A3, B3 | RBC | 43 | NOS | 45 |
| 15 | C1 | 35S/ Aquaporin | 41/44 | NOS | 45 |
| 16 | C2 | 35S/ Aquaporin | 41/44 | NOS | 45 |
| 17 | C3 | 35S/ Aquaporin | 41/44 | NOS | 45 |
| 18 | C3 | 35S/ Aquaporin | 41/44 | NOS | 45 |

DR—Down regulation. OE—Over expression.

a. Down Regulation Constructs Under a Constitutive Promoter

A schematic of the structure of dsRNA down regulation constructs comprising fragments from one or more of the three gXu DELLA genes is shown in FIGS. 5A and 5B. Down regulation constructs contain an expression cassette comprising fragments from at least one of the gXu DELLA genes which are fused and synthesized in inverted repeats, separated by a loop sequence. See cassette P1-T1 in FIGS. 5A and 5B. Transcription of this cassette (initiated at promoter P1 and terminated at T1) produces a hairpin RNA, containing a dsRNA section, formed by annealing of the inverted-repeat sequences of the DELLA gene fragment, and a loop region. See schematics B1-B3.

(i) dsRNA DELLA1 Down Regulation Construct (Construct DEL1)

Construct DEL1 is shown schematically in FIG. 5A, schematics A1 and B1. The DEL1 construct comprised an expression cassette comprising respective 300 bp fragments of the DELLA1 encoding polynucleotide which were fused and synthesized in inverted repeats separated by 108 bp of a loop sequence. Transcription initiation was driven by the 35S CaMV promoter (SEQ ID NO: 41). Transcription termination was provided by the NOS Terminator (SEQ ID NO: 45). Transcription of construct DEL1 yielded a hairpin RNA (hpRNA) with a stem formed by the reverse complementary sequences of the DELLA1 300 bp sequences, to down regulate the corresponding DELLA1 gene.

The respective hpRNA sequences correspond to the following elements: Nucleotides 1-300 and 409-708: Respective sense and reverse complement sequences of SEQ ID NO: 23, corresponding to 300 nucleotides of SEQ ID NO: 2. Nucleotides 301-408: 108 bp loop fragment (SEQ ID NO: 26) based on partial random intron sequence. (Table 2, cassette no.1).

(iii) dsRNA DELLA2 Down Regulation Construct (Construct DEL2)

Construct DEL2 is shown schematically in FIG. 5A, schematics A1 and B1. The DEL2 construct comprised an expression cassette comprising respective 396 bp fragments of the DELLA2 encoding polynucleotide which were fused and synthesized in inverted repeats separated by 108 bp of a loop sequence. Transcription initiation was driven by the 35S CaMV promoter (SEQ ID NO: 41). Transcription termination was provided by the NOS Terminator (SEQ ID NO: 45). Transcription of construct DEL2 yielded a hpRNA with a stem formed by the reverse complementary sequences of the DELLA2 396 bp sequences, to down regulate the corresponding DELLA2 gene.

The respective hpRNA sequences correspond to the following elements: Nucleotides 1-396 and 505-900: Respective sense and reverse complement sequences of SEQ ID NO: 24, corresponding to 396 nucleotides of SEQ ID NO: 4. Nucleotides 397-504: 108 bp loop fragment (SEQ ID NO: 26) based on partial random intron sequence. (Table 2, cassette no.2).

(iv) dsRNA DELLA1 and DELLA2 Down Regulation Construct (Construct DEL1/2)

Construct DEL1/2 is shown schematically in FIG. 5A, schematics A2 and B2. The DEL1/2 construct comprised an expression cassette comprising respective 300 bp fragments of the DELLA1 encoding polynucleotide and 396 bp of the DELLA2 encoding polynucleotide which were fused and synthesized in inverted repeats separated by 108 bp of a loop sequence. Transcription initiation was driven by the 35S CaMV promoter (SEQ ID NO: 41). Transcription termination was provided by the NOS Terminator (SEQ ID NO: 45). Transcription of construct DEL1/2 yielded a hpRNA with a stem formed by the reverse complementary sequences of the DELLA sequences, to down regulate the corresponding DELLA1 and DELLA2 genes.

The respective hpRNA sequences correspond to the following elements: Nucleotides 1-300 and 1201-1500: Respective sense and reverse complement sequences of SEQ ID NO: 23, corresponding to nucleotides of the gXu DELLA1, SEQ ID NO: 2. Nucleotides 301-696 and 805-1200: Respective sense and reverse complement sequences of SEQ ID NO: 24, corresponding to nucleotides of the gXu DELLA2, SEQ ID NO: 4. Nucleotides 697-804: 108 bp loop fragment (SEQ ID NO: 26) based on partial random intron sequence. (Table 2, cassette no.4).

(v) dsRNA DELLA1 and DELLA3 Down Regulation Construct (Construct DEL1/3)

Construct DEL1/3 is shown schematically in FIG. 5A, schematics A2 and B2. The DEL1/3 construct comprised an expression cassette comprising respective 300 bp fragments of the DELLA1 encoding polynucleotide and 300 bp of the DELLA3 encoding polynucleotide which were fused and synthesized in inverted repeats separated by 108 bp of a loop sequence. Transcription initiation was driven by the 35S CaMV promoter (SEQ ID NO: 41). Transcription termination was provided by the NOS Terminator (SEQ ID NO: 45). Transcription of construct DEL1/3 yielded a hpRNA with a stem formed by the reverse complementary sequences of the DELLA sequences, to down regulate the corresponding DELLA1 and DELLA3 genes.

The respective hpRNA sequences correspond to the following elements: Nucleotides 1-300 and 1009-1308: Respective sense and reverse complement sequences of SEQ ID NO: 23, corresponding to 300 nucleotides of the gXu DELLA1, SEQ ID NO: 2. Nucleotides 301-600 and 709-1008: Respective sense and reverse complement sequences of SEQ ID NO: 25, corresponding to 300 nucleotides of gXu DELLA3, SEQ ID NO: 6. Nucleotides 601-708: 108 bp loop fragment (SEQ ID NO: 26) based on partial random intron sequence. (Table 2, cassette no.5).

(vi) dsRNA DELLA1, DELLA2 and DELLA3 Down Regulation Construct (Construct DEL1/2/3)

Construct DEL1/2/3 is shown schematically in FIG. 5A, schematics A3 and B3. The DEL1/2/3 construct comprised an expression cassette comprising respective 300 bp fragments of the DELLA1 encoding polynucleotide, 396 bp of the DELLA2 encoding polynucleotide and 300 bp of the DELLA3 encoding polynucleotide which were fused and synthesized in inverted repeats separated by 108 bp of a loop sequence. Transcription initiation was driven by the 35S CaMV promoter (SEQ ID NO: 41). Transcription termination was provided by the NOS Terminator (SEQ ID NO: 45). Transcription of construct DEL1/2/3 yielded a hpRNA with a stem formed by the reverse complementary sequences of the DELLA sequences, to down regulate the corresponding DELLA1, DELLA2 and DELLA3 genes.

The respective hpRNA sequences correspond to the following elements: Nucleotides 1-300 and 1801-2100: Respective sense and reverse complement sequences of SEQ ID NO: 23, corresponding to nucleotides of the gXu DELLA1, SEQ ID NO: 2. Nucleotides 301-696 and 1405-1800: Respective sense and reverse complement sequences of SEQ ID NO: 24, corresponding to nucleotides of the gXu DELLA2, SEQ ID NO: 4. Nucleotides 697-996 and 1105-1404: Respective sense and reverse complement sequences of SEQ ID NO: 25, corresponding to nucleotides of the gXu DELLA3, SEQ ID NO: 6. Nucleotides 997-1104: 108 bp loop fragment (SEQ ID NO: 26) based on partial random intron sequence. (Table 2, cassette no.7).

b. Down Regulation Constructs Under a Green Tissue-Specific Promoter

A schematic of the structure of dsRNA down regulation constructs comprising fragments from one or more of the three gXu DELLA genes is shown in FIGS. 5A and 5B. Down regulation constructs contained an expression cassette comprising fragments from at least one of the gXu DELLA genes which were fused and synthesized in inverted repeats, separated by a loop sequence. See cassette P1-T1 in FIGS. 5A and 5B. Transcription of this cassette (initiated at promoter P1 and terminated at T1) produced a hairpin RNA, containing a dsRNA section, formed by annealing of the inverted-repeat sequences of the DELLA gene fragment, and a loop region. See schematics B1-B3.

(i) dsRNA DELLA1 Down Regulation Constructs Under a Green Tissue-Specific promoter (Construct DEL1GT)

Construct DEL1GT is shown schematically in FIG. 5A, schematics A1 and B1. The DEL1GT construct comprised an expression cassette comprising respective 300 bp fragments of the DELLA1 encoding polynucleotide which was fused and synthesized in inverted repeats separated by 108 bp of a loop sequence. Transcription initiation was driven by the RBC promoter. Transcription termination was provided by the NOS Terminator (SEQ ID NO: 45). Transcription of construct DEL 1GT yielded a hpRNA with a stem formed by the reverse complementary sequences of the DELLA1 300 bp sequences, to down regulate the corresponding DELLA1 gene.

The respective hpRNA sequences correspond to the following elements: Nucleotides 1-300 and 409-708: Respective sense and reverse complement sequences of SEQ ID NO: 23, corresponding to 300 nucleotides of SEQ ID NO: 2. Nucleotides 301-408: 108 bp loop fragment (SEQ ID NO: 26) based on partial random intron sequence. (Table 2, cassette no.8).

(ii) dsRNA DELLA1 and DELLA2 Down Regulation Construct under a Green Tissue-Specific Promoter (Construct DEL1/2GT)

Construct DEL1/2GT is shown schematically in FIG. 5A, schematics A2 and B2. The DEL1/2GT construct comprised an expression cassette comprising respective 300 bp fragments of the DELLA1 encoding polynucleotide and 396 bp of the DELLA2 encoding polynucleotide which were fused and synthesized in inverted repeats separated by 108 bp of a loop sequence. Transcription initiation was driven by the RBC promoter. Transcription termination was provided by the NOS Terminator (SEQ ID NO: 45). Transcription of construct DEL1/2 yielded a hpRNA with a stem formed by the reverse complementary sequences of the DELLA sequences, to down regulate the corresponding DELLA1 and DELLA2 genes.

The respective hpRNA sequences correspond to the following elements: Nucleotides 1-300 and 1201-1500: Respective sense and reverse complement sequences of SEQ ID NO: 23, corresponding to nucleotides of the gXu DELLA1, SEQ ID NO: 2. Nucleotides 301-696 and 805-1200: Respective sense and reverse complement sequences of SEQ ID NO: 24, corresponding to nucleotides of the gXu DELLA2, SEQ ID NO: 4. Nucleotides 697-804: 108 bp loop fragment (SEQ ID NO: 26) based on partial random intron sequence. (Table 2, cassette no.11).

(iii) dsRNA DELLA1, DELLA2 and DELLA3 Down Regulation Construct Under a Green Tissue-Specific Promoter (Construct DEL1/2/3GT)

Construct DEL1/2/3GT is shown schematically in FIG. 5A, schematics A3 and B3. The DEL1/2/3GT construct comprised an expression cassette comprising respective 300 bp fragments of the DELLA1 encoding polynucleotide, 396 bp of the DELLA2 encoding polynucleotide and 300 bp of the DELLA3 encoding polynucleotide which were fused and synthesized in inverted repeats separated by 108 bp of a loop sequence. Transcription initiation is driven by the RBC promoter. Transcription termination is provided by the NOS Terminator (SEQ ID NO: 45). Transcription of construct DEL1/2/3GT yielded a hpRNA with a stem formed by the reverse complementary sequences of the DELLA sequences, to down regulate the corresponding DELLA1, DELLA2 and DELLA3 genes.

The respective hpRNA sequences correspond to the following elements: Nucleotides 1-300 and 1801-2100: Respective sense and reverse complement sequences of SEQ ID NO: 23, corresponding to nucleotides of the gXu DELLA1, SEQ ID NO: 2. Nucleotides 301-696 and 1405-1800: Respective sense and reverse complement sequences of SEQ ID NO: 24, corresponding to nucleotides of the gXu DELLA2, SEQ ID NO: 4. Nucleotides 697-996 and 1105-1404: Respective sense and reverse complement sequences of SEQ ID NO: 25, corresponding to nucleotides of the gXu DELLA3, SEQ ID NO: 6. Nucleotides 997-1104: 108 bp loop fragment (SEQ ID NO: 26) based on partial random intron sequence. (Table 2, cassette no.14).

c. Down Regulation and Over Expression (DR/OE) Constructs

Schematics of the structure of DR/OE constructs are shown in FIG. 5B. DR/OE constructs contained both a down regulation cassette for the down regulation of one or more endogenous DELLA polypeptides expression level (cassette P1-T1), and an over expression cassette for overexpression of a DELLA gene in the roots (cassette P2-T2). Cassettes are depicted in Table 2.

(i) DELLA1 Down Regulation and *Arabidopsis* RGA Root Over Expression Construct (Construct DEL1/RGA$_{OE}$)

Construct DEL1/RGA$_{OE}$ is shown schematically in FIG. 5B, schematic C1. The construct comprised the DEL1 down regulation expression cassette comprising respective 300 bp fragments of the DELLA1 encoding polynucleotide fused and synthesized in inverted repeats separated by 108 bp of a loop sequence. Transcription initiation was initiated by the 35S CaMV promoter (SEQ ID NO: 41). Transcription termination was provided by the NOS Terminator (SEQ ID NO: 45). Transcription of construct DEL1 yielded a hpRNA with a stem formed by the reverse complementary sequences of the DELLA1 300 bp sequences, to down regulate the corresponding DELLA1 gene.

The respective hpRNA sequences correspond to the following elements: Nucleotides 1-300 and 409-708: Respective sense and reverse complement sequences of SEQ ID NO: 23, corresponding to 300 nucleotides of SEQ ID NO: 2. Nucleotides 301-408: 108 bp loop fragment (SEQ ID NO: 26) based on partial random intron sequence. (Table 2, cassette no.1).

The DEL1/RGA$_{OE}$ Construct further comprised the RGA$_{OE}$ cassette comprising the polynucleotide encoding the At RGA polypeptide, SEQ ID NO: 16. Transcription initiation was driven by an Aquaporin gene promoter (SEQ ID NO: 44). Transcription termination was provided by the NOS Terminator (SEQ ID NO: 45). (Table 2, cassette no.15).

(ii) DELLA1/3 Down Regulation and *Arabidopsis* RGA Root Over Expression Construct (Construct DEL1/3/RGA$_{OE}$)

Construct DEL1/3 is shown schematically in FIG. 5A, schematics A2 and B2. The DEL1/3 construct comprised an expression cassette comprising respective 300 bp fragments of the DELLA1 encoding polynucleotide and 300 bp of the DELLA3 encoding polynucleotide which were fused and synthesized in inverted repeats separated by 108 bp of a loop sequence. Transcription initiation was driven by the 35S CaMV promoter (SEQ ID NO: 41). Transcription termination was provided by the NOS Terminator (SEQ ID NO: 45). Transcription of construct DEL1/3 yielded a hpRNA with a stem formed by the reverse complementary sequences of the DELLA sequences, to down regulate the corresponding DELLA1 and DELLA3 genes.

The respective hpRNA sequences correspond to the following elements: Nucleotides 1-300 and 1009-1308: Respective sense and reverse complement sequences of SEQ ID NO: 23, corresponding to 300 nucleotides of the gXu DELLA1, SEQ ID NO: 2. Nucleotides 301-600 and 709-1008: Respective sense and reverse complement sequences of SEQ ID NO: 25, corresponding to 300 nucleotides of gXu DELLA3, SEQ ID NO: 6. Nucleotides 601-708: 108 bp loop fragment (SEQ ID NO: 26) based on partial random intron sequence. (Table 2, cassette no.5).

The DEL1/3/$RGA_{OE}$ Construct further comprised the $RGA_{OE}$ cassette comprising the polynucleotide encoding the At RGA polypeptide, SEQ ID NO: 16. Transcription initiation was driven by the Aquaporin gene promoter (SEQ ID NO: 44). Transcription termination was provided by the NOS Terminator (SEQ ID NO: 45). (Table 2, cassette no.15).

(iii) DELLA1/2/3 Down Regulation and *Arabidopsis* RGA Root Over Expression Construct (Construct DEL1/2/3/$RGL_{OE}$)

Construct DEL1/2/3/$RGA_{OE}$ is shown schematically in FIG. 5B, schematic C3. The DEL1/2/3 construct comprised an expression cassette comprising respective 300 bp fragments of the DELLA1 encoding polynucleotide, 396 bp of the DELLA2 encoding polynucleotide and 300 bp of the DELLA3 encoding polynucleotide which were fused and synthesized in inverted repeats separated by 108 bp of a loop sequence. Transcription was initiated by the 35S CaMV promoter (SEQ ID NO: 41). Transcription termination was provided by the NOS Terminator (SEQ ID NO: 45). Transcription of construct DEL1/2/3 yielded a hpRNA with a stem formed by the reverse complementary sequences of the DELLA sequences, to down regulate the corresponding DELLA1, DELLA2 and DELLA3 genes.

The respective hpRNA sequences correspond to the following elements: Nucleotides 1-300 and 1801-2100: Respective sense and reverse complement sequences of SEQ ID NO: 23, corresponding to nucleotides of the gXu DELLA1, SEQ ID NO: 2. Nucleotides 301-696 and 1405-1800: Respective sense and reverse complement sequences of SEQ ID NO: 24, corresponding to nucleotides of the gXu DELLA2, SEQ ID NO: 4. Nucleotides 697-996 and 1105-1404: Respective sense and reverse complement sequences of SEQ ID NO: 25, corresponding to nucleotides of the gXu DELLA3, SEQ ID NO: 6. Nucleotides 997-1104: 108 bp loop fragment (SEQ ID NO: 26) based on partial random intron sequence. (Table 2, cassette no.7).

The DEL1/2/3/$RGA_{OE}$ construct further comprised the $RGA_{OE}$ cassette comprising the polynucleotide encoding the At RGA polypeptide, SEQ ID NO:16. Transcription was initiated by the Aquaporin gene promoter (SEQ ID NO: 44). Transcription termination was provided by the NOS Terminator (SEQ ID NO: 45). (Table 2, cassette no.15).

(iv) DELLA1/2/3 Down Regulation and *Arabidopsis* RGL2 Root Over Expression Construct (Construct DEL1/2/3-RGL/OE)

Construct DEL1/2/3/$RGL_{OE}$ is shown schematically in FIG. 5B, schematic C3. The DEL1/2/3 construct comprised an expression cassette comprising respective 300 bp fragments of the DELLA1 encoding polynucleotide, 396 bp of the DELLA2 encoding polynucleotide and 300 bp of the DELLA3 encoding polynucleotide which were fused and synthesized in inverted repeats separated by 108 bp of a loop sequence. Transcription was initiated by the 35S CaMV promoter (SEQ ID NO: 41). Transcription termination was provided by the NOS Terminator (SEQ ID NO: 45). Transcription of construct DEL1/2/3 yielded a hpRNA with a stem formed by the reverse complementary sequences of the DELLA sequences, to down regulate the corresponding DELLA1, DELLA2 and DELLA3 genes.

The respective hpRNA sequences correspond to the following elements: Nucleotides 1-300 and 1801-2100: Respective sense and reverse complement sequences of SEQ ID NO: 23, corresponding to nucleotides of the gXu DELLA1, SEQ ID NO: 2. Nucleotides 301-696 and 1405-1800: Respective sense and reverse complement sequences of SEQ ID NO: 24, corresponding to nucleotides of the gXu DELLA2, SEQ ID NO: 4. Nucleotides 697-996 and 1105-1404: Respective sense and reverse complement sequences of SEQ ID NO: 25, corresponding to nucleotides of the gXu DELLA3, SEQ ID NO: 6. Nucleotides 997-1104: 108 bp loop fragment (SEQ ID NO: 26) based on partial random intron sequence. (Table 2, cassette no.7).

The DEL1/2/3/$RGL_{OE}$ Construct further comprised the RGL/OE cassette comprising the polynucleotide encoding the At RGL2 polypeptide, SEQ ID NO: 20. Transcription was initiated by the Aquaporin gene promoter (SEQ ID NO: 44). Transcription termination was provided by the NOS Terminator (SEQ ID NO: 45). (Table 2, cassette no.16).

B. Transformation of Constructs into Eucalyptus

RNA constructs were transformed into gXu plants using a protocol essentially as described in Prakash et al., 2009. Briefly, shoots of Eucalyptus were propagated in vitro on Murashige and Skoog (MS) basal salt medium consisting of 3% (w/v) sucrose and 0.8% (w/v) agar. All in vitro plant materials were incubated at 25±2° C. using a 16-h photoperiod with cool white fluorescent lamps with an intensity of 30 11Em-2 s-1. *A. tumefaciens* strain LBA 4404 harboring a binary vector pBI121 containing nptII gene was used for transformation. Bacterial culture collected at late log phase was pelleted and resuspended in MS basal salt medium. Leaves from in vitro material were collected and used as explants for transformation experiments. Explants were precultured on the MS regeneration medium supplemented with 0.5 mg/l 6-Benzylaminopurine (BAP) and 0.1 mg/l NAA for 2 d. Precultured leaf explants were gently shaken in the bacterial suspension for 10 min and blotted dry on a sterile filter paper. Explants were then cocultivated in medium under the preculture conditions for two days. Following cocultivation, explants were washed in MS liquid medium, blotted dry on a sterile filter paper, and transferred to MS regeneration medium containing 0.5 mg/l 6-Benzylaminopurine and 0.1 mg/l 1-Naphthaleneacetic acid supplemented with 40 mg/l kanamycin and 300 mg/l cefotaxime. After 4-5 weeks of culture, regeneration was observed and explants were transferred to liquid elongation medium (MS medium supplemented with 0.5 mg/l BAP, 40 mg/l kanamycin, and 300 mg/l cefotaxime) on paper bridges. The elongated shoots (1.5-2 em) were propagated on MS medium with 0.1 mg/l BAP. Leaf segments were regenerated and elongated shoots were analyzed by PCR and western blot. Positive shoots were multiplied to 10 copies on MS medium containing 0.04 mg/L BAP.

C. PCR Confirmation

Figure 6:
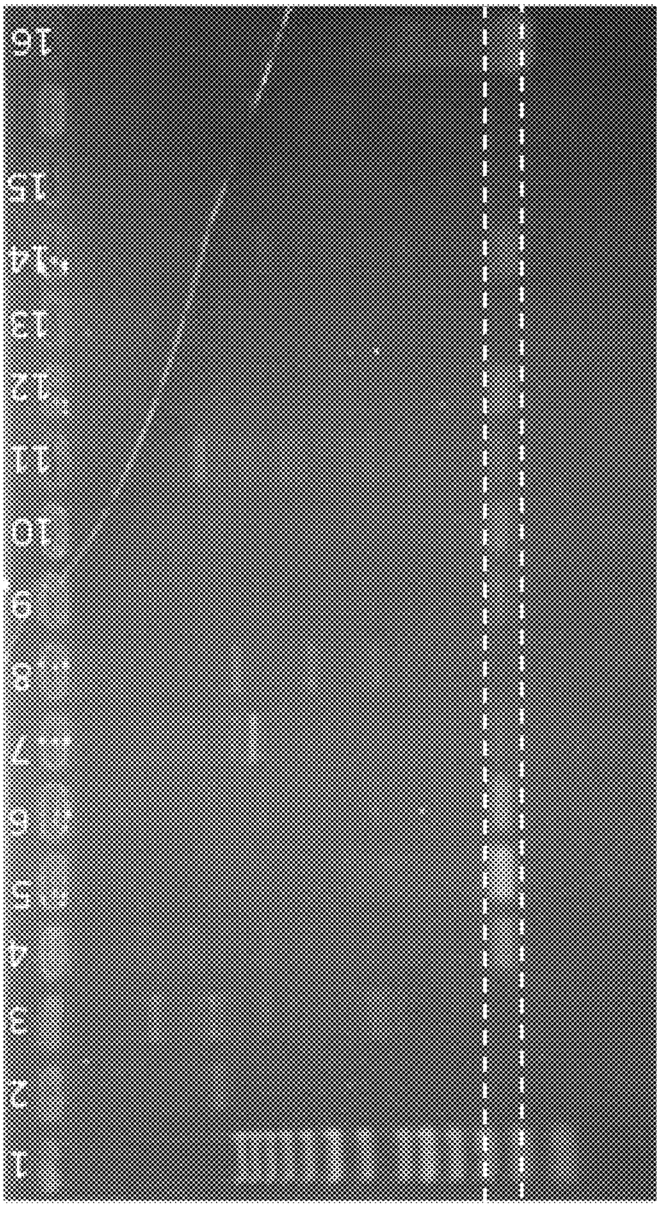
FIG. 6. Transformation verification. Transgenic events were analyzed using PCR to detect the presence of the construct by targeting the loop sequence of the hpRNA silencing construct. Lane 1 is a marker, lane 2 is Buffer mix, lane 3 is the WT, transgenic events are in lanes 4-15, lane 16 is a control. Lanes 4-7, 9-12 and 14 expressed the loop segment.

To detect the presence of the down regulation constructs, PCR was carried out using primer pairs that generate fragments indicative of the presence of the loop segment in the hpRNA construct (FIG. 6). To detect the presence of the over expression constructs, PCR was carried out using primer pairs that generate fragments indicative of the presence of the DELLA genes. The primer pairs are listed in Table 3.

TABLE 3

Primer sequences

| Gene | Primers | Product size |
|---|---|---|
| hpRNA loop (SEQ ID NO: 26) | Forward CGAACGAGCCGACTAATTGTCTT (SEQ ID NO: 33)<br>Reverse CGCGCGAAGATGCCACGC (SEQ ID NO: 34) | Approximately 102 bp |

TABLE 3-continued

| Primer sequences | | |
|---|---|---|
| Gene | Primers | Product size |
| At RGA (SEQ ID NO: 16) | Forward AGCTTAGCCGATCTCGATGC (SEQ ID NO: 35) Reverse TCCACACGATAACCTTGGCC (SEQ ID NO: 36) | Approximately 491 bp |
| At RGL2 (SEQ ID NO: 20) | Forward AGAAGGTCCTTCAATGGCGG (SEQ ID NO: 37) Reverse AACGCAGAAAGACCCGGAAT (SEQ ID NO: 38) | Approximately 342 bp |

TABLE 4

| Real-Time PCR Primer sequences | | |
|---|---|---|
| Gene | Primers | Product size |
| DELLA1 (SEQ ID NO: 2) | Forward GTGCAACGACATCCTCCAGA (SEQ ID NO: 39) Reverse GCGAAGGCTTCAAGAATCGC (SEQ ID NO: 40) | Approximately 96 bp |

Real Time PCR results are summarized in Table 5. The results indicate the DELLA1 transcript levels of events transformed with DEL1 or DEL1/3 compared to the wild-type event transcript levels.

TABLE 5

Real Time PCR results of plants transformed with DEL1 or DEL1/3 constructs

| | A1 | B1 | A2 | WT | B2 | B3 | B4 | B5 | B6 | A3 | A4 | B7 | A5 | B8 | A6 | B9 |
|---|---|---|---|---|---|---|---|---|---|---|---|---|---|---|---|---|
| DELLA1 Relative transcript level | 1 | 0.6 | 0.45 | 1 | 0.5 | 0.785 | 1 | 0.12 | 0.27 | 0.28 | 0.25 | 0.18 | 0.3 | 0.25 | 0.28 | 0.18 |

Example 3: Down Regulation of Eucalyptus DELLAs Expressed in the Leaves

RT PCR analysis of WT gXu, showed that DELLA1 and DELLA3 are expressed in tissue culture leaves, young leaves and mature leaves. DELLA1 had a higher expression level in tissue culture and young leaves compared to DELLA3. DELLA2 expression was not detected in tissue culture leaves or young leaves, and only low expression level was detected in mature leaves. (FIG. 4).

A. Preparation of dsRNA DELLA Down Regulation Construct, Transformation and Confirmation Construct DEL1 and Construct DEL1/3, described in Example 2Aa(i) and 2Aa(iv), were prepared as described above. Eucalyptus plants were transformed with the Constructs DEL1 or DEL1/3 as described in Example 2B. 20 events for each construct were confirmed for stable expression of the transgene by PCR as described in Example 2C.

B. Plant Bioassay: Transcription Levels and Growth Measurements

Transcript levels from tissue culture of each of the transgenic events and wild-type were measured using Real Time PCR. Reverse transcription was performed using 1 μg total RNA, reverse transcriptase, RNAse inhibitor and oligo-dT primers. Gene-specific primers were used for PCR amplification of each gene. A series of cDNA dilutions were prepared (1:2, 1:4, 1:8, 1:16, 1:32, 1:64) and 2 μl of the diluted cDNA was used as template for amplification using SYBR fast mix on an StepOne plus thermocycler (Applied Biosystems). Primers targeting a reference gene were used to normalize the expression data for each gene. The PCR conditions were: 95° C. for 20 sec, followed by 40 cycles of 95° C. for 3 sec and 60° C. for 30 sec. At the end of the experiment dissociation kinetics analysis was performed to check the specificity of annealing. The real time measurements were prepared using primer pairs that generate fragments indicative of the presence and expression of DELLA transgenes. The primer pairs used in Real-Time PCR for the individual genes are listed in Table 4.

Events A1-A6 are gXu plants transformed with construct DELL Events B1-B9 are gXu plants transformed with construct DEL1/3. The DELLA1 transcript levels of events transformed with DEL1 or DEL1/3 was measured and compared to the wild-type event transcript levels.

For greenhouse experiments, 8 replicas for each event were planted and measured. The selected transgenic and wild-type events were grown in a random plot design in the greenhouse under 25-28° C. natural light.

Growth Measurements

Figure 7:
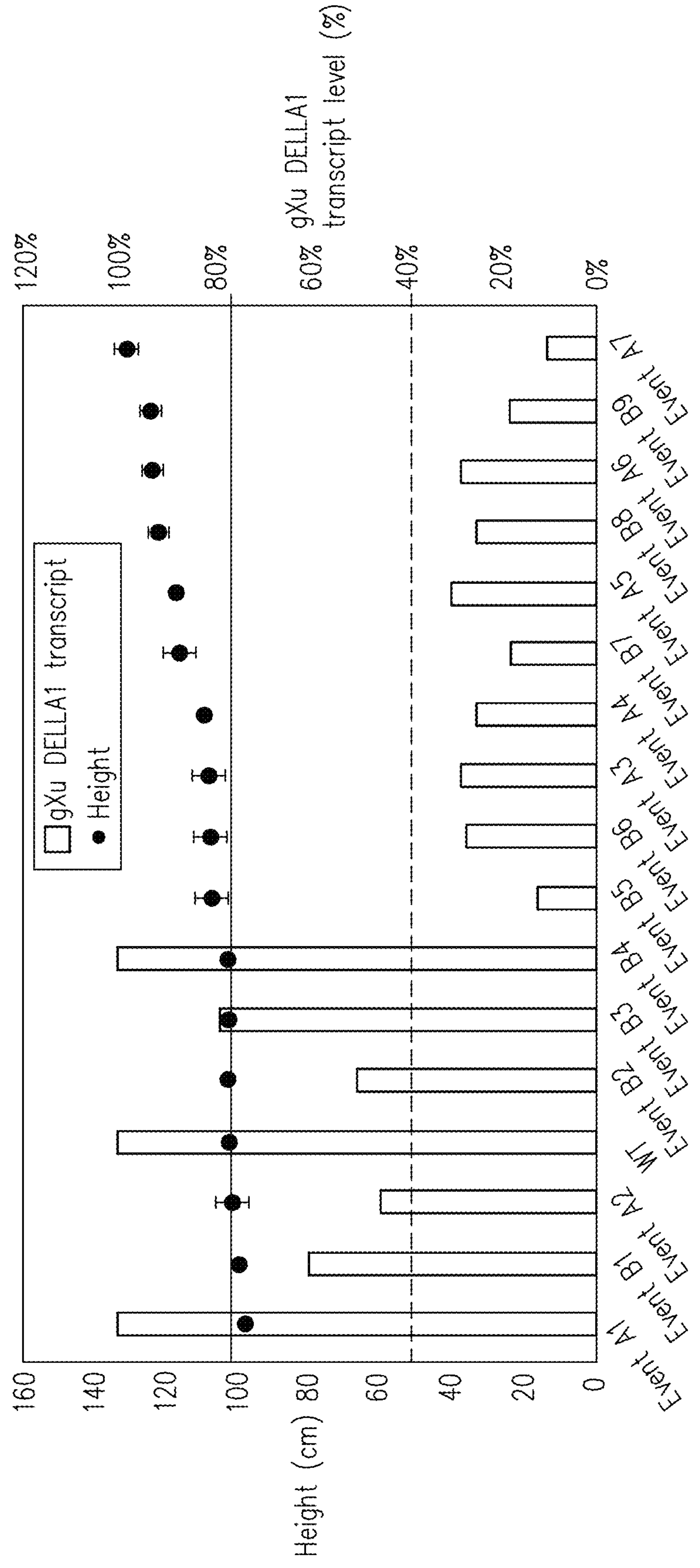
FIG. 7. Average height of gXu *Eucalyptus* plants transformed with DEL1 or DEL1/3 RNAi construct.
Figure 8:
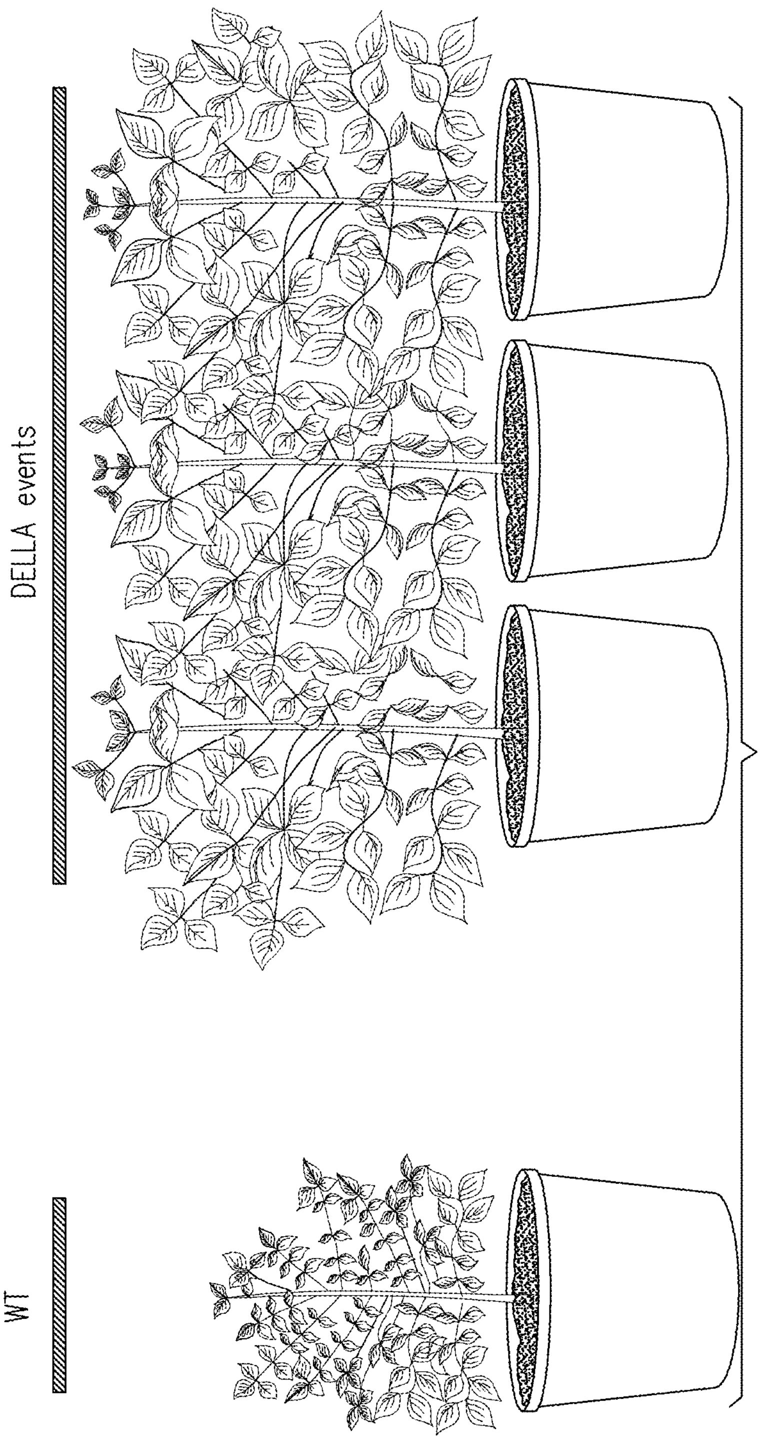
FIG. 8. Phenotypes of wild-type and transgenic DEL1 plants grown in the greenhouse.

After 3 months, canopy height and dry weight were measured. The height was determined by measuring the length of the stem of each transgenic plant from the root crown to the top. Transgenic events, in which the DELLA1 transcript level was lower than 40%, had increased plant height compared to the wild-type. Growth measurements are summarized in FIG. 7 and are also shown in FIG. 8.

Example 4: Down Regulation of DELLA Under a Green Tissue-Specific Promoter

A. Preparation of DELLA Down Regulation Construct, Transformation and Confirmation Constructs DEL1GT, DEL1/2GT and DEL1/2/3GT are prepared as described in Example 2Ab(i)-(iii). Eucalyptus plants are transformed with the Constructs DEL1GT, DEL1/2GT or DEL1/2/3GT as described in Example 2B. 20 events for each construct are confirmed for stable expression of the transgene by PCR as described in Example 2C.

B. Plant Bioassay and Growth Measurements

DELLA1 transcript level from tissue culture plant material of the transgenic events and wild-type is measured using Real Time PCR. Events with reduced transcript levels of DELLA1 compared to the wild-type, are selected for greenhouse trial.

The selected transgenic and wild-type events are grown in a random plot design in the greenhouse under 25-28° C. natural light. Transgenic plants are expected to exhibit improved growth, increase height and increase in dry weight compared to the wild-type.

Example 5: Down Regulation of Endogenous DELLA Polypeptides and Over Expression of Exogenous DELLA in the Roots (DR/OE)

A. DR/OE Construct Preparation, Transformation and Confirmation

Constructs DEL1/$RGA_{OE}$, DEL1/3/$RGA_{OE}$ and DEL1/2/3/$RGA_{OE}$ are prepared as described in Example 2Ac(i)-(iii). Eucalyptus plants are transformed with Constructs DEL1/$RGA_{OE}$, DEL1/3/$RGA_{OE}$ or DEL1/2/3/$RGA_{OE}$ as described in Example 2B. 20 events for each construct are confirmed for stable expression of the transgene by PCR as described in Example 2C.

B. Plant Bioassay and Growth Measurements

After 3 months, canopy height and dry weight are measured. The height is determined by measuring the length of the stem of each transgenic plant from the root crown to the top.

Of note, overexpression DELLA polynucleotide sequences are optimized to Eucalyptus codon usage as published by the Kazusa codon usage database. Eucalyptus codon usage is also generated by counting each codon rate from a full eucalyptus transcriptome library. Computer software that includes the reverse translation option to get the optimized DNA is also used.

Example 6: DELLA Expression Modification in Poplar Plants

A. Identification of DELLA Homologs in *Populous trichocarpa, Populous tremula* and *Populous tremoloides*

To identify possible DELLA homologs in poplar, a known DELLA sequence from *Arabidopsis* is aligned against a *Popolus* genome database found in Phytozome, a plant comparative genomics portal. The RGA sequence from *Arabidopsis thaliana* (SEQ ID NO: 15) is used to search the *Populous trichocarpa* genome in the Phytozome database using the BLAST Protein-Protein search tool. The algorithm parameters are based on a word size 3, and the BLOSUM62 matrix. Four *Popolus trichocarpa* sequences (SEQ ID NO: 46, 47, 48, 49) are identified as likely homologs DELLA genes.

Additional DELLA homologs in poplar, are identified by aligning the RGA sequence from *Arabidopsis thaliana* against a *Populus* genome database found in Popgenie, a plant comparative genomics portal (http://popgenie.org). The RGA sequence is used to search the *Populous tremula* genome and the populous tremoloides genome in the Popgenie database using the BLAST Protein-Protein search tool. The algorithm parameters are based on a word size 3, and the BLOSUM62 matrix. Four *Populus tremula* sequences (SEQ ID NO: 50, 51, 52, 53) and four *Populus* tremoloides sequences (SEQ ID NO: 54, 55, 56, 57) are identified as likely homologs DELLA genes.

B. Construct Preparation

Down regulation constructs comprise an expression cassette comprising a fragment of a sequence encoding for a DELLA target sequence, the reverse complement sequence of the fragment and a loop sequence. Transcription of the constructs produce a hairpin RNA (hpRNA), having a stem comprised of the dsRNA fragment, formed by annealing of the inverted-repeat sequences of the target gene, and a loop region.

a. Down Regulation Constructs Under a Constitutive Promoter or a Green Tissue-Specific Promoter A schematic of the structure of dsRNA down regulation constructs comprising fragments from one or more of the poplar DELLA genes is shown in FIGS. 5A and 5B. Down regulation constructs contain an expression cassette comprising fragments from at least one of the DELLA genes which are fused and synthesized in inverted repeats, separated by a loop sequence. See cassette P1-T1 in FIGS. 5A and 5B. Transcription of this cassette (initiated at promoter P1 and terminated at T1) produce a hairpin RNA, containing a dsRNA section, formed by annealing of the inverted-repeat sequences of the DELLA gene fragment, and a loop region. See schematics B1-B3.

b. Down Regulation and Over Expression (DR/OE) Constructs

Schematics of the structure of DR/OE constructs are shown in FIG. 5B. DR/OE constructs contain both a down regulation cassette for the down regulation of one or more endogenous DELLA polypeptides expression level (cassette P1-T1), and an over expression cassette for overexpression of a DELLA gene in the roots (cassette P2-T2).

C. Transformation of Constructs into Poplar

The transformation is performed using the 'freezethaw' method for direct *Agrobacterium* transformation. Colonies that grow on the selection medium (i.e., 50 mg $1^{-1}$ rifamycin and 50 mg $1^{-1}$ kanamycin) are confirmedas transformants by PCR. Bacterial stock cultures of *A. tumefaciens* strain LBA 4404, carrying the novel constructs, are grown individually overnight at 28° C., on a gyratory shaker (200 rpm) in LB media with rifamycin (50 mg $1^{-1}$) and kanamycin (50 mg $1^{-1}$). Prior to co-cultivation, 1 ml of each bacterial culture is sub-cultured in MSO medium+100 11 μM acetosyringone and grown at 28° C., on a gyratory shaker (200 rpm). *Populus* leaf discs are harvested from four week-old tissue culture-grown plants using a cork borer. Twenty plates containing 25 leaf discs (7 $mm^2$) are co-cultivated with 30 ml of bacterial culture in 50 ml Falcon tubes for 30 minutes at 28° C. in a gyratory shaker (100 rpm). Following co-cultivation, the explants are blotted dry on sterile filter paper and placed abaxially on WPM 0.1 NAA, 0.1 BA and 0.1 TDZ culture medium. The plates are cultured in the dark for two days at room temperature. On the third day, leaf discs are transferred to WPM media containing 250 mg $1^1$ cefotoxine and 500 mg $1^{-1}$ carbenicillin. All plates are kept in the dark for an additional two days. Following this period, explants are transferred to selection media WPM with 250 mg $1^{-1}$ cefotoxine and 500 mg $1^{-1}$ carbenicillin and 25 mg $1^1$ hygromycin. Only one shoot per leaf disc is excised and placed on WPM selection media. After 6 weeks, explants are transferred to fresh medium with the same composition.

D. DELLA Down Regulation Constructs Transformation Confirmation 20 events for each down regulation construct are confirmed for stable expression of the transgene by PCR.

E. Plant Bioassay and Growth Measurements

DELLA transcript level from tissue culture plant material of the transgenic events and wild-type is measured using Real Time PCR. Events with reduced transcript levels of DELLA compared to the wild-type, are selected for greenhouse trial. The plants are subcultured and multiplied on antibiotic free WPM media. Transgenic plants are multiplied in WPM media until approximately ten plants of each line had the same size. The plants are then moved to 2 gallon pots containing perennial soil (50% peat, 25% fine bark and 25% pumice; PH 6.0), and they are maintained on flood tables with supplemental lighting (16 h days) and water daily with fertilized water. Transgenic plants are expected to exhibit improved growth, increase height and increase in dry weight compared to the wild-type.

Example 7: DELLA Expression Modification in Switchgrass

A. Identification of DELLA Homologs in *Brachypodium distachyon* and *Panicum virgatum*

To identify possible DELLA homologs in switchgrasses, a known DELLA sequence from *Arabidopsis* is aligned against a *Brachypodium distachyon* and *Panicum virgatum* genome databases found in Phytozome, a plant comparative genomics portal. The RGA sequence from *Arabidopsis thaliana* (SEQ ID NO: 15) is used to search the Phytozome database using the BLAST Protein-Protein search tool. The algorithm parameters are based on a word size 3, and the BLOSUM62 matrix. One *Brachypodium distachyon* sequence (SEQ ID NO: 58) and two *Panicum virgatum* sequences (SEQ ID NO: 59 and 60) are identified as likely homologs DELLA genes.

B. Construct Preparation

Down regulation constructs comprised an expression cassette comprising a fragment of a sequence encoding for a DELLA target sequence, the reverse complement sequence of the fragment and a loop sequence. Transcription of the constructs produce a hairpin RNA (hpRNA), having a stem comprised of the dsRNA fragment, formed by annealing of the inverted-repeat sequences of the target gene, and a loop region.

C. Down Regulation Constructs Under a Constitutive Promoter or a Green Tissue-Specific Promoter A schematic of the structure of dsRNA down regulation constructs comprising fragments from one or more of the *Brachypodium distachyon* and *Panicum virgatum* DELLA genes is shown in FIGS. 5A and 5B. Down regulation constructs contain an expression cassette comprising fragments from the *Brachypodium distachyon* DELLA gene or at least one of the *Panicum virgatum* DELLA genes which are fused and synthesized in inverted repeats, separated by a loop sequence. See cassette P1-T1 in FIGS. 5A and 5B. Transcription of this cassette (initiated at promoter P1 and terminated at T1) produces a hairpin RNA, containing a dsRNA section, formed by annealing of the inverted-repeat sequences of the DELLA gene fragment, and a loop region. See schematics B1-B3.

D. Down Regulation and Over Expression (DR/OE) Constructs

Schematics of the structure of DR/OE constructs are shown in FIG. 5B. DR/OE constructs contain both a down regulation cassette for the down regulation of one or more endogenous DELLA polypeptides expression level (cassette P1-T1), and an over expression cassette for overexpression of a DELLA gene in the roots (cassette P2-T2).

E. Transformation of the Constructs a. *Brachypodium distachyon* Transformation

*Brachypodium distachyon* transformation is carried out by transforming the constructs into *A. tumefaciens* strain LBA 4404 via electroporation for *Brachypodium distachyon* calli transformations (Handakumbura et al., 2013). Transgenic events are PCR confirmed for the hygromycin resistance gene and propagated for three subsequent generations. The resulting T4 progeny are PCR confirmed for presence of the hygromycin phosphotransferase II gene using a Phire Plant Direct PCR Kit (Thermo Scientific) according to manufactures specifications.

b. *Panicum virgatum* Transformation

*Panicum virgatum* transformation is carried out by transforming embryogenic callus with the expression vector constructs through *Agrobacterium*-mediated transformation (Burris et al., 2009). Antibiotic selection is carried out for about 2 months on 30-50 mg/L hygromycin. Selection is followed by regeneration of orange fluorescent protein reporter (pporRFP; OFP) indicating positive callus sections on regeneration medium containing 400 mg/L timentin (Li and Qu, 2011). Regenerated plants are rooted on MS medium (Murashige and Skoog, 1962) plus 250 mg/L cefotaxime (Grewal et al., 2006).

F. DELLA Down Regulation Constructs Transformation Confirmation 20 events for each down regulation construct are confirmed for stable expression of the transgene by PCR.

G. Plant Bioassay and Growth Measurements

DELLA transcript level from tissue culture plant material of the transgenic events and wild-type is measured using Real Time PCR. Events with reduced transcript levels of DELLA compared to the wild-type, are selected for greenhouse trial. The selected transgenic and wild-type events are grown in a random plot design in the greenhouse. Transgenic plants are expected to exhibit improved growth, increase height and increase in dry weight compared to the wild-type.

Example 8: Genome Editing for DELLA in Eucalyptus

To generate eucalyptus DELLA mutants, CRISPR/Cas9 cassettes targeting different DELLA genes were used for transformation of select eucalyptus clones. DELLA genes in *Eucalyptus* are unique genes with no intron. To create knock-out mutants a genomic locus in the first 800 bp of the coding region was targeted. The sgRNAs were designed using the online tool CRISTA which uses an algorithm to determine the propensity of a genomic site to be cleaved by a given sgRNA and provides a score between 0 and 1. In all constructs, one or two sgRNAs for each gene were selected based on high scores (0.9 and above) and expression was driven by either the full arabidopsis U6 promoter (SEQ ID NO:75) or the modified short version (SEQ ID NO:76). The expression of human codon-optimized *S. pyogenes* Cas9 (hSpCas9, SEQ ID NO:77) is driven by the CaMV 35S promoter (SEQ ID NO:74). Nuclear localization signal (SV40, SEQ ID NO:78) was added to the C terminus of the protein. hSpCas9 target sequence was 20 bp long upstream to NGG Protospacer Adjacent Motif (PAM). DELLA genome editing constructs are schematically shown in FIG. 10. For the editing of the DELLA1 gene in *Grandis*× *Urophylla Eucalyptus* clone, guide sequences 1 and 2 (Table 6) were selected. Both guides were driven by the short U6 promoter. Location of the guides on the DELLA1 gene is shown in FIG. 11.

TABLE 6

Guide RNAs selected by the CRISTA online tools
Guide RNAs

| # | *Eucalyptus* species | Gene | Guide sequence | SEQ ID NO: |
|---|---|---|---|---|
| 1 | *Grandis/* | DELLA1 | GGTCGTCGTTGAAGATGACC | 63 |
| 2 | *Urophylla* | | GGTCCACCAGGACGACCGGC | 64 |
| 3 | | | GATCATCGAGACGCTTGCAG | 65 |
| 4 | | | TCCTCCACCCACTCAATGCC | 66 |
| 5 | | DELLA2 | CCACCACCTCTATCCCCAGA | 67 |
| 6 | | | TCCAAGATGTGGGACGAAGA | 68 |

TABLE 6-continued

Guide RNAs selected by the CRISTA online tools
Guide RNAs

| # | *Eucalyptus* species | Gene | Guide sequence | SEQ ID NO: |
|---|---|---|---|---|
| 7 | | DELLA3 | GCAGCAGCAGCAATTGACGG | 69 |
| 8 | | | GCAGCAGCAGCAGCAATTGA | 70 |
| 9 | *Camaldulensis* | DELLA1 | AGTCGTCGTTGAAGATGACC | 71 |
| 10 | | | TGTCCACCAGGACGACCGGC | 72 |

Selection of Transgenic Events Harboring A Mutation:

*Eucalyptus grandis*×*urophylla* clone was transformed with a construct harboring the first two sgRNA of DELLA1 (Table 6). A total of 10 Cas9-positive transgenic lines were created. The mutations were detected using next generation sequencing (NGS). Seven out of ten events had a mutation in the target gene. The indel patterns differed between events, and all mutations disrupt the reading frame of the sequence (FIG. 12). Event 7 displayed a 189 bp deletion (FIG. 13).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

BIBLIOGRAPHY

Achard P, Gong F, Cheminant S, Alioua M, Hedden P, Genschik P (2008) The cold-inducible CBF1 factor-dependent signaling pathway modulates the accumulation of the growth-repressing DELLA proteins via its effect on gibberellin metabolism. Plant Cell 20: 2117-2129

Achard P, Genschik P (2009) Releasing the brakes of plant growth: how GAs shutdown DELLA proteins. J Exp Bot 60: 1085-1092

Azpiroz-Leehan R, Feldmann K A. T-DNA insertion mutagenesis in *Arabidopsis*: going back and forth. Trends in Genetics. 1997; 13:152-156

Burris J N, Mann D G J, Joyce B L, Stewart C N (2009) An improved tissue culture system for embryogenic callus production and plant regeneration in switchgrass (*Panicum virgatum* L.) BioEnergy Res. 2:267-274

Busov V, Meilan R, Pearce D W, Rood S B, Ma C, Tschaplinski T J, Strauss S H. 2006. Transgenic modification of gai or rgl1 causes dwarfing and alters gibberellins, root growth, and metabolite profiles in *Populus*. Planta 224: 288-299

Busov V, Yordanov Y S, Gou J, Meilan R, Ma C, Regan S, Strauss S (2010) Activation tagging is an effective gene tagging system in *Populus*. Tree Genet Genomes 7: 91-101

Cheng H, Qin L, Lee S, Fu X, Richards D E, Cao D, Luo D, Harberd N P, Peng J (2004) Gibberellin regulates *Arabidopsis* floral development via suppression of DELLA protein function. Development 131: 1055-1064

Daviere J M, Achard P (2013) Gibberellin signaling in plants. Development 140: 1147-1151

Eriksson M E, Israelsson M, Olsson O, Moritz T (2000) Increased gibberellin biosynthesis in transgenic trees promotes growth, biomass production and xylem fiber length. Nature Biotechnology 18: 784-788

Flavell, R B (1994). Inactivation of gene expression in plants as a consequence of specific sequence duplication. Proc. Natl. Acad. Sci. USA 91:3490-3496

Fu X, Harberd N P (2003) Auxin promotes *Arabidopsis* root growth by modulating gibberellin response. Nature 421: 740-743

Grewal D, Gill R, Gosal S S (2006) Influence of antibiotic cefotaxime on somatic embryogenesis and plant regeneration in indica rice. Biotechnol J 1:1158-1162

Harberd N P, Belfield E, Yasumura Y (2009) The angiosperm gibberellin-GID1-DELLA growth regulatory mechanism: how an "inhibitor of an inhibitor" enables flexible response to fluctuating environments. Plant Cell 21: 1328-1339

Handakumbura P, Matos D, Osmont K, Harrington M, Heo K, Kafle K, Kim S, Baskin T, Hazen S (2013) Perturbation of *Brachypodium distachyon* CELLULOSE SYNTHASE A4 or 7 results in abnormal cell walls. BMC Plant Biol 13: 131

Haseloff J, Gerlach W L (1988) Simple RNA enzymes with new and highly specific endoribonuclease activities. Nature 334: 585-591.

King K, Moritz T, Harberd N (2001) Gibberellins are not required for normal stem growth in *Arabidopsis thaliana* in the absence of GAI and RGA. Genetics 159: 767-776

Kooter J M, Mol J N M (1993) Trans-activation of gene expression in plants. Curr. Opin. Biotechnol 4: 166-171

Lee S, Cheng H, King K E, Wang W, He Y, Hussain A, Lo J, Harberd N P, Peng J (2002) Gibberellin regulates *Arabidopsis* seed germination via RGL2, a GAI/RGA-like gene whose expression is up-regulated following imbibition. Genes Dev 16: 646-658

Li R Y, Qu R D, (2011) High throughput *Agrobacterium*-mediated switchgrass transformation. Biomass. Bioenerg 35:1046-1054

Lo S F, Yang S Y, Chen K T, Hsing Y I, Zeevaart J A, Chen L J, Yu S M (2008) A novel class of gibberellin 2-oxidases control semidwarfism, tillering, and root development in rice. The Plant Cell 20: 2603-2618

Murashige T, Skoog F (1962) A revised medium for rapid growth and bioassays with tobacco tissue culture. Physiol Plant 15: 473-497

Napoli C, Lemieux C, Jorgensen R (1990) Introduction of a chimeric chalcone synthase gene into Petunia results in reversible co-suppression of homologous genes in trans. Plant Cell 2: 279-289

Peng J, Carol P, Richards D E, King K E, Cowling R J, Murphy G P, Harberd N P (1997) The *Arabidopsis* GAI gene defines a signaling pathway that negatively regulates gibberellin responses. Genes Dev 11: 3194-3205

Peng J, Richards D E, Moritz T, Cano-Delgado A, Harberd N P (1999) Extragenic suppressors of the *Arabidopsis* gai mutation alter the dose-response relationship of diverse gibberellin responses. Plant Physiol 119: 1199-1208

Silverstone A L, Ciampaglio C N, Sun T-p (1998) The *Arabidopsis* RGA gene encodes a transcriptional regulator repressing the gibberellin signal transduction pathway. Plant Cell 10: 155-169

Smith C J S, Watson C F, Ray J, Bird C R, Morris P C, Schuch W, Grierson D (1988) Antisense RNA inhibition of polygalacturonase gene expression in transgenic tomatoes. Nature 334:724-726.

Smith C J S, Watson C F, Morris P C, Bird C R, Seymouir G B, Gray J E, Arnold C, Tucker G A, Schuch W, Harding S, Grierson D (1990) Inheritance and effect on ripening of antisense polygalacturonase genes in transgenic tomatoes. Plant Mol Biol 14: 369-379

Sun T-p, Gubler F (2004) Molecular mechanism of gibberellin signaling in plants. Annu Rev Plant Biol 55 197-223

Swain S M, Singh D P (2005) Tall tales from sly dwarves: novel functions of gibberellins in plant development. Trends Plant Sci 10 123-129

Tyler L, Thomas S G, Hu J, Dill A, Alonso J M, Ecker J R, Sun T P (2004) DELLA proteins and gibberellin-regulated seed germination and floral development in *Arabidopsis*. Plant Physiol 135: 1008-1019

Wen C-K, Chang C (2002) *Arabidopsis* RGL1 encodes a negative regulator of gibberellin responses. Plant Cell 14: 87-100

Wild M, Davière J-M, Cheminant S, Regnault T, Baumberger N, Heintz D, Baltz R, Genschik P, Achard P (2012) The *Arabidopsis* DELLA RGA-LIKE3 is a direct target of MYC2 and modulates jasmonate signaling responses. Plant Cell 24: 3307-3319

Yamaguchi S (2008) Gibberellin metabolism and its regulation. Annu Rev Plant Biol 59: 225-251

The invention claimed is:

1. A CRISPR/Cas9 construct comprising a polynucleotide sequence encoding Cas9, and at least one guide RNA sequence targeting a target site of a gene encoding a eucalyptus DELLA polypeptide, wherein the DELLA polypeptide is at least 95% identical to SEQ ID NO: 1;

wherein the at least one guide RNA sequence is selected from the group consisting of SEQ ID NOs: 63, 64, 65 and 66; and wherein the construct reduces the expression level of the DELLA polypeptide.

2. The construct of claim 1, wherein the at least one guide RNA sequence comprises two guide RNA sequences.

3. The construct of claim 2, wherein the guide RNA sequences are selected from SEQ ID NO: 63 and SEQ ID NO: 64.

4. The construct of claim 2, wherein the guide RNA sequences are selected from SEQ ID NO: 65 and SEQ ID NO: 66.

5. A host cell comprising the construct of claim 1.

6. The host cell of claim 5, wherein the host cell is a bacterial cell.

7. The host cell of claim 5 wherein the host is an *Agrobacterium*.

8. A plant tissue transformed with the host cell of claim 5.

9. The plant tissue of claim 8, wherein the tissue is a green tissue.

10. A method of producing a eucalyptus plant with reduced expression level of at least one DELLA polypeptide, the at least one DELLA polypeptide being at least 95% identical to SEQ ID NO: 1, the method comprising expressing the construct of claim 1 in the plant.

11. A method of producing a eucalyptus plant with reduced expression level of at least one DELLA polypeptide, the at least one DELLA polypeptide being at least 95% identical to SEQ ID NO: 1, the method comprising:

a. transforming a plant cell with the construct of claim 1, b. regenerating a plant from the transformed plant cell to form a transformed plant, and c. growing the transformed plant, wherein the transformed plant has increased growth compared to a wild-type plant of the same species.

12. A eucalyptus plant cell comprising the construct of claim 1.

13. The construct of claim 1, wherein each of the at least one guide RNA sequence is operably linked to a second promoter selected from the group consisting of SEQ ID NOs: 75 and 76.

14. The construct of claim 1, further comprising a first promoter operably linked to the polynucleotide sequence encoding Cas9.

15. The construct of claim 14, wherein the first promoter is a constitutive promoter.

16. The construct of claim 15, wherein the constitutive promoter is selected from the group consisting of 35S CaMV promoter, CaMV19S promoter, sgFiMV promoter, SVBV promoter, FMV34S promoter, sugarcane bacilliform badnavirus promoter, CsVMV promoter, *Arabidopsis* ACT2/ACT8 actin promoter, *Arabidopsis* ubiquitin UBQ1 promoter, barley leaf thionin BTH6 promoter, rice actin promoter, GOS2 promoter, Rice cyclophilin promoter, and Maize H3 histone promoter.

17. The construct of claim 16, wherein the constitutive promoter is a 35S CaMV promoter.

18. The construct of claim 14, wherein the first promoter is a tissue-specific promoter.

19. The construct of claim 18, wherein the tissue-specific promoter is derived from a tissue selected from the group consisting of leaf tissue, stem tissue, and photosynthetic tissue.

20. The construct of claim 18, wherein the tissue-specific promoter is a ribulose-bisphosphate carboxylase (Rubisco) promoter.

21. A method of engineering a *eucalyptus* plant with DELLA polypeptide expression primarily localized in the roots of the plant, the method comprising:

a. introducing a first expression cassette into the plant, wherein the first expression cassette reduces the expression of at least one endogenous DELLA polypeptide in the plant, the at least one endogenous DELLA polypeptide being at least 95% identical to SEQ ID NO: 1, b. introducing a second expression cassette into the plant, wherein the second expression cassette comprises a polynucleotide encoding a DELLA polypeptide operably linked to a heterologous root-specific promoter, and c. growing the plant, where the expression of the DELLA polypeptides in the plant is primarily localized in the roots of the plant compared to a wild-type plant of the same species.

22. The method of claim 21, wherein the root-specific promoter is selected from the group consisting of PsMTA promoter, Class III Chitinase promoter, phosphate transporter promoter, tonoplast intrinsic aquaporin 2 promoter, Pyk10 promoter, AtFLS5 promoter, btg26 promoter, and *Solanum lycopersicum* root-expressed 2-ODD promoter.

23. The method of claim 21, wherein the DELLA polypeptide b. encoded by the polynucleotide is an *Arabidopsis thaliana* DELLA polypeptide.

24. The method of claim 23, wherein the *Arabidopsis thaliana* DELLA polypeptide b. is SEQ ID NO:15.

25. A eucalyptus plant with DELLA polypeptide expression primarily localized in the roots of the plant, the plant comprising:

a. a first expression cassette that reduces the expression of at least one endogenous DELLA polypeptide in the plant, the at least one endogenous DELLA polypeptide being at least 95% identical to SEQ ID NO: 1, and b. a second expression cassette which comprises a polynucleotide encoding a DELLA polypeptide operably linked to a heterologous root-specific promoter;

wherein the plant is engineered by the method of claim 21.

26. A plant cell of the plant of claim 25, wherein the plant cell comprises the first expression cassette and the second expression cassette.

27. The method of claim 23, wherein the *Arabidopsis thaliana* DELLA polypeptide is SEQ ID NO:13.

28. The method of claim 23, wherein the *Arabidopsis thaliana* DELLA polypeptide is SEQ ID NO:17.

29. The method of claim 23, wherein the *Arabidopsis thaliana* DELLA polypeptide is SEQ ID NO:19.

30. The method of claim 23, wherein the *Arabidopsis thaliana* DELLA polypeptide is SEQ ID NO:21.

31. A method of engineering a eucalyptus plant having DELLA polypeptide expression level that is primarily localized in the roots of the plant compared to an untransformed plant, wherein the plant has a mutation in a gene encoding an endogenous DELLA polypeptide, the endogenous DELLA polypeptide being at least 95% identical to SEQ ID NO: 1, wherein the level of expression of the endogenous DELLA polypeptide is reduced compared to the level of expression of the endogenous DELLA polypeptide in a wild-type plant of the same species, the method comprising:

a. constructing an expression cassette comprising a polynucleotide encoding a DELLA polypeptide, operably linked to a heterologous root-specific promoter;

b. introducing the expression cassette into the plant; and c. growing the plant, where the expression of the DELLA polypeptides in the plant is primarily localized in the roots of the plant compared to a wild-type plant of the same species.

* * * * *

```
                        SEQUENCE LISTING


<160> NUMBER OF SEQ ID NOS: 95

<210> SEQ ID NO 1
<211> LENGTH: 628
<212> TYPE: PRT
<213> ORGANISM: Eucalyptus grandis x urophylla

<400> SEQUENCE: 1

Met Lys Arg Asp His Arg Asp Ala Cys Ser Gly Gly Tyr Gly Gly Gly
1               5                   10                  15

Gly Gly Gly Glu Ala Ser Gly Ala Ser Lys Gly Glu Pro Pro Ser Ser
            20                  25                  30

Ser Ser Thr His Ser Met Pro Gly Ser Gly Lys Ala Lys Met Val Met
        35                  40                  45

Trp Gly Glu Asp Asp Gln Asp Pro Ser Gly Gly Gly Gly Gly Gly Met
    50                  55                  60

Asp Glu Leu Leu Ala Val Leu Gly Tyr Lys Val Arg Ser Ser Asp Met
65                  70                  75                  80

Ala Glu Val Ala Gln Lys Leu Glu Gln Leu Glu Met Val Met Gly Ser
                85                  90                  95

Ala Gln Glu Asp Gly Ile Ser His Leu Ser Tyr Asp Ala Val His Tyr
            100                 105                 110

Asn Pro Ser Asp Leu Ser Ser Trp Val Gln Ser Met Leu Phe Glu Leu
        115                 120                 125

Asn Pro Pro Pro Pro Pro Gln Gln Val Ala Asp Ala Val Leu Ala Ala
    130                 135                 140

Ala Glu Ser Ser Ser Thr Ile Ala Gln His His Arg Ser His Leu Gly
145                 150                 155                 160

Ser Arg Ser Gln Thr Gln Thr Arg Thr Leu Ser Gln Thr Ser Ala Pro
                165                 170                 175

Thr Gln Thr Gln Ser Gln Val Ile Phe Asn Asp Asp Ser Glu Tyr Asp
            180                 185                 190

Leu Arg Ala Ile Pro Gly Val Ala Ala Phe Pro Gln Gly Asp Ser Asp
        195                 200                 205

Phe Glu Ser Ala Ala Arg Lys Lys Met Lys Thr Leu Asn Gly Gly Ser
    210                 215                 220

Asn Ser Leu Ser Ser Ser Ser Ser Ser Ser Ala Ala Gly Ala Ala Pro
225                 230                 235                 240

Ser Glu Ser Thr Arg Pro Val Val Leu Val Asp Thr Gln Glu Thr Gly
                245                 250                 255

Val Arg Leu Val His Thr Leu Met Ala Cys Ala Glu Ala Val Gln Gln
            260                 265                 270
```

```
Glu Asn Leu Lys Leu Ala Asp Ala Leu Val Lys His Ile Gly Leu Leu
        275                 280                 285

Ala Ala Ser Gln Asn Gly Ala Met Arg Lys Val Ala Thr Tyr Phe Ala
    290                 295                 300

Glu Ala Leu Ala Arg Arg Ile Tyr Arg Ile Tyr Pro Asn Asp Gly Ser
305                 310                 315                 320

Leu Asp Ser Ser Cys Asn Asp Ile Leu Gln Met His Phe Tyr Glu Thr
                325                 330                 335

Cys Pro Tyr Leu Lys Phe Ala His Phe Thr Ala Asn Gln Ala Ile Leu
            340                 345                 350

Glu Ala Phe Ala Thr Ala Ser Arg Val His Val Ile Asp Phe Gly Leu
        355                 360                 365

Lys Gln Gly Met Gln Trp Pro Ala Leu Met Gln Ala Leu Ala Leu Arg
    370                 375                 380

Pro Gly Gly Pro Pro Ala Phe Arg Leu Thr Gly Ile Gly Pro Pro Gln
385                 390                 395                 400

Pro Asn Asn Thr Asp Ala Leu Gln Gln Val Gly Trp Lys Leu Ala Gln
                405                 410                 415

Leu Ala Asp Thr Ile Gly Val Glu Phe Glu Phe Arg Gly Phe Val Ala
            420                 425                 430

Asn Ser Leu Ala Asp Leu Glu Pro Ala Met Leu Asp Ile Arg Pro Pro
        435                 440                 445

Glu Val Glu Thr Val Ala Val Asn Ser Val Phe Glu Leu His Pro Leu
    450                 455                 460

Leu Ala Arg Pro Gly Ala Ile Asp Lys Val Leu Ser Ser Ile Lys Ala
465                 470                 475                 480

Met Arg Pro Lys Ile Val Thr Met Val Glu Gln Glu Ala Asn His Asn
                485                 490                 495

Gly Pro Gly Phe Val Asp Arg Phe Thr Glu Ala Leu His Tyr Tyr Ser
            500                 505                 510

Ser Leu Phe Asp Ser Leu Glu Gly Ser Gly Val Ala Pro Pro Asn Gln
        515                 520                 525

Asp Leu Val Met Ser Glu Val Tyr Leu Gly Arg Gln Ile Cys Asn Val
    530                 535                 540

Val Ala Cys Glu Gly Pro Asp Arg Val Glu Arg His Glu Thr Leu Val
545                 550                 555                 560

Gln Trp Gln Ala Arg Met Gly Ser Ala Gly Phe Asp Pro Val His Leu
                565                 570                 575

Gly Ser Asn Ala Phe Lys Gln Ala Ser Met Leu Leu Ala Leu Phe Ala
            580                 585                 590

Gly Gly Glu Gly Tyr Arg Val Glu Glu Asn Asp Gly Cys Leu Met Leu
        595                 600                 605

Gly Trp His Thr Arg Pro Leu Ile Ala Thr Ser Ala Trp Gln Leu Ala
    610                 615                 620

Ala Ala Thr Gln
625


<210> SEQ ID NO 2
<211> LENGTH: 1887
<212> TYPE: DNA
<213> ORGANISM: Eucalyptus grandis x urophylla

<400> SEQUENCE: 2

atgaagaggg atcatcgaga cgcttgcagt ggcggctatg gcggcggcgg tggcggggag      60
```

-continued gcgagcggcg cctcgaaggg cgagcccccg tcgtcctcct ccacccactc aatgcccggc 120
tctggcaagg ccaagatggt gatgtggggc gaggacgacc aagatccgag cggcggtggc 180
gggggcggca tggacgagct cctcgcggtg ctcgggtaca aggtgaggtc gtcggacatg 240
gccgaggtgg cgcagaagct ggagcagctc gagatggtga tgggctctgc tcaggaggac 300
ggcatctcgc acctgtccta cgacgccgtc cactacaacc cttccgatct ctcctcgtgg 360
gtccagagca tgctcttcga gctcaacccc cctccgccgc cgcagcaggt ggccgacgcg 420
gtcctcgctg cggccgagtc gtcttccacc atcgcgcagc accaccgttc gcatctcggg 480
tctcggtctc agacgcagac tcggactctg agtcagactt cggctcccac tcagacgcag 540
tcccaggtca tcttcaacga cgactccgag tacgacttga gggcgattcc cggcgtcgcc 600
gctttcccac agggcgactc ggacttcgag agcgccgccc ggaagaagat gaagaccctg 660
aacggcgggt cgaattcgtt gtcgtcctcg tcctcttcgt cggccgccgg agcggcgccc 720
tccgagtcga cccggccggt cgtcctggtg gacacgcagg agactggggt gcggctcgtc 780
cacacgctca tggcctgcgc cgaggcggtc cagcaggaga acctgaagct ggccgatgcg 840
ctcgtcaagc acattggcct gctcgccgct tcgcagaacg gcgcgatgcg caaggtagcg 900
acctacttcg ccgaggcgct cgcccgccgg atttaccgaa tctaccccaa cgacggcagc 960
ctcgactcct cgtgcaacga catcctccag atgcacttct acgagacctg cccgtacctc 1020
aaattcgccc acttcactgc caatcaggcg attcttgaag ccttcgccac cgccagccgc 1080
gtccacgtca tcgatttcgg cctcaagcag ggtatgcagt ggccggccct catgcaggct 1140
ctggccctga ggcccggcgg tccgcccgcc ttccggctca ccgggattgg cccgccgcag 1200
ccgaacaaca ccgacgcctt gcagcaggtc ggctggaagc tggctcaatt ggccgacact 1260
atcggggtcg agttcgaatt ccggggtttc gtggcgaatt cgctggctga tctcgagccc 1320
gccatgctgg acatccgccc tcccgaggtc gagacggtgg ccgtcaactc ggtgtttgag 1380
ctccaccccc tgctcgcccg accgggggcg attgacaagg ttctctcatc gatcaaggcc 1440
atgagaccta agatagtgac gatggtggaa caggaggcga atcacaatgg cccggggttc 1500
gtggaccggt tcacggaagc tttgcattac tactccagcc tgttcgattc gctggaaggg 1560
tctggggtgg ctcccccgaa ccaggatctg gtcatgtccg aggtctactt gggtcggcag 1620
atttgcaatg ttgtggcctg cgagggggccg gatcgagtgg agcggcacga gacgttggtg 1680
cagtggcagg cgcggatggg atcggctggg ttcgacccgg tccatctcgg gtccaacgcg 1740
ttcaagcagg cgagcatgct gctggccctg ttcgcaggtg gagaaggtta ccgggtcgag 1800
gaaaacgatg gttgtctcat gctcggttgg cacacgaggc ctctgatcgc cacttcggcg 1860
tggcaactcg ctgctgcaac tcagtga 1887

<210> SEQ ID NO 3
<211> LENGTH: 634
<212> TYPE: PRT
<213> ORGANISM: Eucalyptus grandis x urophylla

<400> SEQUENCE: 3

Met Lys Arg Glu His His His Leu Tyr Pro Gln Thr Asp Pro Ser Thr
1 5 10 15

Ser Ala Ser Ala Ala Ala Gly Lys Ser Lys Met Trp Asp Glu Asp Gly
20 25 30

Cys Gly Gly Gly Gly Asp Asp Glu Leu Leu Ala Val Leu Gly Tyr Lys
35 40 45

-continued

```
Val Arg Ser Ser Asp Met Ala Glu Val Ala Gln Lys Leu Glu Gln Leu
    50                  55                  60

Glu Glu Val Met Phe Ser Ala Gln Glu Asp Gly Leu Ser His Leu Ala
65                  70                  75                  80

Ser Glu Thr Val His Tyr Asn Pro Ser Asp Leu Ser Ser Trp Leu Glu
                85                  90                  95

Ser Met Leu Ser Glu Phe Asn Pro Leu Pro Pro Pro Pro Gly Gly Phe
            100                 105                 110

Gly Gly Gly Pro Leu Ser Val Pro Val Ala Ala Ala Pro Pro Arg Pro
        115                 120                 125

Gln Pro Val Gly Asp Pro Phe Leu Pro Arg Ala Glu Ser Ser Ser Ile
    130                 135                 140

Thr Thr Val Asp Phe Gly Ala Asp Gln Arg Met Gln Ser Ser Cys Gly
145                 150                 155                 160

Arg Ser Ser Gln Met Asn Glu Pro Arg Pro Glu Ile Gly Ser Ser Gly
                165                 170                 175

Ile Val Phe Asp Glu Glu Ser Ser Ser Asp Tyr Asp Leu Lys Ala Ile
            180                 185                 190

Pro Gly Lys Ala Val Phe Gly Arg Ala Gln Ala Gln Ala Gln Ala Gln
        195                 200                 205

Ala Gln Thr Arg Thr Arg Leu Ala Ser Thr Ser Ser Ser Ser Thr Ser
    210                 215                 220

Ser Ser Ala Val Thr Ala Lys Arg Phe Lys Ser Ser Pro Ser Asp Ala
225                 230                 235                 240

Ala Val Gly Ala Ala Pro Glu Ser Ser Arg Pro Val Val Leu Val Asp
                245                 250                 255

Ser Gln Glu Asn Gly Val Arg Leu Val His Ala Leu Met Ala Cys Ala
            260                 265                 270

Asp Ala Val Gln Gln Asp Asn Leu Ser Ile Ala Glu Ala Leu Val Lys
        275                 280                 285

Gln Ile Gly Phe Leu Ala Ile Ser Gln Ala Gly Ala Met Arg Lys Val
    290                 295                 300

Ala Thr Phe Phe Ala Glu Ala Leu Ala Arg Arg Ile Tyr Arg Val Tyr
305                 310                 315                 320

Pro Gln Asn Pro Pro Leu Asp His Ser Leu Thr Asp Ala Leu Gln Met
                325                 330                 335

His Phe Tyr Glu Thr Cys Pro Tyr Leu Lys Phe Ala His Phe Thr Ala
            340                 345                 350

Asn Gln Ala Ile Leu Glu Ala Phe Glu Gly Lys Ser Arg Val His Val
        355                 360                 365

Ile Asp Phe Ser Met Asn Gln Gly Leu Gln Trp Pro Ala Leu Met Gln
    370                 375                 380

Ala Leu Ala Leu Arg Pro Gly Gly Pro Pro Thr Phe Arg Leu Thr Gly
385                 390                 395                 400

Ile Gly Pro Pro Ala Pro Asp Asn Ser Asp Arg Leu Gln Glu Val Gly
                405                 410                 415

Trp Lys Leu Ala Gln Leu Ala Glu Thr Ile His Val Glu Phe Glu Tyr
            420                 425                 430

Arg Gly Phe Val Ala Asn Ser Leu Ala Asp Leu Asp Ala Ser Ile Leu
        435                 440                 445

Glu Leu Arg Pro Ser Asp Ala Glu Ala Val Ala Val Asn Ser Val Phe
    450                 455                 460
```

```
Glu Leu His Lys Leu Leu Ala Arg Pro Gly Ala Ile Glu Lys Val Leu
465                 470                 475                 480

Gly Val Val Arg Gln Val Arg Pro Ala Ile Val Thr Val Val Glu Gln
                485                 490                 495

Glu Ala Asn His Asn Gly Pro Val Phe Val Asp Arg Phe Asn Glu Ser
            500                 505                 510

Leu His Tyr Tyr Ser Thr Leu Phe Asp Ser Leu Glu Gly Cys Ala Ser
        515                 520                 525

Thr Gln Asp Lys Ala Met Ser Glu Val Tyr Leu Gly Lys Gln Ile Cys
    530                 535                 540

Asn Val Val Ala Cys Glu Gly Ala Asp Arg Val Glu Arg His Glu Thr
545                 550                 555                 560

Leu Ala Gln Trp Arg Ala Arg Leu Gly Gly Ala Gly Phe Val Pro Ala
                565                 570                 575

His Leu Gly Ser Asn Ala Phe Lys Gln Ala Ser Met Leu Leu Ala Leu
            580                 585                 590

Phe Ala Gly Gly Asp Gly Tyr Arg Val Glu Glu Asn Gly Gly Cys Leu
        595                 600                 605

Thr Leu Gly Trp His Thr Arg Pro Leu Ile Ala Thr Ser Ala Trp Arg
    610                 615                 620

Leu Gly Gly Pro Ser Ala Gly Ala Ala His
625                 630


<210> SEQ ID NO 4
<211> LENGTH: 1905
<212> TYPE: DNA
<213> ORGANISM: Eucalyptus grandis x urophylla

<400> SEQUENCE: 4

atgaagcgag agcaccacca cctctatccc cagacggacc cctccacctc ggcctccgcc      60

gccgccggga agtccaagat gtgggacgaa gacggctgcg gcggcggcgg cgacgatgag     120

ctcctggccg tgctgggcta caaggtgcgg tcctccgaca tggccgaggt tgcccagaag     180

ctggagcagc tcgaggaggt catgttcagc gcccaggagg acggcctctc ccacctcgcc     240

tccgagaccg tccactacaa cccctctgac ctctcctcct ggctcgagag catgctgtcc     300

gagtttaatc ccctgccgcc gccccccggc gggttcggcg gcggacccct ctccgtcccc     360

gtcgccgccg cgccgccgcg gccgcagccc gtgggcgacc cgttcctccc ccgcgcggag     420

tcctcctcca tcaccaccgt tgacttcggg gcggaccagc ggatgcagag cagctgcggg     480

aggagctcgc agatgaacga gccgcgcccg gagatcggct cgtccgggat cgtgttcgat     540

gaggagtcgt cttccgatta cgatctcaag gctattcccg gtaaggccgt gttcggccgc     600

gcccaagcgc aagcgcaagc gcaagcgcag acccgcaccc gcctcgcttc tacgtcttct     660

tcttccacct cctcgagcgc cgtcaccgcc aagcgcttca aatcctctcc cagcgacgcg     720

gccgtcggag ccgccccgga atcgagccgg ccggtcgtcc tggtggactc gcaggagaat     780

ggggtccggc tcgtgcacgc gctcatggcc tgcgcggatg ccgtccagca ggacaacctc     840

agcatcgcgg aggcgctggt gaagcaaatc gggttcctgg cgatctcgca ggccggggcg     900

atgaggaagg tcgccacttt cttcgcggag gcgctggcgc ggcggatcta ccgggtctac     960

ccgcagaacc cgccgttgga ccactccctc accgacgccc tccagatgca cttctacgag    1020

acctgtcctt acctcaaatt cgcccacttc accgcgaacc aggccatctt ggaggccttc    1080

gagggcaaga gccgcgtcca cgtcatcgac ttcagcatga accagggcct ccagtggccg    1140
```

-continued gcgctgatgc aggccctcgc cctccgcccc ggtgggccgc ccaccttccg cctcacgggg 1200
atcggccccc ccgccccgga caactccgac cgcctccagg aggtggggtg gaagctggcc 1260
cagctggcgg agaccatcca cgtcgagttc gagtaccgcg ggttcgtcgc caacagcctc 1320
gccgacctcg acgcgtcgat cctggagctg cggccgagcg acgccgaggc ggtggcggtc 1380
aactcggtgt tcgagctgca caagctgctg gcccgcccgg gggcgatcga gaaggttctg 1440
ggcgtggtgc ggcaggtgcg gccggcgatc gtgacggtgg tcgagcagga ggccaaccac 1500
aacgggccgg tcttcgtgga ccgcttcaac gagtcgctgc actactactc caccttgttc 1560
gactccctgg agggctgcgc cagcacgcag gacaaggcca tgtcggaggt ctacctcggg 1620
aagcagatct gcaacgtggt ggcgtgcgag ggcgccgacc gggtcgagcg ccacgagacc 1680
ctcgcccagt ggcgggcccg cctcggcggc gccgggttcg tcccggccca cctcgggtcg 1740
aacgcgttca agcaggcgag catgctgctg gccctgttcg ccggcgggga cgggtaccgg 1800
gtggaggaga acggcggttg cctgacgctc gggtggcaca cgcggccgct catcgccacc 1860
tcggcgtggc ggctcggcgg cccgagcgcc ggagccgccc actga 1905

<210> SEQ ID NO 5
<211> LENGTH: 567
<212> TYPE: PRT
<213> ORGANISM: Eucalyptus grandis x urophylla

<400> SEQUENCE: 5

Met Gly Pro Phe Asp Pro Ser Ala Ala Ala Ala Ala Ala Ala Ala Ala
1 5 10 15

Ala Val Ala Ala Ser Ser Ser Ser Ser Ser Ser Cys Ser Gly Gly Ser
20 25 30

Ala Pro Lys Arg His His His His His His His His Pro Pro Pro Asp
35 40 45

Leu Asp Gly His Leu Ala Cys Ala Gly Tyr Lys Val Arg Ser Ser Glu
50 55 60

Leu His His Val Ala Gln Arg Leu Glu Arg Leu Glu Thr Ala Leu Val
65 70 75 80

Asn Ser Ala Ala His Ile Pro His Leu Ala Ser Asp Ala Val His Tyr
85 90 95

Asn Pro Ser Asp Leu Ala Ser Trp Val Asp Ser Met Leu Ser Glu Leu
100 105 110

Pro Ser Ser Ser Phe Ser Ser Pro Cys Leu Pro Ser Gly Phe Pro Asp
115 120 125

Pro Tyr Ser Pro Ala Ala Ala Ala Leu Gly Gly Gly Trp Val Asp Gln
130 135 140

Pro Ser Cys Ser Pro His Pro Gln Pro His Gln Asn Val Val Val Pro
145 150 155 160

Gln Gln Gln Gln Gln Gln Gln Gln Leu Thr Val Val Thr Ala Leu Glu
165 170 175

Glu Asp Ser Gly Ile Gln Leu Val His Ala Leu Met Thr Cys Ala Glu
180 185 190

Ser Val Gln Arg Gly Asp Ala Ser Leu Ala Gly Ser Leu Val Glu Glu
195 200 205

Met Arg Ala Leu Leu Thr Arg Val Asp Thr Ser Arg Gly Ile Gly Lys
210 215 220

Val Ala Gly Tyr Phe Ile Asp Ala Leu Gly Arg Arg Leu Leu Gly Leu
225 230 235 240

-continued

```
Gly Ser Ala Pro Ala Ser Ala Phe Glu Asn Glu Val Leu Tyr His His
                245                 250                 255

Phe Tyr Glu Ala Cys Pro Tyr Leu Lys Phe Ala His Phe Thr Ala Asn
            260                 265                 270

Gln Ala Ile Leu Glu Ala Phe Asp Gly His Asp Cys Val His Val Ile
        275                 280                 285

Asp Phe Asn Leu Met His Gly Leu Gln Trp Pro Ala Leu Ile Gln Ala
    290                 295                 300

Leu Ala Leu Arg Pro Arg Gly Pro Pro Leu Leu Arg Leu Thr Gly Ile
305                 310                 315                 320

Gly Pro Pro Ser Pro Asp Gly Arg Asp Ala Leu Arg Glu Ile Gly Leu
                325                 330                 335

Arg Leu Ala Glu Leu Ala Arg Ser Val Asn Val Arg Phe Ala Phe Arg
            340                 345                 350

Gly Val Ala Ala Ser Arg Leu Glu Asp Val Lys Pro Trp Met Leu Gln
        355                 360                 365

Val Ser Pro Lys Glu Ala Val Ala Val Asn Ser Ile Met Gln Leu His
    370                 375                 380

Arg Leu Leu Gly Ser Asp Pro Pro Arg Asp Pro Pro Ile Gly Ser Val
385                 390                 395                 400

Leu Pro Trp Ile Arg Ser Leu Asn Pro Lys Ile Met Thr Val Ala Glu
                405                 410                 415

Gln Glu Ala Asn His Asn Arg Pro Gly Phe Leu Asp Arg Phe Thr Glu
            420                 425                 430

Ala Leu Tyr Tyr Tyr Ser Thr Leu Phe Asp Ser Leu Glu Ala Ala Cys
        435                 440                 445

Pro Val Gln Pro Asp Lys Ala Leu Ala Glu Met Tyr Leu Gln Arg Glu
    450                 455                 460

Ile Cys Asn Ile Val Gly Cys Glu Gly Ala Ala Arg Val Glu Arg His
465                 470                 475                 480

Glu Pro Leu Asp Arg Trp Arg Ala Arg Leu Gly Arg Ala Gly Phe Arg
                485                 490                 495

Pro Leu His Leu Gly Ser Asn Ala Phe Lys Gln Ala Ser Met Leu Leu
            500                 505                 510

Thr Leu Phe Ser Thr Glu Gly Tyr Ser Val Glu Glu Asn Glu Gly Cys
        515                 520                 525

Leu Thr Leu Cys Trp His Ser Arg Pro Leu Ile Ala Ala Ser Ala Trp
    530                 535                 540

Gln Ala Ala Pro Thr Val Val Asn Ser Pro Ala Gly Val Ile Asn His
545                 550                 555                 560

Asp Asp Asn Asn Asn Gln Leu
                565


<210> SEQ ID NO 6
<211> LENGTH: 1704
<212> TYPE: DNA
<213> ORGANISM: Eucalyptus grandis x urophylla

<400> SEQUENCE: 6

atgggcccct tcgacccctc cgccgccgcc gccgccgccg ccgcagcagc cgtagccgcc      60

agcagctcct cgtcgtcgtc ctgctccggg ggctcggcgc ccaagcgcca ccaccaccac     120

caccaccacc acccgccgcc ggatctcgac gggcacctcg cctgcgccgg ctacaaggtc     180

cgctcctccg agctccacca cgtggcgcag cggctcgagc ggctcgagac cgccctcgtc     240
```

aactccgccg cccacatccc ccacctcgcc tccgacgctg tccactacaa cccctccgat 300
ctcgcctcct gggtcgactc catgctctcc gagctcccga gctcatcctt ctcctccccc 360
tgcctgccct ccggcttccc cgacccgtac tctccggcgg cggcggcact cggcggcggg 420
tgggtggacc agccctcctg ctcgccgcac ccacagccgc accagaacgt cgttgtcccc 480
cagcagcagc agcagcagca gcaattgacg gtggtgacgg cgctggagga ggattccggc 540
attcagctcg tccacgcgct gatgacgtgt gcggagtcgg tccagcgtgg cgacgcctcg 600
ctggccggct ccctggtcga ggagatgcgg gccctgctga cgcgcgtcga cacctcgcgg 660
ggcatcggga aggtcgccgg ctacttcatc gacgccctcg gccggcggct gctcggcctc 720
ggctcggctc ccgcctccgc cttcgagaac gaggtgctgt accaccactt ctacgaggcc 780
tgcccctatc tcaagttcgc ccacttcacc gccaaccagg ccatcctcga ggccttcgac 840
ggccacgact gcgtccacgt catcgacttc aacctcatgc acggcctgca gtggccggcc 900
ctgatccagg ccctcgccct ccgcccccgc gggcccccgc tcctccgcct caccggcatt 960
ggcccgccct cccccgacgg ccgcgacgct ctccgcgaga tcggcctccg gctcgcggag 1020
ctggcccgct cggtcaacgt ccggttcgcg ttccgcggcg tcgcggcctc gcggctcgag 1080
gacgtgaagc cgtggatgct ccaggtgagc cccaaggagg ccgtggccgt caactccatc 1140
atgcagctcc acaggctcct gggatccgac ccgccccggg accccccccat cgggtcggtc 1200 ctgccctgga tccggagcct gaacccgaag ataatgaccg tggcggagca ggaggcgaac 1260
cacaaccggc ccgggttcct ggaccggttc accgaggcgc tgtactacta ctcgaccctg 1320
ttcgactcgc tcgaggcggc ctgcccggtc cagcccgaca aggccctggc cgagatgtac 1380
cttcaaaggg agatatgcaa catcgtgggc tgcgaggggg cggcccgggt cgagaggcac 1440
gagccgctgg accggtggcg ggcccgcctc gggcgagccg ggttccggcc gctgcacctc 1500
ggctccaacg cgttcaagca agccagcatg ctgctcaccc tgttctcgac cgagggctac 1560
agcgtggagg agaacgaggg ttgcttgacg ctctgctggc acagccggcc cctcatcgcg 1620
gcttcggcgt ggcaagccgc gcctactgta gtgaactcgc cggccggcgt tattaatcac 1680
gatgacaata ataatcagct gtaa 1704

<210> SEQ ID NO 7
<211> LENGTH: 628
<212> TYPE: PRT
<213> ORGANISM: Eucalyptus grandis

<400> SEQUENCE: 7

Met Lys Arg Asp His Arg Asp Ala Cys Ser Gly Gly Tyr Gly Gly Gly
1               5                   10                  15

Gly Gly Gly Glu Ala Ser Gly Ala Ser Lys Gly Glu Pro Pro Ser Ser
            20                  25                  30

Ser Ser Thr His Ser Leu Pro Gly Ser Gly Lys Ala Lys Met Val Met
        35                  40                  45

Trp Gly Glu Asp Asp Gln Asp Pro Ser Gly Gly Gly Gly Gly Gly Met
    50                  55                  60

Asp Glu Leu Leu Ala Val Leu Gly Tyr Lys Val Arg Ser Ser Asp Met
65                  70                  75                  80

Ala Glu Val Ala Gln Lys Leu Glu Gln Leu Glu Met Val Met Gly Ser
                85                  90                  95

Ala Gln Glu Asp Gly Ile Ser His Leu Ser Tyr Asp Ala Val His Tyr
            100                 105                 110

```
Asn Pro Ser Asp Leu Ser Ser Trp Val Gln Ser Met Leu Phe Glu Leu
        115                 120                 125

Asn Pro Pro Pro Pro Pro Gln Gln Val Ala Asp Ala Val Leu Ala Ala
    130                 135                 140

Ala Glu Ser Ser Ser Thr Ile Ala Gln His His Arg Ser His Leu Gly
145                 150                 155                 160

Ser Arg Ser Gln Thr Gln Thr Arg Thr Leu Ser Gln Thr Ser Ala Pro
                165                 170                 175

Thr Gln Thr Gln Ser Gln Val Ile Phe Asn Asp Asp Ser Glu Tyr Asp
            180                 185                 190

Leu Arg Ala Ile Pro Gly Val Ala Ala Phe Pro Gln Gly Asp Ser Asp
        195                 200                 205

Phe Glu Ser Ala Ala Arg Lys Lys Met Lys Thr Leu Asn Gly Gly Ser
    210                 215                 220

Asn Ser Leu Ser Ser Ser Ser Ser Ser Ser Ala Ala Gly Ala Ala Pro
225                 230                 235                 240

Ser Glu Ser Thr Arg Pro Val Val Leu Val Asp Thr Gln Glu Thr Gly
                245                 250                 255

Val Arg Leu Val His Thr Leu Met Ala Cys Ala Glu Ala Val Gln Gln
            260                 265                 270

Glu Asn Leu Lys Leu Ala Asp Ala Leu Val Lys His Ile Gly Leu Leu
        275                 280                 285

Ala Ala Ser Gln Asn Gly Ala Met Arg Lys Val Ala Thr Tyr Phe Ala
    290                 295                 300

Glu Ala Leu Ala Arg Arg Ile Tyr Arg Ile Tyr Pro Asn Asp Gly Ser
305                 310                 315                 320

Leu Asp Ser Ser Cys Asn Asp Ile Leu Gln Met His Phe Tyr Glu Thr
                325                 330                 335

Cys Pro Tyr Leu Lys Phe Ala His Phe Thr Ala Asn Gln Ala Ile Leu
            340                 345                 350

Glu Ala Phe Ala Thr Ala Ser Arg Val His Val Ile Asp Phe Gly Leu
        355                 360                 365

Lys Gln Gly Met Gln Trp Pro Ala Leu Met Gln Ala Leu Ala Leu Arg
    370                 375                 380

Pro Gly Gly Pro Pro Ala Phe Arg Leu Thr Gly Ile Gly Pro Pro Gln
385                 390                 395                 400

Pro Asn Asn Thr Asp Ala Leu Gln Gln Val Gly Trp Lys Leu Ala Gln
                405                 410                 415

Leu Ala Asp Thr Ile Gly Val Glu Phe Glu Phe Arg Gly Phe Val Ala
            420                 425                 430

Asn Ser Leu Ala Asp Leu Glu Pro Ala Met Leu Asp Ile Arg Pro Pro
        435                 440                 445

Glu Val Glu Thr Val Ala Val Asn Ser Val Phe Glu Leu His Pro Leu
    450                 455                 460

Leu Ala Arg Pro Gly Ala Ile Asp Lys Val Leu Ser Ser Ile Lys Ala
465                 470                 475                 480

Met Arg Pro Lys Ile Val Thr Met Val Glu Gln Glu Ala Asn His Asn
                485                 490                 495

Gly Pro Gly Phe Val Asp Arg Phe Thr Glu Ala Leu His Tyr Tyr Ser
            500                 505                 510

Ser Leu Phe Asp Ser Leu Glu Gly Ser Gly Val Ala Pro Pro Asn Gln
        515                 520                 525

Asp Leu Val Met Ser Glu Val Tyr Leu Gly Arg Gln Ile Cys Asn Val
```

-continued 530 535 540

Val Ala Cys Glu Gly Pro Asp Arg Val Glu Arg His Glu Thr Leu Val
545 550 555 560

Gln Trp Gln Ala Arg Met Gly Ser Ala Gly Phe Asp Pro Val His Leu
565 570 575

Gly Ser Asn Ala Phe Lys Gln Ala Ser Met Leu Leu Ala Leu Phe Ala
580 585 590

Gly Gly Glu Gly Tyr Arg Val Glu Glu Asn Asp Gly Cys Leu Met Leu
595 600 605

Gly Trp His Thr Arg Pro Leu Ile Ala Thr Ser Ala Trp Gln Leu Ala
610 615 620

Ala Ala Thr Gln
625

<210> SEQ ID NO 8
<211> LENGTH: 1887
<212> TYPE: DNA
<213> ORGANISM: Eucalyptus grandis

<400> SEQUENCE: 8
atgaagaggg atcatcgaga cgcttgcagt ggcggctatg gcggcggcgg tggcggggag 60
gcgagcggcg cctcgaaggg cgagcccccg tcgtcctcct ccacccactc attgcccggc 120
tctggcaagg ccaagatggt gatgtggggc gaggacgacc aagatccgag cggcggtggc 180
gggggcggca tggacgagct cctcgcggtg ctcgggtaca aggtgaggtc gtcggacatg 240
gccgaggtgg cgcagaagct ggagcagctc gagatggtga tgggctctgc tcaggaggac 300
ggcatctcgc acctgtccta cgacgccgtc cactacaacc cttccgatct ctcctcgtgg 360
gtccagagca tgctcttcga gctcaacccc cctccgccgc cgcagcaggt ggccgacgcg 420
gtcctcgctg cggccgagtc gtcttccacc atcgcgcagc accaccgttc gcatctcggg 480
tctcggtctc agacgcagac tcggactctg agtcagactt cggctcccac tcagacgcag 540
tcccaggtaa tcttcaacga cgactccgag tacgacttga gggcgattcc cggcgtcgcc 600
gctttcccac agggcgactc ggacttcgag agcgccgccc ggaagaagat gaagaccctg 660
aacggcgggt cgaattcgtt gtcgtcctcg tcctcttcgt cggccgccgg agcggcgccc 720
tccgagtcga cccggccggt cgtcctggtg gacacgcagg agactggggt gcggctcgtc 780
cacacgctca tggcctgcgc cgaggcggtc cagcaggaga acctgaagct ggccgatgcg 840
ctcgtcaagc acattggcct gctcgccgct tcgcagaacg gcgcgatgcg caaggtagcg 900
acctacttcg ccgaggcgct cgcccgccgg atttaccgaa tctaccccaa cgacggcagc 960
ctcgactcct cgtgcaacga catcctccag atgcacttct acgagacctg cccgtacctc 1020
aaattcgccc acttcactgc caatcaggcg attcttgaag ccttcgccac cgccagccgc 1080
gtccacgtca tcgatttcgg cctcaagcag ggtatgcagt ggccggccct catgcaggct 1140
ctggccctga ggcccggcgg tccgcccgcc ttccggctca ccgggattgg cccgccgcag 1200
ccgaacaaca ccgacgcctt gcagcaggtc ggctggaagc tggctcaatt ggccgacact 1260
atcggggtcg agttcgaatt ccggggtttc gtggcgaatt cgctggctga tctcgagccc 1320
gccatgctgg acatccgccc tcccgaggtc gagacggtgg ccgtcaactc ggtgtttgag 1380
ctccaccccc tgctcgcccg accgggggcg attgacaagg ttctctcatc gatcaaggcc 1440
atgagaccta agatagtgac gatggtggaa caggaggcga atcacaatgg cccggggttc 1500
gtggaccggt tcacggaagc tttgcattac tactccagcc tgttcgattc gctggaaggg 1560

```
tctggggtgg ctcccccgaa ccaggatctg gtcatgtccg aggtctactt gggtcggcag   1620

atttgcaatg ttgtggcctg cgaggggccg gatcgagtgg agcggcacga gacgttggtg   1680

cagtggcagg cgcggatggg atcggctggg ttcgacccgg tccatctcgg gtccaacgcg   1740

ttcaagcagg cgagcatgct gctggccctg ttcgcaggtg gagaaggtta ccgggtcgag   1800

gaaaacgatg gttgtctcat gctcggttgg cacacgaggc ctctgatcgc cacttcggcg   1860

tggcaactcg ctgctgcaac tcagtga                                       1887


<210> SEQ ID NO 9
<211> LENGTH: 634
<212> TYPE: PRT
<213> ORGANISM: Eucalyptus grandis

<400> SEQUENCE: 9

Met Lys Arg Glu His His His Leu Tyr Pro Gln Thr Asp Pro Ser Thr
1               5                   10                  15

Ser Ala Ser Ala Ala Ala Gly Lys Ser Lys Met Trp Asp Glu Asp Gly
            20                  25                  30

Cys Gly Gly Gly Gly Asp Asp Glu Leu Leu Ala Val Leu Gly Tyr Lys
        35                  40                  45

Val Arg Ser Ser Asp Met Ala Glu Val Ala Gln Lys Leu Glu Gln Leu
    50                  55                  60

Glu Glu Val Met Phe Ser Ala Gln Glu Asp Gly Leu Ser His Leu Ala
65                  70                  75                  80

Ser Glu Thr Val His Tyr Asn Pro Ser Asp Leu Ser Ser Trp Leu Glu
                85                  90                  95

Ser Met Leu Ser Glu Phe Asn Pro Leu Pro Pro Pro Pro Gly Gly Phe
            100                 105                 110

Gly Gly Gly Pro Leu Ser Val Pro Val Ala Ala Ala Pro Pro Arg Pro
        115                 120                 125

Gln Pro Val Gly Asp Pro Phe Leu Pro Arg Ala Glu Ser Ser Ser Ile
    130                 135                 140

Thr Thr Val Asp Phe Gly Ala Asp Gln Arg Met Gln Ser Ser Cys Gly
145                 150                 155                 160

Arg Ser Ser Gln Met Asn Glu Pro Pro Pro Glu Ile Gly Ser Ser Gly
                165                 170                 175

Ile Val Phe Asp Glu Glu Ser Ser Ser Asp Tyr Asp Leu Lys Ala Ile
            180                 185                 190

Pro Gly Lys Ala Val Phe Gly Arg Ala Gln Ala Gln Ala Gln Ala Gln
        195                 200                 205

Ala Gln Thr Arg Thr Arg Leu Ala Ser Thr Ser Ser Ser Ser Thr Ser
    210                 215                 220

Ser Ser Ala Val Thr Ala Lys Arg Phe Lys Ser Ser Pro Ser Asp Ala
225                 230                 235                 240

Ala Val Gly Ala Ala Pro Glu Ser Ser Arg Pro Val Val Leu Val Asp
                245                 250                 255

Ser Gln Glu Asn Gly Val Arg Leu Val His Ala Leu Met Ala Cys Ala
            260                 265                 270

Asp Ala Val Gln Gln Asp Asn Leu Ser Ile Ala Glu Ala Leu Val Lys
        275                 280                 285

Gln Ile Gly Phe Leu Ala Ile Ser Gln Ala Gly Ala Met Arg Lys Val
    290                 295                 300

Ala Thr Phe Phe Ala Glu Ala Leu Ala Arg Arg Ile Tyr Arg Val Tyr
```

-continued

```
305                 310                 315                 320

Pro Gln Asn Pro Pro Leu Asp His Ser Leu Thr Asp Ala Leu Gln Met
                325                 330                 335

His Phe Tyr Glu Thr Cys Pro Tyr Leu Lys Phe Ala His Phe Thr Ala
            340                 345                 350

Asn Gln Ala Ile Leu Glu Ala Phe Glu Gly Lys Ser Arg Val His Val
        355                 360                 365

Ile Asp Phe Ser Met Asn Gln Gly Leu Gln Trp Pro Ala Leu Met Gln
    370                 375                 380

Ala Leu Ala Leu Arg Pro Gly Gly Pro Pro Thr Phe Arg Leu Thr Gly
385                 390                 395                 400

Ile Gly Pro Pro Ala Pro Asp Asn Ser Asp Arg Leu Gln Glu Val Gly
                405                 410                 415

Trp Lys Leu Ala Gln Leu Ala Glu Thr Ile His Val Glu Phe Glu Tyr
            420                 425                 430

Arg Gly Phe Val Ala Asn Ser Leu Ala Asp Leu Asp Ala Ser Ile Leu
        435                 440                 445

Glu Leu Arg Pro Ser Asp Ala Glu Ala Val Ala Val Asn Ser Val Phe
    450                 455                 460

Glu Leu His Lys Leu Leu Ala Arg Pro Gly Ala Ile Glu Lys Val Leu
465                 470                 475                 480

Gly Val Val Arg Gln Val Arg Pro Ala Ile Val Thr Val Val Glu Gln
                485                 490                 495

Glu Ala Asn His Asn Gly Pro Val Phe Val Asp Arg Phe Asn Glu Ser
            500                 505                 510

Leu His Tyr Tyr Ser Thr Leu Phe Asp Ser Leu Glu Gly Cys Ala Ser
        515                 520                 525

Thr Gln Asp Lys Ala Met Ser Glu Val Tyr Leu Gly Lys Gln Ile Cys
    530                 535                 540

Asn Val Val Ala Cys Glu Gly Ala Asp Arg Val Glu Arg His Glu Thr
545                 550                 555                 560

Leu Ala Gln Trp Arg Ala Arg Leu Gly Gly Ala Gly Phe Val Pro Ala
                565                 570                 575

His Leu Gly Ser Asn Ala Phe Lys Gln Ala Ser Met Leu Leu Ala Leu
            580                 585                 590

Phe Ala Gly Gly Asp Gly Tyr Arg Val Glu Glu Asn Gly Gly Cys Leu
        595                 600                 605

Thr Leu Gly Trp His Thr Arg Pro Leu Ile Ala Thr Ser Ala Trp Arg
    610                 615                 620

Leu Gly Gly Pro Ser Ala Gly Ala Ala His
625                 630


<210> SEQ ID NO 10
<211> LENGTH: 1905
<212> TYPE: DNA
<213> ORGANISM: Eucalyptus grandis

<400> SEQUENCE: 10

atgaagcgag agcaccacca cctctatccc cagacggacc cctccacctc ggcctccgcc      60

gccgccggga agtccaagat gtgggacgaa gacggctgcg gcggcggcgg cgacgatgag     120

ctcctggccg tgctgggcta caaggtgcgg tcctccgaca tggccgaggt tgcccagaag     180

ctggagcagc tcgaggaggt catgttcagc gcccaggagg acggcctctc ccacctcgcc     240

tccgagaccg tccactacaa cccctctgac ctctcctcct ggctcgagag catgctgtcc     300
```

```
gagtttaatc ccctgccgcc gcccccggc gggttcggcg gcggacccct ctccgtcccc    360
gtcgccgccg cgccgccgcg gccgcagccc gtgggcgacc cgttcctccc ccgcgcggag    420
tcctcctcca tcaccaccgt tgacttcggg gcggaccagc ggatgcagag cagctgcggg    480
aggagctcgc agatgaacga gccgcccccg gagatcggct cgtccgggat cgtgttcgat    540
gaggagtcgt cttccgatta cgatctcaag gctattcccg gtaaggccgt gttcggccgc    600
gcccaagcgc aagcgcaagc gcaagcgcag acccgcaccc gcctcgcttc tacgtcttct    660
tcttccacct cctcgagcgc cgtcaccgcc aagcgcttca aatcctctcc cagcgacgcg    720
gccgtcggag ccgccccgga atcgagccgg ccggtcgtcc tggtggactc gcaggagaat    780
ggggtccggc tcgtgcacgc gctcatggcc tgcgcggatg ccgtccagca ggacaacctc    840
agcatcgcgg aggcgctggt gaagcaaatc gggttcctgg cgatctcgca ggccggggcg    900
atgaggaagg tcgccacttt cttcgcggag gcgctggcgc ggcggatcta ccgggtctac    960
ccgcagaacc cgccgttgga ccactccctc accgacgccc tccagatgca cttctacgag   1020
acctgtcctt acctcaaatt cgcccacttc accgcgaacc aggccatctt ggaggccttc   1080
gagggcaaga gccgcgtcca cgtcatcgac ttcagcatga accagggcct ccagtggccg   1140
gcgctgatgc aggccctcgc cctccgcccc ggtgggccgc ccaccttccg cctcacgggg   1200
atcggccccc ccgccccgga caactccgac cgcctccagg aggtggggtg gaagctggcc   1260
cagctggcgg agaccatcca cgtcgagttc gagtaccgcg ggttcgtcgc caacagcctc   1320
gccgacctcg acgcgtcgat cctggagctg cggccgagcg acgccgaggc ggtggcggtc   1380
aactcggtgt tcgagctgca caagctgctg gcccgcccgg gggcgatcga gaaggttctg   1440
ggcgtggtgc ggcaggtgcg gccggcgatc gtgacggtgg tcgagcagga ggccaaccac   1500
aacgggccgg tcttcgtgga ccgcttcaac gagtcgctgc actactactc caccttgttc   1560
gactccctgg agggctgcgc cagcacgcag gacaaggcca tgtcggaggt ctacctcggg   1620
aagcagatct gcaacgtggt ggcgtgcgag ggcgccgacc gggtcgagcg ccacgagacc   1680
ctcgcccagt ggcgggcccg cctcggcggc gccgggttcg tcccggccca cctcgggtcg   1740
aacgcgttca agcaggcgag catgctgctg gccctgttcg ccggcgggga cgggtaccgg   1800
gtggaggaga acggcggttg cctgacgctc gggtggcaca cgcggccgct catcgccacc   1860
tcggcgtggc ggctcggcgg cccgagcgcc ggagccgccc actga                   1905
```

<210> SEQ ID NO 11
<211> LENGTH: 567
<212> TYPE: PRT
<213> ORGANISM: Eucalyptus grandis

<400> SEQUENCE: 11

```
Met Gly Pro Phe Asp Pro Ser Ala Ala Ala Ala Ala Ala Ala Ala Ala
1               5                   10                  15

Ala Ala Ser Ser Ser Ser Ser Ser Ser Cys Ser Gly Gly Ser Ala Pro
            20                  25                  30

Lys Arg His His His His His His His His Pro Pro Pro Asp Leu Asp
        35                  40                  45

Gly Leu Leu Ala Gly Ala Gly Tyr Lys Val Arg Ser Ser Glu Leu His
    50                  55                  60

His Val Ala Gln Arg Leu Glu Arg Leu Glu Thr Ala Leu Val Asn Ser
65                  70                  75                  80

Ala Ala His Ile Pro His Leu Ala Ser Asp Ala Val His Tyr Asn Pro
```

-continued

```
                85                  90                  95

Ser Asp Leu Ala Ser Trp Val Asp Ser Met Leu Ser Glu Leu Pro Ser
            100                 105                 110

Ser Ser Phe Ser Ser Pro Cys Leu Pro Ser Gly Phe Pro Asp Pro Tyr
        115                 120                 125

Ser Pro Ala Ala Ala Ala Leu Gly Gly Gly Trp Val Asp His Pro Ser
    130                 135                 140

Cys Ser Pro His Pro Gln Pro His Gln Asn Val Val Val Pro Gln Gln
145                 150                 155                 160

Pro Gln Pro Gln Gln Gln Gln Gln Leu Thr Val Val Thr Ala Leu Glu
                165                 170                 175

Glu Asp Ser Gly Ile Gln Leu Val His Ala Leu Met Thr Cys Ala Glu
            180                 185                 190

Ser Val Gln Arg Gly Asp Ala Ser Leu Ala Gly Ser Leu Val Glu Glu
        195                 200                 205

Met Arg Ala Leu Leu Thr Arg Val Asp Thr Ser Arg Gly Ile Gly Lys
    210                 215                 220

Val Ala Gly Tyr Phe Ile Asp Ala Leu Gly Arg Arg Leu Leu Gly Leu
225                 230                 235                 240

Gly Ser Ala Pro Ala Ser Ala Phe Glu Asn Glu Val Leu Tyr His His
                245                 250                 255

Phe Tyr Glu Ala Cys Pro Tyr Leu Lys Phe Ala His Phe Thr Ala Asn
            260                 265                 270

Gln Ala Ile Leu Glu Ala Phe Asp Gly His Asp Cys Val His Val Ile
        275                 280                 285

Asp Phe Asn Leu Met His Gly Leu Gln Trp Pro Ala Leu Ile Gln Ala
    290                 295                 300

Leu Ala Leu Arg Pro Arg Gly Pro Pro Leu Leu Arg Leu Thr Gly Ile
305                 310                 315                 320

Gly Pro Pro Ser Pro Asp Gly Arg Asp Val Leu Arg Glu Ile Gly Leu
                325                 330                 335

Arg Leu Ala Glu Leu Ala Arg Ser Val Asn Val Arg Phe Ala Phe Arg
            340                 345                 350

Gly Val Ala Ala Ser Arg Leu Glu Asp Val Lys Pro Trp Met Leu Gln
        355                 360                 365

Val Ser Pro Lys Glu Ala Val Ala Val Asn Ser Ile Met Gln Leu His
    370                 375                 380

Arg Leu Leu Gly Ser Asp Pro Pro Arg Asp Pro Pro Ile Gly Ser Val
385                 390                 395                 400

Leu Pro Trp Ile Arg Ser Leu Asn Pro Lys Ile Met Thr Val Ala Glu
                405                 410                 415

Gln Glu Ala Asn His Asn Arg Pro Gly Phe Leu Asp Arg Phe Thr Glu
            420                 425                 430

Ala Leu Tyr Tyr Tyr Ser Thr Leu Phe Asp Ser Leu Glu Ala Ala Cys
        435                 440                 445

Pro Val Gln Pro Asp Lys Ala Leu Ala Glu Met Tyr Leu Gln Arg Glu
    450                 455                 460

Ile Cys Asn Ile Val Gly Cys Glu Gly Ala Ala Arg Val Glu Arg His
465                 470                 475                 480

Glu Pro Leu Asp Arg Trp Arg Ala Arg Leu Gly Arg Ala Gly Phe Arg
                485                 490                 495

Pro Leu His Leu Gly Ser Asn Ala Phe Lys Gln Ala Ser Met Leu Leu
            500                 505                 510
```

-continued

```
Thr Leu Phe Ser Thr Glu Gly Tyr Ser Val Glu Glu Asn Glu Gly Cys
        515                 520                 525

Leu Thr Leu Cys Trp His Ser Arg Pro Leu Ile Ala Ala Ser Ala Trp
    530                 535                 540

Gln Ala Ala Pro Thr Val Val Asn Ser Pro Ala Gly Val Ile Asn His
545                 550                 555                 560

Asp Asp Asn Asn Asn Gln Leu
                565


<210> SEQ ID NO 12
<211> LENGTH: 1704
<212> TYPE: DNA
<213> ORGANISM: Eucalyptus grandis

<400> SEQUENCE: 12

atgggcccct tcgacccctc cgccgccgcc gccgccgccg ccgccgcagc cgccagcagc      60

tcctcctcgt cgtcctgctc cgggggctcg gcgcccaagc gccaccacca ccaccaccac     120

caccacccgc cgccggatct cgacgggctc ctcgccggcg ccggctacaa ggtccgctcc     180

tccgagctcc accacgtggc gcagcggctc gagcggctcg agaccgccct cgtcaactcc     240

gccgcccaca tcccccacct cgcctccgac gccgtccact acaacccctc cgatctcgcc     300

tcctgggtcg actccatgct ctccgagctc ccgagctcat ccttctcctc cccctgcctg     360

ccctccggct tccccgaccc gtactctccg gcggcggcgg cactcggcgg cgggtgggtg     420

gaccacccct cctgctcgcc gcacccacag ccgcaccaga acgtcgtcgt cccccagcag     480

ccgcagccgc agcagcagca gcaattgacg gtggtgacgg cgctggagga ggattccggc     540

attcagctcg tccacgcgct gatgacgtgc gcggagtcgg tccagcgtgg cgacgcctcg     600

ctggccggct ccctggtcga ggagatgcgg gccctgctga cgcgcgtcga cacctcgcgg     660

ggcatcggga aggtcgccgg ctacttcatc gacgccctcg gccggcggct gctcggcctc     720

ggctcggctc ccgcctcggc cttcgagaac gaggtgctgt accaccactt ctacgaggcc     780

tgcccctatc tcaagttcgc ccacttcacc gccaaccagg ccatcctcga ggccttcgac     840

ggccacgact gcgtccacgt catcgacttc aacctcatgc acggcctgca gtggccggcc     900

ctgatccagg ccctcgccct ccgcccccgc gggcccccgc tcctccgcct caccggcatt     960

ggcccgccct cccccgacgg ccgcgacgtg ctccgcgaga tcggcctccg gctcgcggag    1020

ctggcccgct cggtcaacgt ccggttcgcg ttccgcggcg tcgcggcctc gcggctcgag    1080

gacgtgaagc cgtggatgct ccaggtgagc cccaaggagg ccgtggccgt caactccatc    1140

atgcagctcc acaggctcct gggatccgac ccgccccggg acccccccat cgggtcggtc    1200

ctgccctgga tccggagcct gaacccgaag ataatgaccg tggcggagca ggaggcgaac    1260

cacaaccggc ccgggttcct ggaccggttc accgaggcgc tgtactacta ctcgaccctg    1320

ttcgactcgc tcgaggcggc ctgcccggtc cagcccgaca aggccctggc cgagatgtac    1380

cttcaaaggg agatatgcaa catcgtgggc tgcgaggggg cggcccgggt cgagaggcac    1440

gagccgctgg accggtggcg ggcccgcctc gggcgagccg ggttccggcc gctgcacctc    1500

ggctccaacg cgttcaagca agccagcatg ctgctcaccc tgttctcgac cgagggctac    1560

agcgtggagg agaacgaggg ttgcttgacg ctctgctggc acagccggcc cctcatcgcg    1620

gcttcggcgt ggcaagccgc gcctactgta gtgaactcgc cggccggcgt tattaatcac    1680

gatgacaata ataatcagct gtaa                                           1704
```

<210> SEQ ID NO 13
<211> LENGTH: 533
<212> TYPE: PRT
<213> ORGANISM: Arabidopsis thaliana

<400> SEQUENCE: 13

```
Met Lys Arg Asp His His His His His His Gln Asp Lys Lys Thr Met
1               5                   10                  15

Met Met Asn Glu Glu Asp Asp Gly Asn Gly Met Asp Glu Leu Leu Ala
            20                  25                  30

Val Leu Gly Tyr Lys Val Arg Ser Ser Glu Met Ala Asp Val Ala Gln
        35                  40                  45

Lys Leu Glu Gln Leu Glu Val Met Met Ser Asn Val Gln Glu Asp Asp
    50                  55                  60

Leu Ser Gln Leu Ala Thr Glu Thr Val His Tyr Asn Pro Ala Glu Leu
65                  70                  75                  80

Tyr Thr Trp Leu Asp Ser Met Leu Thr Asp Leu Asn Pro Pro Ser Ser
                85                  90                  95

Asn Ala Glu Tyr Asp Leu Lys Ala Ile Pro Gly Asp Ala Ile Leu Asn
            100                 105                 110

Gln Phe Ala Ile Asp Ser Ala Ser Ser Ser Asn Gln Gly Gly Gly Gly
        115                 120                 125

Asp Thr Tyr Thr Thr Asn Lys Arg Leu Lys Cys Ser Asn Gly Val Val
    130                 135                 140

Glu Thr Thr Thr Ala Thr Ala Glu Ser Thr Arg His Val Val Leu Val
145                 150                 155                 160

Asp Ser Gln Glu Asn Gly Val Arg Leu Val His Ala Leu Leu Ala Cys
                165                 170                 175

Ala Glu Ala Val Gln Lys Glu Asn Leu Thr Val Ala Glu Ala Leu Val
            180                 185                 190

Lys Gln Ile Gly Phe Leu Ala Val Ser Gln Ile Gly Ala Met Arg Lys
        195                 200                 205

Val Ala Thr Tyr Phe Ala Glu Ala Leu Ala Arg Arg Ile Tyr Arg Leu
    210                 215                 220

Ser Pro Ser Gln Ser Pro Ile Asp His Ser Leu Ser Asp Thr Leu Gln
225                 230                 235                 240

Met His Phe Tyr Glu Thr Cys Pro Tyr Leu Lys Phe Ala His Phe Thr
                245                 250                 255

Ala Asn Gln Ala Ile Leu Glu Ala Phe Gln Gly Lys Lys Arg Val His
            260                 265                 270

Val Ile Asp Phe Ser Met Ser Gln Gly Leu Gln Trp Pro Ala Leu Met
        275                 280                 285

Gln Ala Leu Ala Leu Arg Pro Gly Gly Pro Pro Val Phe Arg Leu Thr
    290                 295                 300

Gly Ile Gly Pro Pro Ala Pro Asp Asn Phe Asp Tyr Leu His Glu Val
305                 310                 315                 320

Gly Cys Lys Leu Ala His Leu Ala Glu Ala Ile His Val Glu Phe Glu
                325                 330                 335

Tyr Arg Gly Phe Val Ala Asn Thr Leu Ala Asp Leu Asp Ala Ser Met
            340                 345                 350

Leu Glu Leu Arg Pro Ser Glu Ile Glu Ser Val Ala Val Asn Ser Val
        355                 360                 365

Phe Glu Leu His Lys Leu Leu Gly Arg Pro Gly Ala Ile Asp Lys Val
    370                 375                 380
```

-continued

Leu Gly Val Val Asn Gln Ile Lys Pro Glu Ile Phe Thr Val Val Glu
385 390 395 400

Gln Glu Ser Asn His Asn Ser Pro Ile Phe Leu Asp Arg Phe Thr Glu
405 410 415

Ser Leu His Tyr Tyr Ser Thr Leu Phe Asp Ser Leu Glu Gly Val Pro
420 425 430

Ser Gly Gln Asp Lys Val Met Ser Glu Val Tyr Leu Gly Lys Gln Ile
435 440 445

Cys Asn Val Val Ala Cys Asp Gly Pro Asp Arg Val Glu Arg His Glu
450 455 460

Thr Leu Ser Gln Trp Arg Asn Arg Phe Gly Ser Ala Gly Phe Ala Ala
465 470 475 480

Ala His Ile Gly Ser Asn Ala Phe Lys Gln Ala Ser Met Leu Leu Ala
485 490 495

Leu Phe Asn Gly Gly Glu Gly Tyr Arg Val Glu Glu Ser Asp Gly Cys
500 505 510

Leu Met Leu Gly Trp His Thr Arg Pro Leu Ile Ala Thr Ser Ala Trp
515 520 525

Lys Leu Ser Thr Asn
530

<210> SEQ ID NO 14
<211> LENGTH: 1602
<212> TYPE: DNA
<213> ORGANISM: Arabidopsis thaliana

<400> SEQUENCE: 14
atgaagagag atcatcatca tcatcatcat caagataaga agactatgat gatgaatgaa 60
gaagacgacg gtaacggcat ggatgagctt ctagctgttc ttggttacaa ggttaggtca 120
tccgaaatgg ctgatgttgc tcagaaactc gagcagcttg aagttatgat gtctaatgtt 180
caagaagacg atctttctca actcgctact gagactgttc actataatcc ggcggagctt 240
tacacgtggc ttgattctat gctcaccgac cttaatcctc cgtcgtctaa cgccgagtac 300
gatcttaaag ctattcccgg tgacgcgatt ctcaatcagt tcgctatcga ttcggcttct 360
tcgtctaacc aaggcggcgg aggagatacg tatactacaa acaagcggtt gaaatgctca 420
aacggcgtcg tggaaaccac tacagcgacg gctgagtcaa ctcggcatgt tgtcctggtt 480
gactcgcagg agaacggtgt gcgtctcgtt cacgcgcttt tggcttgcgc tgaagctgtt 540
cagaaagaga atctgactgt agcggaagct ctggtgaagc aaatcggatt cttagccgtt 600
tctcaaatcg gagcgatgag aaaagtcgct acttacttcg ccgaagctct cgcgcggcgg 660
atttaccgtc tctctccgtc gcagagtcca atcgaccact ctctctccga tactcttcag 720
atgcacttct acgagacttg tccttatctc aagttcgctc acttcacggc gaatcaagcg 780
attctcgaag cttttcaagg gaagaaaaga gttcatgtca ttgatttctc tatgagtcaa 840
ggtcttcaat ggccggcgct tatgcaggct cttgcgcttc gacctggtgg tcctcctgtt 900
ttccggttaa ccggaattgg tccaccggca ccggataatt tcgattatct tcatgaagtt 960
gggtgtaagc tggctcattt agctgaggcg attcacgttg agtttgagta cagaggattt 1020
gtggctaaca ctttagctga tcttgatgct tcgatgcttg agcttagacc aagtgagatt 1080
gaatctgttg cggttaactc tgttttcgag cttcacaagc tcttgggacg acctggtgcg 1140
atcgataagg ttcttggtgt ggtgaatcag attaaaccgg agattttcac tgtggttgag 1200
caggaatcga accataatag tccgattttc ttagatcggt ttactgagtc gttgcattat 1260
tactcgacgt tgtttgactc gttggaaggt gtaccgagtg gtcaagacaa ggtcatgtcg 1320
gaggtttact tgggtaaaca gatctgcaac gttgtggctt gtgatggacc tgaccgagtt 1380
gagcgtcatg aaacgttgag tcagtggagg aaccggttcg ggtctgctgg gtttgcggct 1440
gcacatattg gttcgaatgc gtttaagcaa gcgagtatgc ttttggctct gttcaacggc 1500
ggtgagggtt atcgggtgga ggagagtgac ggctgtctca tgttgggttg gcacacacga 1560
ccgctcatag ccacctcggc ttggaaactc tccaccaatt ag 1602

<210> SEQ ID NO 15
<211> LENGTH: 587
<212> TYPE: PRT
<213> ORGANISM: Arabidopsis thaliana

<400> SEQUENCE: 15

Met Lys Arg Asp His His Gln Phe Gln Gly Arg Leu Ser Asn His Gly
1 5 10 15

Thr Ser Ser Ser Ser Ser Ser Ile Ser Lys Asp Lys Met Met Met Val
20 25 30

Lys Lys Glu Glu Asp Gly Gly Gly Asn Met Asp Asp Glu Leu Leu Ala
35 40 45

Val Leu Gly Tyr Lys Val Arg Ser Ser Glu Met Ala Glu Val Ala Leu
50 55 60

Lys Leu Glu Gln Leu Glu Thr Met Met Ser Asn Val Gln Glu Asp Gly
65 70 75 80

Leu Ser His Leu Ala Thr Asp Thr Val His Tyr Asn Pro Ser Glu Leu
85 90 95

Tyr Ser Trp Leu Asp Asn Met Leu Ser Glu Leu Asn Pro Pro Pro Leu
100 105 110

Pro Ala Ser Ser Asn Gly Leu Asp Pro Val Leu Pro Ser Pro Glu Ile
115 120 125

Cys Gly Phe Pro Ala Ser Asp Tyr Asp Leu Lys Val Ile Pro Gly Asn
130 135 140

Ala Ile Tyr Gln Phe Pro Ala Ile Asp Ser Ser Ser Ser Ser Asn Asn
145 150 155 160

Gln Asn Lys Arg Leu Lys Ser Cys Ser Ser Pro Asp Ser Met Val Thr
165 170 175

Ser Thr Ser Thr Gly Thr Gln Ile Gly Gly Val Ile Gly Thr Thr Val
180 185 190

Thr Thr Thr Thr Thr Thr Thr Thr Ala Ala Gly Glu Ser Thr Arg Ser
195 200 205

Val Ile Leu Val Asp Ser Gln Glu Asn Gly Val Arg Leu Val His Ala
210 215 220

Leu Met Ala Cys Ala Glu Ala Ile Gln Gln Asn Asn Leu Thr Leu Ala
225 230 235 240

Glu Ala Leu Val Lys Gln Ile Gly Cys Leu Ala Val Ser Gln Ala Gly
245 250 255

Ala Met Arg Lys Val Ala Thr Tyr Phe Ala Glu Ala Leu Ala Arg Arg
260 265 270

Ile Tyr Arg Leu Ser Pro Pro Gln Asn Gln Ile Asp His Cys Leu Ser
275 280 285

Asp Thr Leu Gln Met His Phe Tyr Glu Thr Cys Pro Tyr Leu Lys Phe
290 295 300

-continued

```
Ala His Phe Thr Ala Asn Gln Ala Ile Leu Glu Ala Phe Glu Gly Lys
305                 310                 315                 320

Lys Arg Val His Val Ile Asp Phe Ser Met Asn Gln Gly Leu Gln Trp
                325                 330                 335

Pro Ala Leu Met Gln Ala Leu Ala Leu Arg Glu Gly Gly Pro Pro Thr
            340                 345                 350

Phe Arg Leu Thr Gly Ile Gly Pro Pro Ala Pro Asp Asn Ser Asp His
        355                 360                 365

Leu His Glu Val Gly Cys Lys Leu Ala Gln Leu Ala Glu Ala Ile His
    370                 375                 380

Val Glu Phe Glu Tyr Arg Gly Phe Val Ala Asn Ser Leu Ala Asp Leu
385                 390                 395                 400

Asp Ala Ser Met Leu Glu Leu Arg Pro Ser Asp Thr Glu Ala Val Ala
                405                 410                 415

Val Asn Ser Val Phe Glu Leu His Lys Leu Leu Gly Arg Pro Gly Gly
            420                 425                 430

Ile Glu Lys Val Leu Gly Val Val Lys Gln Ile Lys Pro Val Ile Phe
        435                 440                 445

Thr Val Val Glu Gln Glu Ser Asn His Asn Gly Pro Val Phe Leu Asp
    450                 455                 460

Arg Phe Thr Glu Ser Leu His Tyr Tyr Ser Thr Leu Phe Asp Ser Leu
465                 470                 475                 480

Glu Gly Val Pro Asn Ser Gln Asp Lys Val Met Ser Glu Val Tyr Leu
                485                 490                 495

Gly Lys Gln Ile Cys Asn Leu Val Ala Cys Glu Gly Pro Asp Arg Val
            500                 505                 510

Glu Arg His Glu Thr Leu Ser Gln Trp Gly Asn Arg Phe Gly Ser Ser
        515                 520                 525

Gly Leu Ala Pro Ala His Leu Gly Ser Asn Ala Phe Lys Gln Ala Ser
    530                 535                 540

Met Leu Leu Ser Val Phe Asn Ser Gly Gln Gly Tyr Arg Val Glu Glu
545                 550                 555                 560

Ser Asn Gly Cys Leu Met Leu Gly Trp His Thr Arg Pro Leu Ile Thr
                565                 570                 575

Thr Ser Ala Trp Lys Leu Ser Thr Ala Ala Tyr
            580                 585


<210> SEQ ID NO 16
<211> LENGTH: 1764
<212> TYPE: DNA
<213> ORGANISM: Arabidopsis thaliana

<400> SEQUENCE: 16

atgaagagag atcatcacca attccaaggt cgattgtcca accacgggac ttcttcttca      60

tcatcatcaa tctctaaaga taagatgatg atggtgaaaa aagaagaaga cggtggaggt     120

aacatggacg acgagcttct cgctgtttta ggttacaaag ttaggtcatc ggagatggcg     180

gaggttgctt tgaaactcga acaattagag acgatgatga gtaatgttca agaagatggt     240

ttatctcatc tcgcgacgga tactgttcat tataatccgt cggagcttta ttcttggctt     300

gataatatgc tctctgagct taatcctcct cctcttccgg cgagttctaa cggtttagat     360

ccggttcttc cttcgccgga gatttgtggt tttccggctt cggattatga ccttaaagtc     420

attcccggaa acgcgattta tcagtttccg gcgattgatt cttcgtcttc gtcgaataat     480

cagaacaagc gtttgaaatc atgctcgagt cctgattcta tggttacatc gacttcgacg     540
```

```
ggtacgcaga ttggtggagt cataggaacg acggtgacga caaccaccac gacaacgacg    600

gcggcgggtg agtcaactcg ttctgttatc ctggttgact cgcaagagaa cggtgttcgt    660

ttagtccacg cgcttatggc ttgtgcagaa gcaatccagc agaacaattt gactctagcg    720

gaagctcttg tgaagcaaat cggatgctta gctgtgtctc aagccggagc tatgagaaaa    780

gtggctactt acttcgccga agctttagcg cggcggatct accgtctctc tccgccgcag    840

aatcagatcg atcattgtct ctccgatact cttcagatgc acttttacga gacttgtcct    900

tatcttaaat tcgctcactt cacggcgaac caagcgattc tcgaagcttt tgaaggtaag    960

aagagagtac acgtcattga tttctcgatg aaccaaggtc ttcaatggcc tgcacttatg   1020

caagctcttg cgcttcgaga aggaggtcct ccaactttcc ggttaaccgg aattggtcca   1080

ccggcgccgg ataattctga tcatcttcat gaagttggtt gtaaattagc tcagcttgcg   1140

gaggcgattc acgtagaatt cgaataccgt ggattcgttg ctaacagctt agccgatctc   1200

gatgcttcga tgcttgagct tagaccgagc gatacggaag ctgttgcggt gaactctgtt   1260

tttgagctac ataagctctt aggtcgtccc ggtgggatag agaaagttct cggcgttgtg   1320

aaacagatta aaccggtgat tttcacggtg gttgagcaag aatcgaacca taacggaccg   1380

gttttcttag accggtttac tgaatcgtta cattattatt cgactctgtt tgattcgttg   1440

gaaggagttc cgaatagtca agacaaagtc atgtctgaag tttacttagg gaaacagatt   1500

tgtaatctgg tggcttgtga aggtcctgac agagtcgaga gacacgaaac gttgagtcaa   1560

tggggaaacc ggtttggttc gtccggttta gcgccggcac atcttgggtc taacgcgttt   1620

aagcaagcga gtatgctttt gtctgtgttt aatagtggcc aaggttatcg tgtggaggag   1680

agtaatggat gtttgatgtt gggttggcac actcgtccac tcattaccac ctccgcttgg   1740

aaactctcga cggcggcgta ctga                                          1764
```

<210> SEQ ID NO 17
<211> LENGTH: 511
<212> TYPE: PRT
<213> ORGANISM: Arabidopsis thaliana

<400> SEQUENCE: 17

```
Met Lys Arg Glu His Asn His Arg Glu Ser Ser Ala Gly Glu Gly Gly
1               5                   10                  15

Ser Ser Ser Met Thr Thr Val Ile Lys Glu Glu Ala Ala Gly Val Asp
            20                  25                  30

Glu Leu Leu Val Val Leu Gly Tyr Lys Val Arg Ser Ser Asp Met Ala
        35                  40                  45

Asp Val Ala His Lys Leu Glu Gln Leu Glu Met Val Leu Gly Asp Gly
    50                  55                  60

Ile Ser Asn Leu Ser Asp Glu Thr Val His Tyr Asn Pro Ser Asp Leu
65                  70                  75                  80

Ser Gly Trp Val Glu Ser Met Leu Ser Asp Leu Asp Pro Thr Arg Ile
                85                  90                  95

Gln Glu Lys Pro Asp Ser Glu Tyr Asp Leu Arg Ala Ile Pro Gly Ser
            100                 105                 110

Ala Val Tyr Pro Arg Asp Glu His Val Thr Arg Arg Ser Lys Arg Thr
        115                 120                 125

Arg Ile Glu Ser Glu Leu Ser Ser Thr Arg Ser Val Val Val Leu Asp
    130                 135                 140

Ser Gln Glu Thr Gly Val Arg Leu Val His Ala Leu Leu Ala Cys Ala
```

-continued

```
145                 150                 155                 160

Glu Ala Val Gln Gln Asn Asn Leu Lys Leu Ala Asp Ala Leu Val Lys
                165                 170                 175

His Val Gly Leu Leu Ala Ser Ser Gln Ala Gly Ala Met Arg Lys Val
            180                 185                 190

Ala Thr Tyr Phe Ala Glu Gly Leu Ala Arg Arg Ile Tyr Arg Ile Tyr
        195                 200                 205

Pro Arg Asp Asp Val Ala Leu Ser Ser Phe Ser Asp Thr Leu Gln Ile
    210                 215                 220

His Phe Tyr Glu Ser Cys Pro Tyr Leu Lys Phe Ala His Phe Thr Ala
225                 230                 235                 240

Asn Gln Ala Ile Leu Glu Val Phe Ala Thr Ala Glu Lys Val His Val
                245                 250                 255

Ile Asp Leu Gly Leu Asn His Gly Leu Gln Trp Pro Ala Leu Ile Gln
            260                 265                 270

Ala Leu Ala Leu Arg Pro Asn Gly Pro Pro Asp Phe Arg Leu Thr Gly
        275                 280                 285

Ile Gly Tyr Ser Leu Thr Asp Ile Gln Glu Val Gly Trp Lys Leu Gly
    290                 295                 300

Gln Leu Ala Ser Thr Ile Gly Val Asn Phe Glu Phe Lys Ser Ile Ala
305                 310                 315                 320

Leu Asn Asn Leu Ser Asp Leu Lys Pro Glu Met Leu Asp Ile Arg Pro
                325                 330                 335

Gly Leu Glu Ser Val Ala Val Asn Ser Val Phe Glu Leu His Arg Leu
            340                 345                 350

Leu Ala His Pro Gly Ser Ile Asp Lys Phe Leu Ser Thr Ile Lys Ser
        355                 360                 365

Ile Arg Pro Asp Ile Met Thr Val Val Glu Gln Glu Ala Asn His Asn
    370                 375                 380

Gly Thr Val Phe Leu Asp Arg Phe Thr Glu Ser Leu His Tyr Tyr Ser
385                 390                 395                 400

Ser Leu Phe Asp Ser Leu Glu Gly Pro Pro Ser Gln Asp Arg Val Met
                405                 410                 415

Ser Glu Leu Phe Leu Gly Arg Gln Ile Leu Asn Leu Val Ala Cys Glu
            420                 425                 430

Gly Glu Asp Arg Val Glu Arg His Glu Thr Leu Asn Gln Trp Arg Asn
        435                 440                 445

Arg Phe Gly Leu Gly Gly Phe Lys Pro Val Ser Ile Gly Ser Asn Ala
    450                 455                 460

Tyr Lys Gln Ala Ser Met Leu Leu Ala Leu Tyr Ala Gly Ala Asp Gly
465                 470                 475                 480

Tyr Asn Val Glu Glu Asn Glu Gly Cys Leu Leu Leu Gly Trp Gln Thr
                485                 490                 495

Arg Pro Leu Ile Ala Thr Ser Ala Trp Arg Ile Asn Arg Val Glu
            500                 505                 510
```

<210> SEQ ID NO 18
<211> LENGTH: 1536
<212> TYPE: DNA
<213> ORGANISM: Arabidopsis thaliana

<400> SEQUENCE: 18

```
atgaagagag agcacaacca ccgtgaatca tccgccggag aaggtgggag ttcatcaatg      60

acgacggtga ttaaagaaga agctgccgga gttgacgagc ttttggttgt tttaggttac     120
```

-continued

```
aaagttcgat catccgacat ggctgacgtg gcacacaagc ttgaacagtt agagatggtt    180
cttggtgatg gaatctcgaa tctttctgat gaaactgttc attacaatcc ttctgatctc    240
tctggttggg tcgaaagcat gctctcggat cttgacccga cccggattca agaaaagcct    300
gactcagagt acgatcttag agctattcct ggctctgcag tgtatccacg tgacgagcac    360
gtgactcgtc ggagcaagag gacgagaatt gaatcggagt tatcctctac gcgctctgtg    420
gtggttttgg attctcaaga aactggagtg cgtttagtcc acgcgctatt agcttgtgct    480
gaagctgttc aacagaacaa tttgaagtta gccgacgcgc tcgtgaagca cgtggggtta    540
ctcgcgtcct ctcaagctgg tgctatgagg aaagtcgcga cttacttcgc tgaagggctt    600
gcgagaagga tttaccgtat ttaccctcga gacgatgtcg cgttgtcttc gttttcggac    660
actcttcaga ttcatttcta tgagtcttgt ccgtatctca agtttgcgca ttttacggcg    720
aatcaagcga tacttgaggt ttttgctacg gcggagaagg ttcatgttat tgatttagga    780
cttaaccatg gtttacaatg gccggctttg attcaagctc ttgctttacg tcctaatggt    840
ccaccggatt ttcggttaac cgggatcggt tattcgttaa ccgatattca agaagttggt    900
tggaaacttg gtcagcttgc gagtactatt ggtgtcaatt tcgaattcaa gagcattgct    960
ttaaacaatt tgtctgatct taaaccggaa atgctagaca ttagacccgg tttagaatca   1020
gtggcggtta actcggtctt cgagcttcat cgcctcttag ctcatcccgg ttccatcgat   1080
aagtttttat cgacaatcaa atcaatccga ccggatataa tgactgtggt cgagcaagaa   1140
gcaaaccata acggtaccgt atttctcgat cggttcacgg aatcgctaca ttactattcg   1200
agcttattcg actcgctcga gggcccgcca agccaagacc gagtgatgtc ggagttattc   1260
ctaggacggc agatactaaa ccttgtggca tgcgaaggag aagaccgggt agagaggcat   1320
gagactttaa atcagtggag aaaccggttc ggtttaggag gatttaaacc ggttagtatc   1380
ggttcgaacg cgtataagca agcaagcatg ttgttggcac tttatgccgg ggctgatggg   1440
tataatgtgg aagagaatga aggttgtttg ttgcttggat ggcaaacgcg accgcttatt   1500
gcaacatctg cgtggcgaat caatcgtgtg gaataa                             1536
```

<210> SEQ ID NO 19
<211> LENGTH: 547
<212> TYPE: PRT
<213> ORGANISM: Arabidopsis thaliana

<400> SEQUENCE: 19

```
Met Lys Arg Gly Tyr Gly Glu Thr Trp Asp Pro Pro Pro Lys Pro Leu
1               5                   10                  15

Pro Ala Ser Arg Ser Gly Glu Gly Pro Ser Met Ala Asp Lys Lys Lys
            20                  25                  30

Ala Asp Asp Asp Asn Asn Asn Ser Asn Met Asp Asp Glu Leu Leu Ala
        35                  40                  45

Val Leu Gly Tyr Lys Val Arg Ser Ser Glu Met Ala Glu Val Ala Gln
    50                  55                  60

Lys Leu Glu Gln Leu Glu Met Val Leu Ser Asn Asp Asp Val Gly Ser
65                  70                  75                  80

Thr Val Leu Asn Asp Ser Val His Tyr Asn Pro Ser Asp Leu Ser Asn
                85                  90                  95

Trp Val Glu Ser Met Leu Ser Glu Leu Asn Asn Pro Ala Ser Ser Asp
            100                 105                 110

Leu Asp Thr Thr Arg Ser Cys Val Asp Arg Ser Glu Tyr Asp Leu Arg
```

-continued

```
        115                 120                 125

Ala Ile Pro Gly Leu Ser Ala Phe Pro Lys Glu Glu Glu Val Phe Asp
    130                 135                 140

Glu Glu Ala Ser Ser Lys Arg Ile Arg Leu Gly Ser Trp Cys Glu Ser
145                 150                 155                 160

Ser Asp Glu Ser Thr Arg Ser Val Val Leu Val Asp Ser Gln Glu Thr
                165                 170                 175

Gly Val Arg Leu Val His Ala Leu Val Ala Cys Ala Glu Ala Ile His
            180                 185                 190

Gln Glu Asn Leu Asn Leu Ala Asp Ala Leu Val Lys Arg Val Gly Thr
        195                 200                 205

Leu Ala Gly Ser Gln Ala Gly Ala Met Gly Lys Val Ala Thr Tyr Phe
    210                 215                 220

Ala Gln Ala Leu Ala Arg Arg Ile Tyr Arg Asp Tyr Thr Ala Glu Thr
225                 230                 235                 240

Asp Val Cys Ala Ala Val Asn Pro Ser Phe Glu Glu Val Leu Glu Met
                245                 250                 255

His Phe Tyr Glu Ser Cys Pro Tyr Leu Lys Phe Ala His Phe Thr Ala
            260                 265                 270

Asn Gln Ala Ile Leu Glu Ala Val Thr Thr Ala Arg Arg Val His Val
        275                 280                 285

Ile Asp Leu Gly Leu Asn Gln Gly Met Gln Trp Pro Ala Leu Met Gln
    290                 295                 300

Ala Leu Ala Leu Arg Pro Gly Gly Pro Pro Ser Phe Arg Leu Thr Gly
305                 310                 315                 320

Ile Gly Pro Pro Gln Thr Glu Asn Ser Asp Ser Leu Gln Gln Leu Gly
                325                 330                 335

Trp Lys Leu Ala Gln Phe Ala Gln Asn Met Gly Val Glu Phe Glu Phe
            340                 345                 350

Lys Gly Leu Ala Ala Glu Ser Leu Ser Asp Leu Glu Pro Glu Met Phe
        355                 360                 365

Glu Thr Arg Pro Glu Ser Glu Thr Leu Val Val Asn Ser Val Phe Glu
    370                 375                 380

Leu His Arg Leu Leu Ala Arg Ser Gly Ser Ile Glu Lys Leu Leu Asn
385                 390                 395                 400

Thr Val Lys Ala Ile Lys Pro Ser Ile Val Thr Val Val Glu Gln Glu
                405                 410                 415

Ala Asn His Asn Gly Ile Val Phe Leu Asp Arg Phe Asn Glu Ala Leu
            420                 425                 430

His Tyr Tyr Ser Ser Leu Phe Asp Ser Leu Glu Asp Ser Tyr Ser Leu
        435                 440                 445

Pro Ser Gln Asp Arg Val Met Ser Glu Val Tyr Leu Gly Arg Gln Ile
    450                 455                 460

Leu Asn Val Val Ala Ala Glu Gly Ser Asp Arg Val Glu Arg His Glu
465                 470                 475                 480

Thr Ala Ala Gln Trp Arg Ile Arg Met Lys Ser Ala Gly Phe Asp Pro
                485                 490                 495

Ile His Leu Gly Ser Ser Ala Phe Lys Gln Ala Ser Met Leu Leu Ser
            500                 505                 510

Leu Tyr Ala Thr Gly Asp Gly Tyr Arg Val Glu Glu Asn Asp Gly Cys
        515                 520                 525

Leu Met Ile Gly Trp Gln Thr Arg Pro Leu Ile Thr Thr Ser Ala Trp
    530                 535                 540
```

-continued

Lys Leu Ala
545

<210> SEQ ID NO 20
<211> LENGTH: 1644
<212> TYPE: DNA
<213> ORGANISM: Arabidopsis thaliana

<400> SEQUENCE: 20
atgaagagag gatacggaga aacatgggat ccgccaccaa aaccactacc agcttctcgt 60
tccggagaag gtccttcaat ggcggataag aagaaggctg atgatgacaa caacaacagc 120
aacatggatg atgagcttct tgctgttctt ggctacaagg ttcgatcttc tgagatggct 180
gaagtagcac agaagcttga acaacttgag atggtcttgt ctaatgatga tgttggttct 240
actgtcttaa acgactctgt tcattataac ccatctgatc tctctaactg ggtcgagagc 300
atgctttctg agctgaacaa cccggcttct tcggatcttg acacgacccg aagttgtgtg 360
gatagatccg aatacgatct cagagcaatt ccgggtcttt ctgcgtttcc aaaggaagag 420
gaagtctttg acgaggaagc tagcagcaag aggatccgac tcggatcgtg gtgcgaatcg 480
tcggacgagt caactcggtc cgtggtgctc gttgactctc aggagaccgg agttagactt 540
gtccacgcac tagtggcgtg cgctgaggcg attcaccagg agaatctcaa cttagctgac 600
gcgctggtga aacgcgtggg aacactcgcg ggttctcaag ctggagctat gggaaaagtc 660
gctacgtatt ttgctcaagc cttggctcgt cgtatttacc gtgattacac ggcggagacg 720
gacgtttgcg cggcggtgaa cccatctttc gaagaggttt tggagatgca cttttacgag 780
tcttgccctt acctgaagtt cgctcatttc acggcgaacc aagcgattct agaagctgtt 840
acgacggcgc gtagagttca cgtcattgat ttagggctta atcaagggat gcaatggcct 900
gctttaatgc aagctttagc tctccgaccc ggtggacctc cgtcgtttcg tctcaccgga 960
atcggaccac cgcagacgga gaattcagat tcgcttcaac agttaggttg gaaattagct 1020
caattcgctc agaacatggg cgttgaattc gaattcaaag gcttagccgc tgagagttta 1080
tcggatcttg aacccgaaat gttcgaaacc cgacccgaat ctgaaacctt agtggttaat 1140
tcggtatttg agctccaccg gttattagcc cgatccggtt caatcgaaaa gcttctcaat 1200
acggttaaag ctattaaacc gagtatcgta acggtggttg agcaagaagc gaaccacaac 1260
ggaatcgtct tcctcgatag gttcaacgaa gcgcttcatt actactcgag cttgtttgac 1320
tcgctcgaag acagttatag tttaccgagt caagaccgag ttatgtcaga agtgtactta 1380
gggagacaga tactcaacgt tgttgcggcg gaagggtccg atcgggtcga gcggcacgag 1440
acggctgcac agtggaggat tcggatgaaa tccgctgggt ttgacccgat tcatctcgga 1500
tctagcgcgt ttaaacaagc gagtatgctt ttatcgcttt acgctaccgg agatggatac 1560
agagttgaag aaaatgacgg atgtttaatg atagggtggc agacgcgacc actcatcaca 1620
acctcggcgt ggaaactcgc ctga 1644

<210> SEQ ID NO 21
<211> LENGTH: 523
<212> TYPE: PRT
<213> ORGANISM: Arabidopsis thaliana

<400> SEQUENCE: 21

Met Lys Arg Ser His Gln Glu Thr Ser Val Glu Glu Glu Ala Pro Ser
1 5 10 15

-continued

```
Met Val Glu Lys Leu Glu Asn Gly Cys Gly Gly Gly Gly Asp Asp Asn
            20                  25                  30

Met Asp Glu Phe Leu Ala Val Leu Gly Tyr Lys Val Arg Ser Ser Asp
        35                  40                  45

Met Ala Asp Val Ala Gln Lys Leu Glu Gln Leu Glu Met Val Leu Ser
    50                  55                  60

Asn Asp Ile Ala Ser Ser Ser Asn Ala Phe Asn Asp Thr Val His Tyr
65                  70                  75                  80

Asn Pro Ser Asp Leu Ser Gly Trp Ala Gln Ser Met Leu Ser Asp Leu
                85                  90                  95

Asn Tyr Tyr Pro Asp Leu Asp Pro Asn Arg Ile Cys Asp Leu Arg Pro
            100                 105                 110

Ile Thr Asp Asp Asp Glu Cys Cys Ser Ser Asn Ser Asn Ser Asn Lys
        115                 120                 125

Arg Ile Arg Leu Gly Pro Trp Cys Asp Ser Val Thr Ser Glu Ser Thr
    130                 135                 140

Arg Ser Val Val Leu Ile Glu Glu Thr Gly Val Arg Leu Val Gln Ala
145                 150                 155                 160

Leu Val Ala Cys Ala Glu Ala Val Gln Leu Glu Asn Leu Ser Leu Ala
                165                 170                 175

Asp Ala Leu Val Lys Arg Val Gly Leu Leu Ala Ala Ser Gln Ala Gly
            180                 185                 190

Ala Met Gly Lys Val Ala Thr Tyr Phe Ala Glu Ala Leu Ala Arg Arg
        195                 200                 205

Ile Tyr Arg Ile His Pro Ser Ala Ala Ala Ile Asp Pro Ser Phe Glu
    210                 215                 220

Glu Ile Leu Gln Met Asn Phe Tyr Asp Ser Cys Pro Tyr Leu Lys Phe
225                 230                 235                 240

Ala His Phe Thr Ala Asn Gln Ala Ile Leu Glu Ala Val Thr Thr Ser
                245                 250                 255

Arg Val Val His Val Ile Asp Leu Gly Leu Asn Gln Gly Met Gln Trp
            260                 265                 270

Pro Ala Leu Met Gln Ala Leu Ala Leu Arg Pro Gly Gly Pro Pro Ser
        275                 280                 285

Phe Arg Leu Thr Gly Val Gly Asn Pro Ser Asn Arg Glu Gly Ile Gln
    290                 295                 300

Glu Leu Gly Trp Lys Leu Ala Gln Leu Ala Gln Ala Ile Gly Val Glu
305                 310                 315                 320

Phe Lys Phe Asn Gly Leu Thr Thr Glu Arg Leu Ser Asp Leu Glu Pro
                325                 330                 335

Asp Met Phe Glu Thr Arg Thr Glu Ser Glu Thr Leu Val Val Asn Ser
            340                 345                 350

Val Phe Glu Leu His Pro Val Leu Ser Gln Pro Gly Ser Ile Glu Lys
        355                 360                 365

Leu Leu Ala Thr Val Lys Ala Val Lys Pro Gly Leu Val Thr Val Val
    370                 375                 380

Glu Gln Glu Ala Asn His Asn Gly Asp Val Phe Leu Asp Arg Phe Asn
385                 390                 395                 400

Glu Ala Leu His Tyr Tyr Ser Ser Leu Phe Asp Ser Leu Glu Asp Gly
                405                 410                 415

Val Val Ile Pro Ser Gln Asp Arg Val Met Ser Glu Val Tyr Leu Gly
            420                 425                 430

Arg Gln Ile Leu Asn Leu Val Ala Thr Glu Gly Ser Asp Arg Ile Glu
```

-continued

```
        435                 440                 445

Arg His Glu Thr Leu Ala Gln Trp Arg Lys Arg Met Gly Ser Ala Gly
    450                 455                 460

Phe Asp Pro Val Asn Leu Gly Ser Asp Ala Phe Lys Gln Ala Ser Leu
465                 470                 475                 480

Leu Leu Ala Leu Ser Gly Gly Gly Asp Gly Tyr Arg Val Glu Glu Asn
                485                 490                 495

Asp Gly Ser Leu Met Leu Ala Trp Gln Thr Lys Pro Leu Ile Ala Ala
            500                 505                 510

Ser Ala Trp Lys Leu Ala Ala Glu Leu Arg Arg
        515                 520


<210> SEQ ID NO 22
<211> LENGTH: 1572
<212> TYPE: DNA
<213> ORGANISM: Arabidopsis thaliana

<400> SEQUENCE: 22

atgaaacgaa gccatcaaga aacgtctgta gaagaagaag ctccttcaat ggtggagaag     60

ttagaaaatg gttgtggtgg tggtggagac gataacatgg acgagtttct tgctgttttg    120

ggttacaagg ttcgatcttc agacatggca gatgttgcac agaagcttga acagcttgaa    180

atggtcttgt ccaatgatat tgcctcttct agtaatgcct tcaatgacac cgttcattac    240

aatccttctg atctctccgg ttgggctcag agcatgctct cggatcttaa ttactacccg    300

gatcttgacc cgaaccggat ttgcgatctg agaccaatca cagacgacga tgagtgttgc    360

agtagcaata gtaacagcaa caagaggatt cgactcggtc cttggtgtga ctcagtgacc    420

agcgagtcaa ctcgttccgt ggtgcttatc gaggagacag gagttagact cgttcaggcg    480

ctagtggcct gcgccgaggc ggttcagctg gagaatctga gcctcgcgga tgctctcgtc    540

aagcgcgtgg gattactcgc ggcttctcaa gccggagcca tggggaaagt cgctacctac    600

ttcgccgaag ccctagctcg tcgaatttac cggattcatc cttccgccgc cgccattgat    660

ccttccttcg aagagattct tcagatgaac ttctacgact cgtgtcccta cctgaaattc    720

gctcatttca cggccaatca ggcgattcta gaagctgtta cgacgtcgcg tgtcgtacac    780

gtaatcgatc tagggcttaa tcaaggtatg caatggccgg cgttaatgca agccttagct    840

ctccgacccg gtggtccacc gtcgtttcgt ctcaccggcg ttgggaatcc gtcgaatcga    900

gaagggattc aagagttagg ttggaagcta gctcagctgg ctcaagccat cggcgtcgaa    960

ttcaaattca atggtctaac gacggagagg ttatccgatt tagaaccgga tatgttcgag   1020

acccgaaccg aatcggagac tctagtggtt aattcggttt tcgagcttca cccggtttta   1080

tcccaacccg gttcgatcga aaagctgtta gcgacggtta aggcggttaa accgggtctc   1140

gtaacagtgg tggaacaaga agcgaaccat aacggtgacg ttttcttaga ccggtttaac   1200

gaagcgcttc actattactc gagcttgttc gactcgctcg aagatggtgt tgtgataccg   1260

agtcaagacc gagtcatgtc ggaggtttac ttagggagac agatattgaa cttggtggcg   1320

acggaaggaa gcgataggat cgagcgacac gagacgctgg ctcagtggcg aaaacgtatg   1380

ggatccgccg ggtttgaccc ggttaacctc ggatcagacg cgtttaagca agcgagtttg   1440

ctattggcgt tatctggcgg tggagatgga tacagagtgg aggagaacga cggaagccta   1500

atgcttgcgt ggcaaacgaa acctctaatc gctgcatcgg cgtggaaact agcggcggag   1560

ttgcggcggt ag                                                       1572
```

<210> SEQ ID NO 23
<211> LENGTH: 300
<212> TYPE: DNA
<213> ORGANISM: Artificial Sequence
<220> FEATURE:
<223> OTHER INFORMATION: Reverse complementary sequence of the DELLA1
300 bp sequences

<400> SEQUENCE: 23
agattgtgac gatggtggaa caggaggcga atcacaatgg cccggggttc gtggaccggt 60
tcacggaagc tttgcattac tactccagcc tgttcgattc gctggaaggg tctggggtgg 120
ctcccccgaa ccaggatctg gtcatgtccg aggtctactt gggtcggcag atttgcaatg 180
ttgtggcctg cgaggggccg gatcgagtgg agcggcacga gacgttggtg cagtggcagg 240
cgcggatggg atcggctggg ttcgacccgg tccatctcgg gtccaacgcg ttcaagcagg 300

<210> SEQ ID NO 24
<211> LENGTH: 396
<212> TYPE: DNA
<213> ORGANISM: Artificial Sequence
<220> FEATURE:
<223> OTHER INFORMATION: Reverse complementary sequence of the DELLA2
396 bp sequence

<400> SEQUENCE: 24
cagctcgagg aggtcatgtt cagcgcccag gaggacggcc tctcccacct cgcctccgag 60
accgtccact acaacccctc tgacctctcc tcctggctcg agagcatgct gtccgagttt 120
aatcccctgc cgccgccccc cggcgggttc ggcggcggac ccctctccgt ccccgtcgcc 180
gccgcgccgc cgcggccgca gcccgtgggc gacccgttcc tcccccgcgc ggagtcctcc 240
tccatcacca ccgttgactt cggggcggac cagcggatgc agagcagctg cgggaggagc 300
tcgcagatga acgagccgcg cccggagatc ggctcgtccg ggatcgtgtt cgatgaggag 360
tcgtcttccg attacgatct caaggctatt cccggt 396

<210> SEQ ID NO 25
<211> LENGTH: 300
<212> TYPE: DNA
<213> ORGANISM: Artificial Sequence
<220> FEATURE:
<223> OTHER INFORMATION: Reverse complementary sequence of the DELLA3
300 bp sequence

<400> SEQUENCE: 25
aggtgagccc caaggaggcc gtggccgtca actccatcat gcagctccac aggctcctgg 60
gatccgaccc gccccgggac ccccccatcg ggtcggtcct gccctggatc cggagcctga 120
acccgaagat aatgaccgtg gcggagcagg aggcgaacca caaccggccc gggttcctgg 180
accggttcac cgaggcgctg tactactact cgaccctgtt cgactcgctt gaggcggcct 240
gcccggtcca gcccgacaag gccctggccg agatgtacct tcaaagggag atatgcaaca 300

<210> SEQ ID NO 26
<211> LENGTH: 108
<212> TYPE: DNA
<213> ORGANISM: Artificial Sequence
<220> FEATURE:
<223> OTHER INFORMATION: Partial random intron sequence

<400> SEQUENCE: 26
ggctcgaacg agccgactaa ttgtctttaa acgcgcgata taagcgcaca atgggcgcgc 60

-continued caaacgataa actctatcgc tctgtcgcgt gcgtggcatc ttcgcgcg 108

<210> SEQ ID NO 27
<211> LENGTH: 18
<212> TYPE: DNA
<213> ORGANISM: Artificial Sequence
<220> FEATURE:
<223> OTHER INFORMATION: Forward primer

<400> SEQUENCE: 27
gtgacgatgg tggaacag 18

<210> SEQ ID NO 28
<211> LENGTH: 18
<212> TYPE: DNA
<213> ORGANISM: Artificial Sequence
<220> FEATURE:
<223> OTHER INFORMATION: Reverse primer

<400> SEQUENCE: 28
catgctcgcc tgcttgaa 18

<210> SEQ ID NO 29
<211> LENGTH: 18
<212> TYPE: DNA
<213> ORGANISM: Artificial Sequence
<220> FEATURE:
<223> OTHER INFORMATION: Forward primer

<400> SEQUENCE: 29
ccccggacaa ctccgacc 18

<210> SEQ ID NO 30
<211> LENGTH: 16
<212> TYPE: DNA
<213> ORGANISM: Artificial Sequence
<220> FEATURE:
<223> OTHER INFORMATION: Reverse primer

<400> SEQUENCE: 30
cggtccacga agaccg 16

<210> SEQ ID NO 31
<211> LENGTH: 21
<212> TYPE: DNA
<213> ORGANISM: Artificial Sequence
<220> FEATURE:
<223> OTHER INFORMATION: Forward primer

<400> SEQUENCE: 31
cctgaacccg aagataatga c 21

<210> SEQ ID NO 32
<211> LENGTH: 19
<212> TYPE: DNA
<213> ORGANISM: Artificial Sequence
<220> FEATURE:
<223> OTHER INFORMATION: Reverse primer

<400> SEQUENCE: 32
atgctggctt gcttgaacg 19

<210> SEQ ID NO 33
<211> LENGTH: 23
<212> TYPE: DNA
<213> ORGANISM: Artificial Sequence

```
<220> FEATURE:
<223> OTHER INFORMATION: Forward primer

<400> SEQUENCE: 33

cgaacgagcc gactaattgt ctt                                        23


<210> SEQ ID NO 34
<211> LENGTH: 18
<212> TYPE: DNA
<213> ORGANISM: Artificial Sequence
<220> FEATURE:
<223> OTHER INFORMATION: Reverse primer

<400> SEQUENCE: 34

cgcgcgaaga tgccacgc                                              18


<210> SEQ ID NO 35
<211> LENGTH: 20
<212> TYPE: DNA
<213> ORGANISM: Artificial Sequence
<220> FEATURE:
<223> OTHER INFORMATION: Forward primer

<400> SEQUENCE: 35

agcttagccg atctcgatgc                                            20


<210> SEQ ID NO 36
<211> LENGTH: 20
<212> TYPE: DNA
<213> ORGANISM: Artificial Sequence
<220> FEATURE:
<223> OTHER INFORMATION: Reverse primer

<400> SEQUENCE: 36

tccacacgat aaccttggcc                                            20


<210> SEQ ID NO 37
<211> LENGTH: 20
<212> TYPE: DNA
<213> ORGANISM: Artificial Sequence
<220> FEATURE:
<223> OTHER INFORMATION: Forward primer

<400> SEQUENCE: 37

agaaggtcct tcaatggcgg                                            20


<210> SEQ ID NO 38
<211> LENGTH: 20
<212> TYPE: DNA
<213> ORGANISM: Artificial Sequence
<220> FEATURE:
<223> OTHER INFORMATION: Reverse primer

<400> SEQUENCE: 38

aacgcagaaa gacccggaat                                            20


<210> SEQ ID NO 39
<211> LENGTH: 20
<212> TYPE: DNA
<213> ORGANISM: Artificial Sequence
<220> FEATURE:
<223> OTHER INFORMATION: Forward primer

<400> SEQUENCE: 39

gtgcaacgac atcctccaga                                            20
```

<210> SEQ ID NO 40
<211> LENGTH: 20
<212> TYPE: DNA
<213> ORGANISM: Artificial Sequence
<220> FEATURE:
<223> OTHER INFORMATION: Reverse primer

<400> SEQUENCE: 40
gcgaaggctt caagaatcgc 20

<210> SEQ ID NO 41
<211> LENGTH: 914
<212> TYPE: DNA
<213> ORGANISM: Artificial Sequence
<220> FEATURE:
<223> OTHER INFORMATION: Constitutive promoter

<400> SEQUENCE: 41
agattagcct tttcaatttc agaaagaatg ctaacccaca gatggttaga gaggcttacg 60
cagcaggtct catcaagacg atctacccga gcaataatct ccaggaaatc aaataccttc 120
ccaagaaggt taaagatgca gtcaaaagat tcaggactaa ctgcatcaag aacacagaga 180
aagatatatt tctcaagatc agaagtacta ttccagtatg gacgattcaa ggcttgcttc 240
acaaaccaag gcaagtaata gagattggag tctctaaaaa ggtagttccc actgaatcaa 300
aggccatgga gtcaaagatt caaatagagg acctaacaga actcgccgta aagactggcg 360
aacagttcat acagagtctc ttacgactca atgacaagaa gaaaatcttc gtcaacatgg 420
tggagcacga cacacttgtc tactccaaaa atatcaaaga tacagtctca gaagaccaaa 480
gggcaattga gacttttcaa caaagggtaa tatccggaaa cctcctcgga ttccattgcc 540
cagctatctg tcactttatt gtgaagatag tggaaaagga aggtggctcc tacaaatgcc 600
atcattgcga taaaggaaag gccatcgttg aagatgcctc tgccgacagt ggtcccaaag 660
atggaccccc acccacgagg agcatcgtgg aaaaagaaga cgttccaacc acgtcttcaa 720
agcaagtgga ttgatgtgat atctccactg acgtaaggga tgacgcacaa tcccactatc 780
cttcgcaaga cccttcctct atataaggaa gttcatttca tttggagaga acacggggga 840
ctctagatat ttttacaaca attaccaaca acaacaaaca acaaacaaca ttacaattac 900
tatttacaat taca 914

<210> SEQ ID NO 42
<211> LENGTH: 301
<212> TYPE: DNA
<213> ORGANISM: Artificial Sequence
<220> FEATURE:
<223> OTHER INFORMATION: Constitutive promoter

<400> SEQUENCE: 42
tttacagtaa gaactgataa caaaaatttt acttatttcc ttagaattaa tcttaaaggt 60
gatagtaaac aaggacgatt agtccgttgg caaaattggt tcagcaagta tcaatttgat 120
gtcgaacatc ttgaaggtgt aaaaaacgtt ttagcagatt gcctcacgag agattttaat 180
gcttaaaaac gtaagcgctg acgtatgatt tcaaaaaacg cagctataaa agaagccctc 240
cagcttcaaa gttttcatca acacaaattc taaaaacaaa attttttaga gagggggagt 300
g 301

<210> SEQ ID NO 43
<211> LENGTH: 1501

<212> TYPE: DNA
<213> ORGANISM: Artificial Sequence
<220> FEATURE:
<223> OTHER INFORMATION: Green tissue promoter

<400> SEQUENCE: 43
tgcgttatac taaagatatt cagatcaatc tatgtcaatc tattcacgaa aacccggaga 60
gtctaatgag gagagttgca tcttggcaat atagttttta agaatggata tccagatccc 120
tacgaactgg attcacacag tcactgctgt aagctctggt ttttttagc ttaggaagca 180 ggttatgatc aaacatgatt aaaccatcgc gtgtttgcca gccatcagaa atggaaaggc 240
gaatgttgtt atagtgatgg acagatcatg ctgagatgat tgattatgaa tcttactgat 300
gactgtcatt tatgttatcg cactctgtgt gcgtgggtgt gtgttatgag taatatcaaa 360
ttaaccagac gataggtgtt gaagattagc tgttgggcca ccgtggcgaa aggtgtctta 420
tacaagccat cggcagtgac gcagaactgt agagaaccgc tctaacaagt cttcgaatgc 480
attcttttaa tgtacagcac gacatgaagg gggttcgagt gtagcgaaca gttcgtgcga 540
gaaagatcat tttcaatagc ataaaagagt ctgctttctg ctgcaaacat ggaaagaact 600
tacatttcaa tcattgagga gaagattata acaaatccta aatggttgag attttagtta 660
gtccattcga actaaagtgg cgaagatgtc agtttttcaa gtggatgata tttctcatgt 720
atgttccgca gaggcaatca ccttgtttgt aactagacat ctagagaacc taacaaggat 780
tgatgggggt gaggtgaaat gtctgtttcc tctttaatat ggatccagcg atgccttaca 840
gagcggatgg atggcactgg caagtcttaa tccttagctc gaatgtttga ttggtaacag 900
atgccttttc tttcttttca atcacagctg acaaatgcaa atatctaaaa ccattggttg 960
tttggtgctt gcaagtctgg attaccccac tttatgtttc acctttcaat aatgaataac 1020
aaggtactcg ggaaaaaaag gaaagggaaa ttcgcacaac caaagttgct atgcagaagt 1080
caactcaatc ctaatcaagt tgatgagagt gttgggccct attttctgca gcaaacatga 1140
atctcgattc atctccctcg caaaagataa ggaagctgca aaagctttcc tcctaagttt 1200
gttggcaagc aaattgattt tgtaccagaa ataaatacaa agtgaaaccc aagcaatcac 1260
gcatggcctg atttgtgcca tgtccatttg atctccctct actatttttc ctgctttctc 1320
aagcaaacta gttgctgtaa cagtgaatga tccccggct ctctctctct ctctctctct 1380
ctccatttat tccatccatg tttttgcttt tcgcacaaca cttatcattg aggtgctaac 1440
tactgaattc ccctaactaa aaattggaac ctctcaccta atttcatttt ctcccacttt 1500
g 1501

<210> SEQ ID NO 44
<211> LENGTH: 1149
<212> TYPE: DNA
<213> ORGANISM: Artificial Sequence
<220> FEATURE:
<223> OTHER INFORMATION: Root promoter

<400> SEQUENCE: 44
gccggctgat catgtttatt cttcgctaat gaaaaatatt tagctctcaa gggaccgtca 60
attcaggatc gtgaagttac gtgcgctagt aaagttcatc gactagtagt agatgcggat 120
gacaagtaaa tctacacaag cgagacatag gcaagtcgtt tcaacctcct atcccattca 180
taattaatga aatgagatct tctaaaacga gtcatcgcag tctgttcttc tatctactaa 240
ccatatgatg tttgctttaa taggcaagtc attccctcac tctgcatgac tttcataaat 300

```
ttttcaccgt ctctgtgtta catttcttta tcatagagca ttaagactag atactgagat    360

aggcaaacta gataccttca ttatgccccc gaagatgaag ccgagataaa gaaattaact    420

tgacatgaat cgggatggca aacctctaag aacagtgggg gcaaggttgg gcaactcgcc    480

cggcccgctc tacttcattc cattccattc cattccatta ccattccatt accattacca    540

ttaccattcc cattccccat atcttcatga aaggttggtg gacaatagtg gtgcttatct    600

cgatcgtacc tttccgctat tttattcatg caaatagccc ttcggcgcgt ccattctcat    660

gtcacgagga aaatgacata aggacatgat tagggtcgat ggtcctttgc ttccgcgaat    720

tattccctct aaaaccgcat ttaataatct cccggaagag cgacagggac tcgcttgtct    780

cgttgcacgt aaattactag ttaagctggt tgtccttatg cccataatcg cccattatta    840

cacatttaag aattcatcgg cggttggtcg gcgcccaacc accgcgctcc actgcatccc    900

cggtcccaat gggcggtgcc ggctgtgccc tcctcgtcca tctctagcta atatatactc    960

gaattagcct gataaaagat taaggagatg gattaaaata agaaagccac tattcgaaag   1020

gatgccttta gggcgagtat atatgcgcgt cttgttcgcc ggacttgacg cacaagctca   1080

ctgcgaagca tagctaagcg agttctcttt ctaaaagtgg ttgattctag ttctttcgat   1140

cgagcaaac                                                           1149


<210> SEQ ID NO 45
<211> LENGTH: 253
<212> TYPE: DNA
<213> ORGANISM: Artificial Sequence
<220> FEATURE:
<223> OTHER INFORMATION: Terminator

<400> SEQUENCE: 45

gatcgttcaa acatttggca ataaagtttc ttaagattga atcctgttgc cggtcttgcg     60

atgattatca tataatttct gttgaattac gttaagcatg taataattaa catgtaatgc    120

atgacgttat ttatgagatg ggtttttatg attagagtcc cgcaattata catttaatac    180

gcgatagaaa acaaaatata gcgcgcaaac taggataaat tatcgcgcgc ggtgtcatct    240

atgttactag atc                                                       253


<210> SEQ ID NO 46
<211> LENGTH: 607
<212> TYPE: PRT
<213> ORGANISM: Populus balsamifera subsp. trichocarpa

<400> SEQUENCE: 46

Met Lys Arg Asp His Gln Glu Thr Ile Gly Gly Gly Ile Gly Asn Arg
1               5                   10                  15

Ala Glu Ser Ser Ser Ser Ser Met Glu Thr Gly Lys Gly Lys Ser Trp
            20                  25                  30

Val Glu Asp Asp Gln Asp Ala Gly Gly Met Asp Glu Leu Leu Ala Val
        35                  40                  45

Leu Gly Tyr Lys Ile Lys Ser Ser Asp Met Ala Asp Val Ala Gln Lys
    50                  55                  60

Leu Glu Gln Leu Glu Met Val Leu Gly Ser Glu Asp Gly Ile Ser His
65                  70                  75                  80

Leu Ala Ser Asp Thr Val His Tyr Asn Pro Ser Asp Leu Ser Gly Trp
                85                  90                  95

Val Gln Ser Met Leu Ser Glu Phe Asn Asn Leu Pro Ser Thr Asp Leu
            100                 105                 110
```

-continued

```
Asp Ser Ser Ile Leu Leu Ser Asn Asn Arg Asp Ser Leu Leu Gly Gln
        115                 120                 125

Pro Ser Thr Ile Thr Pro Leu Asp Phe Pro Ser Asn Ser Gln Ser Lys
    130                 135                 140

Val Phe Ala Asp Asp Ser Glu Tyr Asp Leu Arg Ala Ile Pro Gly Val
145                 150                 155                 160

Ala Ala Tyr Pro Gln Gln Glu Leu Asp Lys Ser Asn Asp Arg Lys Arg
                165                 170                 175

Met Lys Leu Thr Pro Ile Gly Ser Asn Ile Ala Pro Ala Pro Ser Val
            180                 185                 190

Asn Ser Leu Gln Ser Pro Thr Ala Ser Ser Thr Ser Ser Ser Ser Pro
        195                 200                 205

Gln Ala Met Ala Val Ser Gly Thr Leu Ser Glu Pro Thr Arg Pro Val
    210                 215                 220

Val Leu Val Asp Ser Gln Glu Thr Gly Val Arg Leu Val His Thr Leu
225                 230                 235                 240

Leu Ala Cys Ala Glu Ala Ile Gln Gln Glu Asn Leu Lys Leu Ala Asp
                245                 250                 255

Ala Leu Val Lys His Ile Gly Leu Leu Ala Ala Ser Gln Thr Gly Ala
            260                 265                 270

Met Arg Lys Val Ala Thr Tyr Phe Ala Glu Ala Leu Ala Arg Arg Ile
        275                 280                 285

Tyr Lys Ile Phe Pro Gln Asp Tyr Cys Leu Asp Ser Ser Cys Ser Asp
    290                 295                 300

Thr Leu Glu Met His Phe Tyr Glu Thr Cys Pro Tyr Leu Lys Phe Ala
305                 310                 315                 320

His Phe Thr Ala Asn Gln Ala Ile Leu Glu Ala Phe Ala Asn Ala Ser
                325                 330                 335

Arg Val His Val Ile Asp Phe Gly Leu Lys Gln Gly Met Gln Trp Pro
            340                 345                 350

Ala Leu Met Gln Ala Leu Ala Leu Arg Pro Gly Gly Pro Pro Ala Phe
        355                 360                 365

Arg Leu Thr Gly Ile Gly Pro Pro Gln Pro Asp Asn Thr Asp Ala Leu
    370                 375                 380

Gln Gln Val Gly Trp Lys Leu Ala Gln Leu Ala Gln Thr Ile Gly Val
385                 390                 395                 400

Glu Phe Glu Phe Arg Gly Phe Val Ala Asn Ser Leu Ala Asp Leu Asp
                405                 410                 415

Ala Glu Met Leu Gly Leu Leu Pro Pro Glu Val Glu Ala Val Ala Val
            420                 425                 430

Asn Ser Val Phe Glu Leu His Arg Leu Leu Gly Arg Pro Gly Gly Ile
        435                 440                 445

Asp Lys Val Leu Glu Ser Ile Lys Ala Met Arg Pro Lys Ile Val Thr
    450                 455                 460

Ile Val Glu Gln Glu Ala Asn His Asn Gly Pro Val Phe Leu Asp Arg
465                 470                 475                 480

Phe Thr Glu Ala Leu His Tyr Tyr Ser Ser Leu Phe Asp Ser Leu Glu
                485                 490                 495

Gly Ser Gly Leu Thr Pro Pro Ser Gln Asp Leu Val Met Ser Glu Leu
            500                 505                 510

Tyr Leu Gly Arg His Ile Cys Asn Val Val Ala Cys Glu Gly Ala Asp
        515                 520                 525

Arg Val Glu Arg His Glu Thr Leu Ala Gln Trp Arg Thr Arg Phe Asp
```

```
    530                 535                 540

Ser Ala Gly Phe Asp Pro Val His Leu Gly Ser Asn Ala Phe Lys Gln
545                 550                 555                 560

Ala Ser Met Leu Leu Ala Leu Phe Ala Gly Gly Asp Gly Tyr Arg Val
                565                 570                 575

Glu Glu Asn Asn Gly Cys Leu Met Leu Gly Trp His Thr Arg Pro Leu
            580                 585                 590

Ile Ala Thr Ser Ala Trp Gln Leu Ala Ala Gly Asp Ser Gln Gln
        595                 600                 605


<210> SEQ ID NO 47
<211> LENGTH: 600
<212> TYPE: PRT
<213> ORGANISM: Populus balsamifera subsp. trichocarpa

<400> SEQUENCE: 47

Met Lys Arg Glu His Pro Asn Leu His Pro Gln Gln Ile Ser Asp Pro
1               5                   10                  15

Ser Thr Leu Ala Ala Ala Gly Tyr Ser Thr Ser Thr Ser Ala Met Ala
            20                  25                  30

Pro His Asn Gly Lys Ala Lys Ile Trp Glu Glu Gly Glu Gly His Gln
        35                  40                  45

Ala Asp Gly Gly Met Asp Glu Leu Leu Ala Val Leu Gly Tyr Lys Val
    50                  55                  60

Arg Ser Ser Asp Met Ala Glu Val Ala Gln Lys Leu Glu Gln Leu Glu
65                  70                  75                  80

Glu Val Met Gly His Ala Gln Glu Asp Gly Leu Ser His Leu Ala Ser
                85                  90                  95

Asp Ser Val His Tyr Asn Pro Ser Asp Leu Ser Thr Trp Leu Glu Ser
            100                 105                 110

Met Ile Ser Glu Leu Asn Pro Asn Leu Asn Phe Asp Pro Ser Ala Asp
        115                 120                 125

Ser Leu Leu Ala Pro Ala Glu Ser Ser Thr Ile Thr Ser Ile Asp Phe
    130                 135                 140

Ser Asp His Lys His His Gln Gln Gln Lys Leu Phe Glu Glu Ser Ser
145                 150                 155                 160

Ser Ser Asp Tyr Asp Leu Lys Val Ile Pro Gly Lys Ala Val Phe Ser
                165                 170                 175

Gln Thr Gln Ile Asp Ser Arg Glu Ser Lys Arg Leu Lys Thr Asp Leu
            180                 185                 190

Tyr Gln Thr Ser Ser Ser Ser Ser Leu Ser Ser Ala Thr Thr Leu Gly
        195                 200                 205

Ser Phe Gly Ile Ser Thr Glu Ser Thr Arg Pro Val Val Leu Val Asp
    210                 215                 220

Ser Gln Glu Asn Gly Ile Arg Leu Val His Leu Leu Met Ala Cys Ala
225                 230                 235                 240

Glu Ala Val Gln Glu Ser Asn Phe Thr Leu Ala Glu Ala Leu Val Lys
                245                 250                 255

Gln Ile Gly Phe Leu Ala Val Ser Gln Ala Gly Val Met Arg Lys Val
            260                 265                 270

Ala Thr Tyr Phe Ala Glu Ala Leu Ala Arg Arg Ile Tyr Lys Leu Cys
        275                 280                 285

Pro Gln Asn Ser Thr Asp His Ser Leu Ser Asp Ile Leu Gln Ile His
    290                 295                 300
```

```
Phe Tyr Glu Thr Cys Pro Tyr Leu Lys Phe Ala His Phe Thr Ala Asn
305                 310                 315                 320

Gln Ala Ile Leu Glu Ala Phe Glu Gly Lys Lys Arg Val His Val Ile
                325                 330                 335

Asp Phe Ser Met Asn Gln Gly Met Gln Trp Pro Ala Leu Met Gln Ala
            340                 345                 350

Leu Ala Val Arg Pro Gly Gly Pro Pro Ala Phe Arg Leu Thr Gly Ile
        355                 360                 365

Gly Pro Pro Ala His Asp Asn Thr Asp His Leu Gln Glu Val Gly Trp
    370                 375                 380

Lys Leu Ala Gln Leu Ala Glu Thr Ile His Val Glu Phe Glu Tyr Arg
385                 390                 395                 400

Gly Phe Val Ala Asn Ser Leu Ala Asp Leu Asp Ala Ser Met Leu Glu
                405                 410                 415

Leu Arg Pro Thr Glu Ser Val Ala Val Asn Ser Val Phe Glu Leu His
            420                 425                 430

Lys Leu Leu Ser Arg Pro Gly Ala Ile Glu Lys Val Leu Ser Val Val
        435                 440                 445

Lys Gln Met Lys Pro Glu Ile Val Thr Val Val Glu Gln Glu Ala Asn
    450                 455                 460

His Asn Gly Pro Ile Phe Leu Asp Arg Phe Thr Glu Ser Leu His Tyr
465                 470                 475                 480

Tyr Ser Thr Leu Phe Asp Ser Leu Glu Gly Ser Val Ser Thr Gln Asp
                485                 490                 495

Lys Ile Met Ser Glu Val Tyr Leu Gly Lys Gln Ile Cys Asn Val Val
            500                 505                 510

Ala Cys Glu Gly Pro Asp Arg Val Glu Arg His Glu Thr Leu Thr Gln
        515                 520                 525

Trp Arg Thr Arg Leu Gly Ser Ala Gly Phe Ala Pro Val His Leu Gly
    530                 535                 540

Ser Asn Ala Phe Lys Gln Ala Ser Met Leu Leu Ala Leu Phe Ala Gly
545                 550                 555                 560

Gly Asp Gly Tyr Arg Val Glu Glu Asn Asn Gly Cys Leu Met Leu Gly
                565                 570                 575

Trp His Thr Arg Pro Leu Ile Ala Thr Ser Ala Trp Arg Leu Asn Thr
            580                 585                 590

Asn Gln Pro Val Val Gly Ala Ala
        595                 600
```

<210> SEQ ID NO 48
<211> LENGTH: 602
<212> TYPE: PRT
<213> ORGANISM: Populus balsamifera subsp. trichocarpa

<400> SEQUENCE: 48

```
Met Lys Arg Glu His Ser Asn Leu His Pro Gln Gln Leu Thr Asn Pro
1               5                   10                  15

Ser Ser Leu Ala Ala Gly Gly Tyr Ser Leu Thr Ser Thr Gly Thr Met
            20                  25                  30

Thr Ser Asn Asn Gly Lys Ala Lys Thr Trp Glu Glu Glu Lys Gly Arg
        35                  40                  45

Gln Ala Asp Gly Gly Met Asp Glu Leu Leu Ala Val Leu Gly Tyr Lys
    50                  55                  60

Val Arg Ser Ser Asp Met Ala Glu Val Ala Gln Lys Leu Glu Gln Leu
65                  70                  75                  80
```

```
Glu Glu Val Met Gly His Ala Gln Glu Asp Gly Leu Ser His Leu Ala
                85                  90                  95

Ser Asp Ser Val His Tyr Asn Pro Ser Asp Leu Ser Thr Trp Leu Glu
            100                 105                 110

Ser Met Leu Ser Glu Leu Asn Pro Asn His His Phe Asp Leu Ser Ala
        115                 120                 125

Asp Ser Leu Leu Ala Pro Ala Glu Ser Ser Thr Val Thr Ser Ile Asp
    130                 135                 140

Phe Thr Asp Arg Lys His His Gln Gln Pro Lys Leu Phe Glu Glu Ser
145                 150                 155                 160

Ser Ser Ser Glu Tyr Asp Leu Lys Val Ile Pro Gly Lys Ala Val Phe
                165                 170                 175

Ser Pro Thr Gln Ile Asp Ser Arg Glu Ser Lys Arg Leu Lys Thr Asp
            180                 185                 190

Leu Tyr Gln Thr Ser Ser Ser Pro Ser Ser Ser Ser Thr Thr Leu Gly
        195                 200                 205

Ser Leu Val Ala Ser Thr Glu Ser Thr Arg Pro Val Val Leu Val Asp
    210                 215                 220

Ser Gln Glu Asn Gly Val Arg Leu Val His Leu Leu Met Ala Cys Ala
225                 230                 235                 240

Glu Ala Val Gln Glu Asn Asn Leu Asn Leu Ala Glu Ala Leu Val Lys
                245                 250                 255

Gln Ile Gly Phe Leu Ala Val Ser Gln Ala Gly Ala Met Arg Lys Val
            260                 265                 270

Ala Thr Tyr Phe Ala Glu Ala Leu Ala Arg Arg Ile Tyr Lys Leu Tyr
        275                 280                 285

Pro Gln Asn Ser Thr Asp His Ser Leu Ser Asp Ile Leu Gln Ile His
    290                 295                 300

Phe Tyr Glu Thr Cys Pro Tyr Leu Lys Phe Ala His Phe Thr Ala Asn
305                 310                 315                 320

Gln Ala Ile Leu Glu Ala Phe Glu Gly Lys Lys Arg Val His Val Ile
                325                 330                 335

Asp Phe Ser Met Asn Gln Gly Met Gln Trp Pro Ala Leu Met Gln Ala
            340                 345                 350

Leu Ala Leu Arg Pro Gly Gly Pro Pro Ala Phe Arg Leu Thr Gly Ile
        355                 360                 365

Gly Pro Pro Ala His Asp Asn Thr Asp Gln Leu Gln Glu Val Gly Trp
    370                 375                 380

Lys Leu Ala Gln Leu Ala Glu Thr Ile His Val Glu Phe Glu Tyr Arg
385                 390                 395                 400

Gly Phe Val Ala Asn Ser Leu Ala Asp Leu Asp Ala Ser Met Leu Glu
                405                 410                 415

Leu Arg Pro Thr Glu Phe Glu Ser Val Ala Val Asn Ser Ile Phe Glu
            420                 425                 430

Phe His Lys Leu Leu Ala Ile Pro Gly Ala Met Lys Lys Val Leu Ser
        435                 440                 445

Val Val Lys Gln Met Lys Pro Glu Ile Val Thr Val Val Glu Gln Glu
    450                 455                 460

Ala Asn His Asn Gly Pro Val Phe Leu Asp Arg Phe Thr Glu Ser Leu
465                 470                 475                 480

His Tyr Tyr Ser Thr Leu Phe Asp Ser Leu Glu Gly Ser Val Ser Thr
                485                 490                 495
```

Gln Asp Lys Val Met Ser Glu Val Tyr Leu Ala Lys Gln Ile Cys Asn
500 505 510

Val Val Ala Cys Glu Gly Ser Ser Arg Val Glu Arg His Glu Thr Leu
515 520 525

Thr Gln Trp Arg Thr Arg Leu Ser Ser Ala Gly Phe Ala Pro Val His
530 535 540

Leu Gly Ser Asn Ala Phe Lys Gln Ala Ser Met Leu Leu Ala Leu Phe
545 550 555 560

Ala Gly Gly Asp Gly Tyr Arg Val Glu Glu Asn Asn Gly Cys Leu Met
565 570 575

Leu Gly Trp His Thr Arg Pro Leu Ile Ala Thr Ser Ala Trp Arg Val
580 585 590

Asn Asn His His Pro Val Gly Gly Ala Ala
595 600

<210> SEQ ID NO 49
<211> LENGTH: 619
<212> TYPE: PRT
<213> ORGANISM: Populus balsamifera subsp. trichocarpa

<400> SEQUENCE: 49

Met Lys Arg Asp His Gln Glu Thr Ile Gly Gly Ala Gly Asn Ser Ile
1 5 10 15

Gly Asn Lys Ala Glu Ser Ser Ser Ser Ser Met Ala Thr Gly Lys Gly
20 25 30

Lys Leu Trp Val Glu Asp Asp Gln Asp Ala Gly Gly Met Asp Glu Leu
35 40 45

Leu Ala Val Leu Gly Tyr Lys Ile Lys Ser Ser Glu Met Ala Asp Val
50 55 60

Ala Gln Lys Leu Glu Gln Leu Glu Met Val Leu Gly Ser Glu Asp Gly
65 70 75 80

Ile Ser His Leu Ala Ser Asp Thr Val His Tyr Asn Pro Ser Asp Leu
85 90 95

Ser Gly Trp Val Gln Ser Met Leu Ser Glu Leu Asn Asn Leu Pro Ser
100 105 110

Ser Asp Leu Asp Ser Ser Thr Leu Leu Ser Asn Asn Gln Asp Ser Asn
115 120 125

Pro Ser Thr Met Thr Ser Leu Asp Phe Pro Asn Asn Ser Gln Ser Lys
130 135 140

Ala Phe Val Asp Asp Ser Glu Tyr Asp Leu Arg Ala Ile Pro Gly Val
145 150 155 160

Ala Ala Tyr Pro Gln Gln Glu Phe Asp Lys Ser Asn Asp Arg Lys Arg
165 170 175

Met Lys Leu Thr Leu Val Gly Ser Asn Thr Ala Pro Thr Leu Ala Val
180 185 190

Asn Ser Leu Gln Ser Ser Asn Ser Ser Cys Thr Pro Ser Ser Pro Gln
195 200 205

Ala Ile Met Ala Val Ser Gly Thr Leu Ser Glu Pro Thr Arg Pro Val
210 215 220

Val Leu Ile Asp Ser Gln Glu Thr Gly Val Arg Leu Val His Thr Leu
225 230 235 240

Leu Ala Cys Ala Glu Ala Ile Gln Gln Glu Asn Leu Lys Leu Ala Asp
245 250 255

Ala Leu Val Lys His Ile Gly Val Leu Ala Ala Ser Gln Ala Gly Ala
260 265 270

Met Arg Lys Val Ala Thr Tyr Phe Ala Glu Ala Leu Ala Arg Arg Ile
275 280 285

Tyr Lys Ile Phe Pro Gln Asp His Cys Leu Asp Ser Ser Tyr Ser Asp
290 295 300

Thr Leu Glu Met His Phe Tyr Glu Thr Cys Pro Tyr Leu Lys Phe Ala
305 310 315 320

His Phe Thr Ala Asn Gln Ala Ile Leu Glu Ala Phe Ala Asn Ala Ser
325 330 335

Arg Val His Val Ile Asp Phe Gly Leu Lys Gln Gly Met Gln Trp Pro
340 345 350

Ala Leu Met Gln Ala Leu Ala Leu Arg Pro Gly Gly Pro Pro Ala Phe
355 360 365

Arg Leu Thr Gly Ile Gly Pro Pro Gln Pro Asp Asn Thr Asp Ala Leu
370 375 380

Gln Gln Val Gly Trp Lys Leu Ala Gln Leu Ala Gln Thr Ile Gly Val
385 390 395 400

Glu Phe Glu Phe Arg Gly Phe Val Ala Ser Ser Leu Ala Asp Leu Glu
405 410 415

Ala Glu Met Leu Asp Leu Arg Pro Pro Glu Val Glu Ala Val Ala Val
420 425 430

Asn Ser Val Phe Glu Leu His Arg Leu Leu Asp Arg Pro Gly Gly Ile
435 440 445

Asp Lys Val Leu Gly Ser Ile Lys Ala Met Arg Pro Lys Ile Val Thr
450 455 460

Ile Val Glu Gln Glu Ala Asn His Asn Gly Pro Val Phe Leu Asp Arg
465 470 475 480

Phe Thr Glu Ala Leu His Tyr Tyr Ser Ser Leu Phe Asp Ser Leu Glu
485 490 495

Gly Ser Gly Val Thr Pro Thr Ser Gln Asp Leu Val Met Ser Glu Leu
500 505 510

Tyr Leu Gly Arg Gln Ile Cys Asn Val Val Ala Cys Glu Gly Ala Asp
515 520 525

Arg Val Glu Arg His Glu Thr Leu Ala Gln Trp Arg Thr Arg Phe Asp
530 535 540

Ser Ala Gly Phe Asp Pro Val His Leu Gly Ser Asn Ala Phe Lys Gln
545 550 555 560

Ala Ser Met Leu Leu Ala Leu Phe Ala Gly Gly Asp Gly Tyr Arg Val
565 570 575

Glu Glu Asn Asn Gly Cys Leu Met Leu Gly Trp His Thr Arg Pro Leu
580 585 590

Ile Ala Thr Ser Ala Trp Gln Leu Ala Ala Gly Asp Ser Arg Leu Arg
595 600 605

Val Asn Ser Ala Glu Phe Glu Leu Pro Ser Gln
610 615

<210> SEQ ID NO 50
<211> LENGTH: 607
<212> TYPE: PRT
<213> ORGANISM: Populus tremula x Populus tremuloides

<400> SEQUENCE: 50

Met Lys Arg Asp His Gln Glu Thr Ile Gly Gly Gly Ile Gly Asn Arg
1 5 10 15

Gly Glu Ser Ser Ser Ser Ser Met Glu Thr Gly Lys Gly Lys Ser Trp

-continued

```
            20                  25                  30

Val Glu Asp Asp Gln Asp Ala Gly Gly Met Asp Glu Leu Leu Ala Val
        35                  40                  45

Leu Gly Tyr Lys Ile Lys Ser Ser Asp Met Ala Asp Val Ala Gln Lys
    50                  55                  60

Leu Glu Gln Leu Glu Met Ala Leu Gly Ser Glu Asp Gly Ile Ser His
65                  70                  75                  80

Leu Ala Ser Asp Thr Val His Tyr Asn Pro Ser Asp Leu Ser Gly Trp
                85                  90                  95

Val Gln Ser Met Leu Ser Glu Phe Asn Asn Leu Pro Ser Thr Asp Leu
            100                 105                 110

Asp Ser Ser Ile Leu Leu Ser Asn Asn Arg Asp Ser Leu Leu Gly Gln
        115                 120                 125

Pro Ser Thr Ile Thr Pro Leu Asp Phe Pro Ser Asn Ser Gln Ser Lys
    130                 135                 140

Val Phe Ala Asp Asp Ser Glu Tyr Asp Leu Arg Ala Ile Pro Gly Val
145                 150                 155                 160

Ala Ala Tyr Pro Gln Gln Glu Leu Asp Lys Ser Asn Asp Arg Lys Arg
                165                 170                 175

Met Lys Leu Asn Pro Ile Gly Ser Asn Ile Ala Thr Ala Pro Ser Val
            180                 185                 190

Asn Ser Leu Gln Ser Pro Thr Ala Ser Pro Ala Ser Ser Ser Ser Pro
        195                 200                 205

Gln Ala Met Ala Val Ser Gly Thr Leu Ser Glu Ser Thr Arg Pro Val
    210                 215                 220

Val Leu Val Asp Ser Gln Glu Thr Gly Val Arg Leu Val His Thr Leu
225                 230                 235                 240

Leu Gly Cys Ala Glu Ala Ile Gln Gln Glu Asn Leu Lys Leu Ala Asp
                245                 250                 255

Ala Leu Val Lys Gln Ile Gly Leu Leu Ala Ala Ser Gln Thr Gly Ala
            260                 265                 270

Met Arg Lys Val Ala Thr Tyr Phe Ala Glu Ala Leu Ala Arg Arg Ile
        275                 280                 285

Tyr Lys Ile Phe Pro Gln Asp Tyr Cys Leu Asp Ser Ser Cys Ser Asp
    290                 295                 300

Thr Leu Glu Met His Phe Tyr Glu Thr Cys Pro Tyr Leu Lys Phe Ala
305                 310                 315                 320

His Phe Thr Ala Asn Gln Ala Ile Leu Glu Ala Phe Ala Asn Ala Ser
                325                 330                 335

Arg Val His Val Ile Asp Phe Gly Leu Lys Gln Gly Met Gln Trp Pro
            340                 345                 350

Ala Leu Ile Gln Ala Leu Ala Leu Arg Pro Gly Gly Pro Pro Ala Phe
        355                 360                 365

Arg Leu Thr Gly Ile Gly Pro Pro Gln Pro Asp Asn Thr Asp Ala Leu
    370                 375                 380

Gln Gln Val Gly Trp Lys Leu Ala Gln Leu Ala Glu Thr Ile Gly Val
385                 390                 395                 400

Glu Phe Lys Phe Arg Gly Phe Val Ala Asn Ser Leu Ala Asp Leu Asp
                405                 410                 415

Ala Glu Met Leu Gly Leu Leu Pro Pro Glu Val Glu Ala Val Ala Val
            420                 425                 430

Asn Ser Val Phe Glu Leu His Arg Leu Leu Gly Arg Pro Gly Gly Ile
        435                 440                 445
```

```
Asp Lys Val Leu Gly Ser Ile Lys Ala Met Arg Pro Lys Ile Val Thr
    450                 455                 460

Ile Val Glu Gln Glu Ala Asn His Asn Gly Pro Val Phe Leu Asp Arg
465                 470                 475                 480

Phe Thr Glu Ala Leu His Tyr Tyr Ser Thr Leu Phe Asp Ser Leu Glu
                485                 490                 495

Gly Ser Gly Leu Thr Pro Pro Ser Gln Asp Leu Ala Met Ser Glu Leu
            500                 505                 510

Tyr Leu Gly Arg His Ile Cys Asn Val Val Ala Cys Glu Gly Ala Asp
        515                 520                 525

Arg Val Glu Arg His Glu Thr Leu Ala Gln Trp Arg Thr Arg Phe Asp
    530                 535                 540

Ser Ala Gly Phe Asp Pro Val His Leu Gly Ser Asn Ala Phe Lys Gln
545                 550                 555                 560

Ala Ser Met Leu Leu Ala Leu Phe Ala Gly Gly Asp Gly Tyr Arg Val
                565                 570                 575

Glu Glu Asn Asn Gly Cys Leu Met Leu Gly Trp His Thr Arg Pro Leu
            580                 585                 590

Ile Ala Thr Ser Ala Trp Gln Leu Ala Ala Gly Asp Ser Gln Gln
        595                 600                 605


<210> SEQ ID NO 51
<211> LENGTH: 622
<212> TYPE: PRT
<213> ORGANISM: Populus tremula x Populus tremuloides

<400> SEQUENCE: 51

Met Lys Arg Asp His Gln Glu Thr Ile Gly Gly Ala Gly Asn Ser Ile
1               5                   10                  15

Gly Asn Lys Ala Glu Ser Ser Ser Ser Ser Met Thr Thr Gly Lys Gly
            20                  25                  30

Lys Leu Trp Val Glu Asp Asp Gln Asp Ala Gly Gly Met Asp Glu Leu
        35                  40                  45

Leu Ala Val Leu Gly Tyr Lys Ile Lys Ser Ser Glu Met Ala Asp Val
    50                  55                  60

Ala Gln Lys Leu Glu Gln Leu Glu Met Val Leu Gly Ser Glu Asp Gly
65                  70                  75                  80

Ile Ser His Leu Ala Ser Asp Thr Val His Tyr Asn Pro Ser Asp Leu
                85                  90                  95

Ser Gly Trp Val Gln Ser Met Leu Ser Glu Phe Asn Asn Leu Pro Ser
            100                 105                 110

Thr Asp Leu Asp Ser Ser Thr Leu Leu Ser Asn Asn Gln Asp Ser Asn
        115                 120                 125

Pro Ser Thr Met Thr Ser Leu Asp Phe Ser Asn Asn Ser Gln Ser Lys
    130                 135                 140

Ala Phe Val Asp Asp Ser Glu Tyr Asp Leu Arg Ala Ile Pro Gly Val
145                 150                 155                 160

Ala Ala Tyr Pro Gln Gln Glu Phe Asp Lys Ser Asn Asp Arg Lys Arg
                165                 170                 175

Met Lys Leu Thr Leu Ala Gly Ser Asn Thr Ala Pro Ala Pro Ala Leu
            180                 185                 190

Ala Val Asn Ser Leu Gln Ser Ser Ser Ser Ser Cys Thr Pro Ser Ser
        195                 200                 205

Ser Pro Gln Ala Ile Met Ala Val Ser Gly Thr Leu Ser Glu Pro Thr
```

-continued

```
    210                 215                 220

Arg Pro Val Val Leu Ile Asp Ser Gln Glu Thr Gly Val Arg Leu Val
225                 230                 235                 240

His Thr Leu Leu Ala Cys Ala Glu Ala Ile Gln Gln Glu Asn Leu Lys
                245                 250                 255

Leu Ala Asp Ala Leu Val Lys His Ile Gly Val Leu Ala Ala Ser Gln
            260                 265                 270

Ala Gly Ala Met Arg Lys Val Ala Thr Tyr Phe Ala Glu Ala Leu Ala
        275                 280                 285

Arg Arg Ile Tyr Lys Ile Phe Pro Gln Asn His Cys Leu Asp Ser Ser
    290                 295                 300

Tyr Ser Asp Thr Leu Glu Met His Phe Tyr Glu Thr Cys Pro Tyr Leu
305                 310                 315                 320

Lys Phe Ala His Phe Thr Ala Asn Gln Ala Ile Leu Glu Ala Phe Ala
                325                 330                 335

Asn Ala Ser Arg Val His Val Ile Asp Phe Gly Leu Lys Gln Gly Met
            340                 345                 350

Gln Trp Pro Ala Leu Met Gln Ala Leu Ala Leu Arg Pro Gly Gly Pro
        355                 360                 365

Pro Ala Phe Arg Leu Thr Gly Ile Gly Pro Pro Gln Pro Asp Asn Thr
    370                 375                 380

Asp Ala Leu Gln Gln Val Gly Trp Lys Leu Ala Gln Leu Ala Arg Thr
385                 390                 395                 400

Ile Gly Val Glu Phe Glu Phe Arg Gly Phe Val Ala Ser Ser Leu Ala
                405                 410                 415

Asp Leu Glu Ala Glu Met Leu Asp Leu Arg Pro Pro Glu Val Glu Ala
            420                 425                 430

Val Ala Val Asn Ser Val Phe Glu Leu His Arg Leu Leu Asp Arg Pro
        435                 440                 445

Gly Gly Ile Asp Lys Val Leu Gly Ser Ile Lys Ala Met Arg Pro Lys
    450                 455                 460

Ile Val Thr Ile Val Glu Gln Glu Ala Asn His Asn Gly Pro Val Phe
465                 470                 475                 480

Leu Asp Arg Phe Thr Glu Ala Leu His Tyr Tyr Ser Ser Leu Phe Asp
                485                 490                 495

Ser Leu Glu Gly Ser Gly Val Thr Pro Thr Ser Gln Asp Leu Val Met
            500                 505                 510

Ser Glu Leu Tyr Leu Gly Arg Gln Ile Cys Asn Val Val Ala Cys Glu
        515                 520                 525

Gly Ala Asp Arg Val Glu Arg His Glu Thr Leu Ala Gln Trp Arg Thr
    530                 535                 540

Arg Phe Asp Ser Ala Gly Phe Asp Pro Val His Leu Gly Ser Asn Ala
545                 550                 555                 560

Phe Lys Gln Ala Ser Met Leu Leu Ala Leu Phe Ala Gly Gly Asp Gly
                565                 570                 575

Tyr Arg Val Glu Glu Asn Asn Gly Cys Leu Met Leu Gly Trp His Thr
            580                 585                 590

Arg Pro Leu Ile Ala Thr Ser Ala Trp Arg Leu Ala Ala Gly Asp Ser
        595                 600                 605

Arg Leu Arg Val Asn Ser Ala Glu Phe Glu Leu Pro Ser Gln
    610                 615                 620
```

<210> SEQ ID NO 52

```
<211> LENGTH: 602
<212> TYPE: PRT
<213> ORGANISM: Populus tremula x Populus tremuloides

<400> SEQUENCE: 52

Met Lys Arg Glu His Pro Asn Leu His His Gln Gln Ile Ser Asp Pro
1               5                   10                  15

Ala Ser Leu Ala Ala Ala Gly Tyr Ser Ala Ser Thr Ser Thr Ser Ala
            20                  25                  30

Met Ala Pro Asn Asn Gly Lys Ala Lys Ile Trp Ala Glu Gly Glu Gly
        35                  40                  45

His Gln Ala Asp Gly Gly Val Asp Glu Leu Leu Ala Val Leu Gly Tyr
    50                  55                  60

Lys Val Arg Ser Ser Asp Met Ala Glu Val Ala Gln Lys Leu Glu Gln
65                  70                  75                  80

Leu Glu Glu Val Met Gly His Ala Gln Glu Asp Gly Leu Ser His Leu
                85                  90                  95

Ala Ser Asp Ser Val His Tyr Asn Pro Ser Asp Leu Ser Thr Trp Leu
            100                 105                 110

Gln Ser Met Ile Ser Glu Leu Asn Pro Asn Leu Asn Phe Asp Pro Ser
        115                 120                 125

Ala Asp Ser Leu Leu Ala Pro Ala Glu Ser Ser Thr Ile Thr Ser Ile
    130                 135                 140

Asp Phe Ser Asp His Lys Tyr His Gln Gln Gln Lys Leu Phe Glu Glu
145                 150                 155                 160

Ser Ser Ser Ser Asp Tyr Asp Leu Lys Val Ile Pro Gly Lys Ala Val
                165                 170                 175

Phe Ser Gln Thr His Ile Asp Ser Arg Glu Ser Lys Arg Leu Lys Thr
            180                 185                 190

Asp Leu Tyr Gln Thr Ser Ser Ser Ser Ser Leu Ser Ser Ala Thr Thr
        195                 200                 205

Leu Gly Ser Phe Gly Ile Ser Thr Glu Ser Ala Arg Pro Val Val Leu
    210                 215                 220

Val Asp Ser Gln Glu Asn Gly Ile Arg Leu Val His Leu Leu Met Ala
225                 230                 235                 240

Cys Ala Glu Ala Val Gln Asp Ser Asn Phe Thr Leu Ala Glu Ala Leu
                245                 250                 255

Val Lys Gln Ile Gly Phe Leu Ala Val Ser Gln Ala Gly Val Met Arg
            260                 265                 270

Lys Val Ala Thr Tyr Phe Ala Glu Ala Leu Ala Arg Arg Ile Tyr Lys
        275                 280                 285

Leu Cys Pro Gln Asn Ser Thr Asp His Ser Leu Ser Glu Ile Leu Gln
    290                 295                 300

Ile His Phe Tyr Glu Thr Cys Pro Tyr Leu Lys Phe Ala His Phe Thr
305                 310                 315                 320

Ala Asn Gln Ala Ile Leu Glu Ala Phe Glu Gly Lys Lys Arg Val His
                325                 330                 335

Val Ile Asp Phe Ser Met Asn Gln Gly Met Gln Trp Pro Ala Leu Met
            340                 345                 350

Gln Ala Leu Ala Leu Arg Pro Gly Gly Pro Pro Ala Phe Arg Leu Thr
        355                 360                 365

Gly Ile Gly Pro Pro Ala His Asp Asn Thr Asp His Leu Gln Glu Val
    370                 375                 380

Gly Trp Lys Leu Ala Gln Leu Ala Glu Thr Ile His Val Glu Phe Glu
```

385 390 395 400

Tyr Arg Gly Phe Val Ala Asn Ser Leu Ala Asp Leu Asp Ala Ser Met
405 410 415

Leu Glu Leu Arg Pro Thr Glu Ser Val Ala Val Asn Ser Val Phe Glu
420 425 430

Leu His Lys Leu Leu Ser Arg Pro Gly Ala Ile Glu Lys Val Leu Ser
435 440 445

Val Val Lys Gln Met Lys Pro Glu Ile Val Thr Val Val Glu Gln Glu
450 455 460

Ala Asn His Asn Gly Pro Ile Phe Leu Asp Arg Phe Thr Glu Ser Leu
465 470 475 480

His Tyr Tyr Ser Thr Leu Phe Asp Ser Leu Glu Gly Ser Val Ser Thr
485 490 495

Gln Asp Lys Ile Met Ser Glu Val Tyr Leu Gly Lys Gln Ile Cys Asn
500 505 510

Val Val Ala Cys Glu Gly Pro Asp Arg Val Glu Arg His Glu Thr Leu
515 520 525

Thr Gln Trp Arg Thr Arg Leu Gly Ser Ala Gly Phe Ala Pro Val His
530 535 540

Leu Gly Ser Asn Ala Phe Lys Gln Ala Ser Met Leu Leu Ala Leu Phe
545 550 555 560

Ala Gly Gly Asp Gly Tyr Arg Val Glu Glu Asn Asn Gly Cys Leu Met
565 570 575

Leu Gly Trp His Thr Arg Pro Leu Ile Ala Thr Ser Ala Trp Arg Leu
580 585 590

Asn Thr Asn Gln Pro Val Val Gly Ala Ala
595 600

<210> SEQ ID NO 53
<211> LENGTH: 566
<212> TYPE: PRT
<213> ORGANISM: Populus tremula x Populus tremuloides

<400> SEQUENCE: 53

Met Lys Arg Glu His Ser Asn Leu His Pro Gln Gln Leu Thr Asn Pro
1 5 10 15

Ser Ser Leu Ala Ala Gly Gly Tyr Ser Phe Thr Ser Thr Gly Thr Met
20 25 30

Thr Ser Asn Asn Gly Lys Ala Thr Thr Trp Glu Glu Glu Lys Gly Arg
35 40 45

Gln Ala Asp Gly Gly Met Asp Glu Leu Leu Ala Val Leu Gly Tyr Lys
50 55 60

Val Arg Ser Ser Asp Met Ala Glu Val Ala Gln Lys Leu Glu Gln Leu
65 70 75 80

Glu Glu Val Met Gly His Ala Gln Glu Asp Gly Leu Ser His Leu Ala
85 90 95

Ser Asp Ser Val His Tyr Asn Pro Ser Asp Leu Ser Thr Trp Leu Glu
100 105 110

Ser Met Leu Ser Glu Leu Asn Pro Asn His His Phe Asp Leu Ser Ala
115 120 125

Asp Ser Leu Leu Gly Pro Ala Glu Ser Ser Thr Val Thr Ser Ile Asp
130 135 140

Phe Thr Asp Arg Lys His His Gln Gln Pro Lys Leu Phe Glu Glu Ser
145 150 155 160

-continued

```
Ser Ser Ser Glu Tyr Asp Leu Lys Val Ile Pro Gly Lys Ala Val Phe
                165                 170                 175

Ser Pro Thr Gln Ile Asp Ser Arg Glu Ser Lys Arg Leu Lys Thr Asp
            180                 185                 190

Leu Tyr Gln Thr Ser Ser Ser Pro Ser Ser Ser Ser Thr Thr Leu Gly
        195                 200                 205

Ser Leu Val Ala Ser Thr Glu Ser Thr Arg Pro Val Val Leu Val Asp
    210                 215                 220

Ser Gln Glu Asn Gly Val Arg Leu Val His Leu Leu Met Ala Cys Ala
225                 230                 235                 240

Glu Ala Val Gln Gly Asp Asn Leu Asn Leu Ala Glu Ala Leu Val Lys
                245                 250                 255

Gln Ile Gly Phe Leu Ala Val Ser Gln Ala Gly Ala Met Arg Lys Val
            260                 265                 270

Ala Thr Tyr Phe Ala Glu Ala Leu Ala Arg Arg Ile Tyr Lys Leu Tyr
        275                 280                 285

Pro Gln Asn Ser Ile Asp His Ser Leu Ser Asp Ile Leu Gln Ile His
    290                 295                 300

Phe Tyr Glu Thr Cys Pro Tyr Leu Lys Phe Ala His Phe Thr Ala Asn
305                 310                 315                 320

Gln Ala Ile Leu Glu Ala Phe Glu Gly Lys Lys Arg Val His Val Ile
                325                 330                 335

Asp Phe Ser Met Asn Gln Gly Met Gln Trp Pro Ala Leu Met Gln Ala
            340                 345                 350

Leu Ala Leu Arg Pro Gly Gly Pro Pro Ala Phe Arg Leu Thr Gly Ile
        355                 360                 365

Gly Pro Pro Ala His Asp Asn Thr Asp Gln Leu Gln Glu Val Gly Trp
    370                 375                 380

Lys Leu Ala Gln Leu Ala Glu Thr Ile His Val Glu Phe Glu Tyr Arg
385                 390                 395                 400

Gly Phe Val Ala Asn Ser Leu Ala Asp Leu Asp Ala Ser Met Leu Glu
                405                 410                 415

Leu Arg Pro Pro Gln Phe Glu Ser Val Ala Val Asn Ser Ile Phe Glu
            420                 425                 430

Phe His Lys Leu Leu Ala Ile Pro Gly Asp Met Lys Lys Val Leu Ser
        435                 440                 445

Val Val Lys Gln Met Lys Pro Glu Ile Val Thr Val Val Glu Gln Glu
    450                 455                 460

Ala Asn His Asn Gly Pro Val Phe Leu Asp Arg Phe Thr Glu Ser Leu
465                 470                 475                 480

His Tyr Tyr Ser Thr Leu Phe Asp Ser Leu Glu Gly Ser Ala Ser Thr
                485                 490                 495

Gln Asp Lys Val Met Ser Glu Val Tyr Leu Ala Lys Gln Ile Cys Asn
            500                 505                 510

Val Val Ala Cys Glu Gly His Ser Arg Val Glu Arg His Glu Thr Leu
        515                 520                 525

Thr Gln Trp Arg Thr Arg Leu Ser Ser Ala Gly Phe Ala Pro Val His
    530                 535                 540

Leu Gly Ser Asn Ala Phe Lys Gln Ala Ser Met Leu Leu Ala Leu Phe
545                 550                 555                 560

Ala Gly Gly Glu Gly Val
                565
```

-continued

<210> SEQ ID NO 54
<211> LENGTH: 632
<212> TYPE: PRT
<213> ORGANISM: Populus tremuloides

<400> SEQUENCE: 54

```
Met Lys Arg Asp His Gln Glu Thr Ile Gly Gly Gly Ile Gly Asn Arg
1               5                   10                  15

Gly Glu Ser Ser Ser Ser Ser Met Glu Thr Gly Lys Gly Lys Ser Trp
            20                  25                  30

Val Glu Asp Asp Gln Asp Ala Gly Gly Met Asp Glu Leu Leu Ala Val
        35                  40                  45

Leu Gly Tyr Lys Ile Lys Ser Ser Asp Met Ala Asp Val Ala Gln Lys
    50                  55                  60

Leu Glu Gln Leu Glu Met Ala Leu Gly Ser Glu Asp Gly Ile Ser His
65                  70                  75                  80

Leu Ala Ser Asp Thr Val His Tyr Asn Pro Ser Asp Leu Ser Gly Trp
                85                  90                  95

Val Gln Ser Met Leu Ser Glu Phe Asn Asn Leu Pro Ser Thr Asp Leu
            100                 105                 110

Asp Ser Ser Ile Leu Leu Ser Asn Asn Arg Asp Ser Leu Leu Gly Gln
        115                 120                 125

Pro Ser Thr Ile Thr Pro Leu Asp Phe Pro Ser Asn Ser Gln Ser Lys
    130                 135                 140

Val Phe Ala Asp Asp Ser Glu Tyr Asp Leu Arg Ala Ile Pro Gly Val
145                 150                 155                 160

Ala Ala Tyr Pro Gln Gln Glu Leu Asp Lys Ser Asn Asp Arg Lys Arg
                165                 170                 175

Met Lys Leu Asn Pro Ile Gly Ser Asn Ile Ala Pro Ala Pro Ser Val
            180                 185                 190

Asn Ser Leu Gln Ser Pro Thr Ala Ser Pro Ala Ser Ser Ser Ser Pro
        195                 200                 205

Gln Ala Met Ala Val Ser Gly Thr Leu Ser Glu Pro Thr Arg Pro Val
    210                 215                 220

Val Leu Val Asp Ser Gln Glu Thr Gly Val Arg Leu Val His Thr Leu
225                 230                 235                 240

Leu Gly Cys Ala Glu Ala Ile Gln Gln Glu Asn Leu Lys Leu Ala Asp
                245                 250                 255

Ala Leu Val Lys Gln Ile Gly Leu Leu Ala Ala Ser Gln Thr Gly Ala
            260                 265                 270

Met Arg Lys Val Ala Thr Tyr Phe Ala Glu Ala Leu Ala Arg Arg Ile
        275                 280                 285

Tyr Lys Ile Phe Pro Gln Asp Tyr Cys Leu Asp Ser Ser Cys Ser Asp
    290                 295                 300

Thr Leu Glu Met His Phe Tyr Glu Thr Cys Pro Tyr Leu Lys Phe Ala
305                 310                 315                 320

His Phe Thr Ala Asn Gln Ala Ile Leu Glu Ala Phe Ala Asn Ala Ser
                325                 330                 335

Arg Val His Val Ile Asp Phe Gly Leu Lys Gln Gly Met Gln Trp Pro
            340                 345                 350

Ala Leu Met Gln Ala Leu Ala Leu Arg Pro Gly Gly Pro Pro Ala Phe
        355                 360                 365

Arg Leu Thr Gly Ile Gly Pro Pro Gln Pro Asp Asn Thr Asp Ala Leu
    370                 375                 380
```

-continued

Gln Gln Val Gly Trp Lys Leu Ala Gln Leu Ala Glu Thr Ile Gly Val
385 390 395 400

Glu Phe Lys Phe Arg Gly Phe Val Ala Asn Ser Leu Ala Asp Leu Asp
405 410 415

Ala Glu Met Leu Gly Leu Leu Pro Pro Glu Val Glu Ala Val Ala Val
420 425 430

Asn Ser Val Phe Glu Leu His Arg Leu Leu Gly Arg Pro Gly Gly Ile
435 440 445

Asp Lys Val Leu Gly Ser Ile Lys Ala Met Arg Pro Lys Ile Val Thr
450 455 460

Ile Val Glu Gln Glu Ala Asn His Asn Gly Pro Val Phe Leu Asp Arg
465 470 475 480

Phe Thr Glu Ala Leu His Tyr Tyr Ser Thr Leu Phe Asp Ser Leu Glu
485 490 495

Gly Ser Gly Leu Thr Pro Pro Ser Gln Asp Leu Ala Met Ser Glu Leu
500 505 510

Tyr Leu Gly Arg His Ile Cys Asn Val Val Ala Cys Glu Gly Ala Asp
515 520 525

Arg Val Glu Arg His Glu Thr Leu Ala Gln Trp Arg Thr Arg Phe Asp
530 535 540

Ser Ala Gly Phe Asp Pro Val His Leu Gly Ser Asn Ala Phe Lys Gln
545 550 555 560

Ala Ser Met Leu Leu Ala Leu Phe Ala Gly Gly Asp Gly Tyr Arg Val
565 570 575

Glu Glu Asn Asn Gly Cys Leu Met Leu Gly Trp His Thr Arg Pro Leu
580 585 590

Ile Ala Thr Ser Ala Trp Gln Leu Ala Ala Gly Asn Gly Gly His Met
595 600 605

Trp Arg Ile Leu Leu Leu Pro Cys His Leu Arg Arg Glu Lys Ile Leu
610 615 620

Thr Ala Leu Ser Ser Ser Arg Arg
625 630

<210> SEQ ID NO 55
<211> LENGTH: 669
<212> TYPE: PRT
<213> ORGANISM: Populus tremuloides

<400> SEQUENCE: 55

Met Lys Arg Asp His Gln Glu Thr Ile Gly Gly Ala Gly Asn Ser Ile
1 5 10 15

Gly Asn Lys Ala Glu Ser Pro Ser Ser Ser Met Thr Thr Gly Lys Gly
20 25 30

Lys Leu Trp Val Glu Asp Asp Gln Asp Ala Gly Gly Met Asp Glu Leu
35 40 45

Leu Ala Val Leu Gly Tyr Lys Ile Lys Ser Ser Glu Met Ala Asp Val
50 55 60

Ala Gln Lys Leu Glu Gln Leu Glu Met Val Leu Gly Ser Glu Asp Gly
65 70 75 80

Ile Ser His Leu Ala Ser Asp Thr Val His Tyr Asn Pro Ser Asp Leu
85 90 95

Ser Gly Trp Val Gln Ser Met Leu Ser Glu Phe Asn Asn Leu Pro Ser
100 105 110

Thr Asp Leu Asp Ser Ser Thr Leu Leu Ser Asn Asn Gln Asp Ser Asn
115 120 125

Pro Ser Thr Met Thr Ser Leu Asp Phe Ser Asn Asn Ser Gln Ser Lys
    130                 135                 140

Ala Phe Val Asp Asp Ser Glu Tyr Asp Leu Arg Ala Ile Pro Gly Val
145                 150                 155                 160

Ala Ala Tyr Pro Gln Gln Glu Phe Asp Lys Ser Asn Asp Arg Lys Arg
                165                 170                 175

Met Lys Leu Thr Leu Val Gly Ser Asn Thr Ala Pro Ala Pro Ala Leu
            180                 185                 190

Ala Val Asn Ser Leu Gln Ser Ser Arg Ser Ser Cys Thr Pro Ser Ser
        195                 200                 205

Ser Pro Gln Ala Ile Met Thr Val Ser Gly Thr Leu Ser Glu Pro Thr
    210                 215                 220

Arg Pro Val Val Leu Ile Asp Ser Gln Glu Thr Gly Val Arg Leu Val
225                 230                 235                 240

His Thr Leu Leu Ala Cys Ala Glu Ala Ile Gln Gln Glu Asn Leu Lys
                245                 250                 255

Leu Ala Asp Ala Leu Val Lys His Ile Gly Val Leu Ala Ala Ser Gln
            260                 265                 270

Ala Gly Ala Met Arg Lys Val Ala Thr Tyr Phe Ala Glu Ala Leu Ala
        275                 280                 285

Arg Arg Ile Tyr Lys Ile Phe Pro Gln Asn His Cys Leu Asp Ser Ser
    290                 295                 300

Tyr Ser Asp Thr Leu Glu Met His Phe Tyr Glu Thr Cys Pro Tyr Leu
305                 310                 315                 320

Lys Phe Ala His Phe Thr Ala Asn Gln Ala Ile Leu Glu Ala Phe Ala
                325                 330                 335

Asn Ala Ser Arg Val His Val Ile Asp Phe Gly Leu Lys Gln Gly Met
            340                 345                 350

Gln Trp Pro Ala Leu Met Gln Ala Leu Ala Leu Arg Pro Gly Gly Pro
        355                 360                 365

Pro Ala Phe Arg Leu Thr Gly Ile Gly Pro Pro Gln Pro Asp Asn Thr
    370                 375                 380

Asp Ala Leu Gln Gln Val Gly Trp Lys Leu Ala Gln Leu Ala Arg Thr
385                 390                 395                 400

Ile Gly Val Glu Phe Glu Phe Arg Gly Phe Val Ala Ser Ser Leu Ala
                405                 410                 415

Asp Leu Glu Ala Glu Met Leu Asp Leu Arg Pro Pro Glu Val Glu Ala
            420                 425                 430

Val Ala Val Asn Ser Val Phe Glu Leu His Arg Leu Leu Asp Arg Pro
        435                 440                 445

Gly Gly Ile Asp Lys Val Leu Gly Ser Ile Lys Ala Met Arg Pro Lys
    450                 455                 460

Ile Val Thr Ile Val Glu Gln Glu Ala Asn His Asn Gly Pro Val Phe
465                 470                 475                 480

Leu Asp Arg Phe Thr Glu Ala Leu His Tyr Tyr Ser Ser Leu Phe Asp
                485                 490                 495

Ser Leu Glu Gly Ser Gly Val Thr Pro Thr Ser Gln Asp Leu Val Met
            500                 505                 510

Ser Glu Leu Tyr Leu Gly Arg Gln Ile Cys Asn Val Val Ala Cys Glu
        515                 520                 525

Gly Ala Asp Arg Val Glu Arg His Glu Thr Leu Ala Gln Trp Arg Thr
    530                 535                 540

Arg Phe Asp Ser Ala Gly Phe Asp Pro Val His Leu Gly Ser Asn Ala
545 550 555 560

Phe Lys Gln Ala Ser Met Leu Leu Ala Leu Phe Ala Gly Gly Asp Gly
565 570 575

Tyr Arg Val Glu Glu Asn Ser Gly Cys Leu Met Leu Gly Trp His Thr
580 585 590

Arg Pro Leu Ile Ala Thr Ser Ala Trp Arg Leu Ala Ala Gly Asp Ser
595 600 605

Arg Leu Arg Val Asn Ser Ala Glu Phe Glu Leu Pro Asn Ser Gln Met
610 615 620

Asp Gln Glu Ser Phe Phe Tyr Leu Leu Leu Ser Gly Cys Pro Arg Phe
625 630 635 640

Leu Ser Ala Cys Ile Phe Phe Gly Leu Ala Phe Asp Ile Ser Ser Leu
645 650 655

Glu Thr Leu Ala Ser Phe Ser Phe Val Thr Thr Ser Ala
660 665

<210> SEQ ID NO 56
<211> LENGTH: 636
<212> TYPE: PRT
<213> ORGANISM: Populus tremuloides

<400> SEQUENCE: 56

Met Lys Arg Glu His Ser Asn Leu His Pro Gln Gln Leu Thr Asn Pro
1 5 10 15

Ser Ser Leu Ala Ala Gly Gly Tyr Ser Phe Thr Ser Thr Gly Thr Met
20 25 30

Thr Ser Asn Asn Gly Lys Ala Thr Thr Trp Glu Glu Glu Lys Gly Arg
35 40 45

Gln Ala Asp Gly Gly Met Asp Glu Leu Leu Ala Val Leu Gly Tyr Lys
50 55 60

Val Lys Ser Ser Asp Met Ala Glu Val Ala Gln Lys Leu Glu Gln Leu
65 70 75 80

Glu Glu Val Met Gly His Ala Gln Glu Asp Gly Leu Ser His Leu Ala
85 90 95

Ser Asp Ser Val His Tyr Asn Pro Ser Asp Leu Ser Thr Trp Leu Glu
100 105 110

Ser Met Leu Ser Glu Leu Asn Pro Asn His His Phe Asp Leu Ser Ala
115 120 125

Glu Ser Leu Leu Gly Pro Ala Glu Ser Ser Thr Val Thr Ser Ile Asp
130 135 140

Phe Thr Asp Arg Lys His His Gln Gln Pro Lys Leu Phe Glu Glu Ser
145 150 155 160

Ser Ser Ser Glu Tyr Asp Leu Lys Val Ile Pro Gly Lys Ala Val Phe
165 170 175

Ser Pro Thr Gln Ile Asp Ser Arg Glu Ser Lys Arg Leu Lys Thr Asp
180 185 190

Leu Tyr Gln Thr Ser Ser Ser Pro Ser Ser Ser Ser Thr Thr Leu Gly
195 200 205

Ser Leu Val Ala Ser Thr Glu Ser Thr Arg Pro Val Val Leu Val Asp
210 215 220

Ser Gln Glu Asn Gly Val Arg Leu Val His Leu Leu Met Ala Cys Ala
225 230 235 240

Glu Ala Val Gln Gly Asp Asn Leu Ser Leu Ala Glu Ala Leu Val Lys
245 250 255

```
Gln Ile Gly Phe Leu Ala Val Ser Gln Ala Gly Ala Met Arg Lys Val
            260                 265                 270

Ala Thr Tyr Phe Ala Glu Ala Leu Ala Arg Arg Ile Tyr Lys Leu Tyr
        275                 280                 285

Pro Gln Asn Ser Ile Asp His Ser Leu Ser Asp Ile Leu Gln Ile His
    290                 295                 300

Phe Tyr Glu Thr Cys Pro Tyr Leu Lys Phe Ala His Phe Thr Ala Asn
305                 310                 315                 320

Gln Ala Ile Leu Glu Ala Phe Glu Gly Lys Lys Arg Val His Val Ile
                325                 330                 335

Asp Phe Ser Met Asn Gln Gly Met Gln Trp Pro Ala Leu Met Gln Ala
            340                 345                 350

Leu Ala Leu Arg Pro Gly Gly Pro Pro Ala Phe Arg Leu Thr Gly Ile
        355                 360                 365

Gly Pro Pro Ala His Asp Asn Thr Asp Gln Leu Gln Glu Val Gly Trp
    370                 375                 380

Lys Leu Ala Gln Leu Ala Glu Thr Ile His Val Glu Phe Glu Tyr Arg
385                 390                 395                 400

Gly Phe Val Ala Asn Ser Leu Ala Asp Leu Asp Ala Ser Met Leu Glu
                405                 410                 415

Leu Arg Pro Pro Gln Phe Glu Ser Val Ala Val Asn Ser Ile Phe Glu
            420                 425                 430

Phe His Lys Leu Leu Ala Ile Pro Gly Asp Met Lys Lys Val Leu Ser
        435                 440                 445

Val Val Lys Gln Met Lys Pro Glu Ile Val Thr Val Val Glu Gln Glu
    450                 455                 460

Ala Asn His Asn Gly Pro Val Phe Leu Asp Arg Phe Thr Glu Ser Leu
465                 470                 475                 480

His Tyr Tyr Ser Thr Leu Phe Asp Ser Leu Glu Gly Ser Ala Ser Thr
                485                 490                 495

Gln Asp Lys Val Met Ser Glu Val Tyr Leu Ala Lys Gln Ile Cys Asn
            500                 505                 510

Val Val Ala Cys Glu Gly Pro Ser Arg Val Glu Arg His Glu Thr Leu
        515                 520                 525

Thr Gln Trp Arg Thr Arg Leu Ser Ser Ala Gly Phe Ala Pro Val His
    530                 535                 540

Leu Gly Ser Asn Ala Phe Lys Gln Ala Ser Met Leu Leu Ala Leu Phe
545                 550                 555                 560

Ala Gly Gly Asp Gly Tyr Arg Val Glu Glu Asn Asn Gly Cys Leu Met
                565                 570                 575

Leu Gly Trp His Thr Arg Pro Leu Ile Ala Thr Ser Ala Trp Arg Val
            580                 585                 590

Asn Asn His Tyr Pro Gly Ile Ser Glu Asn Pro Pro Phe Met Ser Gly
        595                 600                 605

Lys Gln Thr His Thr Glu Met Ile Lys Val Pro Leu Leu Pro Thr Leu
    610                 615                 620

Leu Arg Met Arg Phe Cys Cys Cys Ser Cys Cys Cys
625                 630                 635
```

<210> SEQ ID NO 57
<211> LENGTH: 571
<212> TYPE: PRT
<213> ORGANISM: Populus tremuloides

<400> SEQUENCE: 57

```
Met Lys Arg Glu His Pro Asn Leu His Pro Gln Gln Ile Ser Asp Pro
1               5                   10                  15

Ala Ser Leu Ala Ala Ala Gly Tyr Ser Ala Ser Thr Ser Thr Ser Ala
            20                  25                  30

Met Ala Pro Asn Asn Gly Lys Ala Lys Ile Trp Ala Glu Gly Glu Gly
        35                  40                  45

His Gln Ala Asp Gly Gly Val Asp Glu Leu Leu Ala Val Leu Gly Tyr
    50                  55                  60

Lys Val Arg Ser Ser Asp Met Ala Glu Val Ala Gln Lys Leu Glu Gln
65                  70                  75                  80

Leu Glu Glu Val Met Gly His Ala Gln Glu Asp Gly Leu Ser His Leu
                85                  90                  95

Ala Ser Asp Ser Val His Tyr Asn Pro Ser Asp Leu Ser Thr Trp Leu
            100                 105                 110

Gln Ser Met Ile Ser Glu Leu Asn Pro Asn Leu Asn Phe Asp Pro Ser
        115                 120                 125

Ala Asp Ser Leu Leu Ala Pro Ala Glu Ser Ser Thr Ile Thr Ser Ile
    130                 135                 140

Asp Phe Ser Asp His Lys His His Gln Gln Gln Lys Leu Phe Glu Glu
145                 150                 155                 160

Ser Ser Ser Ser Asp Tyr Asp Leu Lys Val Ile Pro Gly Lys Ala Val
                165                 170                 175

Phe Ser Gln Thr His Ile Asp Ser Arg Glu Ser Lys Arg Leu Lys Thr
            180                 185                 190

Asp Leu Tyr Gln Thr Ser Ser Ser Ser Ser Leu Ser Ser Ala Thr Thr
        195                 200                 205

Leu Gly Ser Phe Gly Ile Ser Thr Glu Ser Ala Arg Pro Val Val Leu
    210                 215                 220

Val Asp Ser Gln Glu Asn Gly Ile Arg Leu Val His Leu Leu Met Ala
225                 230                 235                 240

Cys Ala Glu Ala Val Gln Asp Ser Asn Phe Thr Leu Ala Glu Ala Leu
                245                 250                 255

Val Lys Gln Ile Gly Phe Leu Ala Val Ser Gln Ala Gly Val Met Arg
            260                 265                 270

Lys Ile His Phe Tyr Glu Thr Cys Pro Tyr Leu Lys Phe Ala His Phe
        275                 280                 285

Thr Ala Asn Gln Ala Ile Leu Glu Ala Phe Glu Gly Lys Lys Arg Val
    290                 295                 300

His Val Ile Asp Phe Ser Met Asn Gln Gly Met Gln Trp Pro Ala Leu
305                 310                 315                 320

Met Gln Ala Leu Ala Leu Arg Pro Gly Gly Pro Pro Ala Phe Arg Leu
                325                 330                 335

Thr Gly Ile Gly Pro Pro Ala His Asp Asn Thr Asp His Leu Gln Glu
            340                 345                 350

Val Gly Trp Lys Leu Ala Gln Leu Ala Glu Thr Ile His Val Glu Phe
        355                 360                 365

Glu Tyr Arg Gly Phe Val Ala Asn Ser Leu Ala Asp Leu Asp Ala Ser
    370                 375                 380

Met Leu Glu Leu Arg Pro Thr Glu Ser Val Ala Val Asn Ser Val Phe
385                 390                 395                 400

Glu Leu His Lys Leu Leu Ser Arg Pro Gly Ala Ile Glu Lys Val Leu
                405                 410                 415
```

```
Ser Val Val Lys Gln Met Lys Pro Glu Ile Val Thr Val Val Glu Gln
            420                 425                 430

Glu Ala Asn His Asn Gly Pro Ile Phe Leu Asp Arg Phe Thr Glu Ser
        435                 440                 445

Leu His Tyr Tyr Ser Thr Leu Phe Asp Ser Leu Glu Gly Ser Val Ser
    450                 455                 460

Thr Gln Asp Lys Ile Met Ser Glu Val Tyr Leu Gly Lys Gln Ile Cys
465                 470                 475                 480

Asn Val Val Ala Cys Glu Gly Pro Asp Arg Val Glu Arg His Glu Thr
                485                 490                 495

Leu Thr Gln Trp Arg Thr Arg Leu Gly Ser Ala Gly Phe Ala Pro Val
            500                 505                 510

His Leu Gly Ser Asn Ala Phe Lys Gln Ala Ser Met Leu Leu Ala Leu
        515                 520                 525

Phe Ala Gly Gly Asp Gly Tyr Arg Val Glu Glu Asn Asn Gly Cys Leu
    530                 535                 540

Met Leu Gly Trp His Thr Arg Pro Leu Ile Ala Thr Ser Ala Trp Arg
545                 550                 555                 560

Leu Asn Thr Asn Gln Pro Val Val Gly Ala Ala
                565                 570


<210> SEQ ID NO 58
<211> LENGTH: 623
<212> TYPE: PRT
<213> ORGANISM: Brachypodium distachyon

<400> SEQUENCE: 58

Met Lys Arg Glu Tyr Gln Asp Gly Gly Gly Ser Arg Gly Gly Gly Asp
1               5                   10                  15

Met Gly Ser Ser Lys Asp Lys Met Met Val Ala Ala Pro Ala Glu Glu
            20                  25                  30

Glu Asp Met Asp Glu Leu Leu Ala Ala Leu Gly Tyr Lys Val Arg Ala
        35                  40                  45

Ser Asp Met Ala Asp Val Ala Gln Lys Leu Glu Gln Leu Glu Met Ala
    50                  55                  60

Met Gly Met Gly Gly Val Gly Ala Gly Ala Ala Pro Asp Asp Ser Phe
65                  70                  75                  80

Val Ala His Leu Ala Thr Asp Thr Val His Ser Asn Pro Ser Asp Leu
                85                  90                  95

Ser Ser Trp Val Glu Ser Met Leu Ser Glu Leu Asn Ala Pro Pro Pro
            100                 105                 110

Pro Leu Pro Pro Ala Pro Gln Ala Pro Arg Leu Ser Ser Asn Ser Ser
        115                 120                 125

Thr Val Thr Gly Gly Gly Gly Ser Gly Gly Gly Tyr Phe Asp Gly Leu
    130                 135                 140

Pro Pro Ser Val Asp Ser Ser Ser Ser Thr Tyr Ala Leu Arg Pro Ile
145                 150                 155                 160

Pro Ser Pro Val Val Thr Pro Ala Glu Pro Ser Ala Asp Pro Ala Arg
                165                 170                 175

Glu Pro Lys Arg Met Arg Thr Gly Gly Gly Ser Thr Ser Ser Ser Ser
            180                 185                 190

Ser Ser Ser Ser Ser Leu Gly Gly Gly Gly Thr Met Ser Ser Val Val
        195                 200                 205

Glu Ala Ala Pro Pro Ala Ala Pro Ala Ser Ala Ala Ala Asn Ala Pro
```

```
    210                 215                 220

Ala Leu Pro Val Val Val Val Asp Thr Gln Glu Ala Gly Ile Arg Leu
225                 230                 235                 240

Val His Ala Leu Leu Ala Cys Ala Glu Ala Val Gln Gln Glu Asn Leu
                245                 250                 255

Ser Ala Ala Glu Ala Leu Val Lys Gln Ile Pro Leu Leu Ala Ala Ser
            260                 265                 270

Gln Gly Gly Ala Met Arg Lys Val Ala Ala Tyr Phe Gly Glu Ala Leu
        275                 280                 285

Ala Arg Arg Val Phe Arg Phe Arg Pro Gln Pro Asp Ser Ser Leu Leu
    290                 295                 300

Asp Ala Ala Phe Ala Asp Leu Leu His Ala His Phe Tyr Glu Ser Cys
305                 310                 315                 320

Pro Tyr Leu Lys Phe Ala His Phe Thr Ala Asn Gln Ala Ile Leu Glu
                325                 330                 335

Ala Phe Ala Gly Cys Arg Arg Val His Val Val Asp Phe Gly Ile Lys
            340                 345                 350

Gln Gly Met Gln Trp Pro Ala Leu Leu Gln Ala Leu Ala Leu Arg Pro
        355                 360                 365

Gly Gly Pro Pro Ser Phe Arg Leu Thr Gly Val Gly Pro Pro Gln Pro
    370                 375                 380

Asp Glu Thr Asp Ala Leu Gln Gln Val Gly Trp Lys Leu Ala Gln Phe
385                 390                 395                 400

Ala His Thr Ile Arg Val Asp Phe Gln Tyr Arg Gly Leu Val Ala Ala
                405                 410                 415

Thr Leu Ala Asp Leu Glu Pro Phe Met Leu Gln Pro Glu Gly Glu Glu
            420                 425                 430

Asp Pro Asn Glu Glu Pro Glu Val Ile Ala Val Asn Ser Val Phe Glu
        435                 440                 445

Met His Arg Leu Leu Ser Gln Pro Gly Ala Leu Glu Lys Val Leu Gly
    450                 455                 460

Thr Val Arg Ala Val Arg Pro Arg Ile Val Thr Val Val Glu Gln Glu
465                 470                 475                 480

Ala Asn His Asn Ser Gly Ser Phe Leu Asp Arg Phe Thr Glu Ser Leu
                485                 490                 495

His Tyr Tyr Ser Thr Met Phe Asp Ser Leu Glu Gly Ala Gly Ser Gly
            500                 505                 510

Gln Ser Glu Ile Ser Pro Gly Ala Ala Ala Gly Ala Thr Asp Gln Val
        515                 520                 525

Met Ser Glu Val Tyr Leu Gly Arg Gln Ile Cys Asn Val Val Ala Cys
    530                 535                 540

Glu Gly Pro Glu Arg Thr Glu Arg His Glu Thr Leu Gly Gln Trp Arg
545                 550                 555                 560

Gly Arg Leu Gly Gln Ala Gly Phe Glu Thr Val His Leu Gly Ser Asn
                565                 570                 575

Ala Tyr Lys Gln Ala Ser Thr Leu Leu Ala Leu Phe Ala Gly Gly Asp
            580                 585                 590

Gly Tyr Lys Val Glu Glu Lys Asp Gly Cys Leu Thr Leu Gly Trp His
        595                 600                 605

Thr Arg Pro Leu Ile Ala Thr Ser Ala Trp Arg Met Ala Ala Pro
    610                 615                 620
```

<210> SEQ ID NO 59

<211> LENGTH: 621
<212> TYPE: PRT
<213> ORGANISM: Panicum virgatum

<400> SEQUENCE: 59

```
Met Lys Arg Glu Tyr Gln Asp Ala Gly Gly Ser Gly Gly Asp Met Gly
1               5                   10                  15

Ser Ser Lys Asp Lys Met Met Ala Ala Ala Ala Gly Glu Gln Asp Glu
            20                  25                  30

Glu Val Asp Glu Leu Leu Ala Ala Leu Gly Tyr Lys Val Arg Ser Ser
        35                  40                  45

Asp Met Ala Asp Val Ala Gln Lys Leu Glu Gln Leu Glu Met Ala Met
    50                  55                  60

Gly Met Gly Gly Val Gly Gly Ala Ala Thr Ala Val Asp Asp Gly Phe
65                  70                  75                  80

Val Ser His Leu Ala Thr Asp Thr Val His Tyr Asn Pro Ser Asp Leu
                85                  90                  95

Ser Ser Trp Val Glu Ser Met Leu Ser Glu Leu Asn Ala Pro Pro Pro
            100                 105                 110

Pro Leu Pro Thr Ala Pro Pro Ala Pro Arg Leu Ala Ser Thr Ser Ser
        115                 120                 125

Thr Val Thr Gly Gly Ala Ala Ala Gly Gly Gly Tyr Phe Asp Leu Pro
    130                 135                 140

Pro Ala Val Asp Ser Ser Ser Ser Thr Tyr Ala Leu Lys Pro Ile Pro
145                 150                 155                 160

Ser Pro Val Ala Ala Ser Ala Asp Pro Ser Thr Asp Ser Thr Arg Glu
                165                 170                 175

Pro Lys Arg Met Arg Thr Gly Gly Gly Ser Thr Ser Ser Ser Ser Ser
            180                 185                 190

Ser Ser Ser Ser Leu Asp Gly Gly Arg Thr Arg Ser Ser Val Val Glu
        195                 200                 205

Ala Ala Pro Pro Ala Thr Gln Ala Ser Ala Ala Ala Asn Ala Pro Ala
    210                 215                 220

Val Pro Val Val Val Val Asp Thr Gln Glu Ala Gly Ile Arg Leu Val
225                 230                 235                 240

His Ala Leu Leu Ala Cys Ala Glu Ala Val Gln Gln Glu Asn Phe Thr
                245                 250                 255

Ala Ala Glu Ala Leu Val Lys Gln Ile Pro Met Leu Ala Ser Ser Gln
            260                 265                 270

Gly Gly Ala Met Arg Lys Val Ala Ala Tyr Phe Gly Glu Ala Leu Ala
        275                 280                 285

Arg Arg Val Tyr Arg Phe Arg Pro Ala Pro Asp Ser Ser Leu Leu Asp
    290                 295                 300

Ala Ala Phe Ala Asp Leu Leu His Ala His Phe Tyr Glu Ser Cys Pro
305                 310                 315                 320

Tyr Leu Lys Phe Ala His Phe Thr Ala Asn Gln Ala Ile Leu Glu Ala
                325                 330                 335

Phe Ala Gly Cys Arg Arg Val His Val Val Asp Phe Gly Ile Lys Gln
            340                 345                 350

Gly Met Gln Trp Pro Ala Leu Leu Gln Ala Leu Ala Leu Arg Pro Gly
        355                 360                 365

Gly Pro Pro Ser Phe Arg Leu Thr Gly Val Gly Pro Pro Gln Pro Asp
    370                 375                 380

Glu Thr Asp Ala Leu Gln Gln Val Gly Trp Lys Leu Ala Gln Phe Ala
```

-continued

```
385                 390                 395                 400

His Thr Ile Arg Val Asp Phe Gln Tyr Arg Gly Leu Val Ala Ala Thr
                405                 410                 415

Leu Ala Asp Leu Glu Pro Phe Met Leu Gln Pro Asp Gly Glu Asp Thr
            420                 425                 430

Asp Asp Glu Pro Glu Val Ile Ala Val Asn Ser Val Phe Glu Leu His
        435                 440                 445

Arg Leu Leu Ala Gln Pro Gly Ala Leu Glu Lys Val Leu Gly Thr Val
    450                 455                 460

Arg Ala Val Arg Pro Arg Ile Val Thr Val Val Glu Gln Glu Ala Asn
465                 470                 475                 480

His Asn Ser Val Ser Phe Leu Asp Arg Phe Thr Glu Ser Leu His Tyr
                485                 490                 495

Tyr Ser Thr Met Phe Asp Ser Leu Glu Gly Ala Gly Ser Gly Gln Ser
            500                 505                 510

Ala Asp Ala Ala Pro Ala Ala Ala Gly Gly Thr Asp Gln Val Met Ser
        515                 520                 525

Glu Val Tyr Leu Gly Arg Gln Ile Cys Asn Val Val Ala Cys Glu Gly
    530                 535                 540

Ala Glu Arg Thr Glu Arg His Glu Thr Leu Gly Gln Trp Arg Asn Arg
545                 550                 555                 560

Leu Gly Gly Ala Gly Phe Glu Pro Val His Leu Gly Ser Asn Ala Tyr
                565                 570                 575

Lys Gln Ala Ser Thr Leu Leu Ala Leu Phe Ala Gly Gly Asp Gly Tyr
            580                 585                 590

Arg Val Glu Glu Lys Asp Gly Cys Leu Thr Leu Gly Trp His Thr Arg
        595                 600                 605

Pro Leu Ile Ala Thr Ser Ala Trp Arg Val Ala Ala Pro
    610                 615                 620


<210> SEQ ID NO 60
<211> LENGTH: 603
<212> TYPE: PRT
<213> ORGANISM: Panicum virgatum

<400> SEQUENCE: 60

Met Lys Arg Glu Tyr Gln Asp Ala Gly Gly Ser Gly Gly Asp Met Gly
1               5                   10                  15

Ser Ser Lys Asp Asn Met Met Ala Ala Ala Ala Gly Glu Gln Asn Glu
            20                  25                  30

Glu Val Asp Glu Leu Leu Ala Ala Leu Gly Tyr Lys Val Arg Ser Ser
        35                  40                  45

Asp Met Ala Asp Val Ala Gln Lys Leu Glu Gln Leu Glu Met Ala Met
    50                  55                  60

Gly Met Gly Gly Val Gly Gly Ala Gly Ala Ala Ala Asp Asp Gly Phe
65                  70                  75                  80

Val Ser His Leu Val Thr Asp Thr Val His Tyr Asn Pro Ser Asp Leu
                85                  90                  95

Ser Ser Trp Val Glu Asn Met Leu Ser Glu Leu Asn Ala Pro Pro Pro
            100                 105                 110

Arg Ser Arg Arg Leu Arg Gly Ser Arg Tyr Phe Asp Leu Pro Pro Ala
        115                 120                 125

Val Asp Ser Ser Ser Ser Thr Tyr Ala Leu Lys Pro Ile Pro Ser Pro
    130                 135                 140
```

-continued

```
Val Ala Ala Ser Ala Asp Pro Ser Thr Asp Ser Thr Arg Glu Pro Lys
145                 150                 155                 160

Arg Met Arg Thr Gly Gly Gly Ser Thr Ser Ser Ser Ser Ser Ser Ser
                165                 170                 175

Ser Ser Leu Asp Gly Gly Arg Thr Arg Ser Ser Ala Val Glu Ala Ala
            180                 185                 190

Pro Pro Ala Thr Gln Ala Ser Ala Ala Ala Asn Ala Pro Ala Val Pro
        195                 200                 205

Val Val Val Val Asp Thr Gln Glu Ala Gly Ile Arg Leu Val His Ala
    210                 215                 220

Leu Leu Ala Cys Ala Glu Ala Val Gln Gln Glu Asn Phe Thr Ala Ala
225                 230                 235                 240

Glu Ala Leu Val Lys Gln Ile Pro Met Leu Ala Ser Ser Gln Gly Gly
                245                 250                 255

Ala Met Arg Lys Val Ala Ala Tyr Phe Gly Glu Ala Leu Ala Arg Arg
            260                 265                 270

Val Tyr Arg Phe Arg Pro Ala Pro Asp Ser Ser Leu Leu Asp Ala Ala
        275                 280                 285

Phe Ala Asp Leu Leu His Ala His Phe Tyr Glu Ser Cys Pro Tyr Leu
    290                 295                 300

Lys Phe Ala His Phe Thr Ala Asn Gln Ala Ile Leu Glu Ala Phe Ala
305                 310                 315                 320

Gly Cys Arg Arg Val His Val Val Asp Phe Gly Ile Lys Gln Gly Met
                325                 330                 335

Gln Trp Pro Ala Leu Leu Gln Ala Leu Ala Leu Arg Pro Gly Gly Pro
            340                 345                 350

Pro Ser Phe Arg Leu Thr Gly Val Gly Pro Pro Gln Pro Asp Glu Thr
        355                 360                 365

Asp Ala Leu Gln Gln Val Gly Trp Lys Leu Ala Gln Phe Ala His Thr
    370                 375                 380

Ile Arg Val Asp Phe Gln Tyr Arg Gly Leu Val Ala Ala Thr Leu Ala
385                 390                 395                 400

Asp Leu Glu Pro Phe Met Leu Gln Pro Asp Gly Glu Asp Thr Asp Asp
                405                 410                 415

Glu Pro Glu Val Ile Ala Val Asn Ser Val Phe Glu Leu His Arg Leu
            420                 425                 430

Leu Ala Gln Pro Gly Ala Leu Glu Lys Val Leu Gly Thr Val Arg Ala
        435                 440                 445

Val Arg Pro Arg Ile Val Thr Val Val Glu Gln Glu Ala Asn His Asn
    450                 455                 460

Ser Gly Ser Phe Leu Asp Arg Phe Thr Glu Ser Leu His Tyr Tyr Ser
465                 470                 475                 480

Thr Met Phe Asp Ser Leu Glu Gly Ala Gly Ala Gly Gln Ser Ala Asp
                485                 490                 495

Ala Ala Pro Ala Ala Ala Gly Gly Thr Asp Gln Val Met Ser Glu Val
            500                 505                 510

Tyr Leu Gly Arg Gln Ile Cys Asn Val Val Ala Cys Glu Gly Ala Glu
        515                 520                 525

Arg Thr Glu Arg His Glu Thr Leu Gly Gln Trp Arg Asn Arg Leu Gly
    530                 535                 540

Arg Ala Gly Phe Glu Pro Val His Leu Gly Ser Asn Ala Tyr Lys Gln
545                 550                 555                 560

Ala Ser Thr Leu Leu Ala Leu Phe Ala Gly Gly Asp Gly Tyr Arg Val
```

```
                565                 570                 575

Glu Glu Lys Asp Gly Cys Leu Thr Leu Gly Trp His Thr Arg Pro Leu
            580                 585                 590

Ile Ala Thr Ser Ala Trp Arg Leu Ala Ala Pro
        595                 600
```

<210> SEQ ID NO 61
<211> LENGTH: 1566
<212> TYPE: DNA
<213> ORGANISM: Artificial Sequence
<220> FEATURE:
<223> OTHER INFORMATION: Green tissue promoter

<400> SEQUENCE: 61

```
gtgaggaggg ggtgaaacac taaatcaagc gagatgcaat gtcaaccgag cctttccttg     60
aggaagaaag caaggtgatg gaggaggcaa ttgtcaactg agatgcaaag tcaactttaa    120
ccggaaatca tccactcgtc caattggctg gcggaggtgg gggccccgag ccaggagcaa    180
accttaccca aattagcttg cgaggttgag aggatcccat ccaattaggt gtcgaatgtc    240
gattgttgtt ggctccacct cggagatcac aagccatcat tgacatgata gattgatata    300
tcttatttct tccaattttg tggtgataga tctcagcaac ctttcaaatc actacactgt    360
gcaaaggatg atgttatttg tgttatttat ccggaatcca aaatcagtat taagttattt    420
gaagaaacat atagttagac gagttgtgtc atcttgatag atttcatatg atgaaattga    480
gatgtctcgt gaaattaaat gggtgactct taatcataca ttttatgtga tacatatata    540
tattatgtgc cttattgatt agttttctta cggtttatat tttcagaacc aaagatttac    600
ctaccatgaa atcggagcat aaattatgaa ttcaaattcc tttggctcat ggtttttagg    660
aaaaaaaaag atttaatgag aggaactttc gcattttcac cgtttgtttg tgtaagttaa    720
gtaaattttg attcaagagt cacactggaa atgatctaaa agtgacacca accttggttt    780
tttccatttg tgcgaatgaa aaattaaact atatattgat gttaaagaaa aattagacag    840
ggatgtcgct taaccttatg aaatcatgac caaaaacctt atgaagccgg ttttacctct    900
atggtcatgt caacgggagt ttttgtagca tttagcacgt gtaacgattt ctttttgtcg    960
aaagtgcatt tgaacttgac acaatgcatt tttaataagt tattgcacat tatcaagagt   1020
agttagtgca ttgaaaatcg agaagtttcc gtaaccaaat tctaagctat tcgttagtaa   1080
tatctcccaa gatattcatt aaaaacatct ggtacttcgt tttcctcaaa cctcctaact   1140
cttgattatc aatcctggac ataaatctca acatccactt gaaatgcatc ctctgttctt   1200
tttcccctaa caagaagcaa acgatcctca atttcaccaa agcggggcca aagaaccatc   1260
actcataatc aacaaggata tctcatctat cttccaacca aattaaaccc caaacatctc   1320
taaagcagca tcgaaaagaa aacagtccgg aagtctctag ctcaaaaact gtaaccccgt   1380
acctaattcc agttgtctct gattacatca attctcatgt cttaacactc cattcgcacc   1440
tccacaataa atagatcggc ccttcatctc cccttaccat caaatccaat cccaaaaaca   1500
cttgctcaga caccatcaaa tccttcgcaa agtctttttc ttacaaaaaa acaaacgaaa   1560
gcaaca                                                              1566
```

<210> SEQ ID NO 62
<211> LENGTH: 1720
<212> TYPE: DNA
<213> ORGANISM: Artificial Sequence
<220> FEATURE:
<223> OTHER INFORMATION: Green tissue promoter

<400> SEQUENCE: 62
ttttatcctg tgatgccaca ttaatcagaa tatatttttt tctaaatagt taatgtttgg 60
gttcggcaag gatattcaaa attaaatat gaataaaata tagaataaaa aaattttgtt 120
cttgactact cgtgggttct tgttcaatct aggccttggg tctaagttat gggttaaatt 180
ggatattaac aaaacattaa aggatatgat aaatatgaaa agttaacctg aatttacttg 240
agtatttttt tttgtttttt ttttaattta atattttaat tttaatttta ttatttatca 300
ttgggttgat cgagaattga tttttttat ggttttatga ttcgtgtcgt gaatttaaca 360
agttaattca atttgattta atattttatc ttctcattat tttaaaaaat aatagcatcc 420
aatatatcga tatttgaaaa tgatggcatc taatcttaat catattttga gtctatggtt 480
gttattattt ttagaaaata agttagcaat actttaatat tttttatata ttaaaacaat 540
ttaatctatc ccgcaaacac atcgcaagtt aatgatctaa ttataactat aataaaactt 600
gatttgagca aaattcaatc tcaaatatac aatatatagc attaatattg agttgaaatc 660
aattatccac caaatctata ttgttgtttc aaaatacatt tttgagtaaa ggttttttcc 720 ccttttggt tcaatgcctt ttattcttcc aaattaattt caatattttg tatccggagg 780
aacatatttg tttcaaaagg tgtcagaaaa tcaaagccca ttgaaaatat ataaacatat 840
atagatataa aaactcaagg attcattcca aaatataaga acaaactgat tgaattaatt 900
tgttatttta agaacactgt ctatatgttt atatagtggt aggtagtgtt tttaaaatca 960
tatactaact tattataaaa ataaatcata aaaaaggaac ctcaagcatc cctttgtaag 1020
ctcgtatgta ggaatactcg gagatcaaat gtccgaatgt caaatgttaa ggcaagtgaa 1080
atatccctaa ctttttagca agcaaattgt tgagtagcta aaatgaatta ttttaatatt 1140
tttaaatcat tttaatatat taatattaaa aaaaattaaa tattttttt aatacatttt 1200 caataacaaa cactttaaaa tataatcttt gtcacactct taaacagtaa cagcagaaag 1260
catatgtgag tgatatagct atagttgctg tttgacacgg acaatctcca tctaaattca 1320
tgaataataa agttttgcct acacacccac ttgaaatctc ctcctagttt tcctgatttg 1380
ccatgctaac tacaagaaca agatgctagc tagtatcttg ttctgtctct cgctctctct 1440
ctatctctcc agttgatagt tgatagttga tagttgatag ctgatacact cccacctttc 1500
ccagaaagat gattgaggaa ctagtcactg tgttcgtgta actaatactg ttcatggcac 1560
ctaacttgat cctctcttca ccagaccact ataaaaaccc tatctgtcct cctcataatc 1620
atctcactac acccaacact tctgcaagca caactccatt caagaacatc aagagtatag 1680
gccgccactg caacaaaaca gcactcctag ctacttcaag 1720

<210> SEQ ID NO 63
<211> LENGTH: 20
<212> TYPE: DNA
<213> ORGANISM: Artificial Sequence
<220> FEATURE:
<223> OTHER INFORMATION: Guide RNA

<400> SEQUENCE: 63
ggtcgtcgtt gaagatgacc 20

<210> SEQ ID NO 64
<211> LENGTH: 20
<212> TYPE: DNA
<213> ORGANISM: Artificial Sequence
<220> FEATURE:

<223> OTHER INFORMATION: Guide RNA

<400> SEQUENCE: 64
ggtccaccag gacgaccggc 20

<210> SEQ ID NO 65
<211> LENGTH: 20
<212> TYPE: DNA
<213> ORGANISM: Artificial Sequence
<220> FEATURE:
<223> OTHER INFORMATION: Guide RNA

<400> SEQUENCE: 65
gatcatcgag acgcttgcag 20

<210> SEQ ID NO 66
<211> LENGTH: 20
<212> TYPE: DNA
<213> ORGANISM: Artificial Sequence
<220> FEATURE:
<223> OTHER INFORMATION: Guide RNA

<400> SEQUENCE: 66
tcctccaccc actcaatgcc 20

<210> SEQ ID NO 67
<211> LENGTH: 20
<212> TYPE: DNA
<213> ORGANISM: Artificial Sequence
<220> FEATURE:
<223> OTHER INFORMATION: Guide RNA

<400> SEQUENCE: 67
ccaccacctc tatccccaga 20

<210> SEQ ID NO 68
<211> LENGTH: 20
<212> TYPE: DNA
<213> ORGANISM: Artificial Sequence
<220> FEATURE:
<223> OTHER INFORMATION: Guide RNA

<400> SEQUENCE: 68
tccaagatgt gggacgaaga 20

<210> SEQ ID NO 69
<211> LENGTH: 20
<212> TYPE: DNA
<213> ORGANISM: Artificial Sequence
<220> FEATURE:
<223> OTHER INFORMATION: Guide RNA

<400> SEQUENCE: 69
gcagcagcag caattgacgg 20

<210> SEQ ID NO 70
<211> LENGTH: 20
<212> TYPE: DNA
<213> ORGANISM: Artificial Sequence
<220> FEATURE:
<223> OTHER INFORMATION: Guide RNA

<400> SEQUENCE: 70
gcagcagcag cagcaattga 20

<210> SEQ ID NO 71
<211> LENGTH: 20
<212> TYPE: DNA
<213> ORGANISM: Artificial Sequence
<220> FEATURE:
<223> OTHER INFORMATION: Guide RNA

<400> SEQUENCE: 71
agtcgtcgtt gaagatgacc 20

<210> SEQ ID NO 72
<211> LENGTH: 20
<212> TYPE: DNA
<213> ORGANISM: Artificial Sequence
<220> FEATURE:
<223> OTHER INFORMATION: Guide RNA

<400> SEQUENCE: 72
tgtccaccag gacgaccggc 20

<210> SEQ ID NO 73
<211> LENGTH: 426
<212> TYPE: DNA
<213> ORGANISM: Artificial Sequence
<220> FEATURE:
<223> OTHER INFORMATION: CaMV 35S promoter

<400> SEQUENCE: 73
caacatggtg gagcacgaca ctctcgtcta ctccaagaat atcaaagata cagtctcaga 60
agaccaaagg gctattgaga cttttcaaca aagggtaata tcgggaaacc tcctcggatt 120
ccattgccca gctatctgtc acttcatcaa aaggacagta gaaaaggaag gtggcaccta 180
caaatgccat cattgcgata aaggaaaggc tatcgttcaa gatgcctctg ccgacagtgg 240
tcccaaagat ggacccccac ccacgaggag catcgtggaa aaagaagacg ttccaaccac 300
gtcttcaaag caagtggatt gatgtgatat ctccactgac gtaagggatg acgcacaatc 360
ccactatcct tcgcaagacc cttcctctat ataaggaagt tcatttcatt tggagaggac 420
acgctg 426

<210> SEQ ID NO 74
<211> LENGTH: 835
<212> TYPE: DNA
<213> ORGANISM: Artificial Sequence
<220> FEATURE:
<223> OTHER INFORMATION: CaMV 35S promoter

<400> SEQUENCE: 74
agattagcct tttcaatttc agaaagaatg ctaacccaca gatggttaga gaggcttacg 60
cagcaggtct catcaagacg atctacccga gcaataatct ccaggaaatc aaataccttc 120
ccaagaaggt taaagatgca gtcaaaagat tcaggactaa ctgcatcaag aacacagaga 180
aagatatatt tctcaagatc agaagtacta ttccagtatg gacgattcaa ggcttgcttc 240
acaaaccaag gcaagtaata gagattggag tctctaaaaa ggtagttccc actgaatcaa 300
aggccatgga gtcaaagatt caaatagagg acctaacaga actcgccgta aagactggcg 360
aacagttcat acagagtctc ttacgactca atgacaagaa gaaaatcttc gtcaacatgg 420
tggagcacga cacacttgtc tactccaaaa atatcaaaga tacagtctca gaagaccaaa 480
gggcaattga gacttttcaa caaagggtaa tatccggaaa cctcctcgga ttccattgcc 540
cagctatctg tcactttatt gtgaagatag tggaaaagga aggtggctcc tacaaatgcc 600

-continued atcattgcga taaaggaaag gccatcgttg aagatgcctc tgccgacagt ggtcccaaag 660
atggaccccc acccacgagg agcatcgtgg aaaaagaaga cgttccaacc acgtcttcaa 720
agcaagtgga ttgatgtgat atctccactg acgtaaggga tgacgcacaa tcccactatc 780
cttcgcaaga cccttcctct atataaggaa gttcatttca tttggagaga acacg 835

<210> SEQ ID NO 75
<211> LENGTH: 442
<212> TYPE: DNA
<213> ORGANISM: Arabidopsis thaliana

<400> SEQUENCE: 75
cgttgaacaa cggaaactcg acttgccttc cgcacaatac atcatttctt cttagctttt 60
tttcttcttc ttcgttcata cagttttttt ttgtttatca gcttacattt tcttgaaccg 120
tagctttcgt tttcttcttt ttaactttcc attcggagtt tttgtatctt gtttcatagt 180
ttgtcccagg attagaatga ttaggcatcg aaccttcaag aatttgattg aataaaacat 240
cttcattctt aagatatgaa gataatcttc aaaaggcccc tgggaatctg aaagaagaga 300
agcaggccca tttatatggg aaagaacaat agtatttctt atataggccc atttaagttg 360
aaaacaatct tcaaaagtcc cacatcgctt agataagaaa acgaagctga gtttatatac 420
agctagagtc gaagtagtga tt 442

<210> SEQ ID NO 76
<211> LENGTH: 72
<212> TYPE: DNA
<213> ORGANISM: Arabidopsis thaliana

<400> SEQUENCE: 76
tgatcaaaag tcccacatcg atcaggtgat atatagcagc ttagtttata taatgataga 60
gtcgacatag cg 72

<210> SEQ ID NO 77
<211> LENGTH: 4116
<212> TYPE: DNA
<213> ORGANISM: Streptococcus pyogenes

<400> SEQUENCE: 77
atggacaaga agtactccat tgggctcgat atcggcacaa acagcgtcgg ctgggccgtc 60
attacggacg agtacaaggt gccgagcaaa aaattcaaag ttctgggcaa taccgatcgc 120
cacagcataa agaagaacct cattggcgcc ctcctgttcg actccgggga gacggccgaa 180
gccacgcggc tcaaaagaac agcacggcgc agatataccc gcagaaagaa tcggatctgc 240
tacctgcagg agatctttag taatgagatg gctaaggtgg atgactcttt cttccatagg 300
ctggaggagt cctttttggt ggaggaggat aaaaagcacg agcgccaccc aatctttggc 360
aatatcgtgg acgaggtggc gtaccatgaa aagtacccaa ccatatatca tctgaggaag 420
aagcttgtag acagtactga taaggctgac ttgcggttga tctatctcgc gctggcgcat 480
atgatcaaat ttcggggaca cttcctcatc gagggggacc tgaacccaga caacagcgat 540
gtcgacaaac tctttatcca actggttcag acttacaatc agcttttcga agagaacccg 600
atcaacgcat ccggagttga cgccaaagca atcctgagcg ctaggctgtc caaatcccgg 660
cggctcgaaa acctcatcgc acagctccct ggggagaaga agaacggcct gtttggtaat 720
cttatcgccc tgtcactcgg gctgaccccc aactttaaat ctaacttcga cctggccgaa 780
gatgccaagc ttcaactgag caaagacacc tacgatgatg atctcgacaa tctgctggcc 840

-continued

```
cagatcggcg accagtacgc agaccttttt ttggcggcaa agaacctgtc agacgccatt    900
ctgctgagtg atattctgcg agtgaacacg gagatcacca aagctccgct gagcgctagt    960
atgatcaagc gctatgatga gcaccaccaa gacttgactt tgctgaaggc ccttgtcaga   1020
cagcaactgc ctgagaagta caaggaaatt ttcttcgatc agtctaaaaa tggctacgcc   1080
ggatacattg acggcggagc aagccaggag gaattttaca aatttattaa gcccatcttg   1140
gaaaaaatgg acggcaccga ggagctgctg gtaaagctta acagagaaga tctgttgcgc   1200
aaacagcgca ctttcgacaa tggaagcatc ccccaccaga ttcacctggg cgaactgcac   1260
gctatcctca ggcggcaaga ggatttctac cccttttga aagataacag ggaaaagatt   1320
gagaaaatcc tcacatttcg gataccctac tatgtaggcc ccctcgcccg gggaaattcc   1380
agattcgcgt ggatgactcg caaatcagaa gagactatca ctccctggaa cttcgaggaa   1440
gtcgtggata agggggcctc tgcccagtcc ttcatcgaaa ggatgactaa ctttgataaa   1500
aatctgccta acgaaaaggt gcttcctaaa cactctctgc tgtacgagta cttcacagtt   1560
tataacgagc tcaccaaggt caaatacgtc acagaaggga tgagaaagcc agcattcctg   1620
tctggagagc agaagaaagc tatcgtggac ctcctcttca agacgaaccg gaaagttacc   1680
gtgaaacagc tcaaagaaga ttatttcaaa aagattgaat gtttcgactc tgttgaaatc   1740
agcggagtgg aggatcgctt caacgcatcc ctgggaacgt atcacgatct cctgaaaatc   1800
attaaagaca aggacttcct ggacaatgag gagaacgagg acattcttga ggacattgtc   1860
ctcaccctta cgttgtttga agatagggag atgattgaag aacgcttgaa aacttacgct   1920
catctcttcg acgacaaagt catgaaacag ctcaagaggc gccgatatac aggatggggg   1980
cggctgtcaa gaaaactgat caatgggatc cgagacaagc agagtggaaa gacaatcctg   2040
gattttctta agtccgatgg atttgccaac cggaacttca tgcagttgat ccatgatgac   2100
tctctcacct ttaaggagga catccagaaa gcacaagttt ctggccaggg ggacagtctc   2160
cacgagcaca tcgctaatct tgcaggtagc ccagctatca aaaagggaat actgcagacc   2220
gttaaggtcg tggatgaact cgtcaaagta atgggaaggc ataagcccga gaatatcgtt   2280
atcgagatgg cccgagagaa ccaaactacc cagaagggac agaagaacag tagggaaagg   2340
atgaagagga ttgaagaggg tataaaagaa ctggggtccc aaatccttaa ggaacaccca   2400
gttgaaaaca cccagcttca gaatgagaag ctctacctgt actacctgca gaacggcagg   2460
gacatgtacg tggatcagga actggacatc aatcggctct ccgactacga cgtggatcat   2520
atcgtgcccc agtcttttct caaagatgat tctattgata ataaagtgtt gacaagatcc   2580
gataaaaata gagggaagag tgataacgtc ccctcagaag aagttgtcaa gaaaatgaaa   2640
aattattggc ggcagctgct gaacgccaaa ctgatcacac aacggaagtt cgataatctg   2700
actaaggctg aacgaggtgg cctgtctgag ttggataaag ccggcttcat caaaaggcag   2760
cttgttgaga cacgccagat caccaagcac gtggcccaaa ttctcgattc acgcatgaac   2820
accaagtacg atgaaaatga caaactgatt cgagaggtga aagttattac tctgaagtct   2880
aagctggttt cagatttcag aaaggacttt cagttttata aggtgagaga gatcaacaat   2940
taccaccatg cgcatgatgc ctacctgaat gcagtggtag gcactgcact tatcaaaaaa   3000
tatcccaagc ttgaatctga atttgtttac ggagactata aagtgtacga tgttaggaaa   3060
atgatcgcaa agtctgagca ggaaataggc aaggccaccg ctaagtactt cttttacagc   3120
aatattatga atttttcaa gaccgagatt acactggcca atggagagat tcggaagcga   3180
```

-continued

```
ccacttatcg aaacaaacgg agaaacagga gaaatcgtgt gggacaaggg tagggatttc   3240

gcgacagtcc ggaaggtcct gtccatgccg caggtgaaca tcgttaaaaa gaccgaagta   3300

cagaccggag gcttctccaa ggaaagtatc ctcccgaaaa ggaacagcga caagctgatc   3360

gcacgcaaaa aagattggga ccccaagaaa tacggcggat tcgattctcc tacagtcgct   3420

tacagtgtac tggttgtggc caaagtggag aaagggaagt ctaaaaaact caaaagcgtc   3480

aaggaactgc tgggcatcac aatcatggag cgatcaagct tcgaaaaaaa ccccatcgac   3540

tttctcgagg cgaaaggata taaagaggtc aaaaaagacc tcatcattaa gcttcccaag   3600

tactctctct ttgagcttga aaacggccgg aaacgaatgc tcgctagtgc gggcgagctg   3660

cagaaaggta acgagctggc actgccctct aaatacgtta atttcttgta tctggccagc   3720

cactatgaaa agctcaaagg atctcccgaa gataatgagc agaagcagct gttcgtggaa   3780

caacacaaac actaccttga tgagatcatc gagcaaataa gcgaattctc caaaagagtg   3840

atcctcgccg acgctaacct cgataaggtg ctttctgctt acaataagca cagggataag   3900

cccatcaggg agcaggcaga aaacattatc cacttgttta ctctgaccaa cttgggcgcg   3960

cctgcagcct tcaagtactt cgacaccacc atagacagaa agcggtacac ctctacaaag   4020

gaggtcctgg acgccacact gattcatcag tcaattacgg ggctctatga aacaagaatc   4080

gacctctctc agctcggtgg agacagcagg gctgac                             4116
```

<210> SEQ ID NO 78
<211> LENGTH: 24
<212> TYPE: DNA
<213> ORGANISM: Artificial Sequence
<220> FEATURE:
<223> OTHER INFORMATION: Nuclear localization signal

<400> SEQUENCE: 78

```
cccaagaaga agaggaaggt gtga                                            24
```

<210> SEQ ID NO 79
<211> LENGTH: 84
<212> TYPE: DNA
<213> ORGANISM: Artificial Sequence
<220> FEATURE:
<223> OTHER INFORMATION: sgRNA scaffold

<400> SEQUENCE: 79

```
gttttagagc tagaaatagc aagttaaaat aaggctagtc cgttatcaac ttgaaaaagt     60

ggcaccgagt cggtgctttt tttt                                            84
```

<210> SEQ ID NO 80
<211> LENGTH: 40
<212> TYPE: DNA
<213> ORGANISM: Artificial Sequence
<220> FEATURE:
<223> OTHER INFORMATION: U6 terminator

<400> SEQUENCE: 80

```
gttttgcaaa attttccaga tcgatttctt cttcctctgt                           40
```

<210> SEQ ID NO 81
<211> LENGTH: 305
<212> TYPE: DNA
<213> ORGANISM: Arabidopsis thaliana

<400> SEQUENCE: 81

```
agaaatctca aaattccggc agaacaattt tgaatctcga tccgtagaaa cgagacggtc     60
```

attgttttag ttccaccacg attatatttg aaatttacgc tgagtgtgag tgagacttgc 120
ataagaaaat aaaatcttta gttgggaaaa aattcaataa tataaatggg cttgagaagg 180
aagcgaggga taggcctttt tctaaaatag gcccatttaa gctattaaca atcttcaaaa 240
gtaccacatc gcttaggtaa agaaagcagc tgagtttata tatggttaga gacgaagtag 300
tgatt 305

<210> SEQ ID NO 82
<211> LENGTH: 319
<212> TYPE: DNA
<213> ORGANISM: Arabidopsis thaliana

<400> SEQUENCE: 82
aaatatcaga gatctcttac agttagtttc gttcttaatc caaactactg cagcctgaca 60
gacaaatgag gatgcaaaca attttaaagt ttatctaacg ctagctgttt tgtttcttct 120
ctctggtgca ccaacgacgg cgttttctca atcataaaga ggcttgtttt acttaaggcc 180
aataatgttg atggatcgaa agaagagggc ttttaataaa cgagcccgtt taagctgtaa 240
acgatgtcaa aaacatccca catcgttcag ttgaaaatag aagctctgtt tatatattgg 300
tagagtcgac taagagatt 319

<210> SEQ ID NO 83
<211> LENGTH: 324
<212> TYPE: DNA
<213> ORGANISM: Arabidopsis thaliana

<400> SEQUENCE: 83
tttactttaa attttttctt atgcagcctg tgatggataa ctgaatcaaa caaatggcgt 60
ctgggtttaa gaagatctgt tttggctatg ttggacgaaa caagtgaact tttaggatca 120
acttcagttt atatatggag cttatatcga gcaataagat aagtgggctt tttatgtaat 180
ttaatgggct atcgtccata gattcactaa tacccatgcc cagtacccat gtatgcgttt 240
catataagct cctaatttct cccacatcgc tcaaatctaa acaaatcttg ttgtatatat 300
aacactgagg gagcaacatt ggtc 324

<210> SEQ ID NO 84
<211> LENGTH: 102
<212> TYPE: DNA
<213> ORGANISM: Arabidopsis thaliana

<400> SEQUENCE: 84
cataagctta tgatttcttt tttcttacga attttgcgtc ccacatcggt aagcgagtga 60
agaaataact gctttatata tggctacaaa gcaccattgg tc 102

<210> SEQ ID NO 85
<211> LENGTH: 373
<212> TYPE: DNA
<213> ORGANISM: Eucalyptus grandis

<400> SEQUENCE: 85
tctccgctgg ctaatttgat taaaatgaaa aggcccatca aagaatttct cttgtcgaag 60
agtaagcttg ggtaggcgga ccacctaccc acccacccac ccacccatgg tgacccaatt 120
caggtgtcgc gaactgcaat aaaaagcttt gctttgggaa tcccgactcg ttcgccaatt 180
gattaccgcc ccacagtttc gggtaggggg aaaaaactcg tacaaggccc gcgccaagga 240

```
aaggtacgag gcccatgggc tgggttcgac tatttagtct tgcacggatc tggcggaaga    300

aaaaaaagtc ccacatcgga ccgcaactga caaattgaac agtttttaag cggggaggag    360

agaattactg ggc                                                       373


<210> SEQ ID NO 86
<211> LENGTH: 467
<212> TYPE: PRT
<213> ORGANISM: Eucalyptus camaldulensis
<220> FEATURE:
<221> NAME/KEY: misc_feature
<222> LOCATION: (66)..(67)
<223> OTHER INFORMATION: Xaa can be any naturally occurring amino acid

<400> SEQUENCE: 86

Met Lys Arg Asp His Arg Asp Ala Cys Ser Gly Gly Tyr Gly Gly Gly
1               5                   10                  15

Gly Gly Gly Glu Ala Ser Gly Ala Ser Lys Gly Glu Pro Pro Ser Ser
            20                  25                  30

Ser Ser Thr His Ser Leu Pro Gly Ser Gly Lys Ala Lys Met Val Met
        35                  40                  45

Trp Gly Glu Asp Asp Gln Asp Pro Ser Gly Gly Gly Gly Gly Gly Met
    50                  55                  60

Asp Xaa Xaa Ser Ser Ser Ser Ser Thr Ala Ala Gly Ala Ala Pro Ser
65                  70                  75                  80

Glu Ser Thr Arg Pro Val Val Leu Val Asp Thr Gln Glu Thr Gly Val
                85                  90                  95

Arg Leu Val His Thr Leu Met Ala Cys Ala Glu Ala Val Gln Gln Glu
            100                 105                 110

Asn Leu Lys Leu Ala Asp Ala Leu Val Lys His Ile Gly Leu Leu Ala
        115                 120                 125

Ala Ser Gln Asn Gly Ala Met Arg Lys Val Ala Thr Tyr Phe Ala Glu
    130                 135                 140

Ala Leu Ala Arg Arg Ile Tyr Arg Ile Tyr Pro His Asp Gly Ser Leu
145                 150                 155                 160

Asp Ser Ser Cys Asn Asp Ile Leu Gln Met His Phe Tyr Glu Thr Cys
                165                 170                 175

Pro Tyr Leu Lys Phe Ala His Phe Thr Ala Asn Gln Ala Ile Leu Glu
            180                 185                 190

Ala Phe Ala Thr Ala Ser Arg Val His Val Ile Asp Phe Gly Leu Lys
        195                 200                 205

Gln Gly Met Gln Trp Pro Ala Leu Met Gln Ala Leu Ala Leu Arg Pro
    210                 215                 220

Gly Gly Pro Pro Ala Phe Arg Leu Thr Gly Ile Gly Pro Pro Gln Pro
225                 230                 235                 240

Asn Asn Thr Asp Ala Leu Gln Gln Val Gly Trp Lys Leu Ala Gln Leu
                245                 250                 255

Ala Asp Thr Ile Gly Val Glu Phe Glu Phe Arg Gly Phe Val Ala Asn
            260                 265                 270

Ser Leu Ala Asp Leu Glu Pro Ala Met Leu Glu Ile Arg Pro Pro Glu
        275                 280                 285

Val Glu Thr Val Ala Val Asn Ser Val Phe Glu Leu His Pro Leu Leu
    290                 295                 300

Ala Arg Pro Gly Ala Ile Asp Lys Val Leu Ser Ser Ile Lys Ala Met
305                 310                 315                 320

Arg Pro Lys Ile Val Thr Met Val Glu Gln Glu Ala Asn His Asn Gly
```

```
                325                 330                 335

Pro Gly Phe Val Asp Arg Phe Thr Glu Ala Leu His Tyr Tyr Ser Ser
            340                 345                 350

Leu Phe Asp Ser Leu Glu Gly Ser Gly Val Ala Pro Pro Asn Gln Asp
        355                 360                 365

Leu Val Met Ser Glu Val Tyr Leu Gly Arg Gln Ile Cys Asn Val Val
    370                 375                 380

Ala Cys Glu Gly Pro Asp Arg Val Glu Arg His Glu Thr Leu Val Gln
385                 390                 395                 400

Trp Gln Ala Arg Met Gly Ser Ala Gly Phe Asp Pro Val His Leu Gly
                405                 410                 415

Ser Asn Ala Phe Lys Gln Ala Ser Met Leu Leu Ala Leu Phe Ala Gly
            420                 425                 430

Gly Glu Gly Tyr Arg Val Glu Glu Asn Asp Gly Cys Leu Met Leu Gly
        435                 440                 445

Trp His Thr Arg Pro Leu Ile Ala Thr Ser Ala Trp Gln Leu Ala Ala
    450                 455                 460

Ala Thr Gln
465


<210> SEQ ID NO 87
<211> LENGTH: 365
<212> TYPE: PRT
<213> ORGANISM: Eucalyptus globulus

<400> SEQUENCE: 87

Met Ala Cys Ala Glu Ala Val Gln Gln Glu Asn Leu Lys Leu Ala Asp
1               5                   10                  15

Ala Leu Val Lys His Ile Gly Leu Leu Ala Ala Ser Gln Asn Gly Ala
            20                  25                  30

Met Arg Lys Val Ala Thr Tyr Phe Ala Glu Ala Leu Ala Arg Arg Ile
        35                  40                  45

Tyr Arg Ile Tyr Pro His Asp Gly Ser Leu Asp Ser Ser Cys Asn Asp
    50                  55                  60

Ile Leu Gln Met His Phe Tyr Glu Thr Cys Pro Tyr Leu Lys Phe Ala
65                  70                  75                  80

His Phe Thr Ala Asn Gln Ala Ile Leu Glu Ala Phe Ala Thr Ala Ser
                85                  90                  95

Arg Val His Val Ile Asp Phe Gly Leu Lys Gln Gly Met Gln Trp Pro
            100                 105                 110

Ala Leu Met Gln Ala Leu Ala Leu Arg Pro Gly Gly Pro Pro Ala Phe
        115                 120                 125

Arg Leu Thr Gly Ile Gly Pro Pro Gln Pro Asn Asn Thr Asp Ala Leu
    130                 135                 140

Gln Gln Val Gly Trp Lys Leu Ala Gln Leu Ala Asp Thr Ile Gly Val
145                 150                 155                 160

Glu Phe Glu Phe Arg Gly Phe Val Ala Asn Ser Leu Ala Asp Leu Glu
                165                 170                 175

Pro Ala Met Leu Asp Ile Arg Pro Pro Glu Val Glu Thr Val Ala Val
            180                 185                 190

Asn Ser Val Phe Glu Leu His Pro Leu Leu Ser Arg Pro Gly Ala Ile
        195                 200                 205

Asp Lys Val Leu Ser Ser Ile Lys Ala Met Arg Pro Lys Ile Val Thr
    210                 215                 220
```

```
Met Val Glu Gln Glu Ala Asn His Asn Gly Pro Val Phe Val Asp Arg
225                 230                 235                 240

Phe Thr Glu Ala Leu His Tyr Tyr Ser Ser Leu Phe Asp Ser Leu Glu
                245                 250                 255

Gly Ser Gly Val Ala Pro Pro Asn Gln Asp Leu Val Met Ser Glu Val
            260                 265                 270

Tyr Leu Gly Arg Gln Ile Cys Asn Val Val Ala Cys Glu Gly Leu Asp
        275                 280                 285

Arg Val Glu Arg His Glu Thr Leu Val Gln Trp Gln Ala Arg Met Gly
    290                 295                 300

Ser Ala Gly Phe Asp Pro Val His Leu Gly Ser Asn Ala Phe Lys Gln
305                 310                 315                 320

Ala Ser Met Leu Leu Ala Leu Phe Ala Gly Gly Glu Gly Tyr Arg Val
                325                 330                 335

Glu Glu Asn Asp Gly Cys Leu Met Leu Gly Trp His Thr Arg Pro Leu
            340                 345                 350

Ile Ala Thr Ser Ala Trp Gln Leu Ala Ala Ala Thr Gln
        355                 360                 365


<210> SEQ ID NO 88
<211> LENGTH: 407
<212> TYPE: PRT
<213> ORGANISM: Eucalyptus globulus

<400> SEQUENCE: 88

Met Lys Arg Glu His His His Leu Tyr Pro Gln Thr Gly Pro Ser Thr
1               5                   10                  15

Ser Ala Ser Ala Ala Gly Gly Lys Ser Lys Met Trp Asp Glu Asp Gly
            20                  25                  30

Cys Gly Gly Gly Gly Asp Asp Glu Leu Leu Ala Val Leu Gly Tyr Lys
        35                  40                  45

Val Arg Ser Ser Asp Met Ala Glu Val Ala Gln Lys Leu Glu Gln Leu
    50                  55                  60

Glu Glu Val Met Phe Ser Ala Gln Glu Asp Gly Ile Ser His Leu Ala
65                  70                  75                  80

Ser Glu Thr Val His Tyr Asn Pro Ser Asp Leu Ser Ser Trp Leu Glu
                85                  90                  95

Ser Met Leu Ser Glu Phe Asn Pro Leu Pro Pro Pro Pro Gln Pro Pro
            100                 105                 110

Pro Pro Gly Gly Phe Gly Gly Gly Pro Leu Ser Val Pro Val Ala Ala
        115                 120                 125

Ala Pro Pro Arg Pro Gln Pro Val Gly Asp Pro Phe Leu Pro Arg Ala
    130                 135                 140

Glu Ser Ser Ser Ile Thr Thr Val Asp Phe Gly Ala Asp Gln Arg Met
145                 150                 155                 160

Gln Ser Ser Cys Gly Arg Ser Ser Gln Met Asn Glu Pro Arg Pro Glu
                165                 170                 175

Ile Gly Ser Ser Gly Ile Val Phe Asp Glu Glu Ser Ser Ser Asp Tyr
            180                 185                 190

Asp Leu Lys Ala Ile Pro Gly Lys Ala Val Phe Gly Arg Ala Gln Ala
        195                 200                 205

Gln Ala Gln Ala Gln Thr Arg Thr Arg Leu Ala Ser Thr Ser Ser Ser
    210                 215                 220

Ser Thr Ser Ser Ser Ala Val Thr Ala Lys Arg Phe Lys Ser Ser Pro
225                 230                 235                 240
```

```
Ser Asp Ala Ala Val Gly Ala Ala Pro Glu Ser Ser Arg Pro Val Val
                245                 250                 255

Leu Val Asp Ser Gln Glu Asn Gly Val Arg Leu Val His Ala Leu Met
            260                 265                 270

Ala Cys Ala Asp Ala Val Gln Gln Asp Asn Leu Ser Ile Ala Glu Ala
        275                 280                 285

Leu Val Lys Gln Ile Gly Phe Leu Ala Ile Ser Gln Ala Gly Ala Met
    290                 295                 300

Arg Lys Val Ala Thr Phe Phe Ala Glu Ala Leu Ala Arg Arg Ile Tyr
305                 310                 315                 320

Arg Val Tyr Pro Gln Asn Pro Pro Leu Asp His Ser Leu Thr Asp Ala
                325                 330                 335

Leu Gln Met His Phe Tyr Glu Thr Cys Pro Tyr Leu Lys Phe Ala His
            340                 345                 350

Phe Thr Ala Asn Gln Ala Ile Leu Glu Ala Phe Glu Gly Lys Ser Arg
        355                 360                 365

Val His Val Ile Asp Phe Ser Met Asn Gln Gly Leu Gln Trp Pro Ala
    370                 375                 380

Leu Met Gln Ala Leu Ala Leu Arg Pro Gly Gly Pro Pro Thr Phe Arg
385                 390                 395                 400

Leu Thr Gly Ile Gly Pro Pro
                405
```

<210> SEQ ID NO 89
<211> LENGTH: 11
<212> TYPE: DNA
<213> ORGANISM: Artificial Sequence
<220> FEATURE:
<223> OTHER INFORMATION: mutant E. grandis

<400> SEQUENCE: 89
cctggtggac a 11

<210> SEQ ID NO 90
<211> LENGTH: 50
<212> TYPE: DNA
<213> ORGANISM: Artificial Sequence
<220> FEATURE:
<223> OTHER INFORMATION: Mutant E. grandis

<400> SEQUENCE: 90
cctcttcgtc ggccgccgga gcggcgccct ccgagtcgtc ctggtggaca 50

<210> SEQ ID NO 91
<211> LENGTH: 56
<212> TYPE: DNA
<213> ORGANISM: Artificial Sequence
<220> FEATURE:
<223> OTHER INFORMATION: Mutant E. grandis

<400> SEQUENCE: 91
cctcttcgtc ggccgccgga gcggcgccct ccgagtcgac ccggccctgg tggaca 56

<210> SEQ ID NO 92
<211> LENGTH: 56
<212> TYPE: DNA
<213> ORGANISM: Artificial Sequence
<220> FEATURE:
<223> OTHER INFORMATION: Mutant E. grandis

<400> SEQUENCE: 92
cctcttcgtc ggccgccgga gcggcgccct ccgagtcgac ccggtcctgg tggaca 56

<210> SEQ ID NO 93
<211> LENGTH: 59
<212> TYPE: DNA
<213> ORGANISM: Artificial Sequence
<220> FEATURE:
<223> OTHER INFORMATION: Mutant E. grandis

<400> SEQUENCE: 93
cctcttcgtc ggccgccgga gcggcgccct ccgagtcgac ccggccgtcc tggtggaca 59

<210> SEQ ID NO 94
<211> LENGTH: 62
<212> TYPE: DNA
<213> ORGANISM: Artificial Sequence
<220> FEATURE:
<223> OTHER INFORMATION: Mutant E. grandis

<400> SEQUENCE: 94
cctcttcgtc ggccgccgga gcggcgccct ccgagtcgac ccggccgtcg tcctggtgga 60
ca 62

<210> SEQ ID NO 95
<211> LENGTH: 1697
<212> TYPE: DNA
<213> ORGANISM: Artificial Sequence
<220> FEATURE:
<223> OTHER INFORMATION: Mutant E. grandis

<400> SEQUENCE: 95
atgaagaggg atcatcgaga cgcttgcagt ggcggctatg gcggcggcgg tggcggggag 60
gcgagcggcg cctcgaaggg cgagcccccg tcgtcctcct ccacccactc aatgcccggc 120
tctggcaagg ccaagatggt gatgtggggc gaggacgacc aagatccgag cggcggtggc 180
gggggcggca tggacgagct cctcgcggtg ctcgggtaca aggtgaggtc gtcggacatg 240
gccgaggtgg cgcagaagct ggagcagctc gagatggtga tgggctctgc tcaggaggac 300
ggcatctcgc acctgtccta cgacgccgtc cactacaacc cttccgatct ctcctcgtgg 360
gtccagagca tgctcttcga gctcaacccc cctccgccgc cgcagcaggt ggccgacgcg 420
gtcctcgctg cggccgagtc gtcttccacc atcgcgcagc accaccgttc gcatctcggg 480
tctcggtctc agacgcagac tcggactctg agtcagactt cggctcccac tcagacgcag 540
tcccaggtgt cgtcctggtg gacacgcagg agactggggt gcggctcgtc cacacgctca 600
tggcctgcgc cgaggcggtc cagcaggaga acctgaagct ggccgatgcg ctcgtcaagc 660
acattggcct gctcgccgct tcgcagaacg gcgcgatgcg caaggtagcg acctacttcg 720
ccgaggcgct cgcccgccgg atttaccgaa tctaccccaa cgacggcagc ctcgactcct 780
cgtgcaacga catcctccag atgcacttct acgagacctg cccgtacctc aaattcgccc 840
acttcactgc caatcaggcg attcttgaag ccttcgccac cgccagccgc gtccacgtca 900
tcgatttcgg cctcaagcag ggtatgcagt ggccggccct catgcaggct ctggccctga 960
ggcccggcgg tccgcccgcc ttccggctca ccgggattgg cccgccgcag ccgaacaaca 1020
ccgacgcctt gcagcaggtc ggctggaagc tggctcaatt ggccgacact atcggggtcg 1080
agttcgaatt ccggggtttc gtggcgaatt cgctggctga tctcgagccc gccatgctgg 1140
acatccgccc tcccgaggtc gagacggtgg ccgtcaactc ggtgtttgag ctccaccccc 1200

-continued

```
tgctcgcccg accgggggcg attgacaagg ttctctcatc gatcaaggcc atgagaccta   1260

agatagtgac gatggtggaa caggaggcga atcacaatgg cccggggttc gtggaccggt   1320

tcacggaagc tttgcattac tactccagcc tgttcgattc gctggaaggg tctggggtgg   1380

ctcccccgaa ccaggatctg gtcatgtccg aggtctactt gggtcggcag atttgcaatg   1440

ttgtggcctg cgaggggccg gatcgagtgg agcggcacga gacgttggtg cagtggcagg   1500

cgcggatggg atcggctggg ttcgacccgg tccatctcgg gtccaacgcg ttcaagcagg   1560

cgagcatgct gctggccctg ttcgcaggtg gagaaggtta ccgggtcgag gaaaacgatg   1620

gttgtctcat gctcggttgg cacacgaggc ctctgatcgc cacttcggcg tggcaactcg   1680

ctgctgcaac tcagtga                                                  1697
```